United States Patent [19]

Karagueuzian et al.

[11] Patent Number: 6,094,593
[45] Date of Patent: Jul. 25, 2000

[54] METHOD AND APPARATUS FOR DETECTING PROSPENITY FOR VENTRICULAR FIBRILLATION USING ACTION POTENTIAL CURVES

[75] Inventors: Hrayr S. Karagueuzian; George A. Diamond; Steven S. Khan; Timothy A. Denton, all of Los Angeles, Calif.; Steven Evans, Great Neck, N.Y.

[73] Assignee: Cedars-Sinai Medical Center, Los Angeles, Calif.

[21] Appl. No.: 08/948,095

[22] Filed: Oct. 9, 1997

Related U.S. Application Data

[63] Continuation of application No. 08/567,176, Dec. 11, 1995, Pat. No. 5,678,561, which is a continuation of application No. 08/191,099, Feb. 4, 1994, Pat. No. 5,555,889, which is a continuation of application No. 07/701,753, May 17, 1991, abandoned, and application No. 07/716,665, Jun. 4, 1991, abandoned, each is a continuation-in-part of application No.07/541,881, Jun. 20, 1990, abandoned.

[51] Int. Cl.$^7$ .................................................. A61B 5/046
[52] U.S. Cl. ............................................................ 600/518
[58] Field of Search ............................................. 600/518

[56] References Cited

U.S. PATENT DOCUMENTS

| | | |
|---|---|---|
| 3,929,125 | 12/1975 | Barnes . |
| 3,940,692 | 2/1976 | Neilson . |
| 4,085,407 | 4/1978 | Stratbucker et al. . |
| 4,172,451 | 10/1979 | Kline . |
| 4,377,492 | 3/1983 | Aurousseau . |
| 4,384,585 | 5/1983 | Zipes . |
| 4,403,614 | 9/1983 | Engle et al. . |
| 4,523,595 | 6/1985 | Zibell . |
| 4,570,225 | 2/1986 | Lundy . |
| 4,680,708 | 7/1987 | Ambos et al. . |
| 4,924,875 | 5/1990 | Chamoun . |
| 4,934,374 | 6/1990 | Oslund et al. . |
| 4,964,410 | 10/1990 | Leahey et al. . |
| 4,974,598 | 12/1990 | John . |
| 4,979,110 | 12/1990 | Albrecht et al. . |
| 5,000,189 | 3/1991 | Throne et al. . |
| 5,092,341 | 3/1992 | Kelen . |

OTHER PUBLICATIONS

Goldberg et al., Applications of Nonlinear Dynamics to Clinical Cardiology, pp. 195–212, *Annals of the N.Y. Academy of Science*, vol. 504, 1987.

Babloyantz et al., Is the Normal Heart a Periodic Oscillator?, pp. 203–211, *Biol.Cybernetics 58,* (1988).

Berni et al., Detection of Digitalis Toxicity, pp. 29–34, *IEEE Transactions on Biomedical Engineering*, vol. BME–22.

Shimizu et al., *Circulation*, vol. 75 (Suppl I), pp. I–34–I–39 (Jan. 1987).

Paulus et al., *Circulation*, vol. 81, pp. 886–898, (Mar. 1980).

Nave et al., *International Journal of System Science*, vol. 13, pp. 703–706. (Jun. 1982).

Ravelli et al., *Proceedings of Computers in Cardiology; IEEE Computer Society Press*, pp. 501–504, Jerusalem Israel, (Sep. 1989).

Klinger et al., *Proceedings of the 8th Northeast Bioengineering Conference; IEEE Press Conference*, pp. 217–221, New York, US (1980).

Jorne et al., *Mathematical Biosciences*, vol. 37, pp. 51–61, (1977).

Ino et al., Relation of Monophasic Action Potential Recorded with Contact Electrode to Underlying Transmembrane Action Potential Properties in Isolated Cardiac Tissues: A Systematic Microelectrode Validation Study, *Cardiovascular Research*, vol. 22, pp. 255–264 (1988).

*Primary Examiner*—William E. Kamm
*Attorney, Agent, or Firm*—Lyon & Lyon LLP

[57] ABSTRACT

A method for detecting a heart disorder comprises examination of a phase-plane plot (PPP) of a patient electrocardiogram (EKG). The PPP's degree of deterministic chaos may be measured by a processor. Analysis of the PPP may indicate a propensity for fibrillation that is, indicate both the risk of fibrillation and its actual onset (cases where risk is 100 percent). A second method for detecting a heart disorder comprises examination of a frequency-domain transform (such as an FFT) of a patient EKG. An automatic defibrillating device may comprise means for delivering a variable shock, the size of which is determined at least in part by the FFT's peak energy. A method for detecting drug toxicity comprises examination of a parameter time constant for an action-potential duration (APD) restitution curve which is constructed for the patient.

3 Claims, 7 Drawing Sheets

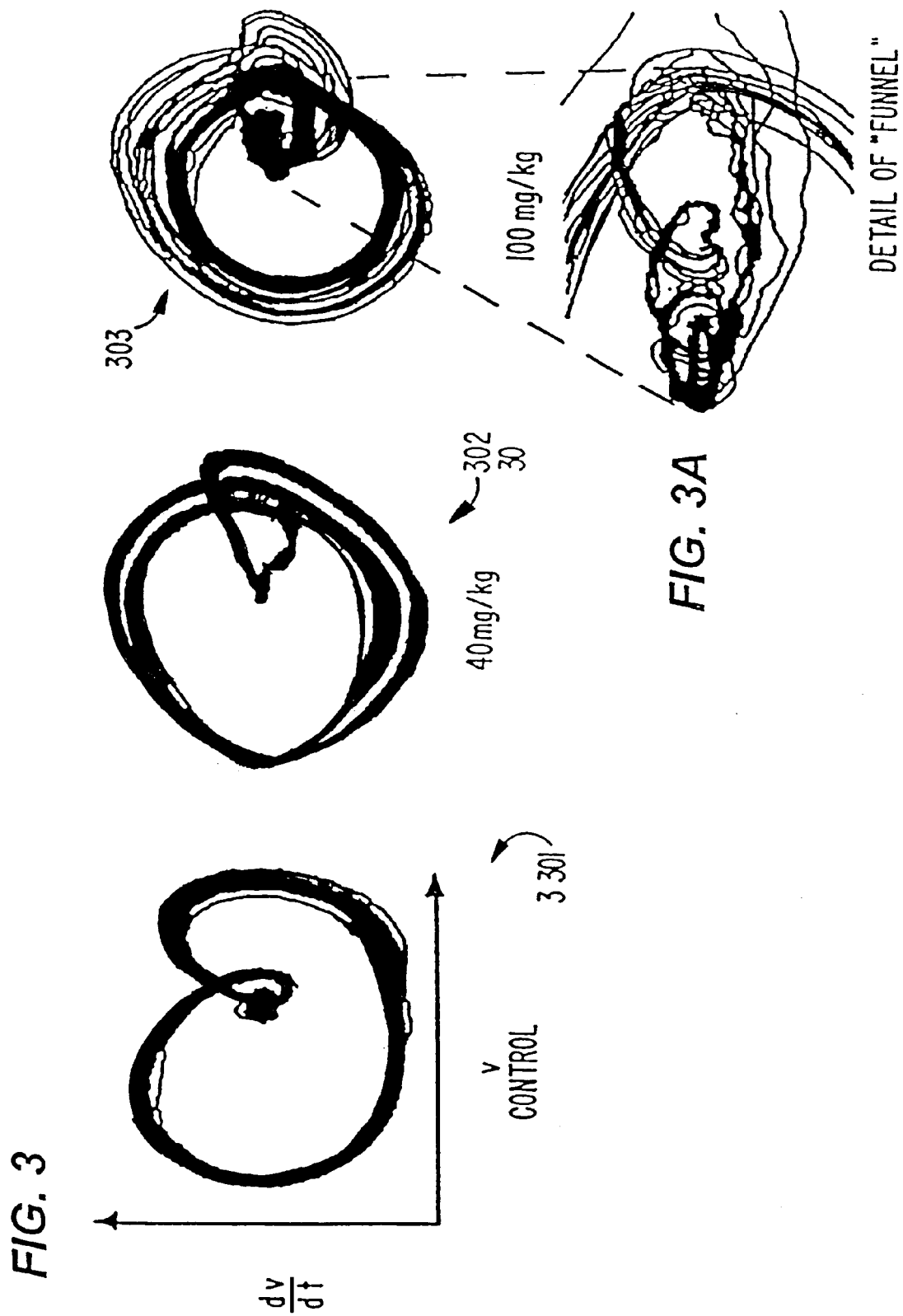

METHOD AND APPARATUS FOR DETECTING PROSPENITY FOR VENTRICULAR FIBRILLATION USING ACTION POTENTIAL CURVES

This is a continuation of Ser. No. 08/567,176, filed Dec. 11, 1995, now U.S. Pat. No. 5,678,561 which in turn is a continuation of application Ser. No. 08/191,099, now U.S. Pat. No. 5,555,889, which is a continuation of Ser. No. 07/701,753 filed May 17, 1991, abandoned, and Ser. No. 07/716,665, filed Jun. 04, 1991, abandoned, which are continuation-in-parts of Ser. No. 07/541,881 filed on Jun. 20, 1990 now abandoned. This application declares its priority from these applications which are also incorporated by reference. This application combines the disclosures of these applications.

BACKGROUND OF THE INVENTION

1. Field of the Invention

This invention relates to heart disorders. More specifically, this invention relates to detecting and evaluating arrhythmia, fibrillation and related disorders by manipulation of an electrocardiogram signal.

2. Description of Related Art

Despite major advances in the diagnosis and treatment of ischemic heart disease over the past decade, a substantial number of patients each year may suffer sudden cardiac death as a consequence of ventricular fibrillation (VF). To date, no reliable predictive or preventive measures have been developed. By all outward appearances, VF is a highly complex, seemingly random phenomenon. So are other related heart disorders, including those stages in heart behavior which typically precede JF (onset of VF). Accordingly, it is difficult for automated devices to determine with any reliability that a patient is undergoing VF or onset of VF. Moreover, onset of VF may also be difficult to determine with any reliability, even for skilled medical personnel.

A method of detecting and evaluating heart disorders would therefore find wide applicability and utility. Patient monitoring devices may summon medical personnel if the patient is undergoing VF or onset of VF. Automatic devices which attempt to counter VF, e.g. automatic implantable cardiac defibrillators (AICDs) may vary their operation based on evaluation of the severity of the patient's condition. Methods for reliably evaluating the risk of VF may also have important utility in monitoring patients undergoing surgery or other critical therapy.

It has been found that some anti-arrhythmic drugs may also have a pro-arrhythmic effect in excess concentrations. For example, quinidine has been known to be toxic in this manner. A method of detecting and evaluating heart disorders would also have wide applicability and utility in determining if a patient as been subjected to a toxic (or partially toxic) dosage of a drug relating to heart condition.

Chaos theory is a recently developed field relating to phenomena which appear to be highly complex and seemingly random, but which may be described as the deterministic result of relatively simple systems. Chaos theory may have potentially wide applications in biologic and other systems involving ambiguity and uncertainty. For example, it has been conjectured that chaos theory may be valuable for describing certain natural processes, including electroencephalogram (EEG) and electrocardiogram (EKG) signals. Techniques for detecting and evaluating aspects of deterministic chaos are known in the field of chaos theory, but have found little application in the medical field.

Accordingly, there is a need for improved methods and devices for detecting and evaluating heart disorders, including ventricular fibrillation (VF) and the onset of VF.

SUMMARY OF THE INVENTION

A first aspect of the invention provides a method for detecting a heart disorder, by examination of a phase-plane plot (PPP) of a patient electrocardiogram (EKG). A normal patient will have a PPP which is relatively smooth; a patient at risk of developing ventricular fibrillation (VF) onset will have a PPP which exhibits features of a chaotic process, such as multiple bands, "forbidden zones", periodicity with period-doubling and phase locking; a patient exhibiting VF will have a PPP which appears noisy and irregular. Differing PPPs may be readily recognized, thus detecting patients with heart disorders.

In a preferred embodiment, the PPP's degree of deterministic chaos may be measured by a processor, such as by graphic and numeric analysis. (1) The processor may measure a Lyapunov exponent or a fractal dimension of the PPP. (2) The processor may determine a Poincare section of the PPP and examine that Poincare section for indicators of deterministic chaos. Also, the processed PPP and Poincare sections may be reviewed by a human operator. The processed PPP and Poincare sections may indicate the propensity for fibrillation.

A second aspect of the invention provides a method for detecting a heart disorder, by examination of a frequency-domain transform (such as an FFT) of a patient EKG. A normal patient will have an FFT with a discrete spectrum, while a patient exhibiting VF will have an FFT with a relatively continuous spectrum and a peak energy at a relatively low frequency (e.g., about 5–6 Hz). A patient exhibiting VF which is difficult to revert with shock will have an FFT with a peak energy at a relatively high frequency (e.g., about 10 Hz or more).

In a preferred embodiment, an automatic defibrillating device may comprise means for delivering a variable shock, the size of which is determined at least in part by the FFT's peak energy. The defibrillating device may also comprise means for signalling an alarm if the FFT's peak energy is at a relatively high frequency.

A third aspect of the invention provides a method for detecting drug toxicity, based on particulars of an action potential duration (APD) restitution curve, or an action-potential amplitude (APA) curve, which is constructed for the patient, such as fitting an exponential relation to that curve or such as a parameter time constant for that curve. The slope of the fitted curve will indicate the patient's possibility of predisposition to arrhythmia. Differences in the parameters of the fitted curve allow one to distinguish between normal and abnormal patients, e.g. those at risk of arrhythmia or ischemia. A normal patient will have a relatively low parameter time constant; a patient who is exhibiting drug toxicity will have a relatively high parameter time constant. A PPP of APD or APA data may also be generated, and the analytical techniques described herein may be utilized to interpret that PPP, to determine and evaluate drug toxicity.

BRIEF DESCRIPTION OF THE DRAWINGS

FIG. 3A shows a detail of the "funnel" area of the PPP corresponding to the third EKG of FIG. 2, taken from a patient exhibiting VF.

DESCRIPTION OF THE PREFERRED EMBODIMENT

I

A first aspect of the invention relates to detection and evaluation of heart disorders by examination of a phase-plane plot (PPP) of a patient electrocardiogram (EKG).

Figure 1:
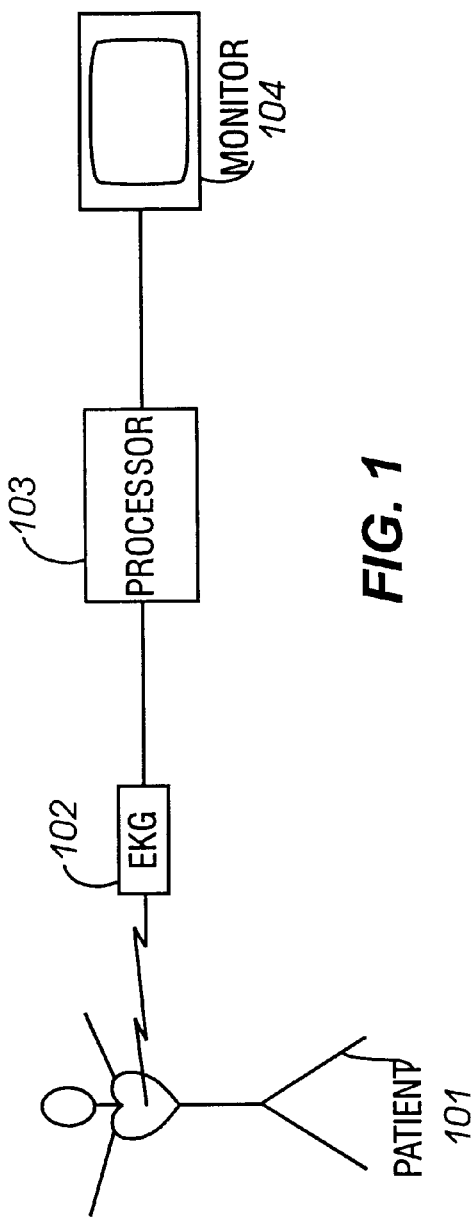
FIG. 1 shows a patient monitoring system.

FIG. 1 shows a patient monitoring system. A patient 101 is coupled to an electrocardiogram (EKG) device 102, which acquires EKG signals and transmits them to a processor 103. The processor 103 may display the EKG signals on a monitor 104 (as is well-known in the art), or it may process the EKG signals and display any results of processing on the monitor 104.

EKG signals are well-known in the art, as are methods of acquiring them. As used herein, an EKG refers to a surface electrocardiogram, but other forms of electrocardiogram would also work with the methods disclosed herein, and are within the scope and spirit of the invention. For example, the EKG shown herein may comprise a surface EKG, an epicardial EKG, an endocardial EKG, or another related signal (or set of signals) measured in or near the heart. Moreover, the signal which is manipulated may be a voltage signal, a current signal, or another related electromagnetic values (or set of values).

Figure 2:
FIG. 2 shows a set of sample EKG signals.

FIG. 2 shows a set of sample EKG signals. A first EKG signal 201 shows a normal patient. A second EKG signal 202 shows a patient in transition to VF. A third EKG signal 203 shows a patient with VF.

The processor 103 may construct a phase-plane plot (PPP) from the EKG signal. A first type of PPP comprises a plot of an EKG variable against its first derivative. In a preferred embodiment, the EKG variable is voltage, v (itself a function of time); its first derivative is dv/dt (also a function of time).

However, it would be clear to one of ordinary skill in the art, after perusal of the specification, drawings and claims herein, that wide latitude in construction of the PPP is possible. The variable chosen for the PPP may be any one of a variety of different parameters, including EKG voltage, current, or another signal value. The chosen variable (v) may be plotted against its first time derivative (dv/dt), its second time derivative $d^2v/dt^2$, or another time derivative $d^n v/dt^n$. Or, an Mth derivative may be plotted against an Nth derivative.

Another type of PPP may comprise a plot of an EKG variable (or an Nth derivative thereof) against a time delayed version of itself, (e.g. v(t) versus v(t−δt)). This type of PPP is sometimes also called a "return map". This type of PPP is led sensitive to EKG signal noise.

Another type of PPP may comprise a plot of three EKG variables (or Nth derivatives thereof) simultaneously (e.g., v, dv/dt, and $d^2v/dt^2$). Such a PPP would be 3-dimensional. Where the PPP is 3-dimensional, it may be displayed stereoscopically, or a 2-dimensional plane "cut" of the 3-dimensional display may be displayed on a 2-dimensional display. It would be clear to one of ordinary skill in the art, that all of these choices described herein, or combinations thereof, would be workable and are within the scope and spirit of the invention.

Figure 3:
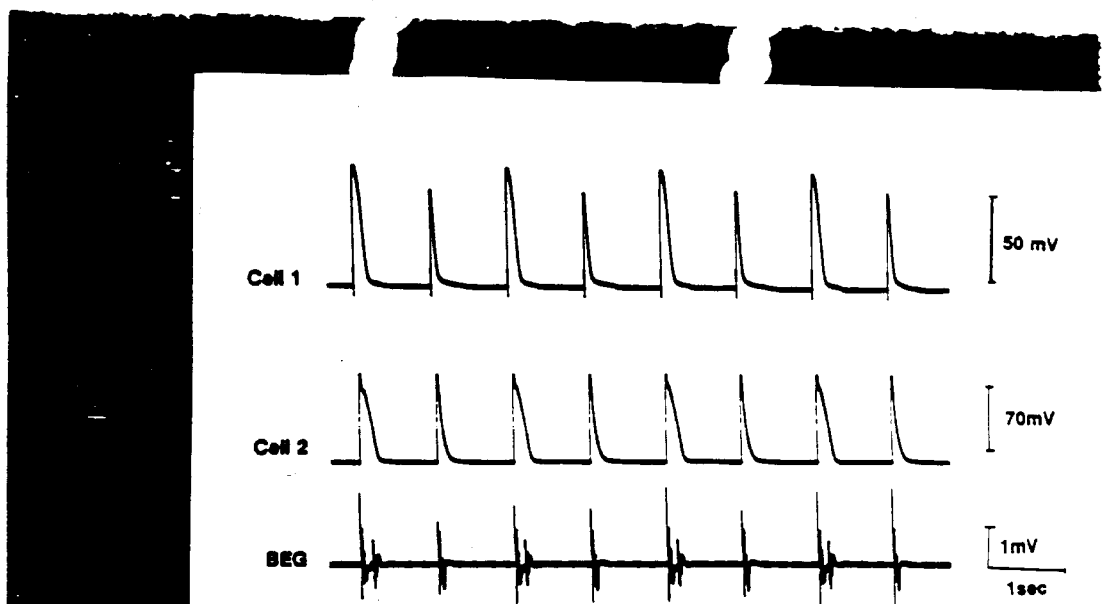
FIG. 3 shows a set of corresponding PPPs for the sample EKG signals of FIG. 2.
Figure 4:
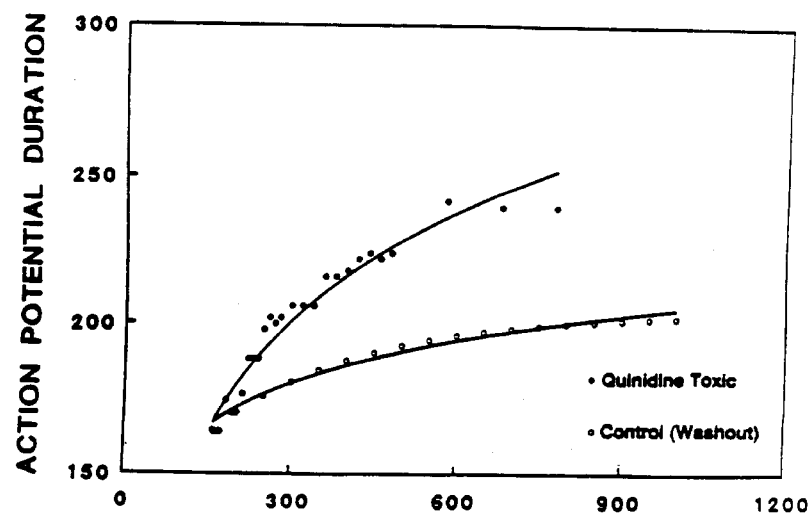
Figure 5:
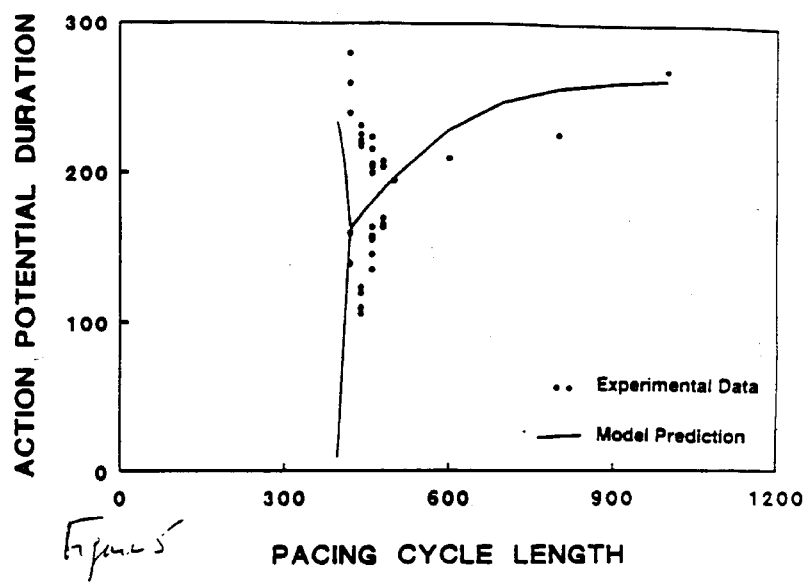

FIG. 3 shows a set of corresponding PPPs for the sample EKG signals of FIG. 2. A first PPP 301 corresponds to the first EKG signal 201. A second PPP 302 corresponds to the second EKG signal 202. A third PPP 303 corresponds to the third EKG 203. FIG. 3a shows a detail of the "funnel" area of the PPP corresponding to the third EKG of FIG. 2, taken from a patient exhibiting VF. The funnel area of the PPP, shown in FIG. 3a, in particular, exhibits an irregular and highly complex pattern, indicative of ventricular fibrillation to even a relatively untrained eye.

Part of this aspect of the invention is the discovery that a normal patient will have a PPP which exhibits the regularity and smoothness of an EKG signal from that normal patient, while a patient undergoing VF will have a PPP which exhibits the irregularity and complexity of an EKG signal which might be deterministic chaos (e.g., aperiodicity, banding and "forbidden zones"). Moreover, a patient in transition from normal into VF (i.e., in VF onset) exhibits a PPP which is consistent with an assessment that the EKG signal for the patient is in transition to deterministic chaos.

A normal patient has a relatively regular beat-to-beat EKG signal. As the patient transitions to VF, the patient's EKG signal at first shows oscillations between pairs of alternant regular beat-to-beat signals. As the transition continues, the patient's EKG signal then shows oscillations between greater and greater numbers of alternate regular signals (e.g., four possible alternants, eight possible alternants, etc.), until it is no longer possible to identify alternant regular signals and the EKG signal is irregular and highly complex. At that point, the patient is generally said to be exhibiting VF.

In like manner, the patient's PPP will transition from a smooth single-banded display, through a multi-banded display (showing multiple alternants) and finally to an irregular and highly complex display. The display change in the PPP is so striking that even a relatively untrained person can see the difference. This is in contrast with display changes in the EKG, which generally requires a skilled cardiologist to evaluate.

There are several possible factors which might cause a patient to transition from normal to VF. These factors may include drug overdose (especially overdose with an antiarrhythmic which has a pro-arrhythmic effect in overdosage, e.g., quinidine intoxication), excessive electrical stimulation, hypothermia, ischemia, and stress. In a preferred embodiment, a patient monitor may examine the patient's PPP so as to determine if the patient is in transition from normal to VF; this could indicate that one of these pro-arrhythmic factors is excessively present.

The processor 103 may further process the PPP so as to measure the PPP's degree of deterministic chaos. Several techniques may be applied for this purpose:

(1) The processor 103 may measure a Lyapunov exponent of the PPP. The Lyapunov exponent of the PPP is a measure of the degree to which nearby paths of the PPP diverge. The Lyapunov exponent is well-known in chaos theory and may be measured with available software. See, e.g., Wolf et al., "Determining Lyapunov exponents from a time series", Physica D 1985; 16: 285317.

(2) The processor 103 may measure a fractal dimension of the PPP. The fractal dimension of the PPP is a measure of the degree to which the PPP forms a "space-filling" curve. The fractal dimension is well-known in chaos theory and may be measured with several techniques (e.g. correlation dimension or box-counting methods), for example as shown below and in FIG. 9:

After the EKG is sensed 901 and the phase plane plot constructed 902, in order to measure the fractal dimension of the PPP the processor of FIG. 1 superimposes a rectilinear grid (comprising a set of boxes) 903 on the PP 903 and counts the number of boxes which are cut by the PPP's trace 904. The processor of FIG. 1 then varies the size of the grid and records each grid size and each count 905. The processor FIG. 1 then computes the constant k in the following relation 906:

$$\ln(\# \text{ of boxes cut}) = k * \ln(\# \text{ of boxes in grid})$$

The constant k is a measure of the fractal dimension of the PPP. A value of k between about 3 and about 7 especially with a fractional component, implies that the PPP is likely to represent a process based on deterministic chaos, and therefore a patient who is close to (or actually in) VF 907. The propensity for ventricular fibrillation is then registered 908.

Figure 10:
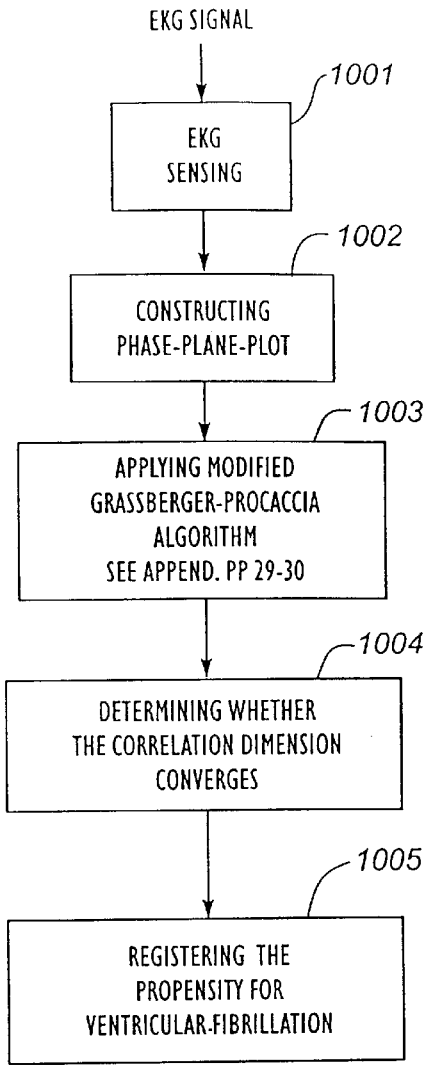
FIG. 10 shows a flow chart for a method of registering a propensity for fibrillation by determining correlation dimension convergence.

The fractal dimension may also be measured with correlation dimension techniques such as shown in FIG. 10 and appendix pp. 29–30. In this process after the EKG is sensed 1001 and the phase-plane plot constructed 1002 the processor of FIG. 1 applies a modified Grassberger-Procaccia algorithm 1003. The correlation dimension is then evaluated for convergence 1004. In the event of convergence the propensity for ventricular fibrillation is registered 1005.

(3) the processor 103 may determine a Poincare section of the PPP and examine that Poincare section for indicators of deterministic chaos, as described herein. The processed PPP and Poincare sections may also be displayed for review by a human operator, whereupon any visible structure will be readily recognized.

Figure 4:
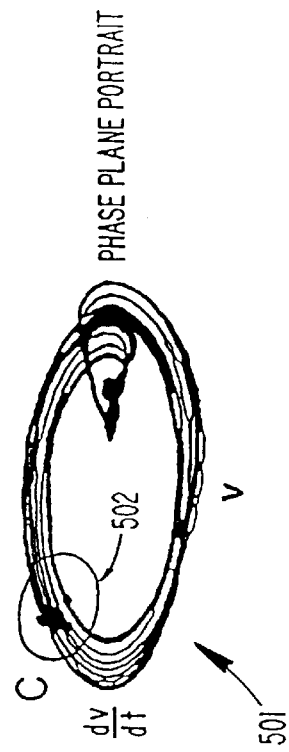
FIG. 4 shows an example PPP and a corresponding Poincare section.

FIG. 4 shows an example PPP 401 and a corresponding Poincare section 402. A Poincare section may comprise a line segment drawn across a part of the PPP. In general, such a line segment will be close to perpendicular to the trajectories of the PPP in a region of interest.

The processor 103 may acquire the data points in each Poincare section or PPP and compute a statistical measure of anisotropy or inhomogeneity of those data points. one such measure is based on the mean and standard deviation of those data points (these may be computed by statistical methods which are well-known in the art). The ratio $$r = (\text{standard deviation})/(\text{expected value}) \quad (403)$$

is a measure of the degree of clumping in the Poincare section.

A greater value for r implies that the PPP is more likely to represent a process based on deterministic chaos, and therefore a patient who is close to (or actually in) VF. The value for r may be displayed for review by a human operator in comparison with a value for r for a normal patient, together with a set of confidence bands, as is well-known in the art, for indicating a degree of variation from a normal patient.

The processor 103 may also compute other statistical measures of the Poincare section.

The processor 103 may also determine a "time-lapse" Poincare section of the PPP.

Figure 5:
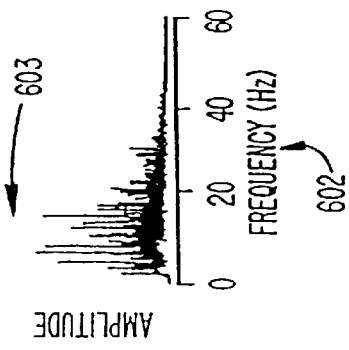
FIG. 5 shows an example PPP and a corresponding time-lapse Poincare section.

FIG. 5 shows an example PPP 501 and a corresponding time-lapse Poincare section 502. A time-lapse Poincare section may comprise a set of data points selected from the PPP by selecting one data point every t seconds. The time-lapse Poincare section may be analyzed in like manner as the other Poincare section disclosed herein.

II

A second aspect of the invention relates to detection and evaluation of heart disorders based on a frequency-domain transform of a patient EKG.

Figure 6A:
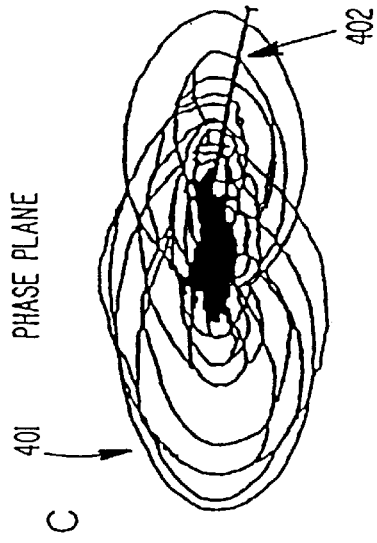
FIG. 6A shows the frequency-domain fast Fourier transform of an EKG from a normal patient.
Figure 6B:
FIG. 6B shows the frequency-domain fast Fourier transform of an EKG from a patient experiencing VF.
Figure 6:
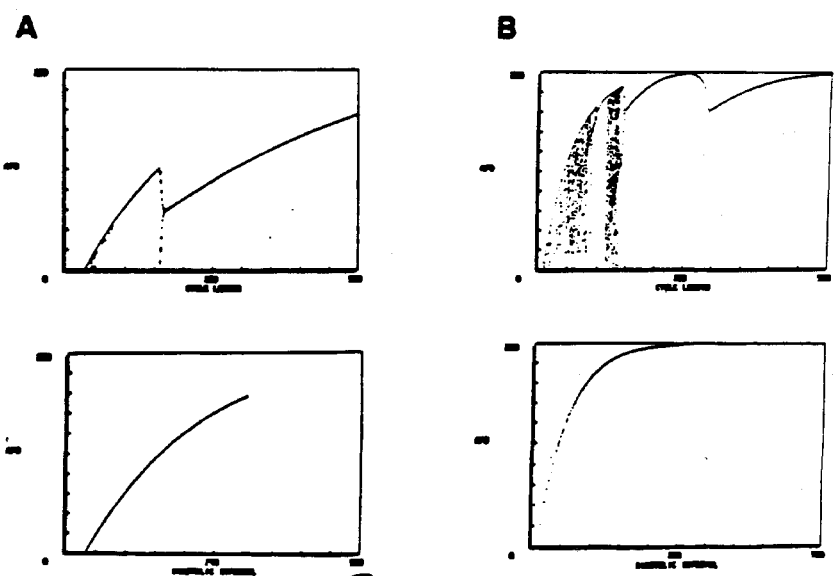
Figure 1:
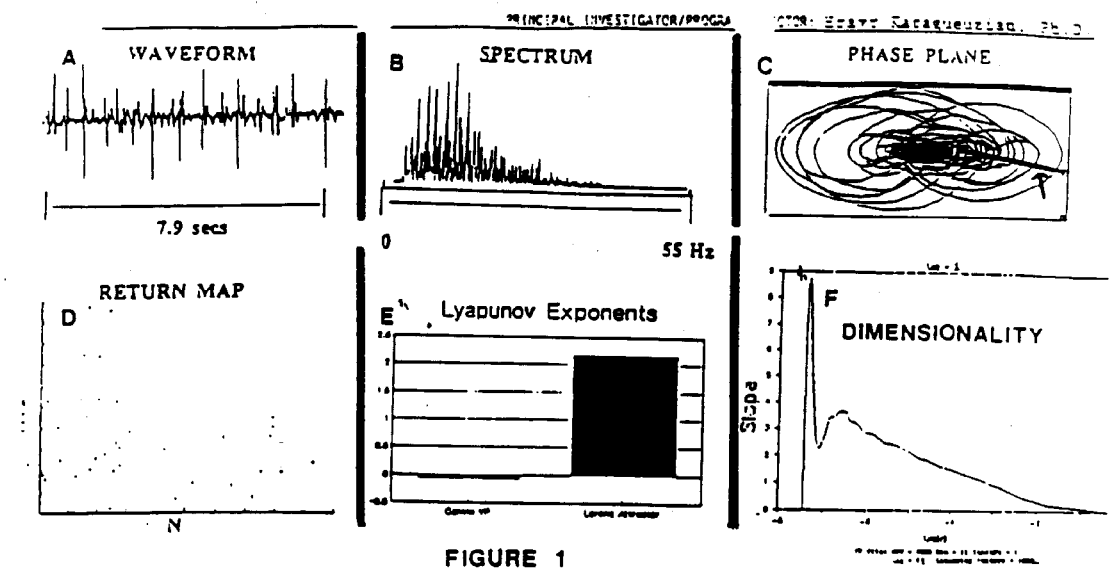
Figure 3:
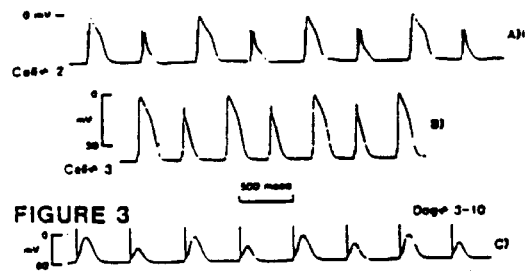
Figure 4:
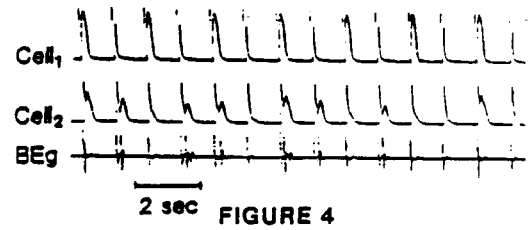
Figure 5:
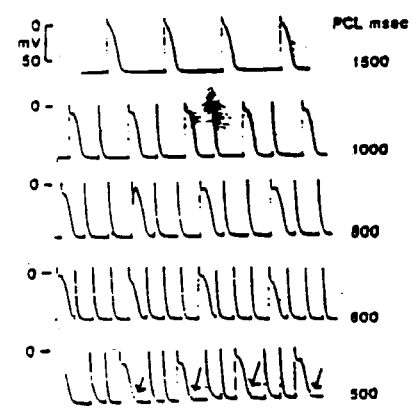
Figure 6:
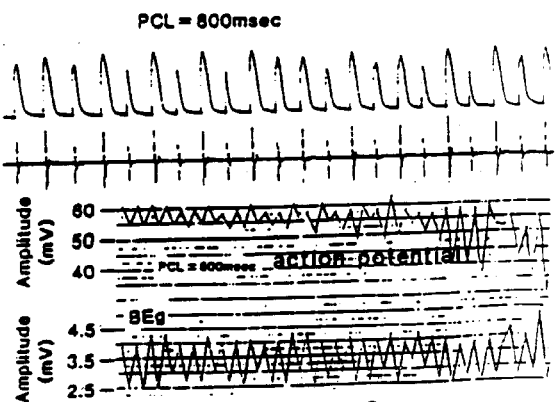
Figure 2:
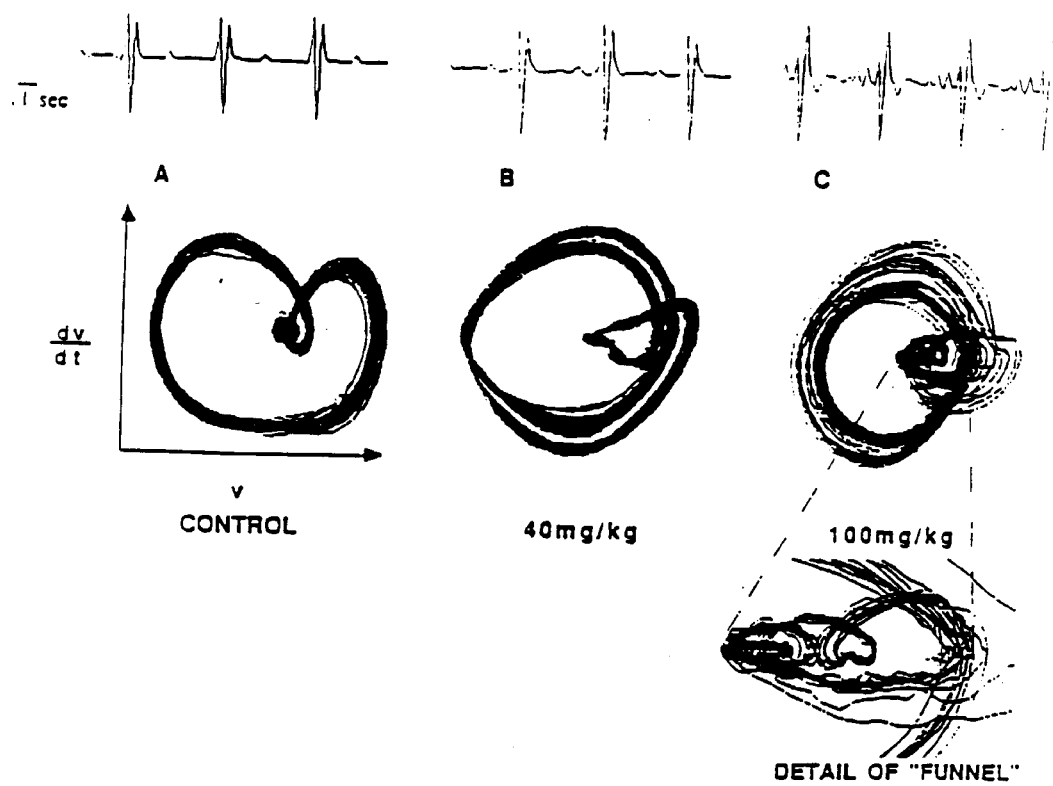
Figure 2:
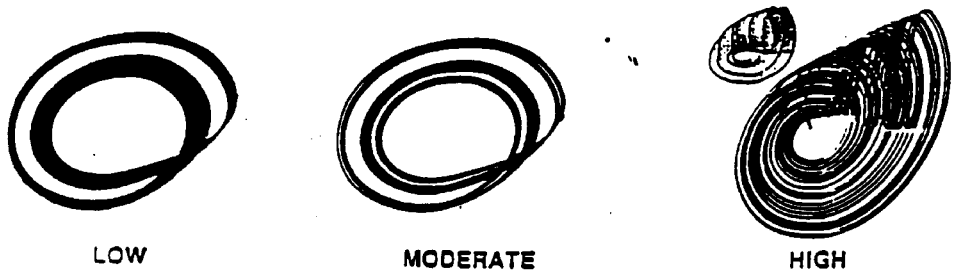
Figure 5:
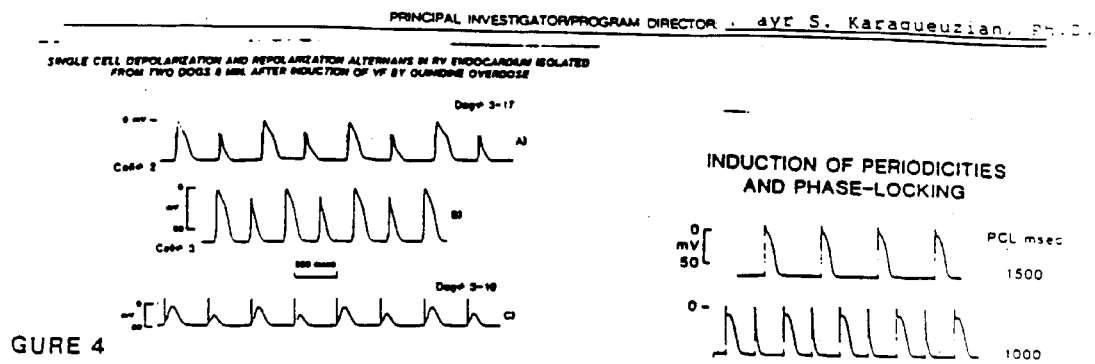
Figure 5:
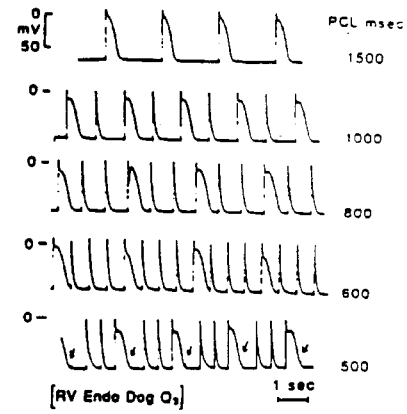
Figure 6:
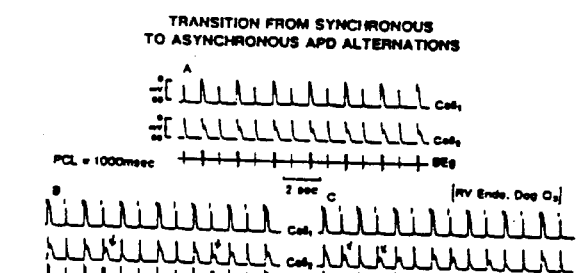
Figure 8:
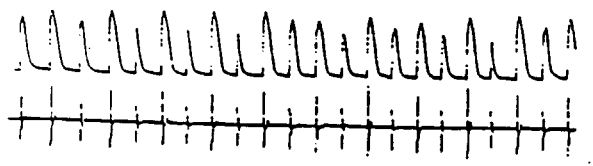
Figure 8:
Figure 3:
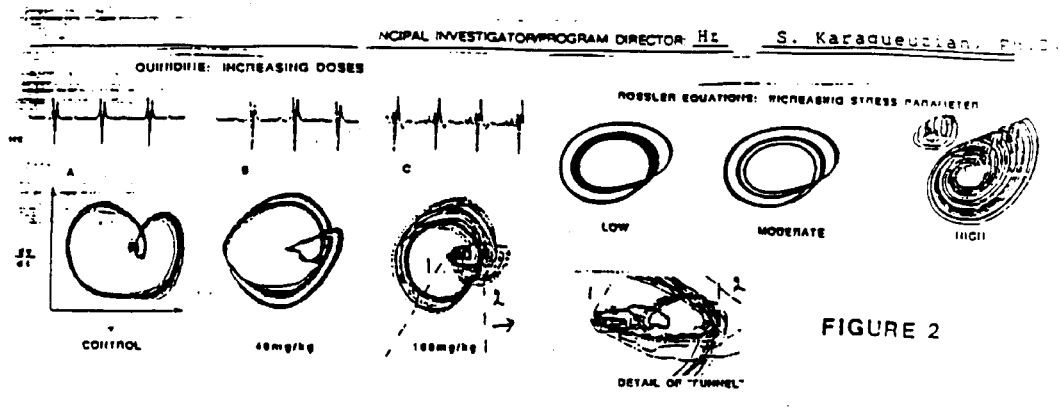
Figure 3:
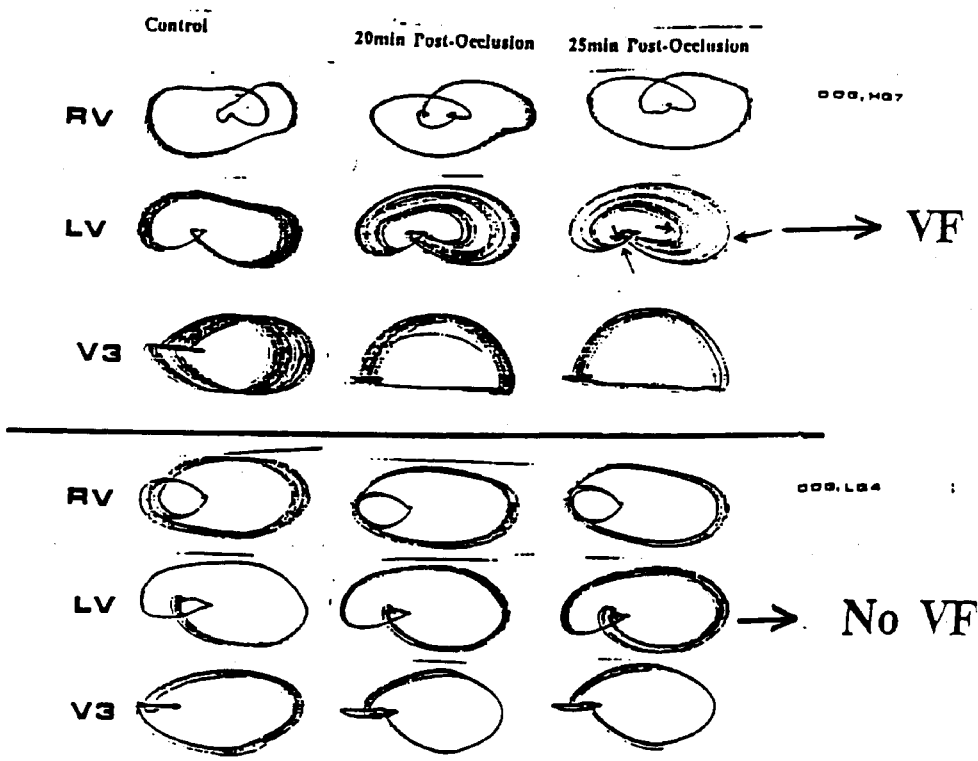
Figure 2:
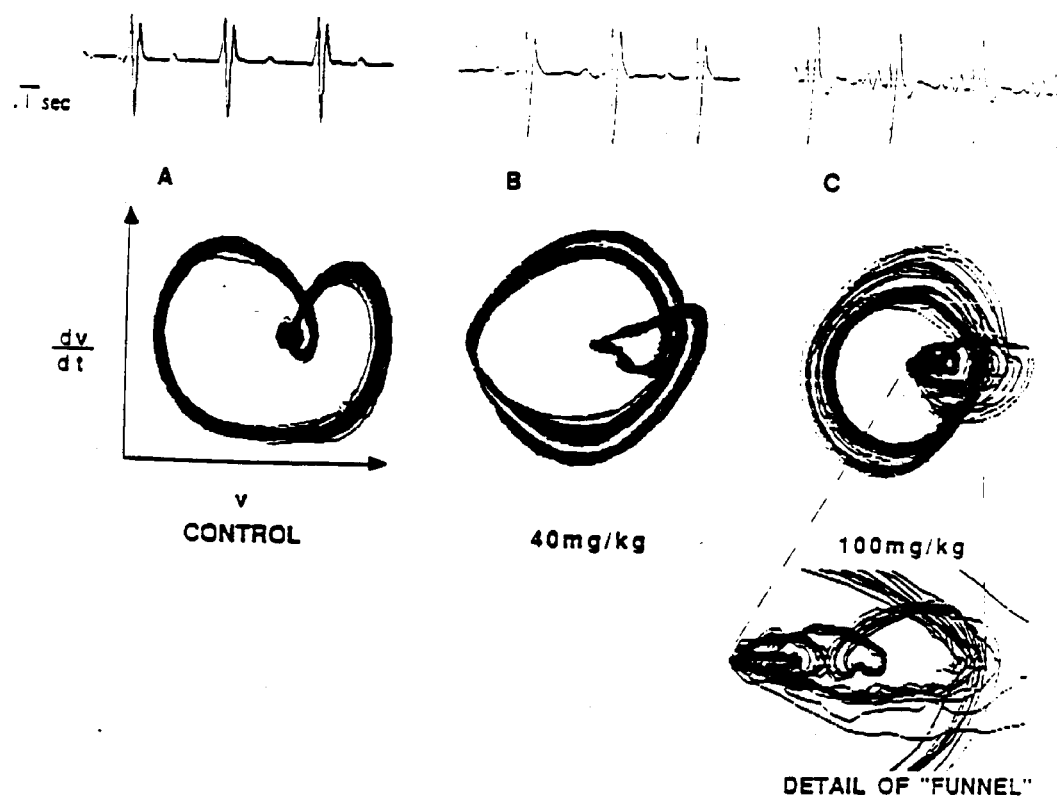
Figure 2:
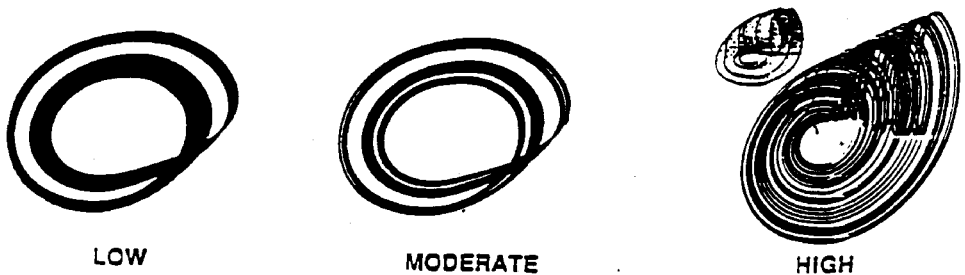
Figure 1:
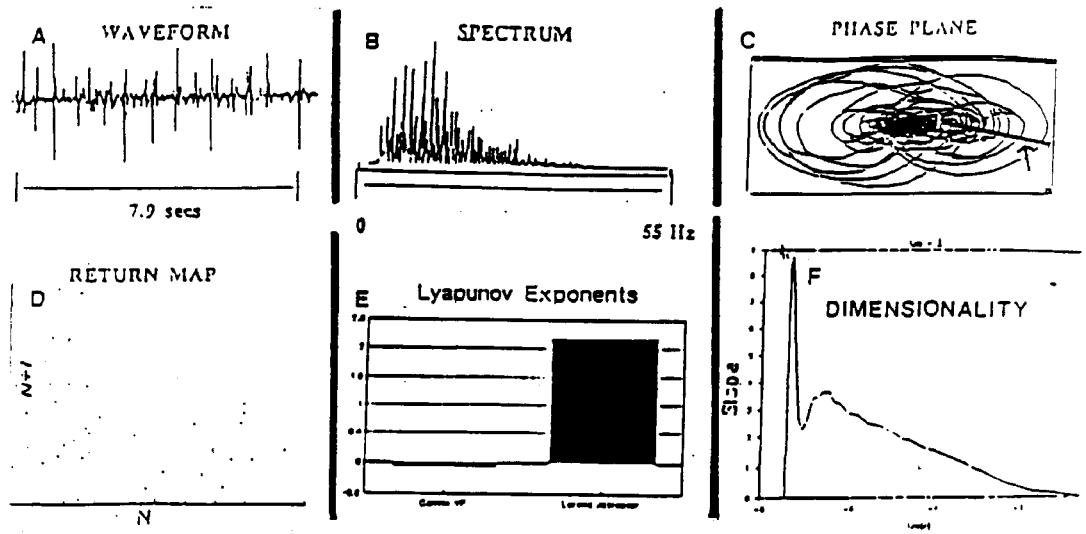
Figure 1:
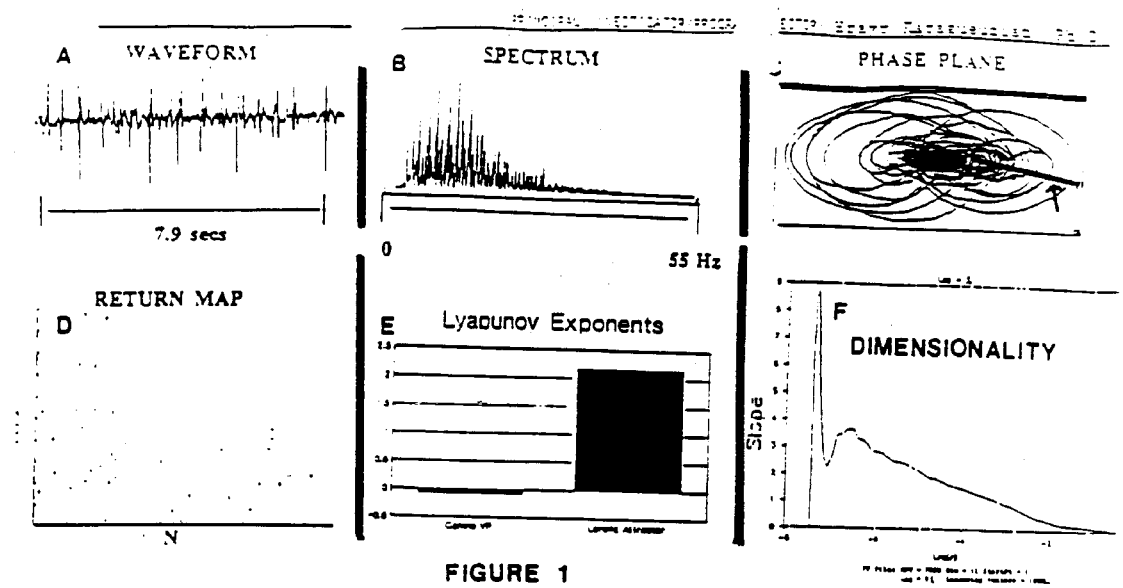
Figure 3:
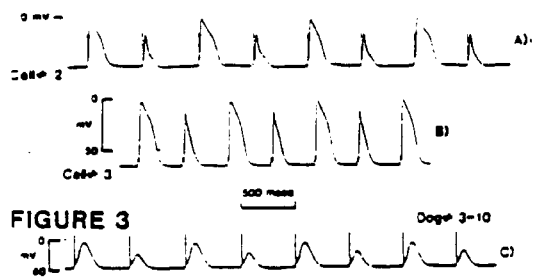
Figure 4:
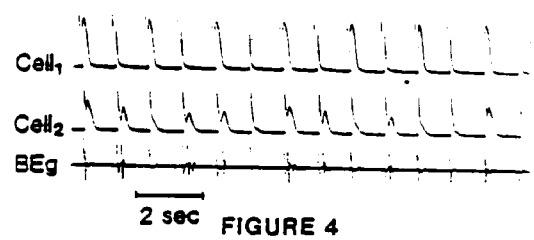
Figure 5:
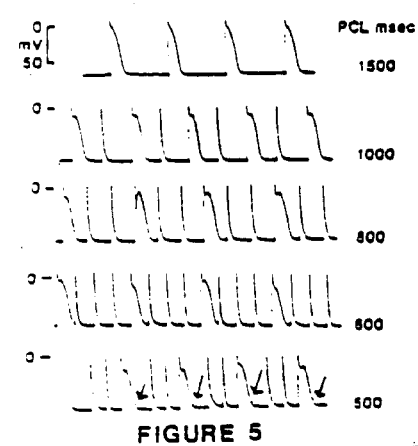
Figure 6:
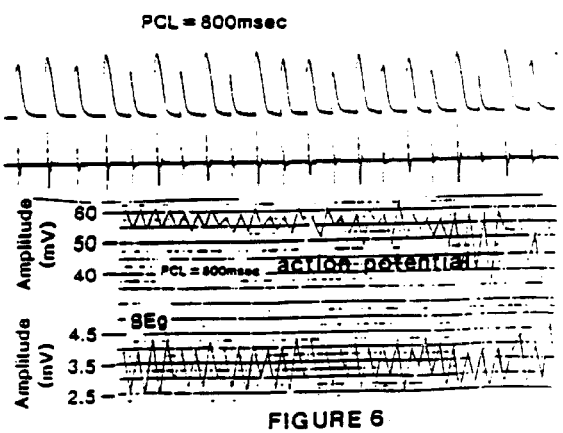
Figure 2:
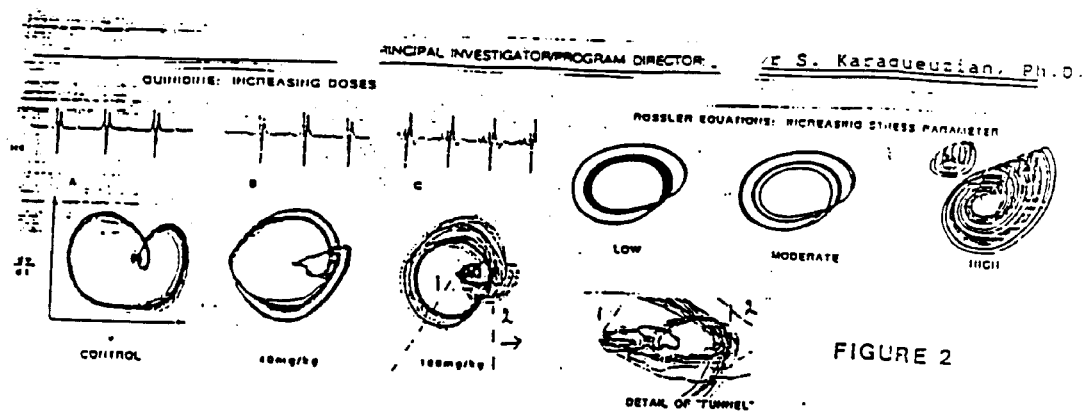
Figure 3:
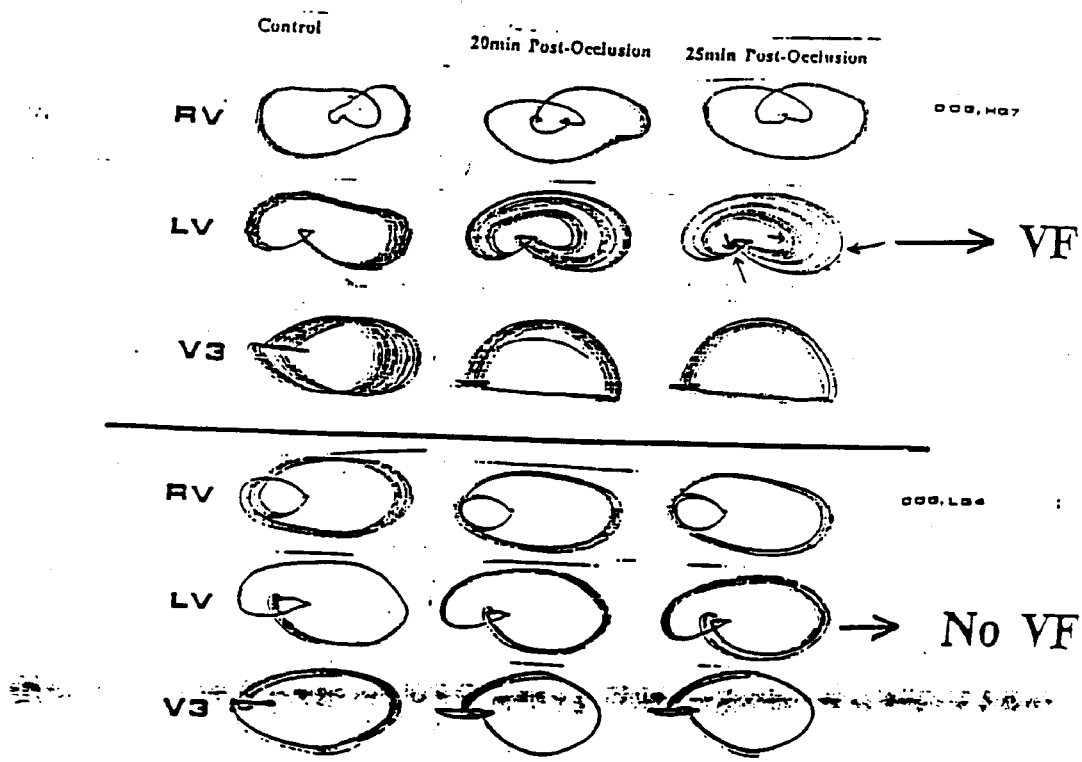
Figure 1:
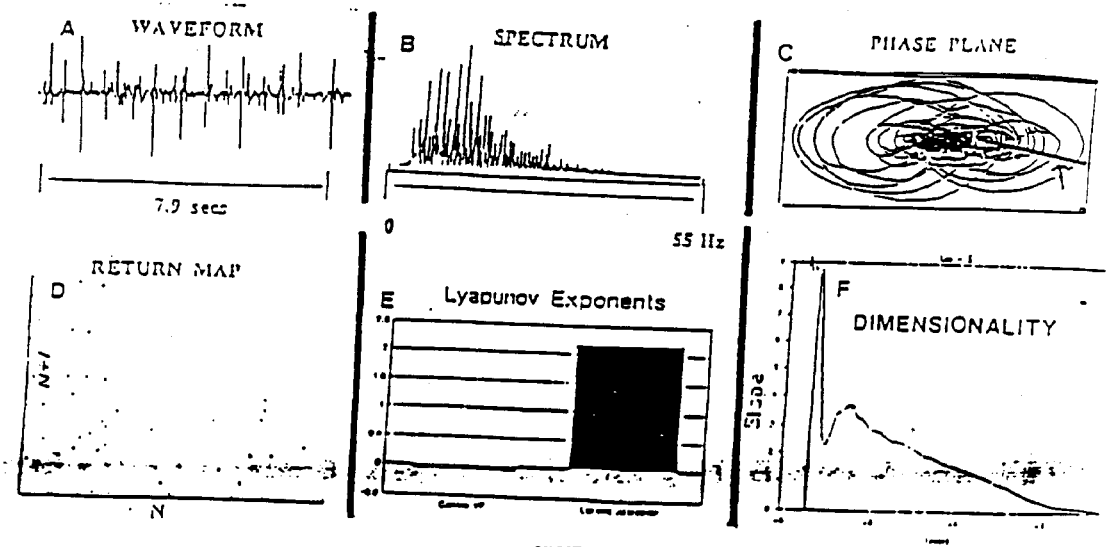
Figure 2:
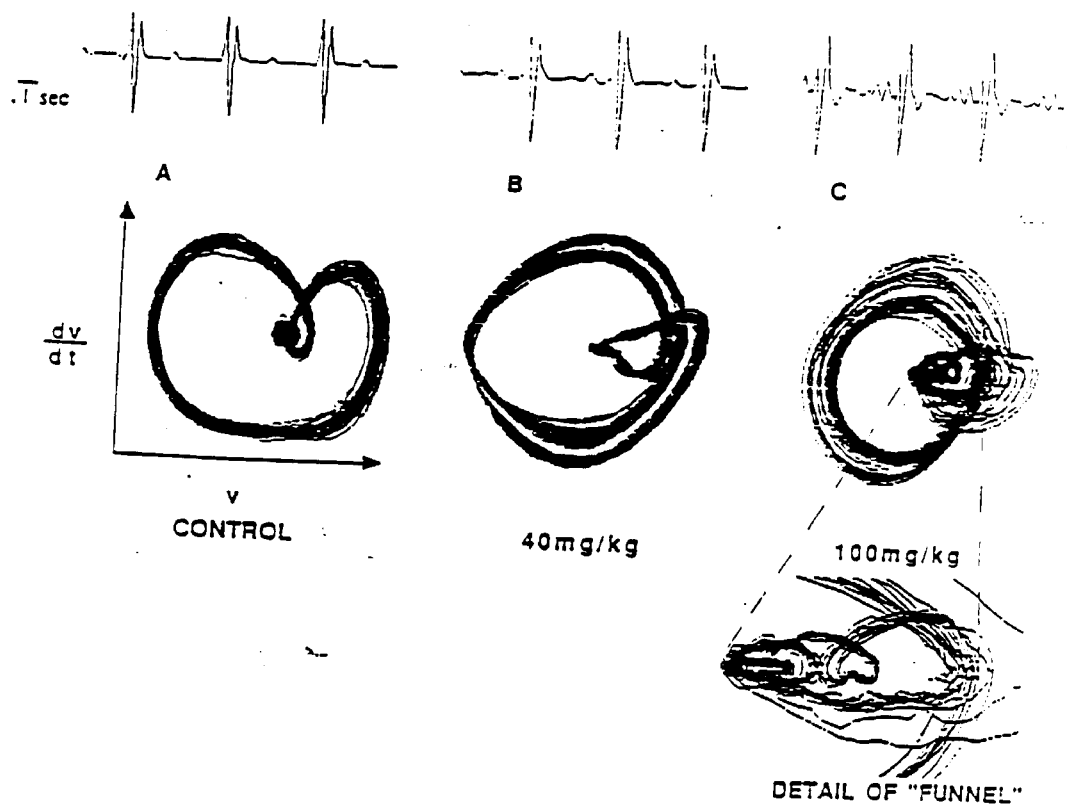
Figure 2:
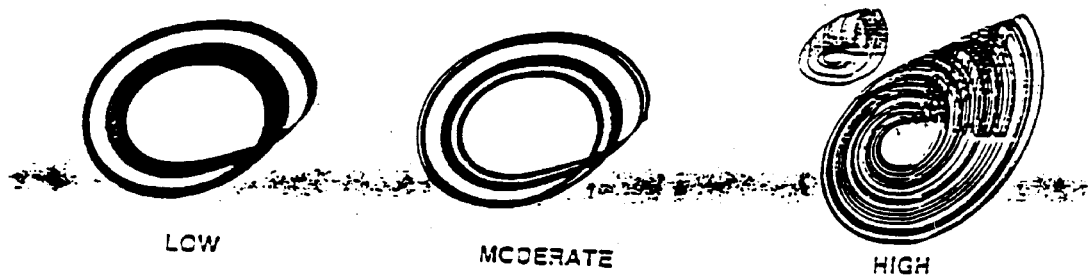
Figure 1:
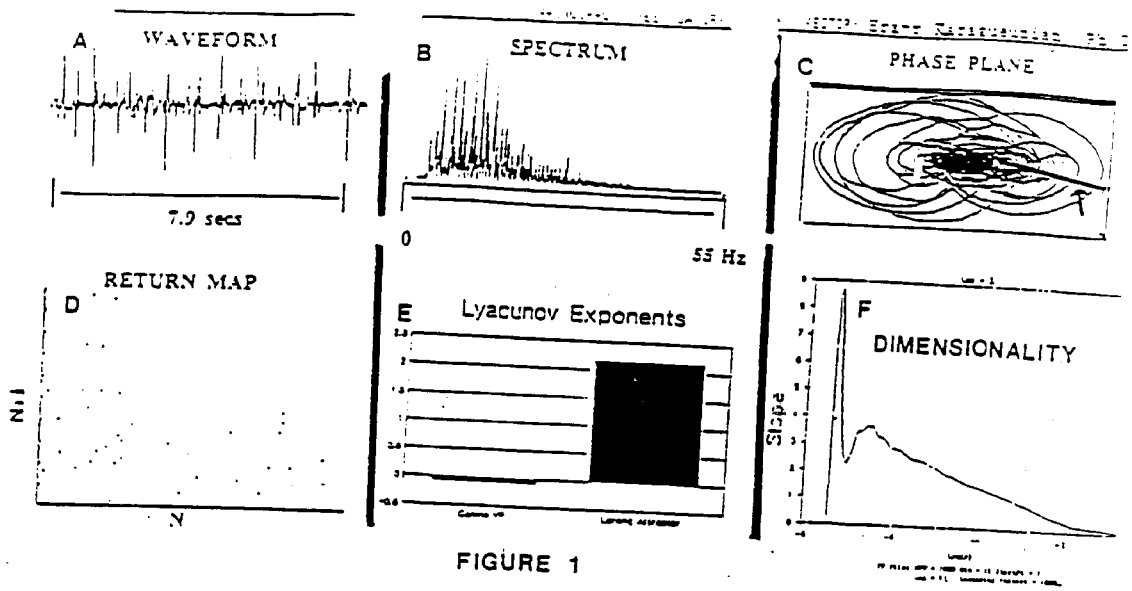
Figure 3:
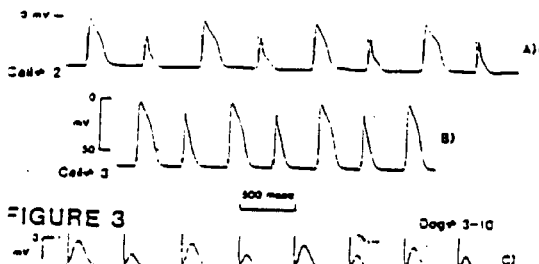
Figure 4:
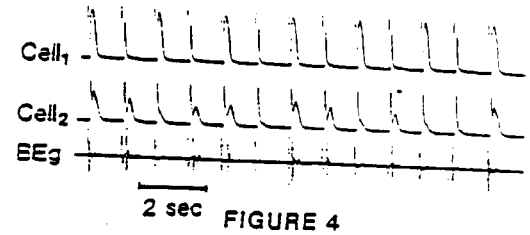
Figure 5:
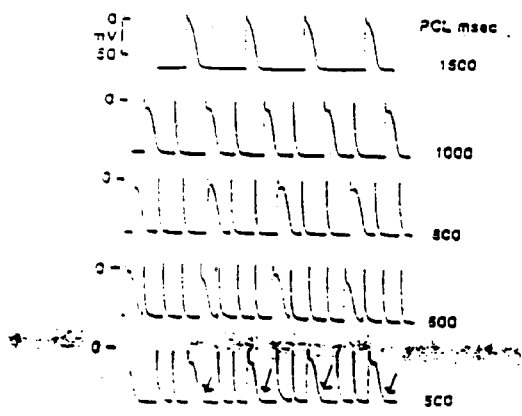
Figure 6:
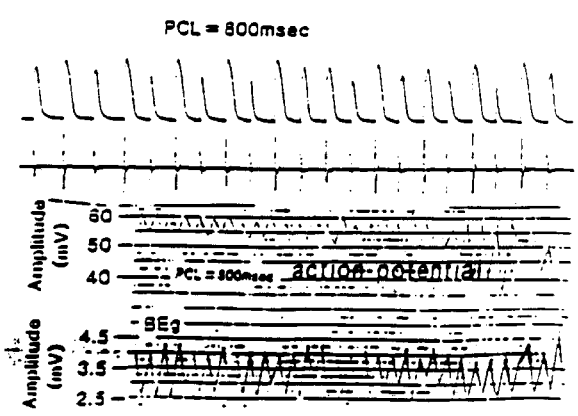

FIG. 6 shows a set of corresponding frequency-domain transforms, obtained by performing an FFT on the EKG signal. A first transform 601 corresponds to a first EKG signal (not shown). A second transform 602 corresponds to a second EKG signal (not shown).

In the first transform 601 of FIG. 6a, representing a normal patient, the frequency spectrum shows that the energy of the corresponding EKG signal occurs primarily at a discrete set of frequencies. In the second transform 602 of FIG. 6b, representing a patient exhibiting VF, the frequency spectrum shows that the energy of the corresponding EKG signal has a continuous spectrum of frequencies, and has an energy peak 603.

Part of this aspect of the invention is the use of both visual and mathematical techniques for analyzing frequency domain transforms, including for example calculation of a harmonic magnitude ratio (HMR). To determine the HMR, a major peak or a central region of energy distribution in a spectrum of a frequency domain transform (such as an FFT) may be identified, and the HMR calculated as follows: A magnitude of the transform in the region of the identified point is determined (e.g., by summing the magnitude of the transform at the identified point and at surrounding points), and is summed with the corresponding magnitude in the region of harmonic values of the frequency for the identified point. This sum is divided by a total magnitude of the transform for the entire signal; the ratio is defined as the HMR.

One method which is known for bringing a patient out of VF ("defibrillating") is to administer an electric shock across the patient's heart. This electric shock must generally have a substantial energy, e.g. 10–20 joules, and may often cause tissue damage to the patient even if it is successful in defibrillating the patient. Multiple shocks may be required, generally of increasing energy. Accordingly, it would be advantageous to use a larger shock only when necessary, and it would be advantageous to use as few shocks as possible.

Part of this aspect of the invention is the discovery that when the energy peak 603 of the frequency-domain transform 602 is at a relatively low frequency, a relatively low energy shock will generally suffice to defibrillate the patient. When the energy peak 603 of the frequency-domain transform 602 is at a relatively high frequency (also, when a secondary energy peak 604 appears in the frequency-domain transform 602 at a relatively high frequency), it will require a relatively high energy shock to defibrillate the patient, if it is possible to defibrillate the patient by means of an electric shock at all.

One application of this discovery is in automated implanted cardiac defibrillators (AICDs), which attempt to automatically detect VF and to automatically administer a shock to defibrillate the patient.

Figure 7:
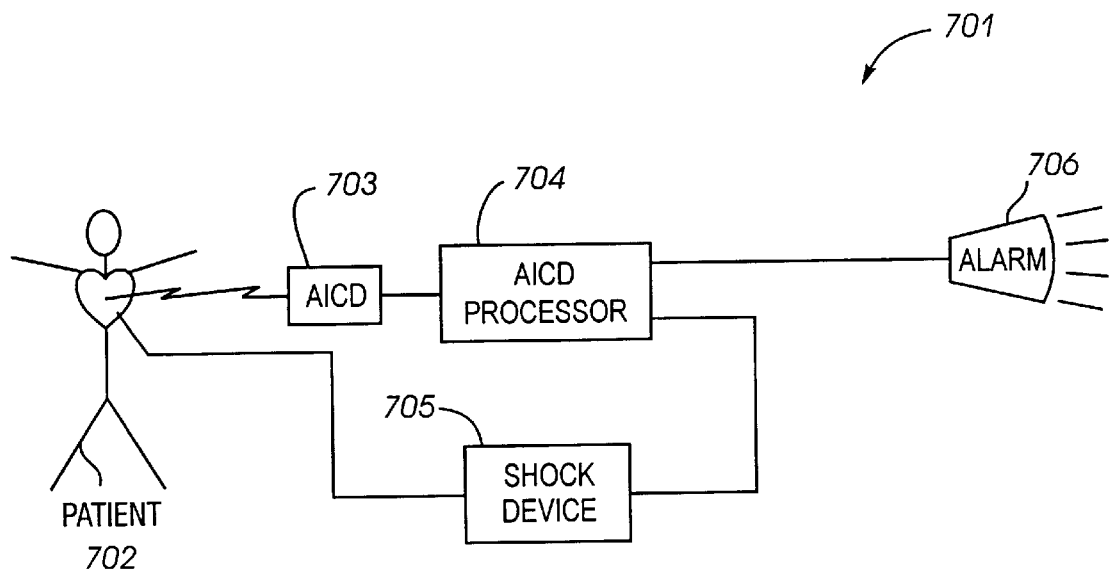
FIG. 7 shows an improved automatic implantable cardiac defibrillator ("AICD").

FIG. 7 shows an improved AICD 701. A patient 702 is coupled to an AICD EKG 703, which acquires EKG signals and transmits them to an AICD processor 704, which controls a shock device 705 for administering a defibrillating shock to the patient 702.

The improved AICD 701 also comprises (e.g., as part of the AICD processor 704) software for determining an FFT of the EKG signal and for determining the energy peak in that FFT. If the energy peak in that FFT is relatively low, the AICD processor 704 controls the shock device 705 to administer a relatively small shock to the patient. If the energy peak in that FFT is relatively high, the AICD processor 704 controls the shock device 705 to administer a relatively large shock to the patient, and may also signal an alarm 706 or other indicator that defibrillation may not be successful.

A third aspect of the invention relates to detection and evaluation of drug toxicity based on a parameter time constant for an action-potential duration (APD) restitution curve or an action-potential amplitude (APA) curve which is constructed for the patient.

Figure 8:
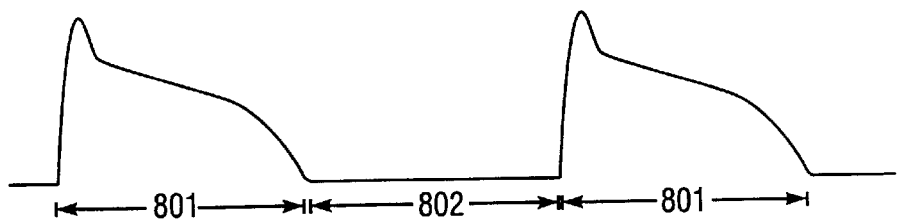
FIG. 8 shows a signal response of an individual heart muscle cell to a stimulus, known in the art as "action potential."

FIG. 8 shows a signal response of an individual heart muscle cell to a stimulus. This individual cell response is known in the art as "action potential".

It is well-known in the art that a time duration for recovery 801 of an individual cell depends on factors including a resting period 802 which the cell has had prior to stimulus. It is also well-known in the art that an APD restitution curve can be constructed for a human patient with the use of an intracardiac catheter. However, the complete relation between the actual time duration for recovery 801 based on the resting period 802 is not known.

Part of this aspect of the invention is the discovery that when the time duration for recovery 801 is plotted against the resting period 802 (diastolic interval), the curve follows an exponential relation:

$$APD = APD_{p1} - A * \exp(-DI/tau) \quad (803)$$

where $APD_{p1}$ is the plateau APD, A is a proportionality constant, DI is the diastolic interval, and tau is the parameter time constant The nonlinear nature of the APD restitution curve may promote deterministic chaos in response to excessive stimulus of the heart muscle cells. When the APD restitution curve is steeper (i.e., the parameter time constant tau is larger), there is accordingly a greater predilection for the heart to enter VF. Thus, another part of this aspect of the invention is the discovery that a normal patient will have a relatively low APD restitution parameter time constant, while a patient who is exhibiting drug toxicity (e.g., quinidine intoxication) will have a relatively high APD restitution parameter time constant. The restitution parameter time constant may also be used in monitoring cardiac stability, and in evaluating efficacy of antiarrhythmic drugs.

Figure 11:
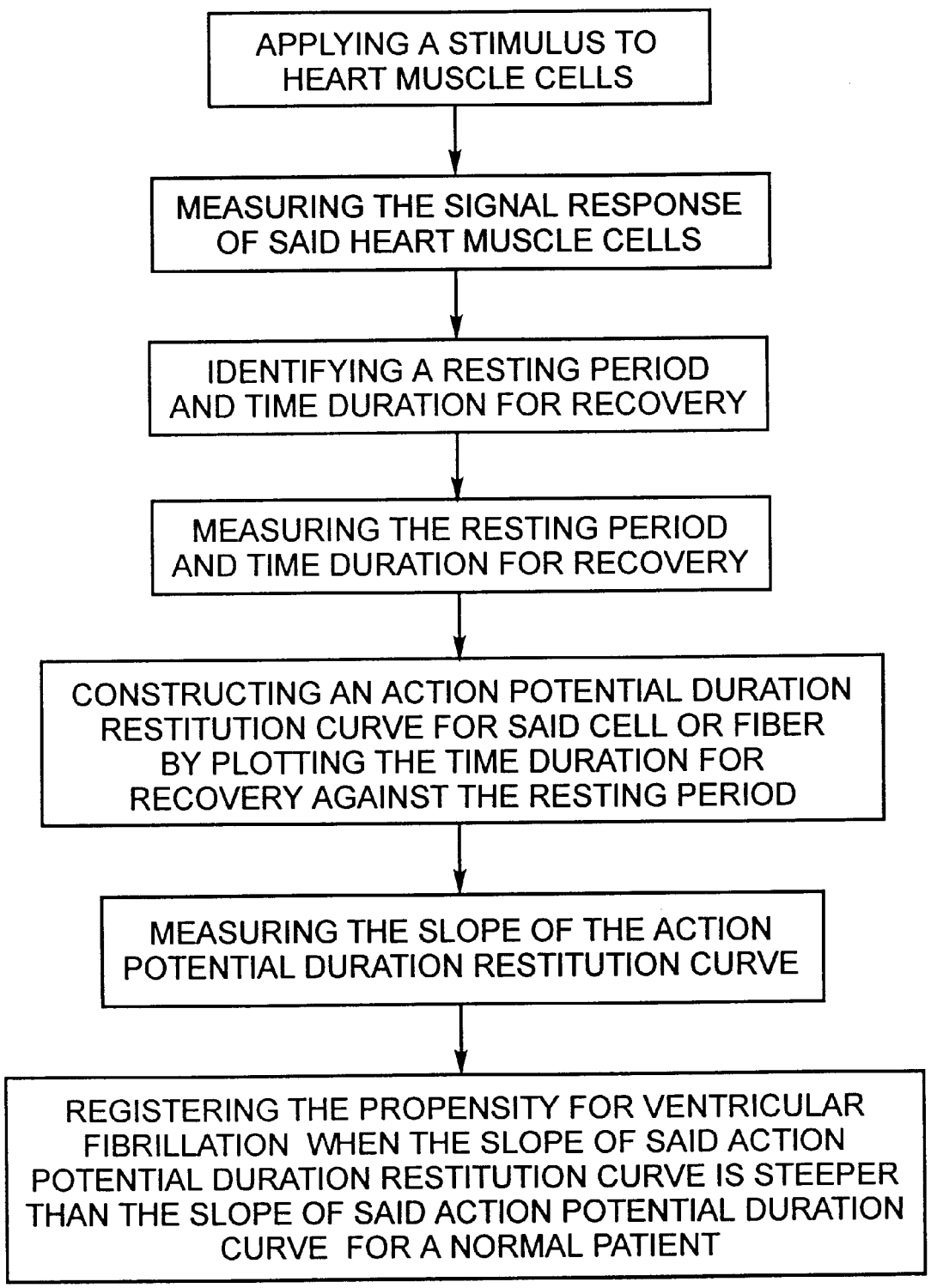
FIG. 11 is a flow chart depicting the method of detecting the propensity for fibrillation by measuring the slope of an action potential duration restitution curve and comparing it to the slope of a normal patient's curve.
Figure 12:
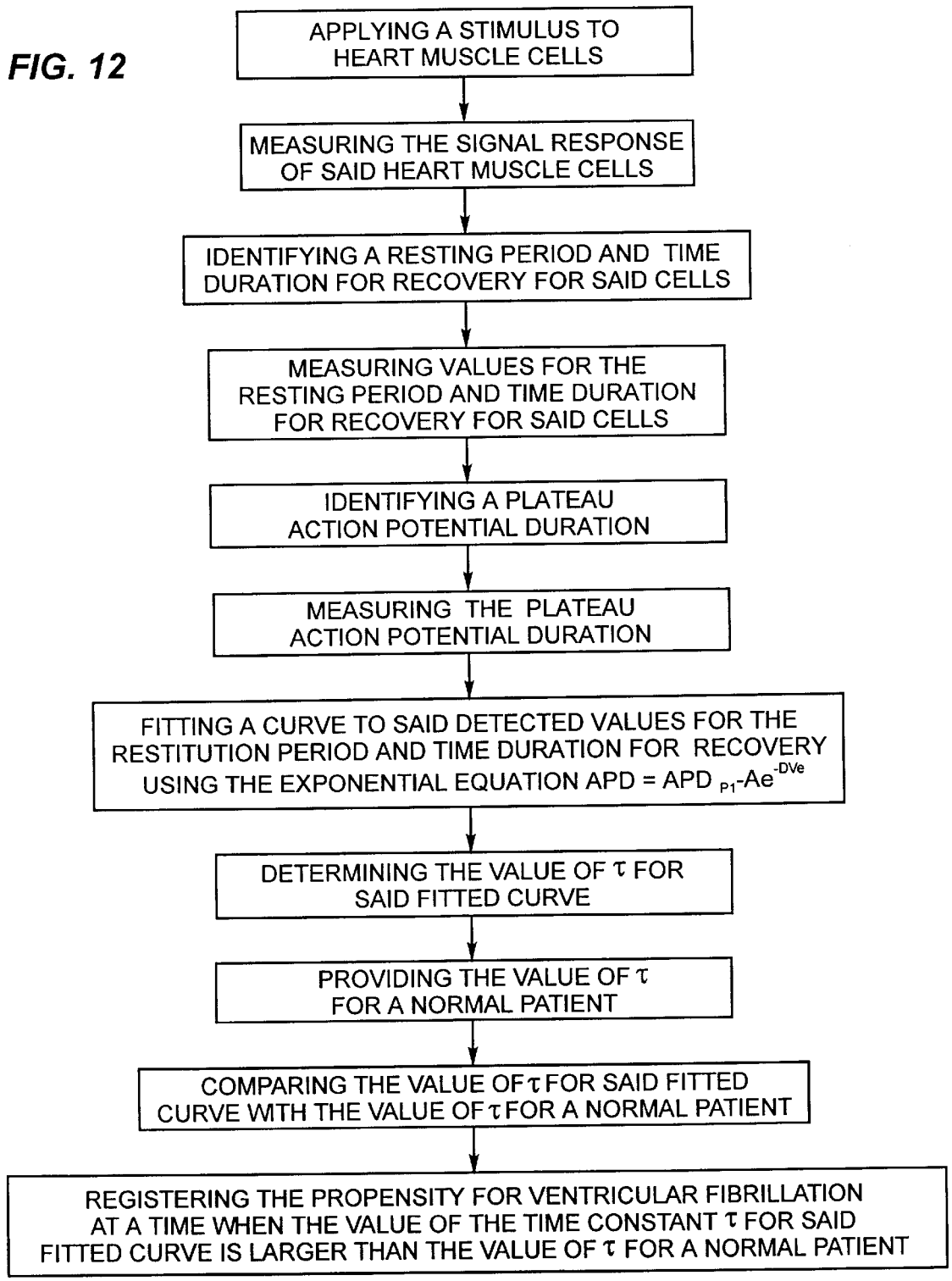
FIG. 12 is a flow chart depicting the method of detecting the propensity for fibrillation by numerically comparing the time parameter constant for the patient's fitted action potential duration restitution curve and the value of the time parameter for a normal patient's curve.
Figure 1:
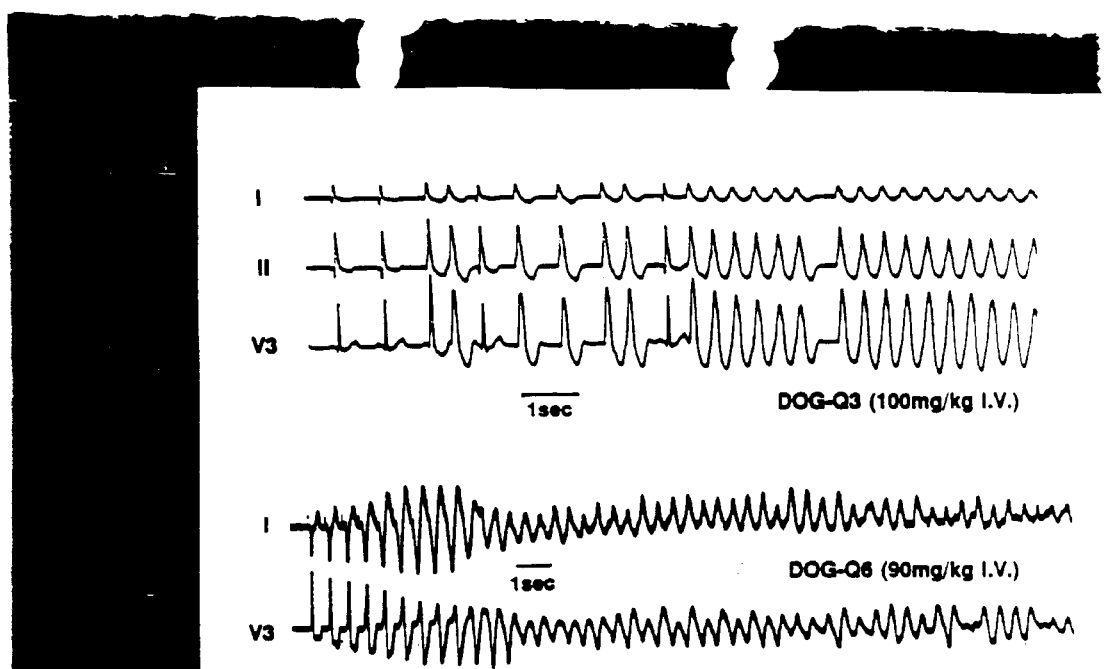
Figure 2:
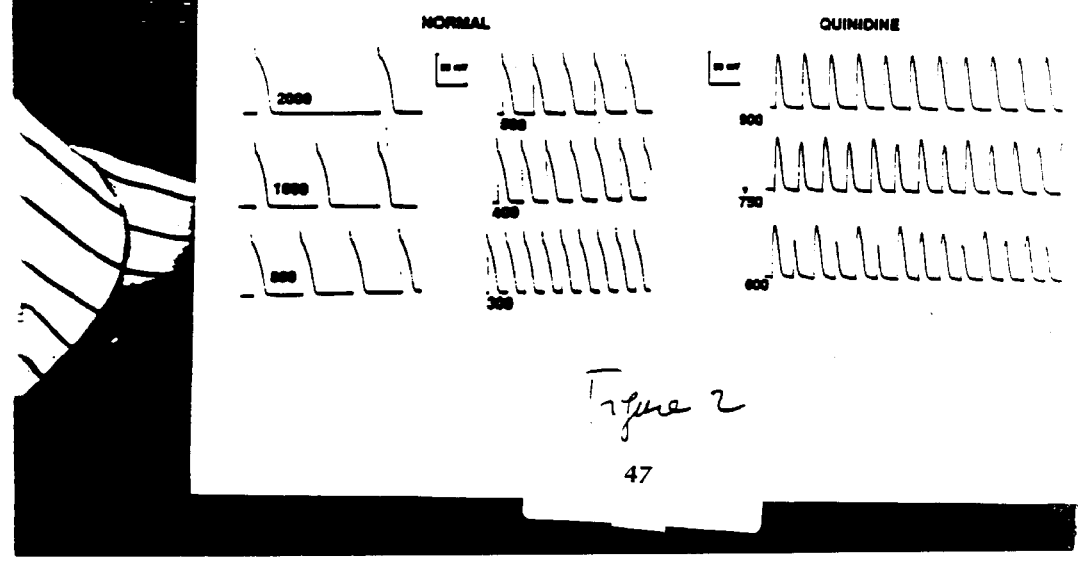

One embodiment for monitoring cardiac stability is shown in FIG. 12 and includes comparing restitution parameter time constraints. This method includes the steps of applying a stimulus to heart muscle cells (1201), measuring the signal response of said heart muscle cells (1202), measuring values for the resting period and time duration for recovery of action potential duration of said cells (1203), fitting a curve to said detected values for the restitution period and time duration for recovery of action potential duration using the exponential equation $APD = APD_{PI} - Ae^{DI/\tau}$ where APD represents the time duration for recovery of action potential duration, $APD_{PI}$ is the plateau action potential duration, A is a proportionality constant, DI is said resting period and $\tau$ is the time constant (1204), determining the aforesaid equation parameters so as to determine the value of $\tau$ for said fitted curve (1205), providing the value of $\tau$ for a normal patient (1206), comparing the value of $\tau$ for said fitted curve with the value of $\tau$ for a normal patient (1207), registering the propensity for ventricular fibrillation at a time when the value of the time constant $\tau$ for said fitted curve is larger than the value of $\tau$ for a normal patient (1208). However, the method may employ any manner of slope measurement of the APD restitution curve such as shown in FIG. 11 by employing the steps of applying a stimulus of heart muscle cells (1101), measuring the signal response of said heart muscle cells (1102), measuring values for the resting period and time duration for recovery of action potential duration for said cells (1103), constructing an action potential duration curve by plotting the time duration for recovery of action potential duration against the said resting period (1104), determining the slope of said constructed curve by fitting a curve to said detected values and using said fitted curve to determine the slope of said constructed curve (1105), providing the slope of the action potential duration curve for a normal patient (1106), comparing the slope of said constructed action potential duration curve with the slope of said action potential duration curve for a normal patient (1107), registering the propensity for ventricular fibrillation where the slope of said constructed curve is at least steeper then the slope of said action potential duration curve for a normal patient (1108).

Experimental verification of the present invention has been achieved by the inventors.

Experiment I.

A mathematical study used PPPs, return maps, Poincare sections, correlation dimension, and spectral analysis to distinguish periodic, chaotic and random signals. PPPs were useful in distinguishing among all three classes of signals. Periodic signals showed clear, widely separated trajectories; chaotic signals showed banding, forbidden zones and sensitive dependence on initial conditions; random signals showed no clear internal structure. With the exception of noise effects, the only major difference between the PPPs and the appropriately lagged return map was a 45 degree rotation. Poincare sections were also able to distinguish among the three classes of signals: periodic signals showed isolated points; chaotic signals showed ordered areas of apparent self-similarity; random signals showed a Gaussian distribution of points. Correlation dimension was more able to distinguish between chaotic and random signals than between chaotic and periodic signals. Spectral analysis using FFTs and harmonic magnitude ratio (HMR) was able to distinguish periodic signals, but were unable to distinguish between random and chaotic signals: HMRs of periodic signals were greater than 97%; HMRs of chaotic signals varied between 17 and 80%; HMRs of random signals were approximately 40%. PPPs were greatly affected by noise, return maps were less affected, while spectral analysis was relatively immune to noise. It was concluded that PPPS, return maps, Poincare sections, correlation dimension and spectral analysis are all useful determinatives of chaotic systems.

Experiment II.

A mathematical study concentrated specifically on ability of spectral analysis to distinguish chaotic from random signals. In this experiment, two series of random signals were generated. The first series comprised 5000 pseudo-random numbers which were smoothed using a method of least-squares approximation. The second series comprised white noise obtained from an analog-to-digital conversion board. Spectral analysis was performed by applying an FFT to the data, and searching for a broad band spectrum or a change from a narrow band to a broad band, which was presumed to be diagnostic of chaos. It was concluded that spectral analysis by itself was insufficient to unequivocally distinguish chaotic signals from random signals, and that additional tests such as PPPs and return maps were necessary for this purpose.

Experiment III.

An experiment examined spectral analysis, visualization of PPPs and correlation dimension analysis, for usefulness in distinguishing between normal sinus rhythm and VF in dogs. Ischemia and re-perfusion were used as stress factors in closed-chest anesthetized dogs. Spectral analysis of the dogs having normal sinus rhythm revealed narrow-band spectra with fundamental frequencies at the sinus rate and harmonics extending beyond 50 Hz. PPPs were consistent with periodic dynamics, and dimension analysis revealed low dimensional behavior (1–2.5). In contrast, spectral analysis of the dogs having VF, revealed broad-band behavior with most of the energy at 6 Hz, and with energy at all frequencies between 1 and 25 Hz. PPPs showed constrained aperiodic behavior, and the dimensional analysis revealed higher dimensions (4–6) than that observed for the normal sinus rhythm dogs. Thus, all three techniques proved useful in distinguishing normal sinus rhythm from VF.

Experiment IV.

An experiment examined spectral analysis, visualization of PPPs, visualization of return maps, and correlation dimension analysis, for their usefulness in identifying VF in humans. These analytical techniques were applied to data from eight hypothermic patients undergoing spontaneous VF, and also to data from three normothermic patients with VF induced during electrophysiology testing. All patients had a broad band frequency spectrum (0–12 Hz), a low dimension (range 2–5), and banding and forbidden zones on PPPs and return maps. It was concluded that spectral analysis, visualization of PPPs, visualization of return maps, and correlation dimension analysis are useful in detecting and evaluating VF.

Experiment V.

An experiment examined spectral analysis, visualization of PPPs and correlation dimension analysis for their usefulness in distinguishing between normal sinus rhythm and VP in humans. VF in eight hypothermic human patients undergoing open-heart surgery was studied. In all patients, first and second order PPPs showed forbidden zones and banding, and an FFT revealed a relatively continuous power spectrum at all frequencies from zero to 25 Hz, with a majority of the power below 12 Hz. In contrast, correlation dimension in all cases was less than 4. It was concluded that multiphasic analysis of the data is preferable to reliance on a single analytical technique such as correlation dimension.

Experiment VI.

An experiment utilized spectral analysis and visualization of PPPs to elucidate the heterogenous nature of atrial fibrillation. In the experiment, the researchers induced acute fibrillation by a rapid train of stimuli to the atria of seven closed-chested dogs. PPPs based on the EKG data often inscribed well defined structures, and an FFT of the digitized EKGs showed peaks mostly below 15 Hz that were either discrete with clear harmonic components, or had continuous spectra that changed in a time- and site-dependent manner. It was concluded that both spectral analysis and visualization of PPPs are useful techniques for analyzing atrial as well as ventricular fibrillation.

Experiment VII.

In an experiment, visual analysis of PPPs and the slope of an APD restitution curve were found to be useful for detecting and evaluating quinidine-induced VF in in vivo hearts. Quinidine was administered at 30 minute intervals over five hours, until either a total of 90–100 mg/kg was administered or until ventricular tachycardia or VF occurred, whichever came first. PPPs of the quinidine intoxicated cells demonstrated sensitive dependence on initial conditions and the presence of forbidden zones, and the corresponding FFTs showed continuous spectra. In contrast, PPPs of cells in a control dog were uniform and densely packed, and the corresponding FFTs showed discrete spectra. The initial slope of the APD restitution curve of quinidine intoxicated cells was much steeper, by at least an order of magnitude, than the slope of normal cells. It was concluded that quinidine toxicity correlates with the slope of the APD restitution curves.

Experiment VIII.

An experiment compared the slope of the APD and APA restitution curves with quinidine intoxication. Quinidine was administered (90–100 mg/kg) to eight dogs over a five hour period. Three untreated dogs served as controls. Ventricular and Purkinje cells from both treated and untreated dogs were then subjected to electrical stimulation with cycles from 900 to below 600 msec. Shortening of the cycle length to 600 msec resulted in irregular dynamics of both APD and APA, including electrical alternants and bifurcation. The slope of an APD restitution curve was calculated, and found to be steeper in quinidine-intoxicated cells for both Purkinje fibers and ventricular muscle cells than the slope during quinidine washout or in normal untreated cells. The curve could be fit by the exponential equation given herein. APA changes were almost always correlated with the APD changes. In the three normal tissue preparations neither ventricular muscle cells nor Purkinje cells showed bifurcative behavior with respect to APD or AA. It was concluded that quinidine toxicity, and presumably other drug-induced pro-arrhythmic effects, correlate with the slope of both APD and APA restitution curves.

Experiment IX.

In an experiment, quinidine-induced ventricular tachycardia and VF in dogs was analyzed using PPPs generated from action potential duration (APD) and action potential amplitude (APA) data. Both PPPs showed forbidden zones and sensitive dependence on initial conditions which are indicative of chaos. It was concluded that PPPs based on either APD or APA are useful in detecting and evaluating quinidine toxicity.

Experiment X.

In an experiment, EKGs of quinidine intoxicated dogs were analyzed by frequency spectra, phase plane plots, Poincare sections, return maps and Lyapunov exponents. In the control state and at therapeutic doses, PPPs were uniformly thick and showed no gaps, indicating that cycle-to-cycle variation was due to normal biological "noise". But as the quinidine dose was increased to intermediate levels (40–50 mg/kg), PPPs showed clear non-uniform thickening, indicating sensitive dependence on initial conditions, and also showed marked banding (densely filled regions separated by divisions or gaps). At these intermediate doses, Lyapunov exponents became positive and Poincare return maps also indicated nonrandom chaos. At still higher doses, PPPs became more complex. In two dogs that did exhibit VF (and not in another) there was a significant change in the PPP at the last pre-fibrillatory dose: the development of a "funnel", a classic mechanism of chaos. Frequency spectra at all pre-fibrillatory doses were discrete, with peaks at a fundamental frequency and multiple harmonics. It was concluded that chaos does occur during progressive quinidine intoxication, and that PPPs, and graphic and numeric analysis based on the PPPs, are better indicators of chaos than frequency spectra.

Experiment XI.

In an experiment, quinidine toxicity in dogs was analyzed using PPPs generated from APA and APD data. EKG recordings were made at various driving rates from 1000 to 500 msec. Increase in the driving rate from 1000 to 500 msec caused the progressive appearance of higher order periodicities (period 3 and 4). Phase locking was seen with a stimulus (S) response (R) pattern repeating periodically in all 4 preparations at S:R ratios of 2:1, 5:3, 3:2. At faster drive rates aperiodic variations in APA and APD were observed. A number of intermediate stages that presage chaos were also seen in the quinidine intoxicated fibers. These results further demonstrate the usefulness of the methods of the present invention to detect both quinidine intoxication and precursor stages to intoxication.

Experiment XII.

In an experiment, quinidine toxicity in dogs was analyzed using PPPs generated from APA and APD data. Electrical stimuli were used to drive cardiac tissue at various rates from 2000 to under 300 msec. These stimuli caused steady alternants (bifurcation) in APD and APA of 108±36 msec and 12±9 millivolts respectively. Further increase in driving rates gave rise to irregular dynamics. This transition was preceded by various repeating stimulus-response ratios (phase-locking) for up to fifty consecutive beats. No such dynamics could be induced in three non treated (control) tissues. The APD restitution curve had significantly ($p<0.05$) steeper slope than six control fibers. Stimulus-response latency remained constant at 6–9 msec. PPPs of the APDs during the irregular dynamics showed sensitive dependence on initial conditions and forbidden zones consistent with chaos theory. These results further demonstrate the usefulness of the methods of the present invention to detect both quinidine intoxication and precursor stages to intoxication.

Experiment XIII.

An experiment used spectral analysis, PPPs, Poincare sections, Lyapunov Exponents and dimension analysis to analyze computer simulated waveforms including sine waves, modulated sine waves, square waves, saw toothed waves, and triangular waves. The researchers added random noise to the waveforms at 1%, 10% and 20%. The experiment further used the same analytical techniques on EKG data from anesthetized dogs in which VF was precipitated by five different interventions: quinidine intoxication; premature electrical stimulation followed by quinidine intoxication; coronary occlusion; reperfusion of acutely ischemic myocardium; and global hypothermia. The preliminary results showed that PPPs and Poincare sections in dogs undergoing ventricular fibrillation were consistent with chaos, while spectral analysis was not suggestive of chaos. The researchers concluded in part that VF can be described as chaotic electrophysiological behavior, but that single methods of analysis are not sufficient to detect such behavior.

III

One conclusion which may be drawn from the research cited herein is that the analytical value of each of the aspects of the invention may be enhanced through combination with one or more of the other aspects of the invention. A preferred embodiment of the present invention may include a combination of the aspects of the invention described herein. One preferred embodiment may comprise multiphasic analysis of a PPP (e.g., visually with a display, graphically with Poincare sections, and numerically with Lyapunov exponents and correlation dimension), frequency spectral analysis, and mathematical analysis of an APD restitution curve.

Alternative Embodiments

While preferred embodiments are disclosed herein, many variations are possible which remain within the concept and scope of the invention, and these variations would become clear to one of ordinary skill in the art after perusal of the specification, drawings and claims herein.

It would also become clear to one of ordinary skill in the art that embodiments of the invention may comprise means for continuous monitoring of drug toxicity, atrial fibrillation, ischemia or other heart conditions, such as during surgery or patient recovery from surgery. Moreover, embodiments of the invention may comprise means for indicating heart conditions which are detected to attending medical personnel or to the patient. In one preferred embodiment of the invention, means may be provided for directing the patient (when a heart disorder is detected) to contact a physician or to proceed to a nearby hospital for treatment.

Bifurcative and Irregular Cardiac Action Potential Dynamics
During Quinidine Toxicity:
Implications to Arrhythmogenesis Hrayr S. Karagueuzian Steven S. Khan William J Mandel George A. Diamond Division of Cardiology and Department of Medicine
Cedars-Sinai Medical Center
and the Department of Medicine
University of California,
Los Angeles, California.
Phone (213) 855-4744 / 6255

Address correspondence to: Hrayr S Karagueuzian, Ph.D., Cedars-Sinai Medical Center, Division of Cardiology, 8700 Beverly Boulevard, Los Angeles CA 90048.

ABSTRACT

Rate-dependent bifurcative and aperiodic dynamic changes in action potential duration and amplitude were observed in periodically stimulated cardiac Purkinje and ventricular muscle cells, isolated from dogs with quinidine-induced ventricular tachycardia and ventricular fibrillation. This nonlinear cellular dynamic behavior was not observed in normal untreated cardiac fibers. A theoretical monoexponential model derived from the experimentally observed relationship between action potential duration and recovery time (restitution curve) predicted these experimental observations. These data suggest that the mechanism of drug-induced temporal heterogeneity of cellular action potential duration has an underlying deterministic dynamical mechanism. Because cellular electrophysiological heterogeneity can result in ventricular fibrillation, these observations may have relevance to the prediction and prevention of sudden cardiac death.

3

Nonlinear dynamical systems are characterized by an intrinsic ability to manifest increasingly complex patterns of behavior when subjected to a constant periodic stress [1]. Similarly, cardiac tissue subjected to constant periodic stimulation (stress) manifests electrophysiologic behavior that can be explained by nonlinear dynamic theory [2]. Bifurcative and irregular cellular action potential dynamics occur in cardiac automatic [2] and quiescent but-regularly driven [3] cells in vitro. Bifurcative dynamics were also seen in the QRS and T waves in in vivo canine hearts stressed by norepinephrine or acute ischemia and in man with myocardial infarction [4]. Recent experimental and theoretical arguments have been put forth to suggest that increased slope of the action potential duration restitution (APD-R) curve (a measure of nonlinearity) promotes oscillation [3,5] and bifurcations that eventually results in chaotic dynamics [3]. It is known that beat to beat variability in action potential duration (APD) and amplitude (APA) could impart to the ventricular myocardium a degree of heterogeneity (i.e. dispersion of repolarization and excitability respectively) that promotes reentry [6]. Since ventricular tachycardia and ventricular fibrillation (VT/VF) are often caused by reentry [7], we hypothesized that cellular heterogeneity brought about by increased slope of APD-R curve and rate-dependent changes in action potential amplitude enhances the vulnerability of the ventricle to VT/VF because such heterogeneity facilitates the emergence of reentry loops. To test this hypothesis, we compared action potential dynamics of ventricular cells isolated from dogs with drug-induced ventricular fibrillation to cells isolated from the ventricles of untreated normal dogs with no ventricular fibrillation.

4

All studies were conducted on right ventricular endocardial tissues; 8 dogs were anesthetized with sodium pentobarbital (35mg/kg intravenously), intubated with cuffed endotracheal tubing and ventilated with room air with a Harvard respirator at 4cm H2O pressure. Teflon catheters (i.d. 1.58mm and o.d.3.17mm) were placed in the right carotid artery to monitor aortic blood pressure, and in the right jugular vein for systemic injections of drugs. A 6F USCI bipolar electrode catheter was inserted through the left jugular vein, and positioned at the right ventricular apex under fluoroscopic control for the purpose of pacing the ventricle. Three untreated dogs served as controls. In the remaining five dogs increasing doses of intravenous quinidine was administered, an antiarrhythmic drug capable of precipitating ventricular tachyarrhythmias if given in high (toxic) doses [8]. This model of global cardiac intoxication was used to assure that individual cells subsequently selected for microelectrode study would be representative. Each dose (10mg/kg) of quinidine (Quinidine Gluconate Injection USP, Lilly) was administered over a 2min period at 30min intervals (a total of 90-100mg/kg over a 5 hrs). Two minutes after each dose, the ventricle was paced using a custom-made digital programmable stimulator, for periods of 5 to 10min, with a constant current (2msec duration and twice diastolic excitability threshold) at cycle lengths of 500 and 300msec to enhance myocardial uptake and toxicity of quinidine [9]. Three dogs developed ventricular fibrillation one spontaneously, and two during pacing at 500msec cycle length when the total dose of quinidine was 100mg/kg (Figure 1). The remaining two dogs developed runs of sustained and non-sustained ventricular tachycardia when the total administered dose of quinidine was 90mg/kg (Figure 1).

Figure 2 illustrates two experiments, one from a control dog, and the other from quinidine intoxicated dog. Recordings were made from right ventricular endocardial muscle cells [10]. Both preparations were first paced at relatively long cycle lengths, followed by shorter ones. In the normal non-intoxicated cell, each stimulus is followed by an action potential that has constant duration and amplitude for the entire range of frequencies (2000-300msec) tested. The same invariance was observed in all six ventricular cells and Purkinje fibers from the 3 control untreated dogs. In the cell from the quinidine-intoxicated dog however, APA and APD exhibited regular alternation, i.e., period doubling bifurcation, when the cycle length of stimulation shortened from 900 to 750msec. Shortening of the cycle length still further to 600msec resulted in irregular dynamics of both APA and APD. During this irregular activity, monitoring of up to 150 consecutive beats failed to discern periodicity. APD alternation, measured to 100% repolarization, ranged from 25-200msec in the 14 ventricular muscle cells sampled, with a mean resting membrane potential of -70.1mV ($\pm 3$). Similar observation were made on 9 Purkinje fibers (mean resting potential of 73.6mV,$\pm 4$), and in 8 cells, whose fiber type could not be ascertained [10], because of their depressed resting potential (-61.3mv,$\pm 3$mV.

It has been shown [11] that APD is linearly correlated in a frequency-dependent manner, with the effective refractory period during both control and quinidine treatment in canine ventricular myocardium. This indicates the usefulness of APD as an index of recovery of excitability [11]. Unlike APD however, APA changes were almost always associated with concomitant APD changes. Only in slow response fibers (resting potential of around -60mV), the predominant dynamic changes were confined to the APA alone (15-25mV). In cells from the control, untreated dogs (Figure 2A), stimulations at cycle lengths of 2000-300msec were always associated with stable APD and APA patterns for both Purkinje fibers and ventricular muscle cells. Rate-dependent, steady-state APD shortening of both fiber types were seen in all three preparations studied, consistent with previous reports [12].

The changes in the APD during periodic stimulation, were independent of latency (stimulus-response interval). The variations in latency were constant in any given preparation and ranged between 6 to 12msec. Furthermore, after a sudden increase in the pacing rate the characteristic new dynamic state was reached after an initial transient lasting 3-24sec.

The alternation of both APD and APA reported in the present study were caused by alternation of individual cell transmembrane ionic kinetics and not the result of spatial (electrotonic) interaction between neighboring cells and/or by spatial variations in conduction pattern [3,13]. The intrinsic cellular nature of such ionic dynamics is evidenced by simultaneous multiple sites recordings (two microelectrodes and one extracellular bipolar electrode [1cm interelectrode distance]) and demonstration of simultaneous occurrence of alternans at all three recording sites (Figure 3). The simultaneous occurrence of alternans at multiple sites was confirmed in two additional quinidine toxic preparations by similar recording arrangements. This suggests that the beat to beat variability of the electrophysiological properties of quinidine intoxicated cells result from beat to beat alternations of cellular transmembrane ionic currents. To shed some light on the possible cellular mechanism(s) of quinidine-induced alternans we constructed APD restitution curve (Figure 4) as it has been suggested that increases in the slope of APD restitution curve could bring about electrical alternans and bifurcation [3,5]. The slope of the APD restitution curve of quinidine intoxicated cells was steeper, particularly at short diastolic intervals, for both Purkinje fibers and ventricular muscle cells than the slope during quinidine washout (Figure 4) or in normal untreated cells. The curve could be fit by a single exponential equation:

$$APD = APD_{pl} - Ae^{(-DI/\tau)}$$

where $APD_{pl}$ is the plateau action potential duration, A is a proportionality constant, DI is the diastolic interval, and tau is the time constant [14]. Unlike in normal cells, quinidine toxicity caused rate-dependent APD bifurcative behavior during stepwise increase in the frequency of stimulation (Figures 2 and 3). Figure 5 shows one such experiment, in which progressive increase in the rate of stimulation caused bifurcation and irregular dynamics of APD. Iteration of the monoexponential equation describing the experimentally derived APD restitution curve, with proper changes of the slope parameter, predicted with reasonable degree of accuracy the experimentally observed similar bifurcative and irregular dynamics of APD (Figure 6).

In the three normal tissue preparations neither ventricular muscle cells nor Purkinje cells have shown such bifurcative behavior with respect to both APD and APA. During each frequency of stimulation (2000-300msec) a constant APD and APA were present (after an initial transient of up to 6-8 beats) for the entire duration of stimulation (2-5 minutes). Similarly, iteration of the monoexponential APD restitution equation with relatively smaller slope factor as in the normal untreated fibers failed to show bifurcative dynamics.

8

In conclusion, rate-dependent bifurcative response pattern of action potential duration and amplitude was found to occur in cells isolated from fibrillating ventricle induced by quinidine intoxication. Irregular, (chaotic) cellular electrical responses, enhance the electrophysiologic heterogeneity of the ventricle (dispersion of refractoriness and non-uniform excitability), that could set the stage for reentrant sustained activation [6,7]. Ventricular fibrillation seen in the present study could well be brought about by such a scenario. Use of nonlinear dynamic concepts may thus have important implications in clinical cardiology [15] for monitoring cardiac electrical stability [13] and drug-induced proarrhythmic effects [16]. Alternatively, the efficacy of an antiarrhythmic drug can be judged by its ability to decrease the strength of electro-dynamic nonlinearity (i.e. the slope of APD restitution curve) of the ventricle. Finally, if an orderly cardiac electro-dynamic transition sequences (bifurcations) can be identified in an in situ ventricle that could serve as harbingers of an impending aperiodic chaotic state, as in other nonlinear physical systems it might provide new insight into the origin and prevention of sudden cardiac death in man [13,17].

9
REFERENCES AND NOTES

1. R. M. May, Nature, 261, 459-467 (1976); H. Swinney, Physica, 7D, 3-15 (1983); L. F. Olson and H. Degn, Q Rev Biophys, 18, 165-225 (1985).

2. M.R. Guevara and L. Glass : J Math Biol, 14, 1-23 (1982); Michaels DC, Chialvo DR, Matyas EP, Jalife J: Circ Res, 65:1350-1360, (1989).

3. D.R. Chialvo and J. Jalife: Nature, 330, 749-752 (1987); R.D.Chialvo, D.C.Michaels, J.Jalife : Circ Res 1990 (In Press)

4. A.L.Ritzenberg, D.R.Adam, R.J.Cohen: Nature, 307,159-161 (1984); J.M. Smith, E.A. Clancy, C.R. Valeri, J.N. Ruskin, R.J. Cohen: Circulation, 77:110-121, 1988.

5. J.B.Nolasco, R.W.Dahlen: J Appl Physiol, 25:191-196, 1968; M.R.Guevara, G.Ward, A.Shrier, L.Glass: Computers in Cardiol, 167-170, 1984.

6. J.Han and G.K.Moe: Circ Res, 14, 44-60 (1964); M.J.Burgess, B.M.Steinhaus, K.W.Spitzer, P.R.Ershler: Circ Res, 62, 233-246 (1988); C.S.Kuo, K.Munakata, C.P.Reddy, B.Surawicz: Circulation, 67, 1356-1367 (1983); W.B.Gough, R.Mehra, M.Restivo, R.H.Zeiler, N.El Sherif: Circ Res, 57:432-442, 1985.

7. D.W.Frazier, P.D.Wolf, J.M.Wharton, A.S.L.Tang, W.M.Smith, R.E.Ideker : J Clin Invest, 83:1039-1052, 1989; P.S.Chen, P.D.Wolf, E.G.Dixon, N.D.Daniely, D.W.Frazier, W.M.Smith, R.E.Ideker: Circ Res, 62:1191-1209, 1988, N.Shibata, P.S.Chen, E.G.Dixon, P.D.Wolf, N.D.Danieley, W.M.Smith, R.E.Ideker: Am J Physiol, 255:H891-H901, 1988.

8. A.Selzer and H.W.Wray: Circulation 30, 17-26 (1964).

9. L.M. Hondeghem and B.G.Katzung: Ann Rev Pharmacol Toxicol, 24,387-423 (1984); J.M.Davidenko, L.Cohen, R.Goodrow, C.Anzelevitch: Circulation 79 674-686 (1989).

10

10. K.Sugi, H.S.Karagueuzian, M.C.Fishbein, A.McCullen, Y.Sato, W.Ganz, W.J.Mandel, T.Peter: Am Heart J, 109, 232-244 (1985); H.S.Karagueuzian, J.J. Fenoglio Jr, M.B.Weiss, A.L.Wit: Am J Physiol, 238, H581-H595 (1980). Methods: All action potentials were first recorded on an analog tape recorder (Bell and Howell, model 4010 CPR), then played back on Honeywell (VR-16), oscilloscopic-photographic recorder at paper speed of 50-100mm/sec. Two by 2cm blocks of right ventricular endocardial tissues were isolated from the dogs and were mounted endocardial surface upward in a tissue bath. Each tissue block isolated from treated and untreated dogs were of similar size and similar locations. The bath was maintained at 37 degrees Celsius, and at pH equal to 7.4. The bath was superfused with Tyrode's solution with the following composition in mM: NaCl 135, KCL 4.5, NaH2PO4 1.8, CaCl2 2.7, MgCl2 0.5, dextrose 5.5, NaHCO3 12 in triple-distilled, deionized water. The preparations were regularly stimulated with bipolar Teflon coated (except at their tips) electrodes (0.12mm in diameter) placed on the surface of the tissue. Transmembrane action potentials were then recorded with glass capillary electrode from single endocardial superficial cells (1 to 4 cell deep), 1-3mm away from the stimulating electrode. The effects of increasing rates of stimulation on the duration and amplitude of subendocardial Purkinje and ventricular muscle cells were evaluated in each isolated tissue preparation. The protocol of these experiments consisted of recording sequentially in each tissue, from both Purkinje and ventricular muscle cells at multiple sites (7 to 12 cells) during progressive increase in the frequency of stimulation (2000-200msec).

11. M.R. Franz and A.Costard: Circulation, 77:1177-1184 (1988)

41

11

12. V.Elharrar, and B.Surawicz: Am J Physiol, 244: H782-H792 (1983); V.Elharrar, H.Atarashi, B.Surawicz: Am J Physiol, 247:936-945, 1984; H.Saitoh, J.C.Bailey, B.Surawicz: Circ Res, 62: 1027-1040 (1988); M.R. Guevara, G. Ward, A. Schrier, L. Glass: Computers in Cardiology, 11: 167-170 (1984)

13. A.L.Ritzenberg, J.M.Smith, M.P.Grumbach, R.J.Cohen: Computers in Cardiology, 171-174, 1984; J.M. Smith, R.J. Cohen; PNAS, 84:233-237, 1984.

14. The parameters were fitted to the data using a nonlinear curve fitting package (BMDP-3V, BMDP Statistical Software, Westwood, CA). The following parameters were used in generating figure 6A: $APDpl = 241$, $A = 300$, and $Tau = 179$ (fitted from Quinidine intoxicated data) and for figure 6B: $APDpl = 250$, $A = 300$, and $tau = 50$ (arbitrary parameters chosen to increase the slope of the restitution curve).

15 A.L. Goldberger and B.J. West: Ann NY Acad Sci, 504:195-213, 1987.

16. J.T.Bigger Jr and D.I.Sahari: Am J Cardiol,59, 2E-9E (1987); M.S.Stanton, E.N.Prystowsky, N.S.Fineberg, W.M.Miles, D.P.Zipes, J.J.Heger: J Am Coll Cardiol, 14:209-215 (1989)

17. A.T.Winfree: "When Time Breaks Down. The Three-Dimensional Dynamics of Electrochemical Waves and Cardiac Arrhythmia". 1987, Princeton University Press, pp 11-339; L. Glass, M.C. Mackey, From Clocks to Chaos: The Rhythms of Life 1988, pp 144-171, Princeton University Press.

42

12

We thank Dr Kichol Hong and Avile McCullen for technical assistance. This work was supported in part by a Research Career Development Award (RCDA) to Dr. Karagueuzian from the National Institutes of Health, Bethesda, Maryland, and by the ECHO Cedars-Sinai Research Fund.

FIGURE LEGENDS

FIGURE 1. Spontaneous ventricular tachycardia (top panel) and ventricular fibrillation induced by ventricular pacing (lower panel) in two closed-chest anesthetized dogs during quinidine intoxication. I II and V3 are electrocardiographic surface leads.

FIGURE 2. Steady-state, rate-dependent shortening of normal (untreated) and quinidine intoxicated canine right endocardial ventricular muscle cell action potential duration (APD). Note the stable and constant action potential duration and amplitude response in the normal tissue at each of the stimulating basic cycle lengths (BCL) tested (i.e., 2000-300msec). In contrast, rate-dependent period doubling bifurcations of both action potential duration and amplitude occurred during shortening of cycle length from 900 to 750 msec. Further shortening of BCL to 600 resulted in aperiodic dynamics of APD and APA (lower recordings). The horizontal bar represents 0.5 seconds for the normal and 1.0 second for the quinidine recordings.

FIGURE 3. Simultaneous recordings of action potentials from two cells 1cm distant from each other (upper recordings), and an extracellular bipolar electrogram (BEG, 1cm interelectrode distance), in a right ventricular endocardial preparation isolated from a dog intoxicated with quinidine. Note the simultaneous, in phase, action potential duration and amplitude alternans at all three recording sites.

FIGURE 4. Action potential duration (APD) restitution curve of a right ventricular endocardial muscle cell isolated from a dog 15min after induction of ventricular fibrillation with quinidine intoxication (filled circles), and after four hours of washout with quinidine-free Tyrode's solution (open circles). The abscissa is diastolic interval and the ordinate, action potential duration for 100% repolarization. The curve was constructed during regular pacing at 500msec cycle length and application of single impulses with diastolic intervals of 150-1000msec. All applied electrical stimuli were twice diastolic current strength and 2msec duration.

FIGURE 5. Bifurcation diagram of action potential duration (APD), in a right endocardial canine ventricular fiber isolated from a dog after (12min) quinidine intoxication (filled circles). Abscissa, pacing cycle length (PCL) of stimulation; ordinate, action potential duration (APD) in msec for 100% repolarization. APD decreased monotonically, as PCL decreased from 2000msec (not shown) to 550msec. After an initial period doubling bifurcation at 480msec PCL, irregular APD dynamics occurred at PCL of 420msec which were present for an observation period of up to 200 beats.

The solid line was derived from iteration of a mono-exponential equation derived from the restitution curve using the technique of Guevara et al (12) and provided a theoretical model for the deterministic nature of the experimental observations. Figure 6 details the relationship of the restitution curve to the dynamics of APD bifurcation.

FIGURE 6. Theoretical bifurcation diagrams demonstrating the induction of chaotic dynamics by increasing the steepness of the restitution curve. The bifurcation curves (upper panels) are obtained using the method of Guevara (12) by iteration of the single exponential equation describing APD restitution (lower panels). The abscissa is diastolic interval and the ordinate is action potential duration. In A, the flatter slope of the action potential duration restitution curve results in only a single bifurcation. However, with an increase in the slope of the restitution curve (lower panel B) the bifurcation diagram progresses to irregular (chaotic) dynamics (upper panel B).

EVIDENCE FOR A LOW-DIMENSIONAL CHAOTIC ATTRACTOR
IN HUMAN VENTRICULAR FIBRILLATION

Steven J. L. Evans[*], M.D., Steven S. Khan[*], M.D., Alan Garfinkel[+], Ph.D.,
Alfonso M. Albano[++], Ph.D., Robert M. Kass[**], M.D., and George A. Diamond[*], M.D.

[*] Division of Cardiology
Cedars-Sinai Medical Center
8700 Beverly Blvd.
Los Angeles, CA 90048    USA

[**] Department of Cardiovascular Surgery
Cedars-Sinai Medical Center
8700 Beverly Blvd.
Los Angeles, CA 90048    USA

[+] Department of Kinesiology
2859 Slichter Hall
University of California, Los Angeles
Los Angeles, CA 90024-1568

[++] Department of Physics
Bryn Mawr College
Bryn Mawr, PA 19010    USA

Address for Correspondence:
Dr. Steven S. Khan
Division of Cardiology
Cedars-Sinai Medical Center
8700 Beverly Blvd., Rm 6215
Los Angeles, CA 90048    USA The normal, healthy human heart contracts periodically, but can undergo a transition to an aperiodic, non-contractile state termed ventricular fibrillation (VF) when diseased. This state, fatal if not immediately terminated, is the leading cause of sudden death in the United States(1). The electrocardiogram during normal heart rhythm gives rise to a periodic waveform, while VF generates an irregular signal(fig. 1) that is classically described as disordered and asynchronous(2). However, recent work has suggested that structure may be present in VF, particularly during the first few seconds after its onset(3). This paradoxical combination of order and disorder suggests that VF may be chaotic(4). If so, non-linear dynamics might provide insight into the mechanisms underlying the onset and perpetuation of VF.

A one-dimensional time series can be used to construct a dynamic trajectory embedded in an n-dimensional phase space (5). If, in a stationary system, the trajectory is restricted to a subset of phase space, this subset is defined as an attractor. An attractor may have an integer dimension. Recently, however, fractal, or strange attractors with non-integer dimensions have also been described(6). Strange attractors are characteristic of systems that exhibit chaotic dynamics. These systems appear random, but are governed by underlying deterministic processes, and manifest sensitive dependence on initial conditions.

The correlation dimension, D2, gives a quantitative characterization of the geometric properties of a system's attractor. It provides a measure of the complexity of the system's behavior, and can help distinguish between random and non-random signals(7). A random signal does not converge, and 'fills' the space in which it is embedded, regardless of the embedding dimension of the space. Thus, establishing that the correlation dimension of a signal converges demonstrates that the signal is not random.

A fractional value of D2 indicates the existence of a strange attractor. In practice, however, the error associated with the estimation of D2 is often too large to determine whether a fractional dimension is present. If the calculated distribution of D2 (mean ± standard deviation) overlaps an integer value of D2 with sufficiently high probability, the system may be either chaotic or quasiperiodic. In this circumstance, examination of the power spectrum is useful: a broadband spectrum in conjunction with a convergent D2 indicates chaotic behavior whereas a spectrum consisting of discrete peaks without a broadband component indicates periodic or quasiperiodic behavior.

The application of non-linear dynamic analysis to a system requires that the system be stationary over the time period subjected to analysis. Previous work attempting to analyze VF by non-linear mathematical techniques has suffered from an inherent lack of stationarity of the systems analyzed(8,9). In this paper, we apply the techniques of dimension calculation, spectral analysis, and phase space analysis to a relatively stationary state of human VF, and demonstrate the presence of a low dimensional, strange attractor.

We studied perfused, hypothermic human VF in 8 patients undergoing open-heart surgery, a state which is more physiologically stable than in non-perfused systems(10). Examination of the VF waveform revealed organized activity at the onset of VF(fig 1), as reported by Chen et al.(3), lasting in some patients for up to 6 seconds. Since this initial organized stage may be a transient state(9), subsequent analysis was performed starting at 7 seconds after the onset of VF in all patients.

A correlation dimension of less than 4 was observed in all patients. Dimension calculations were performed(fig 2) using data segment lengths from 1000 data-points (1-second) to as many as 10,000 data-points(10 seconds). These calculations revealed an attractor which was stable for up to 10 seconds in some patients, and was stable for at least 2 seconds in all patients. A broadband power spectrum was observed in all patients, consistent with results previously reported in hypothermic human VF(11). The majority of the power was below 12 Hz. Power decreased at higher frequencies, but was present at all frequencies up to at least 25 Hz. (fig. 3). Phase space analysis of the time series revealed the presence of underlying non-random structure(fig 4a,4b).

The existence of a low dimensional attractor in association with a broadband power spectrum implies that the attractor is a strange attractor. This, in conjunction with the structure seen in the phase space plots, suggests that the underlying process is chaotic rather than random or quasiperiodic in perfused, hypothermic human VF.

It has been shown that the heart manifests non-linear dynamical behavior (12,13). Goldberger et al(8) were the first to use spectral analysis to examine VF from a viewpoint of non-linear dynamics. They reported that VF was probably not chaotic because of the presence of well-defined peaks in the power spectrum. However, several chaotic systems (for example the Duffing oscillator) have power spectra with one or many peaks superimposed on a broad background, with substantial power at all frequencies. Therefore, although power spectrum analysis is a useful tool to help distinguish an aperiodic chaotic or random signal from a quasiperiodic or periodic signal, it is not sufficient by itself to determine if a system is chaotic(14). Kaplan(9) used similar techniques to analyze VF in canines but found no evidence of a low-dimensional attractor. The systems studied by both Goldberger(8) and Kaplan(9) were not stationary, however, because no attempt was made to perfuse the fibrillating heart or to lower its metabolic demands. Kaplan also started the analysis at a different point in the fibrillatory waveform(1-2 seconds after onset) than our analysis, and analyzed surface electrocardiograms from normothermic canines.

There are 4 possible dynamic patterns for ventricular fibrillation: periodic; quasiperiodic; random; or chaotic. The broad band power spectrum demonstrates that VF is neither periodic or quasiperiodic. The presence of a low-dimensional attractor in VF suggests that the signal is not random. While oversampling of a finite-length random signal can result in a spuriously low dimension (9), the two-dimensional projections of the system's phase space trajectory display considerable structure and spatial non-uniformity (fig 4a, 4b). It is possible that the dynamics may represent an underlying quasiperiodic attractor with added noise. However, the quasiperiodic component would be insignificant compared to the noise in the system, and in this case one would not expect a low-dimensional attractor. Thus our results are most consistent with the conclusion that VF is a chaotic process.

Three important questions are raised by our findings. Firstly, what is the physical basis for the observed low dimension in VF? Structure in VF could exist at both the macroscopic level and the cellular or sub-cellular level. Secondly, how does chaos evolve in VF? Recent work suggests that decreased fibrillatory thresholds may manifest as a subtle electrical alternans(15), similar to the period doubling seen in many systems during their evolution from a periodic to a chaotic state(16). This would have important implications for detecting the progression toward VF, and possibly preventing VF. Thirdly, can this behavior be controlled? If organized structures are present later in VF as well as its onset, they may be susceptible to entrainment and termination using lower energy pacing techniques instead of frank defibrillation. In addition, new modes of approach to the design and testing of antiarrhythmic pharmacologic therapy may be identified(28).

We thank Drs. W. Mandel, R. Helfant, and E. Gang for their invaluable support of this work, and Drs. T. Denton, H. Karagueuzian, and T. Peter for helpful discussions.

REFERENCES

1. Sudden Cardiac Death: The Major Challenge Confronting Contemporary Cardiology. Lown, B. Am J Cardiol 43, 313-328 (1979).

2. Ventricular Fibrillation. Surawicz, B. J Am Coll Cardiol 5, 43B-54B (1985).

3. Mechanism of Ventricular Vulnerability to Single Premature Stimuli in Open-Chest Dogs. Cheng, P-S., Wolf, P.D., Dixon, E.G., Danieley, N., Frazier, D.W., Smith, W.M., and Ideker, R.E. Circ Research 62, 1191-1209 (1988).

4. Simple Mathematical Models With Very Complicated Dynamics. May, R.M. Nature 261, 459-467 (1976).

5. Geometry from a time series. Packard, N.H., Crutchfield, J.P., Farmer, J.D., and Shaw, R.S. Physical Review Letters (USA). 45, 712-716 (1980).

6. Strange Attractors. Ruelle, D. The Mathematical Intelligencer. 2, 126-137 1980.

7. Measuring the Strangeness of Strange Attractors. Grassberger, P. and Procaccia, I. Physica 9D, 189-208 (1983).

8. Some observations on the question: is ventricular fibrillation "chaos"? Goldberger, A.L., Bhargava, V., West, B.J., and Mandell, A.J. Physica 19D, 282-289 (1986).

9. Kaplan, D.T. The Dynamics of Cardiac Electrical Instability. PhD thesis, Harvard University, Cambridge, Massachusetts, (1989).

10. Studies of the effects of hypothermia on regional myocardial blood flow and metabolism during cardiopulmonary bypass. III. Effects of temperature, time, and perfusion pressure in fibrillating hearts. Brazier, J.R., Cooper, N., McConnell, D.H., and Buckberg, G. D. <u>J Cardiovascular Surgery</u> 73, 102-109 (1977).

11. Time Domain and Spectral Analysis of Electrograms in Man During Regular Ventricular Activity and Ventricular Fibrillation. Morkrid, L., Ohm, O-J., and Engedal, H. <u>IEEE Trans Biomedical Engineering</u>, BME-31, 350-355 (1984).

12. Non-linear dynamics of cardiac excitation and impulse propagation. Chialvo, D.R., & Jalife, J. <u>Nature</u> 330, 749-752 (1987).

13. Is the normal heart a periodic oscillator? Babloyantz, A. and Destexhe, A. <u>Biological Cybernetics</u> 58, 203-211 (1988).

14. Berge, P., Pomeau, Y., and Vidal, C. in <u>Order Within Chaos</u>, 146 (Wiley, New York, 1986).

15. Electrical alternans and cardiac electrical instability. Smith, J.M, Clancy, E.A., Valeri, C.R., Ruskin, J.N., and Cohen, R.J. <u>Circulation</u> 77, 110-121 (1988).

16. Chaos, Strange Attractors, and Fractal Basin Boundaries in Nonlinear Dynamics. Grebogi, C., Ott, E., and Yorke, J.A. <u>Science</u> 238, 632-638 (1987).

17. Studies of the effects of hypothermia on regional myocardial blood flow and metabolism during cardiopulmonary bypass. I. The adequately perfused beating, fibrillating, and arrested heart. Buckberg, G. D., Brazier, J.R., Nelson, R.L., Goldstein, S.M., McConnell, D.H., and Cooper, N. J Cardiovasc Surg 73, 87-94 (1977).

18. Singular-value decomposition and the Grassberger-Procaccia algorithm. Albano, A.M., Muench, J., Schwartz, C., Mees, A.L, and Rapp, P.E. Physical Reviews Gen. Phys. (USA). 38, 3017-3026 (1988).

19. Determination of Attractor Dimension and Entropy in Various flows, An Experimentalist's Viewpoint. Caputo, J.G., Malraison, B., and Atten, P. in Dimensions and Entropies in Chaotic Systems, 180-190. Ed. Mayer-Kress, G. (Springer, Berlin, 1986).

20. Spurious dimension from correlation algorithms applied to limited time-series data. Theiler-J. Physical Review A (USA). 34, 2427-2432 (1986).

21. Do climatic attractors exist? Grassberger, P. Nature 323, 609-612 1986.

22. Lasers and Brains: Complex Systems with low dimensional Attractors. Albano, A.M., Abraham, N.B., DeGuzman, G.C., Tarroja, M.S.H., Bandy, D.K., Gioggia, R.S., Rapp, P.E., Zimmerman, I.D., Greenbaum, N.N., and Bayshore, T.R. in Dimensions and Entropies in Chaotic Systems, 231-240 Ed. Mayer-Kress, G. (Springer, Berlin, 1986).

23. Attractor Dimension of non-stationary dynamical systems from small data sets. Havstad, J. and Ehlers, C. Physical Review A 39, 845-853 (1989).

24. Swinney, H.L., personal communication.

25. Calculation of Correlation Dimension from Experimental Data: Progress and Problems. Rapp, P.E., Albano, A.M., and Mees, A.L, in *Dynamic Patterns in Complex Systems*, 191-205, Kelso, J.A.S., Mandell, A.J., and Schlesinger, M.F. eds. (World Scientific, Singapore, 1988).

26. Calculating the Dimension of Attractors from Small Data Sets. Abraham, N.B., Albano, A.M., Das, B., DeGuzman, G., Yong, S., Gioggia, R.S., Puccioni, G.P., and Treddicce, J.R. *Physical Letters* 114A, 217-221 (1986).

27. Extracting qualitative dynamics from experimental data. Broomhead, D.S. and King, G.P. *Physica D (Netherlands)*. 20D, 217-36 (1986).

28. Is the proarrhythmic effect of quinidine a chaotic phenomenon? Garfinkel, A., Karagueuzian, H.S., Khan, S.S., and Diamond, G.A. *J Am Coll Cardiol*, 13(supp.A), 186A (1989).

LEGENDS

Figure 1:

ONSET OF VENTRICULAR FIBRILLATION.

Top tracing: Surface ECG lead II during VF, starting with the last sinus beat (arrow).

Bottom tracing: Simultaneous left ventricular bipolar epicardial electrogram. Note the presence of an organized, spikelike pattern after the initial onset of VF, lasting for 6 seconds. The organized activity is more evident in the epicardial electrogram, even when the surface ECG appears disorganized.

During open heart surgery, patients spontaneously develop VF as they are cooled from 37°C (body temperature) to approximately 25°C. The patient's circulation is supported by an extracorporeal circulatory device, the heart-lung machine, which provides a continuous supply of oxygenated blood to the heart and body. After VF develops, steady perfusion of the heart is maintained by the heart-lung machine(17). This reduces the accumulation of toxic metabolic products and maintains a more stable physiological state than in non-perfused systems(10).

Bipolar stainless steel electrodes were sutured onto the ventricular epicardium of the heart before cooling. The epicardial signals were continuously recorded on magnetic tape (frequency response 0-2500 Hz) during the cooling period, the transition to VF, and for at least 20 seconds thereafter. The recordings were analog antialias filtered (band pass 0-200 Hz) and digitized (12-bit resolution) at a sampling rate of 1 KHz. A single-variable time series $v(t)$ $\{t=1,2...2 \times 10^4\}$ was thus obtained for each patient for 20 seconds after the onset of VF.

Figure 2:
DIMENSION ANALYSIS
Plot of dlnCn(r)/dCn(r) vs. ln(r) for a 7-second data segment (7000 data points).

The correlation dimension D2 of the time series from each patient was calculated using a modified(18) Grassberger-Procaccia algorithm(7). Oversampling a signal, or equivalently, embedding using too small a window length, may underestimate D2 (18,19,20,21), whereas using too large a window length may overestimate D2. To avoid these pitfalls, we chose a window equal to the first zero of the signal's autocorrelation function(22), and used a maximum embedding dimension of 11(18).

When analyzing weakly stationary data(23), a useful guideline is to obtain $10^D$ sufficiently spaced points to resolve an attractor of dimension D2 to an accuracy of 5-10%(24,25). This has been confirmed for a number of mathematical attractors and used in the analysis of laser data (26). We used from 1000-point (1-second) to 10,000-point (10-seconds) data segments to calculate D2. The time series for all patients had autocorrelation functions that reached their first zero at approximately 50 milliseconds, giving at least 950 embedding vectors for each calculation.

The embedding vectors, x(k), were taken to be the rows of a trajectory matrix on which singular value decomposition (SVD) was performed. The embedding vectors were projected along the eigenvectors (principal axes) of the SVD (18), and the projections used to calculate the correlation integral C(r), $$Cn(r) = (1/Np) \sum_{\substack{i,j=1 \\ i \neq j}} \Theta (r-|x(i)-x(j)|)$$

where Np is the number of pairs of embedding vectors x(i) and x(j), $\Theta$ is the Heaviside function which has a value of 1 when its argument is non-negative and zero otherwise, and r is the distance for which the correlation integral is being evaluated. Cn(r) is the fraction, in embedding dimension n, of Euclidean distances between embedding vectors |x(i)-x(j)|, that do not exceed r. Only those vectors that were separated in time by more than 10 sampling times (10 msec) were summed to avoid underestimating D2 (20).

D2 is the limit for small values of r and large values of n of the slope D(n;r), of the graph of lnCn(r)

vs. ln(r). The existence of a limit of this slope as n increases is usually tested by repeating the calculation for increasingly larger n. Instead, we have used the singular values obtained from the SVD of the trajectory matrix as criteria for determining the largest subspace of the embedding space containing the attractor(27). Albano (18) has shown that principal axes with eigenvalues below $10^{-4}Lmax$ (Lmax=largest eigenvalue of the covariance matrix) do not contribute significantly to the correlation integral. This result was also confirmed using our time series of VF. Thus, the high n limit was taken to be the value of the dimension calculated by using the projection of the trajectory in that subspace of the embedding space spanned by principal axes with eigenvalues exceeding $10^{-4}Lmax$.

The low-r limit of $D(n;r)$ is most corrupted by noise. Instead of seeking a low-r limit, we selected a range of r, the 'scaling region' or plateau, $\ln(r_{lower}) <= \ln(r) <= \ln(r_{upper})$, where $D(n;r)$ was approximately constant. If a scaling region was found in the high n limit as described above, then the average value, D2, of $D(n;r)$ in the scaling region was taken to be the correlation dimension. The figure shows a plateau in the scaling region from $\ln(r_{lower})=-4.2$ to $\ln(r_{upper})=-2.7$, with a dimension of $1.8 \pm 0.05$.

Figure 3:

POWER SPECTRUM OF VENTRICULAR FIBRILLATION

The power spectrum for each time series was calculated by performing a fast Fourier transform (FFT) on the digitized signal. The spectrum is broadband, with power at every frequency between 0 and up to over 25 Hz. The majority of power is below 12 Hz. The power spectrum alone can distinguish between periodic or quasiperiodic and random or chaotic signals, but cannot differentiate between random and chaotic signals. However, in conjunction with low dimensionality and ordered phase space plots, a broadband power spectrum suggests the presence of a chaotic, rather than random underlying process.

Figure 4:

PHASE SPACE ANALYSIS a) Plot of $d^2v/dt^2$ vs. $dv/dt$: Phase space plots of the time series were obtained by filtering the time series via the FFT at 0-1 Hz and 60 ± 2 Hz to remove baseline drift and line frequency artifact, and smoothing with a 5-point moving average filter to remove high frequency artifact for plotting purposes only. The first and second derivatives of the smoothed time series were calculated, and phase space plots obtained by graphing v vs $dv/dt$ and $dv/dt$ vs $d^2v/dt^2$. This plot of a 5-second data segment contains regions that are heavily visited by the trajectories and regions that are relatively sparsely visited. This is consistent with an underlying non-random process.

b) Phase space plot obtained via singular value decomposition: The projection of the trajectory on the plane determined by the principal axes of the singular value decomposition corresponding to the largest eigenvalues (squares of the singular values) was plotted. The eigenvectors represent the major directions the trajectories take while traversing phase space. This plot contains a 5 second time sequence, covering the same time span as in figure 4a, and also demonstrates considerable structure. 'Forbidden zones', regions where the trajectory does not appear, and banding, where the region is heavily visited, are seen.

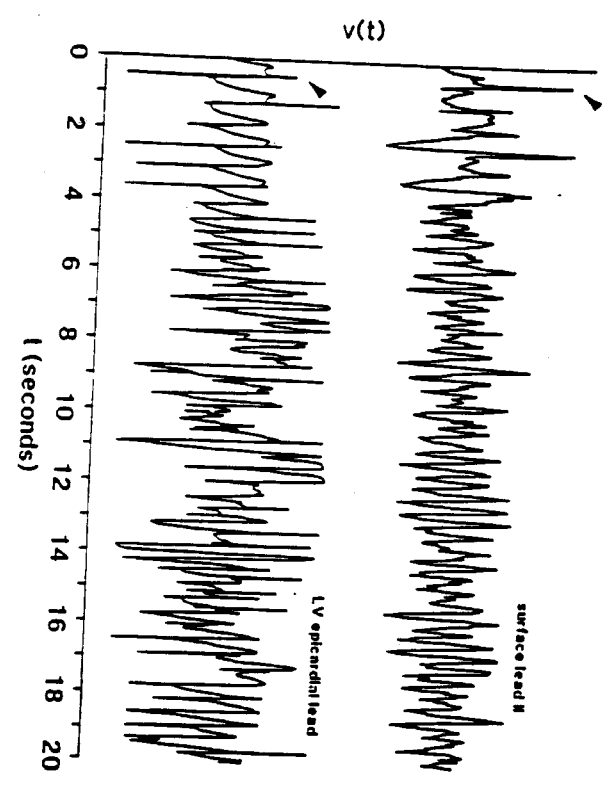
64

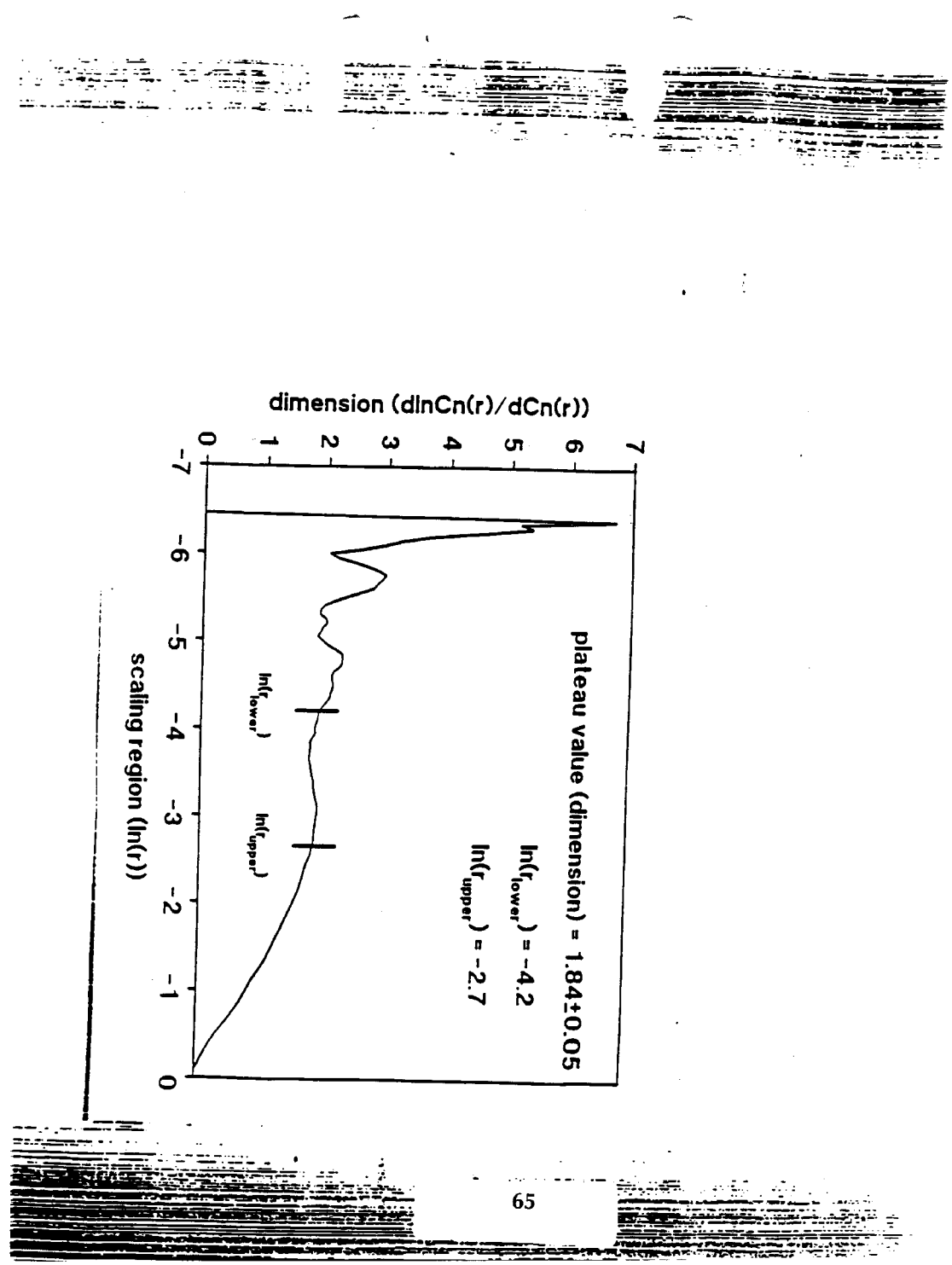

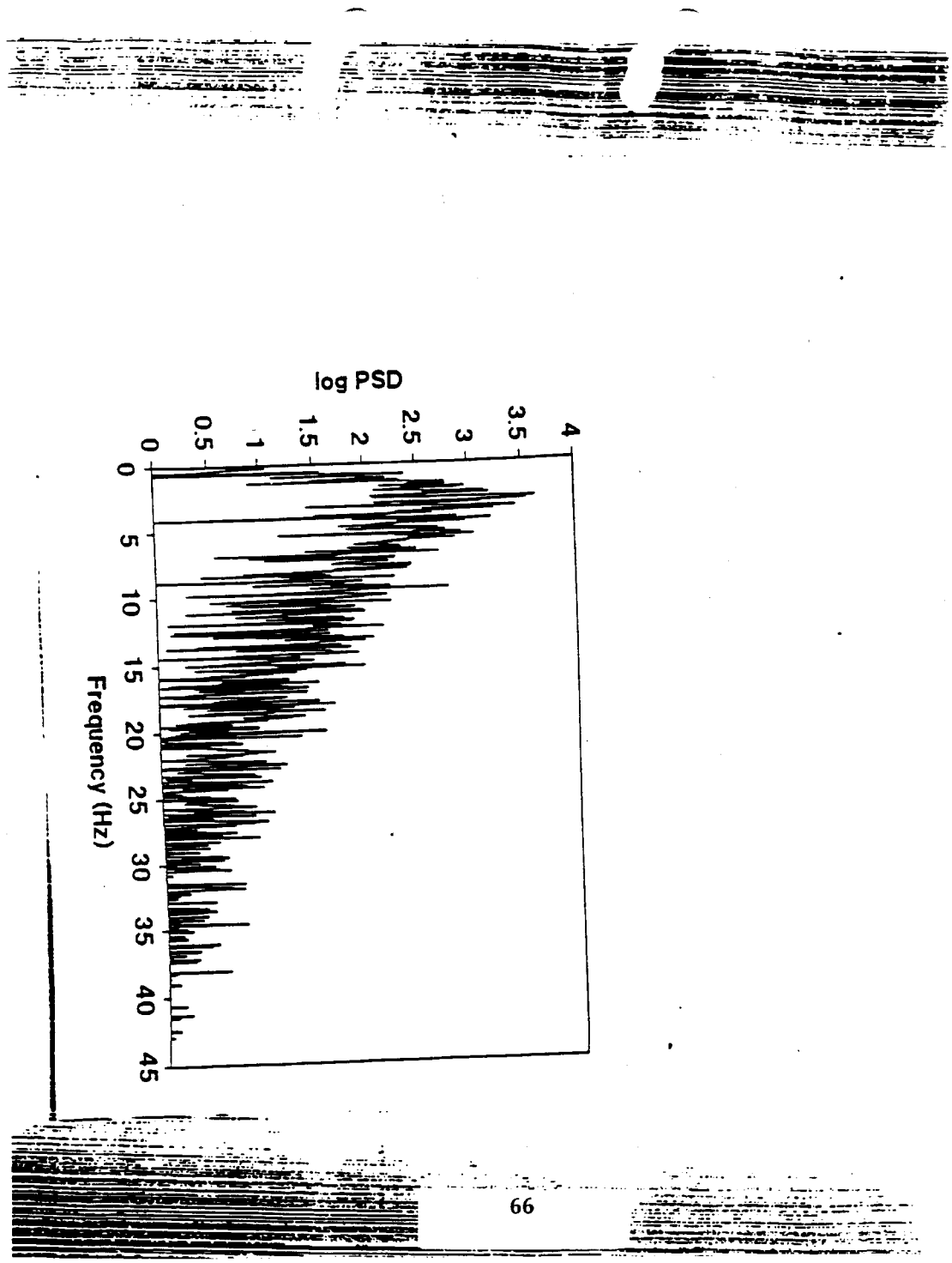
66

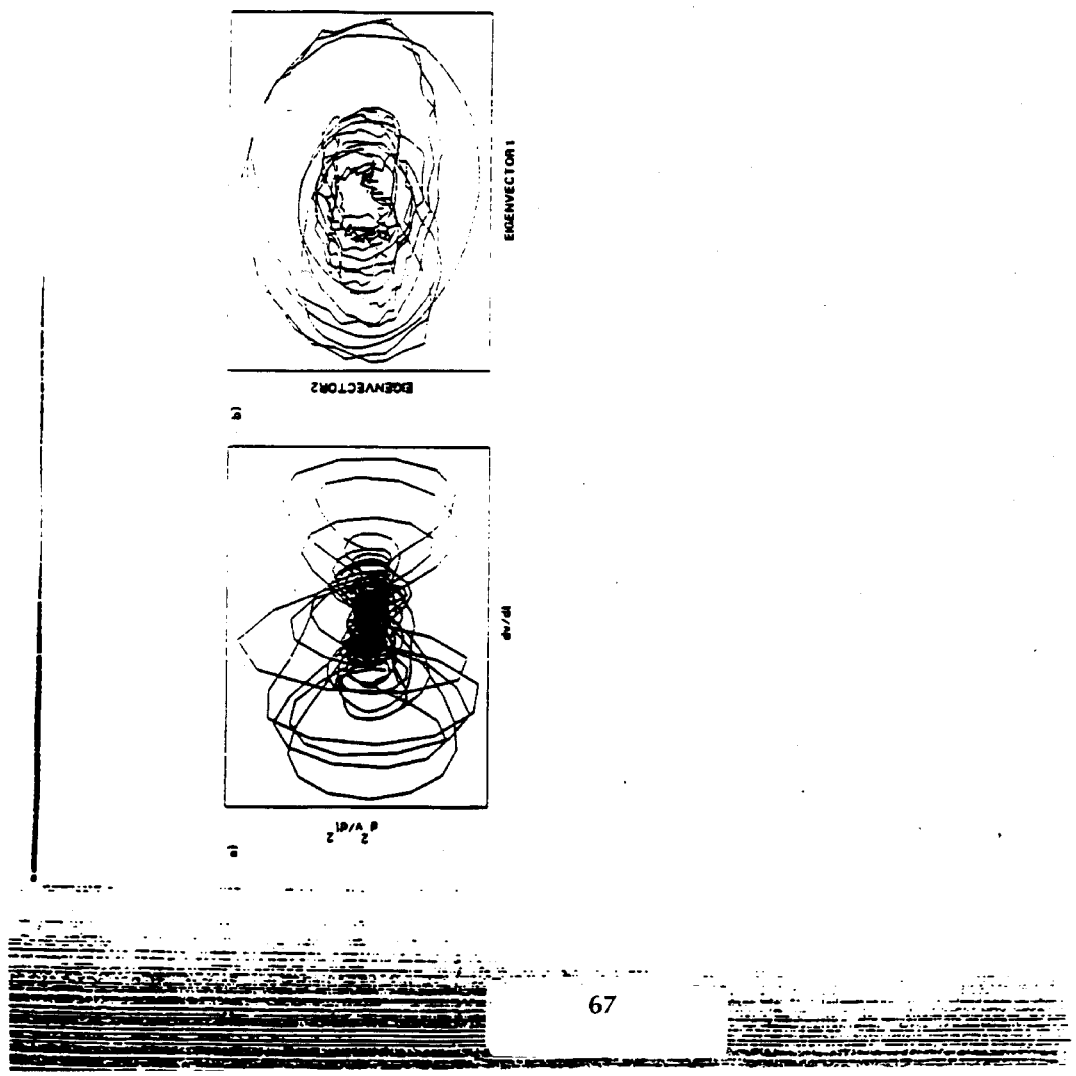

Fascinating Rhythm:

A Primer on Chaos Theory and its
Application to Cardiology

Timothy A. Denton, M.D.
George A. Diamond, M.D.
Richard H. Helfant, M.D.
Steven Khan, M.D.
Hrayr Karagueuzian, Ph.D.

Short Title: Chaos and Cardiology

Key Words: Nonlinear dynamics, Arrhythmia, Dynamic systems, Fractal

From the Division of Cardiology, Cedars-Sinai Medical Center, and
the School of Medicine, University of California, Los Angeles, California This work was supported in part by an NHLBI Training Grant (2T32HL07380) from the National Institutes of Health, Bethesda, Maryland.

Address reprint requests to:
George A. Diamond, M.D.
Cedars-Sinai Medical Center
Division of Cardiology
Becker 210
8700 Beverly Boulevard
Los Angeles, California 90048
Business phone (213) 855-3884

Abstract:

Recent advances in nonlinear mathematics have led to the development of a science called "chaos" and its application to biology and cardiology. We discuss the basics of chaotic behavior, comparing and contrasting it to periodic and random behavior. Also discussed is the way in which nonlinear systems can become chaotic and the applications of chaos to cardiac arrhythmias. Finally, we describe the methods used to study nonlinear systems and seemingly random behavior. Five tools of nonlinear dynamics are described (phase plane plots, return maps, Poincaré sections, fractal dimensions and spectral analysis). A glossary is included that explains much of the basic vocabulary of chaos theory.

*Somehow, a myth has arisen....that detailed mathematical and theoretical analysis are not appropriate in biology....Yet if the complex dynamic phenomena that occur in the human body were to arise in some inanimate physical system....they would be subjected to the most sophisticated experimental and theoretical study[1]*

Prologue

*While caring for a patient with a large pericardial effusion a physician notes that each electrocardiographic R wave and each peak systolic pressure wave is of a different amplitude (Figure 1A and 1B). Although the phenomenon disappears following pericardiocentesis, the physician wonders if there might be a hidden pattern underlying this seemingly random behavior, and therefore plots the height of each wave against the height of the succeeding wave. To the physician's surprise, the relation for R wave amplitude is highly structured (Figure 1C), but that for systolic pressure is not (Figure 1D).*

Although this particular example is completely fanciful, many scientists have made precisely analogous observations over the last 20 years. The explanation for these puzzling findings lies in a new science called chaos. In recent years, this new discipline, based on the mathematics of nonlinear dynamics, has been applied to many areas of physical and biological science[1-7]. Its application to cardiology may provide an innovative tool to aid our understanding of many physiologic phenomena that heretofore were deemed inexplicable using conventional methodologies. Specifically, a better understanding of the mathematical physiology of cardiac rhythms may allow us to predict the onset of lethal arrhythmias, and intervene prior to the development of catastrophic clinical events.

This essay is a primer on the principles of chaos – what it is, what causes it, and how to detect it. As much as possible, we have attempted to write the text in non-mathematical form. We have used a variety of metaphors and hypothetical examples as pedagogic aids to a deeper understanding of the underlying concepts. Our purpose is to provide appreciation without intimidation. Those interested in a more comprehensive review of the subject are referred to a number of excellent books and articles. Gleick[7] and Stewart[8] have written superb nontechnical descriptions of chaos theory, and concise accounts are also available[9-12]. Moon[6] offers a highly accessible technical discussion of the theory, while Thompson[13] and Bergé[14] provide more mathematically rigorous expositions. Those interested in biological aspects of the theory are referred to a technical review by Olsen and Degn[4], and to books by Holden[5], Glass and Mackey[3], and Winfree[15].

The present discussion is divided into three sections. The first is an introduction to nonlinear dynamics and chaos, the second reviews the current status of its application to cardiology, and the third describes some of the methods used to study chaotic activity. A glossary of unfamiliar technical terms is provided as an appendix, and the terms themselves are highlighted in bold lettering when they first appear in the text. The glossary also contains terms not used in this text, but encountered often enough in the references cited to warrant their brief definition here.

An Introduction to Nonlinear Dynamics and Chaos

<u>What is Chaos?</u>

Chaos is best understood by comparing it to two other behaviors with which we are more familiar: randomness and periodicity. Random behavior never repeats itself, and is inherently unpredictable and disorganized except in a very special way. We can predict the average behavior of a collection of gas molecules with absolute precision, but we can never predict the individual behavior of a single molecule. Similarly, we can predict the average change in heart rate as we administer digoxin to a patient in atrial fibrillation, but we cannot predict the individual pattern of R-R intervals. A very simple random series is represented by the number of letters in the first word of each sentence of this paragraph - 5, 6, 2, 9, 1, 5, 8. There is no rule for predicting the seventh number in this series from the preceding six numbers - if there were, the series would not be random. Although one might think otherwise, very few biologic processes are considered fundamentally random (genetic translocation, ovulation, fertilization, receptor binding).

Periodic behavior, on the other hand, is highly predictable because it always repeats itself over some finite time interval. A mathematical sine wave and electrocardiographic normal sinus rhythm are typical examples. Systems exhibiting periodic behavior are governed by an underlying deterministic process. Thus, if we know the amplitude, frequency and phase of a sine wave at any instant, we can predict the amplitude at any other point in time. An example of periodic behavior is given by the following simple mathematical system: $x_{n+1} = |x_n - 7|$. The next number in this series is the absolute value of the preceding number minus seven. With an initial value of 2, we obtain the following series of numbers: 2, 5, 2, 5, 2, 5... The next number in the series (2) can be predicted because you know the rule. Periodic behavior in biological systems is generally considered normal (diurnal variation, sinus rhythm, menstruation, peristalsis), but at least two examples are decidedly abnormal (ventricular tachycardia and petit mal seizures).

Chaos is distinct from periodicity and randomness, but has characteristics of both. Although chaotic behavior looks disorganized (like random behavior), it is really deterministic (like periodic behavior). The Bernoulli map[6] is a simple example of a chaotic system: $x_{n+1} = 2x_n$ (mod 1). The mod 1 means that the integer value of the number x is subtracted from the number to leave only the decimal value (example: mod 1 of 1.73 = 0.73). With an initial value of 0.85, we obtain the following series of numbers - 0.85, 0.7, 0.4, 0.8, 0.6 ... - Although the series <u>seems</u> random, it is completely determined by a very simple rule. If you know the rule, you can predict the next number in the series (0.2) with complete confidence.

A number of physical processes are known to be chaotic (some chemical reactions[15,16], fluid turbulence[17], the orbit of Pluto[18], solar radio emissions[20,21], atomic motion[22], weather[23], polar ice[24]), and a few biological examples have been reported (measles epidemics[25], population biology models[26-30], evolution models[31], stretch reflex[32], models of cardiac behavior[33,34], cardio-pulmonary interactions[35,36], embryology[37,38], sociology of war models[39], hematopoiesis[40,41], some biochemical reactions[42,43] and the electroencephalogram[44-46]).

<u>What Causes Chaos?</u>

Conventional biologic systems are often viewed as linear. A familiar example of a linear system is a straight line graph of some independent variable on the x-axis plotted against a dependent variable on the y-axis - "the more the merrier" is a prosaic representation[7]. The simplicity of linear systems is so attractive that investigators routinely attempt to "linearize" complex sets of data by various transformations of the axes (plotting the logarithm of x against the reciprocal of y, for example). This practice, however, may misrepresent the true state of the system; as a result, the underlying pathologic process, or mechanism, may be overlooked.

The classical Starling curve describing the relation between cardiac output and ventricular filling pressure is one such case. Initially, cardiac output rises as filling pressure is increased, but at some point, further increases in filling pressure result in a fall in cardiac output. This classical nonlinear behavior is readily explained at a molecular level by the physical relation between actin and myosin filaments in the sarcomere. At low levels of resting tension there is only a small stretch on the sarcomere, and little interaction between active sites on the actin and myosin filaments. As tension rises, the sarcomere stretches, interaction between actin and myosin increases, and developed force thereby increases. As tension rises still further, the sarcomere stretches to a point where the overlap between actin and myosin, and the attendant developed force, begins to fall off.

With linear equations, there is always a one-to-one correspondence between values on the x and y axes (Figure 2A). This is often not the case with nonlinear equations. Nonlinear equations are of two types, monotonic and folded. Monotonic equations (those that are always increasing or always decreasing), such as $y = e^x$, always have a one-to-one correspondence between values on the x and y axes. In contrast, folded nonlinear equations (those that change direction) like the Starling curve, exhibit local maxima or minima. As a result, a single value of y can be associated with two (or more) values of x (Figure 2B). As we shall see, this ambiguity gives rise to chaos under some conditions.

Many nonlinear systems can be represented by simple equations. Consider the so-called logistic map[1,2,3,4] based on the simple equation for a parabola: $y = k \cdot x \cdot (1 - x)$; where x is a variable ($0 \leq x \leq 1$) and k is a parameter ($0 \leq k \leq 4$). The logistic equation contains both linear and nonlinear components that are better seen when the equation is expressed in another form: $y = kx - kx^2$. The kx term is the linear portion of the equation, and the $kx^2$ term is the nonlinear portion. If we choose particular values for k and x, we can plug them into the equation and get a value for y. If we now substitute y as the new value for x, we obtain a new value for y (k remains the same). This repetitive process of substituting the solution to an equation back into the same equation to obtain the next solution is called iteration. If we iterate the equation many times and plot each new value of y on the vertical axis, against the number of iterations on the horizontal axis, we will have constructed a graph that represents the dynamic behavior of the system. Depending on the value of k, the behavior can be quite spectacular.

As a specific example, if we choose an initial condition $x = 0.05$, $k = 2.5$, and iterate the equation 50 times, we see that after a short oscillation, the system settles into a predictable and stable output – a flat line (Figure 3A). The system is stable because the linear portion of the equation is dominant. By increasing k to 3.2, and keeping the initial value of x the same, a sudden qualitative change in behavior of the system occurs – it begins to oscillate between two different states, as the nonlinear portion of the equation becomes manifest (Figure 3B). This abrupt transition based, in this case, on a small change in a parameter, is called a bifurcation. Increasing k still further to 3.5, causes another bifurcation to four states (Figure 3C). Suddenly, as we increase k to 3.8, the system begins to exhibit strikingly aperiodic, seemingly random, behavior – chaos - - as the nonlinear term becomes dominant (Figure 3D). The entire range of behavior for the logistic map is summarized in the bifurcation diagram illustrated in Figure 4.

This behavior may be better understood by a graphic demonstration (Figure 5). Start with a parabola. The height of this parabola is directly proportional to the parameter k. Choose an initial value for x (0.05), and find the next value by drawing a horizontal line between x and a diagonal line of identity. From that point on the line of identity, draw a vertical line to the parabola. That new value (y) then becomes the next value for x. Repeat this process as long as you like.

In our earlier numeric example, after some initial instability, the system oscillated between two values, a and b (Figure 3B). Figure 5A demonstrates that with k = 3.2, a transient period of instability, only two points on the parabola are visited (a and b). Figure 5B demonstrates what happens when the parabola height (k) is increased to 4. Note that there is no stability, and that each intersection of the parabola is at a different point.

Nonlinear systems such as the logistic map can pass through a variety of identifiable stages before they become chaotic[6,7], and the identification of these stages might have important clinical implications. Imagine a completely hypothetical example, wherein a patient undergoing coronary artery bypass surgery develops sinus arrest (a logistic map with k = 0) in response to hypothermia, but as body temperature returns to normal, so too does normal sinus rhythm (k = 2.5). On the second post-operative day, atrial bigeminy occurs (k = 3.2), followed by atrial fibrillation (k = 3.8) on the third day. Had the atrial bigeminy been recognized as a harbinger of chaos, and a suitable drug been administered, capable of reducing the value of k, the arrhythmia might have been abolished, and the subsequent atrial fibrillation, prevented.

What are the Characteristics of Chaos?

Chaotic behavior exhibits a number of characteristics that distinguish it from periodic and random behavior. The most important criteria are summarized below:

1. *Chaos is both deterministic and aperiodic.* As with Newtonian physics, there is an underlying system of mathematical equations that controls the behavior of the system. If you know the equations (e.g., the parabola) and the initial conditions (e.g., x and k), you can predict the system's behavior accurately and precisely, no matter how complex it appears (Figure 3D). Unlike Newtonian physics, however, chaotic behavior never repeats itself exactly. There are no identifiable cycles that recur at regular intervals.

2. *Chaotic systems exhibit sensitive dependence on initial conditions*[1,38,39]. This means that very small differences in initial conditions will result in large differences in behavior at a later point in time. For example, the solid line in Figure 6 illustrates the behavior of the logistic map if the initial value of x is 0.5, and the dotted line illustrates the behavior if the initial value x is 0.5000001 instead. The two behaviors are almost identical at the start, but wind up being highly divergent even with initial conditions that differ by only 1 part in a million. The larger the initial difference, the faster the divergence.

The so-called baker's transformation provides a material metaphor of sensitive dependence[34,40]. Take a piece of dough and sprinkle it with raisins, taking note of their initial positions. Stretch and fold the mixture repeatedly. Now compare the final positions of the raisins to the initial positions. Even a small change in the initial position of a particular raisin will result in a very different final position if you do enough stretching and folding. In fact, any two raisins will move apart exponentially with each cycle of stretching and folding (mathematically, the logarithm of the distance separating them increases as a linear function of time).

A simple modification of the baker's transformation allows us to contrast the exponential divergence associated with chaos with the more commonplace linear divergence. Take a piece of dough and sprinkle it with raisins as before, but instead of stretching and folding the mixture, just stretch it. Two raisins will now move apart linearly rather than exponentially (mathematically, the separation itself rather than the logarithm of the separation increases linearly as a function of time). It doesn't take much imagination to see that the apprentice-baker's stretching will not result in very good raisin bread. It's the master-baker's folding of the dough that adds the nonlinear spice; no folding, no chaos, no bread.

The baker's transformation is also demonstrated on the graph of the logistic map (Figure 5B). The solution in Figure 5B starts at the initial value a. Its value is represented on the parabola by b. The value of b is "stretched" to c and c is stretched to d. Point d is stretched still further to e, and from there e is "folded" back on itself (moves to lower values) to point f. In essence, low values on the ascending portion of the parabola are stretched to higher values. When the new stretched value falls on the descending portion of the parabola, it is folded back on itself to low values on the ascending portion of the curve.

Although first described by Poincaré 90 years ago, sensitive dependence on initial conditions in the modern chaotic dynamic sense, was rediscovered by Lorenz[14] in the early 1960's. He developed a mathematical model consisting of three differential equations (now enshrined as the Lorenz equations) to predict the behavior of a simple microclimate over time. Initial conditions were input, and the computer generated a time series of the behavior of the three variables over many months. On one occasion, Lorenz wanted to extend a previous calculation beyond a few months. Because the calculations were time consuming, he saved time by using data from the middle of the previous calculation as initial conditions for his longer calculation. After starting the program, he later observed that the time series did not exactly correspond to the previous calculation. The data corresponded exactly for a while, but then diverged widely from the previous behavior. Later he realized that the computer used six significant digits in its calculations, but he had only input three significant digits (there were only three on the print-out). Based on this experience he concluded that long-term weather forecasting was impossible, and that small changes in a system at one time (the flutter of the wings of a butterfly in Peking) could make large changes in the behavior of a system later (a weather change in New York) -- the so-called "Butterfly effect"[7].

3. *Chaotic behavior is constrained to a relatively narrow range*. Although it appears random, the behavior of the system is bounded, and does not wander off to infinity. In the baker's transformation, for example, the raisins always remain embedded in the dough no matter how long, or how vigorously, we knead it. The behavior tends to wander because of the stretching, but always returns to a small region because it is folded back on itself. In the logistic map, the limits of the behavior are determined by the height and length of the arms of the parabola.

4. *Chaotic behavior has definite form*. Not only is the behavior constrained, but there is a particular pattern to the behavior. Common examples are the swirls seen as cream is mixed in coffee, as cigarette smoke rises in a calm room, and as a running stream is transformed into a rapid[36]. These patterns often take the form of "bands" (regions where behavior preferentially occurs), and "forbidden zones" (regions where it does not). Raisin bread exhibits such a pattern. The raisins are clustered in layers; they are not randomly distributed throughout the bread. This was also seen in the logistic map, where the irregular behavior was constrained by the parabola, and could not move off the curve. The extremes of behavior were limited by the height of the parabola. As we shall see, such patterns represent presumptive - but not definitive - evidence that an underlying process is chaotic rather than random.

Application of Nonlinear Dynamics to Cardiac Arrhythmias

Nonlinear behavior was first identified in cardiac tissue by Guevara and associates in 1981[4,6,8]. They induced both periodic and aperiodic rhythms in spontaneously depolarizing chick embryonic ventricular cell aggregates by intracellular current injection, and observed a variety of phenomena (period-doubling and phase locking) similar to those that are characteristic precursors of chaos in the logistic map. Based on these data, they developed a simple nonlinear mathematical model that described the complex behavior of these heart cell aggregates. Most importantly, they found that the model could reproduce all of the behaviors seen in the heart cell aggregates, and the behavior could be predicted based on measurable parameters. This was an unequivocal demonstration of nonlinear biological behavior. A potential clinical application of this study arises in the phase locking and period-doubling patterns observed. These patterns correspond to those associated with advanced AV nodal disease (2:1, 3:1, 4:1 block[44,45]). The mathematical model developed by these investigators showed how these seemingly irregular conduction processes could be explained and predicted. This is an important first step in the construction of a realistic mathematical model of the AV node itself[46].

Chialvo and Jalife observed these same electrophysiologic phenomena in electrically stimulated adult sheep heart Purkinje fibers that had no pacemaker activity[69]. By gradually increasing stimulation rate, strength of stimulation, and duration they observed phase locking patterns similar to those reported by Guevara and associates. They also subjected these Purkinje fibers to stress in a three chamber superfusion tissue bath. The proximal and distal chambers were superfused with Tyrode's solution, and the center chamber superfused with the electrical uncoupler heptanol or was compressed mechanically. By varying stimulation rate in the proximal chamber, and measuring conduction velocity to the distal chamber, bifurcations in conduction velocity similar to those in the logistic map, and aperiodic dynamics consistent with chaos were observed (Figure 7). These observations clearly show that a biologic system is capable of exhibiting aperiodic behavior under conditions of stress, and that such behavior has many of the characteristics of chaos. Moreover, the experimental design is a reasonable model for a common clinical condition -- an island of ischemic or infarcted tissue (the stressed central chamber) surrounded by normal tissue (the proximal and distal chambers), in which aperiodic behavior (extrasystoles) occurs as a result of variable conduction velocities at various heart rates.

Ritzenberg and associates observed a variety of electrophysiologic and hemodynamic phenomena indicative of prechaotic behavior (QRS alternans, period-doubling, period-tripling, period-quadrupling, and period-quintupling) in anesthetized closed-chested dogs following intravenous noradrenaline[70]. They also reported that hypothermia (29°C) and transient coronary artery occlusion both caused aperiodic changes in the magnitude of the QRS and T waves that followed a pattern of period-doubling similar to that for the logistic map. Whenever this characteristic precursor of chaos was observed, ventricular fibrillation threshold was significantly decreased[71,72]. This work extended the observation of nonlinear biologic behavior from purely electrical, in vitro systems to a mechanical, in vivo system. On the basis of these studies, these investigators developed a simple computer model of ventricular activation capable of beat-to-beat oscillations of period 2, 3, 6 and 24 during progressive increases in the rate of stimulation. This model eventually exhibited a chaotic rhythm that was considered an analog of clinical ventricular fibrillation[73].

Goldberger and associates, on the other hand, have questioned the hypothesis that ventricular fibrillation is chaotic[74,75]. They applied a rapid train of electrical stimuli to the heart of normal, open-chested, anesthetized dogs, and analyzed the resulting ventricular fibrillation by spectral analysis of the hand-digitized electrocardiographic waveforms. They observed that this ventricular fibrillation was associated with a narrow-band frequency spectrum. Because chaos is often characterized by a broad-band frequency spectrum[3], the authors concluded that ventricular fibrillation is not a chaotic process[76].

But recent studies by Chen and associates[77], using a very similar model (canine ventricular fibrillation induced by a single premature stimulus), demonstrated reentrant activation at the very onset of ventricular fibrillation in a figure eight pattern. This highly organized pattern of activation is analogous to sustained monomorphic ventricular tachycardia[78] and might explain the narrow-band frequency spectrum observed by Goldberger and associates[76] at the onset of ventricular fibrillation. Moreover, although investigations aimed at determining if ventricular fibrillation is chaotic have so far relied exclusively on conventional spectral analysis, as we shall see, more sensitive and specific methods of detection are now available[79,80].

Goldberger, in fact, considers normal sinus rhythm rather than ventricular fibrillation to be chaotic[45,74,75,81-82]. This counterintuitive assertion has a reasonable theoretical foundation: The sinus rhythm "system" consists of the SA node (a periodic oscillator) controlled by multiple nonlinear mechanisms (sympathetic tone, parasympathetic tone, hormones, preload, afterload), most of which have long feedback loops compared to the basic sinus cycle length -- a near-perfect substrate for the generation of chaos. Recent data showing a decrease in heart rate variability among patients at high risk for sudden death as a consequence of left ventricular dysfunction[83] provides empirical support for this assertion.

Shrier and associates[84] recently demonstrated nonlinear behavior of the atrioventricular node in the intact human heart. AV nodal recovery curves were generated for seven patients undergoing routine electrophysiologic testing. The curves were constructed by plotting the time of conduction from the extrastimulus (S2) to the His bundle spike – the S2-H2 interval – on the y axis, and the recovery time of the beat prior to the extrastimulus – the H1-S2 interval – on the x axis. Using these curves as templates, two sets of nonlinear equations were generated that described the behavior of the AV node. A variety of complex behaviors such as Wenckebach, reverse Wenckebach, alternating Wenckebach, and other advanced AV rhythms could be reproduced by these equations. This study is a logical extension of the animal models described above, and provides further support for the hypothesis that simple nonlinear mathematical models are capable of predicting – albeit over the short-term – the complex electrodynamic behavior of the intact human heart.

Finally, Winfree has made a remarkable series of predictions regarding the onset and form of ventricular fibrillation based on topological characteristics of biologic oscillators[13,14,16]. He thereby predicted that a depolarization field oriented in a particular way to a repolarization field could produce an unstable state (what he called a "singular point") in the myocardium that would lead to a rotating spiral of reentry – fibrillation. The type of spiral field (circular or figure-of-eight) is a function of the orientation of the depolarizing and repolarizing fields. Various aspects of this hypothesis have been verified experimentally[17,17,18] thereby demonstrating the power of applying abstract principles of mathematical analysis to the problem of cardiac arrhythmias.

Analytic Techniques to Detect Nonlinear Dynamic Behavior

Unfortunately, we usually do not know the underlying mathematical mechanisms that determine the behavior of a biological system. We are instead presented with nothing more than a phenomenological time series of the behavior (the conventional electrocardiogram, or conduction properties through the AV node, for example), and must infer the mechanisms from simple measurements of that time series. The most common ways to look for nonlinear or chaotic behavior involve the study of bifurcations in discrete data. Other less commonly used techniques attempt to detect more complex patterns in continuous data (such as the electrocardiogram). We divide our discussion here in two parts: the first describing the analysis of discrete data, and the second, describing the analysis of continuous data.

Discrete Data

Many nonlinear systems (such as the logistic map) pass through a series of intermediate stages prior to chaotic behavior. Often, these stages are easily recognized as oscillations between two, four, eight or more states. If a biologic system is observed to behave in this manner, then the underlying rules for the behavior might be based on a nonlinear system. Guevara, for example, started with observations of periodic and aperiodic behavior in his model of heart cell aggregates. By carefully stimulating the preparations, repetitive, reproducible behaviors were noted (the multiple combinations of phase-locking responses).

The next step in the analysis was the construction of a mathematical model that could reproduce the behaviors noted in vitro. This is the most difficult aspect of the problem. After developing a general theoretical model, appropriate parameters must be selected that reproduce the behavior. This step is empiric, and multiple models may need to be tried - and many parameters tested - before a successful model is found. Guevara found a very simple model, the Poincaré oscillator, that described much of the behavior. It cannot be sufficiently stressed that the search for a model is an art that is not easily taught.

The final step in the process is proving that the proposed mathematical model accounts for most, if not all, of the behaviors described in the biologic model. By solving the model under many conditions analogous to those in the real biologic system, one may have the basis for studying the biology in a more systematic fashion. In addition, once a reliable model is obtained, ionic, mechanical, or biochemical mechanisms might be inferred from what we know of the biologic system.

9

The application of models to biologic problems has helped explain many inconsistencies in the past. An example is seen in the use of exercise stress testing. Although exercise electrocardiography has a *high* predictive accuracy for the diagnosis of coronary artery disease in symptomatic populations, it has a *low* predictive accuracy in asymptomatic populations. This paradox was resolved by showing that Bayes' theorem provided a theoretical basis for the disparate observations[20].

Continuous Data

The modeling process described above is a general framework that can be applied to many biologic behaviors. In Guevara's work, the variations in behavior were relatively simple - but continuous signals present a more difficult problem. Often, subtle changes in behavior are not visible in the time series; sometimes, the time series appears random. In these cases, more sophisticated techniques are needed to detect the presence of underlying structure in the behavior. We now present a series of techniques commonly used in the analysis of continuous data (and sometimes of discontinuous data) that can reveal underlying structure in complicated behavior. These techniques are only the first step in providing an explanation for complex behavior. Just as in the discontinuous systems described above, once we determine there is underlying structure, we must propose a model or mechanism that fits the behavior, and demonstrate that the model applies to the biologic system. We then have a better understanding of the system, and might be able to intervene to regulate the system.

Figure 9:
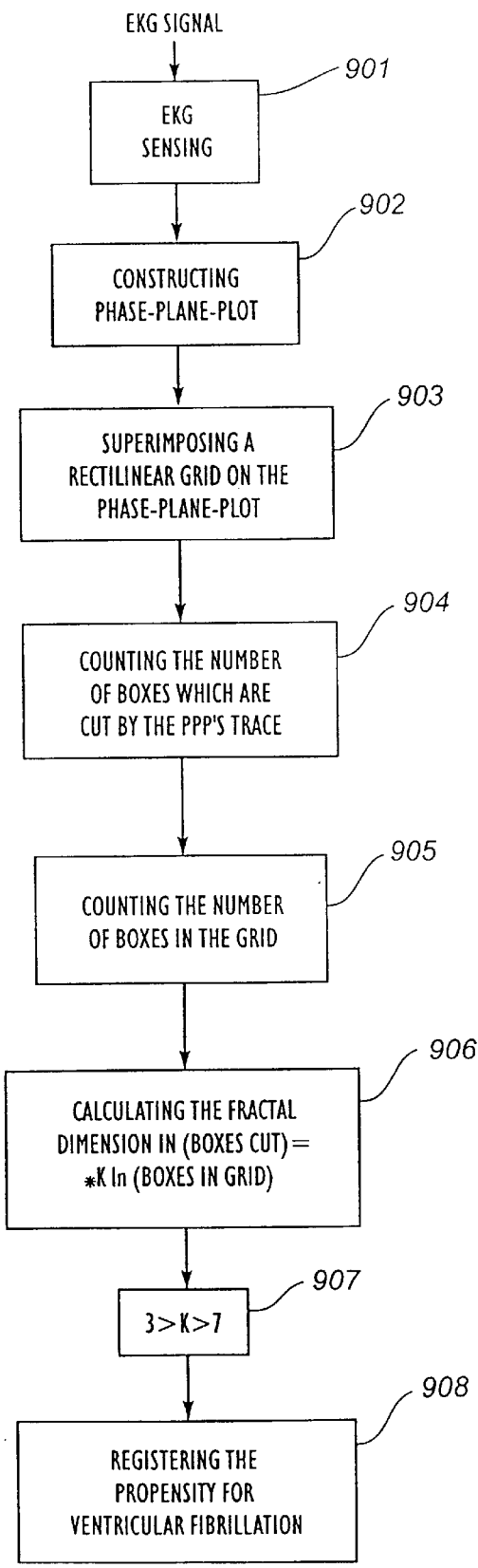
FIG. 9 shows a flow chart for a method of registering a propensity for fibrillation by calculating a fracted dimension using a box counting method.

Phase plane plots. The phase plane plot is a representation of the behavior of a dynamic system in state space (the abstract mathematical area in which a behavior occurs). It typically takes the form of a graph of the position of a signal (its amplitude) on the x-axis, versus the velocity of the signal (its first derivative) on the y-axis. Each cycle, called a trajectory or orbit, represents the behavior of the system over a given period of time[6,11,14,20]. Figure 8 illustrates the phase plane plot of a typical chaotic system and Figure 9 is a phase plane plot based on data obtained from the experiments in Figure 7. Graphs such as these were used widely for some time to assess left ventricular function[n]. Left ventricular wall tension was plotted on the x-axis against a function of its velocity of contraction on the y-axis. An indirect measure of contractility ($V_{max}$) was determined directly from this force-velocity phase plane plot.

The two dimensional phase plane plot is the most common representation of state space, but many others are possible. State space can also be represented in three dimensions, for example, with the axes representing the amplitude of the waveform, its first derivative (velocity), and its second derivative (acceleration). In some multi-dimensional systems, each axis serves to represent a different variable.

Phase plane plots of periodic signals have trajectories that overlap each other precisely (Figure 10B), while those of random signals exhibit no definite pattern (Figure 10J). In contrast, although phase plane plots of chaotic signals do not have periodic trajectories, they do exhibit a definite pattern (Figure 10F). As noted earlier, two particular patterns are highly specific for chaotic behavior. Bands, similar to those in the rings of the planet Saturn, represent groups of nearby non-overlapping trajectories, while forbidden zones represent the empty space between adjacent bands.

A major disadvantage of the phase plane plot is its sensitivity to noise. As little as 1% noise can severely disrupt the structure of a plot (by filling in forbidden zones, for example). Accordingly, the recording system and the data must be as noise free as possible. Although data can be filtered to remove some of this noise, such filtering can also mask identification of an underlying chaotic structure.

Return maps. The return map is similar to the phase plane plot, but the analyzed data must be discrete (digital), or, if not, must be converted to digital form[14,44]. Typically, the return map represents the relation between a given point in a time series plotted on the x-axis, and the next point in the time series plotted on the y-axis (a next-amplitude plot). The temporal difference between the two points is called the lag. The lag

76 acts to smooth away some of the noise in the data, making the return map less sensitive to noise than the phase plane plot. This is especially useful when the data cannot be filtered. Figure 10 illustrates examples of return maps for periodic, chaotic and random signals. These maps are similar to phase plane plots (compare Figures 10F and 10G) because the x-axes are identical (amplitude), while the y-axes are mathematically related (the y-axis of the return map is x + Δx/Δt, and the y-axis of the phase plane plot is dx/dt).

Shaw has used a common water faucet as an example of a chaotic system readily analyzed by construction of a return map[48,49]. Allow the faucet to drip into a container filled with water so that you can easily hear the intervals between drops. Start at a very low rate such that discrete drops fall at regular intervals. As you slowly increase the flow rate, you will note an abrupt change in the interval between the drops such that a long interval alternates with a short interval (the first bifurcation). If you continue to increase the rate of flow you will get to a point where the intervals between drops sound random. But if you plot the relation between one interval and a subsequent interval (a next-interval plot), a remarkably ordered pattern is obtained (Figure 11), indicating that the process is probably chaotic rather than random. With this simple graphic tool, the return map, a seemingly random pattern has been shown to have an underlying ordered structure.

A hypothetical example of the use of a return map was illustrated in the prologue of this report. The R-wave amplitude time series illustrated in Figure 1A is actually the output of the logistic map with k = 3.99, and the return map in Figure 1C reveals the underlying parabolic relation. In contrast, the systolic pressure time series illustrated in Figure 1B is really just a series of computer generated pseudorandom numbers, and the return map in Figure 1D confirms that there is no relation between one number and a neighbor. The return maps clearly distinguish between these chaotic and random signals. Application of this technique to the assessment of the susceptibility to ventricular fibrillation was recently awarded a United States Patent[50].

Poincaré sections. If a phase plane plot does not have a clearly discernable pattern, this ancillary graphical technique can help reveal one[1,14,38,54]. There are two kinds of Poincaré sections.

In the first[43,51,54], we cut a two dimensional phase plane plot by a line roughly perpendicular to the trajectories (Figure 12A). Points on that line represent where each trajectory crossed the line (Figure 12B). A graph is constructed from these points, representing the relation between adjacent trajectories (Figure 12C). Sometimes this graph reveals structure that is not apparent in the phase plane plot itself. As with the phase plane plot, this method too is sensitive to noise.

The second kind of Poincaré section[1,13] is best explained by analogy. Imagine a common house-fly in a large dark room containing only a dresser. Over time, the fly traces a continuous path through space (its plot of state space) as it moves about the room. If you were to take a stroboscopic picture of the fly's position at regular intervals you would generate a discrete pattern that represents where the fly has been. In addition, you would have also amassed information about where the fly has not been. Thus because the dresser takes up space in the center of the room, our graph of where the fly has been is also a graph of a forbidden zone representing the dresser. The existence and form of the dresser is thereby detected without ever detecting the dresser itself. Just as with our analogy, this kind of Poincaré section is obtained by sampling a conventional phase plane plot at regular intervals, and replotting the data as discrete points as an amplitude v.s. first derivative graph.

Lyapunov exponents. This numerical method[13,46,47] is used as an adjunct to the graphical analysis of state space. As noted earlier, chaotic systems characteristically exhibit sensitive dependence on initial conditions. In state space, sensitive dependence manifests itself graphically as adjacent trajectories that diverge widely from their initial close positions. The baker's transformation that was introduced as an example of sensitive dependence is also an example of exponential divergence: two raisins that are initially near each other move apart exponentially with each cycle of stretching and folding. The Lyapunov exponent is a quantitative measure of

77 this rate of separation. The magnitude of this exponent is related to how chaotic the system is; the larger the exponent, the more chaotic the system[97]. In three-dimensional systems, periodic signals have a Lyapunov exponent of zero; there is no divergence or convergence of trajectories because all trajectories overlap. A random signal will also have an exponent of zero because over a long period of time adjacent trajectories will converge and diverge equally. A positive Lyapunov exponent, on the other hand, indicates sensitive dependence on initial conditions and is -- almost without exception[97] -- diagnostic of chaos[1,98].

Lyapunov exponents are not easily measured[98]. The major limitation in their calculation is that currently available algorithms require large amounts of data (on the order of 1000-10,000 cycles). As a result, the computing time itself can be limiting (the processing of only a few thousand points by one member of our group took 27 hours on a fast personal computer). Even then, the system being studied must remain stable over the collection period, and real biological systems virtually never remain stable for any length of time. Clinical ventricular fibrillation serves as a good example. If one records the fibrillation over a short interval (1-2 seconds) there is probably little change in the underlying dynamics of the system, but this represents only 10-30 cycles of fibrillation -- not enough for accurate computation of the exponent. With longer recording periods, adequate data can be collected, but the myocardium becomes progressively ischemic during the collection period thereby changing the underlying dynamics of the system.

Fractal dimension. The word fractal, coined by Benoit Mandelbrot, refers to data sets that are self-similar at all scales[99]. Clouds are a common example; you cannot tell the distance to a large cloud because its overall form is the same at any distance, whether it be 10 miles, or 10 feet. Fractal patterns cannot be thought of in conventional topological terms of three dimensions (the volume of this journal), two dimensions (the plane of this page), one dimension (this line of text), or zero dimensions (the period at the end of this sentence). Consider a ball of twine[7,100]. At a distance of 100 yards the ball is nothing more than a point; one dimension. As you move closer, say 50 feet, it acquires characteristics of a plane -- its spherical shape cannot be appreciated, but it takes up more space than a point; it has two dimensions. Moving closer still, it acquires all the characteristics of a sphere; three dimensions. Moving inside the ball of twine, the strands seem to be three dimensional columns. On a still smaller scale, the individual threads of the strands are a maze of one-dimensional lines. As we magnify or shrink an object, our perception of the object's dimension will vary. A fractal has the same overall structure at all scales. The bifurcation diagram of the logistic map (Figure 4) is a fractal pattern. Though not obvious at first, if you were to magnify the area between k=3.5 and k=3.6, you would see a close replica of the overall diagram; this remarkable phenomenon occurs at any scale.

This is not just an idle abstraction; fractal dimension can be quantified in a meaningful way[7,99,101,102,103,104,105,106,107]. To do this, we observe the object (metaphorically) under many different magnifications; by varying our magnification, and measuring the amount of space the object occupies, we can determine its fractal dimension. Mandelbrot uses the coast of Britain as an example. If you use a meter stick to measure the length of the coastline, you come up with some distance for the total length; but if you use a millimeter stick, you will get a much larger distance. By continuously increasing the magnification (using a smaller stick) and measuring the length of the coastline, you will observe different lengths for each magnification. Over some range, however, there will be a series of magnifications for which the length of the coastline is essentially constant, and a plot of coastline length versus magnification will show a "plateau" area wherein small changes in magnification do not affect length. This plateau corresponds to the quantitative fractal dimension. The more irregular a figure, the more complex its structure, more space it occupies, and the higher its fractal dimension. The fractal dimension of the British coastline is approximately 1.3. It is not a perfect line (dimension = 1), but neither does it fill a plane (dimension = 2).

Computation of fractal dimension is presently something of an art, and the algorithms used for analysis of unknown signals are still evolving. The most common algorithm is that developed by Grassberger and Procaccia[104,105]. We use a particular modification of that algorithm[106], whereby dimension is estimated by the slope of the line showing the relation between the log of the magnification factor (measuring stick length) and

12 the log of the measured distance. As specific examples, the periodic signal in Figure 10 has a fractal dimension of 1.1, the chaotic signal has a dimension of 2.4, and the random signal has a dimension of 3.2 (Figure 13). Chaotic systems often exhibit low dimension because they are often simple systems, but periodic and random signals can also exhibit the same magnitude of dimension. For this reason, a diagnosis of chaos based solely on fractal dimension should be viewed with suspicion.

Spectral analysis. Spectral analysis is used as a diagnostic tool in the study of chaos because it is capable of distinguishing periodicity from the aperiodicity of randomness and chaos. There are many methods of spectral analysis, the fast Fourier transform (FFT) being the most common[38,108,119]. Spectral analysis takes a continuous signal, breaks it into component frequencies, and displays the contribution of each frequency to the total signal. A pure sine wave of 8 Hz will have an isolated spike at 8 Hz (Figure 10D), while a modulated sine wave (one that varies in a periodic manner) will have more than one spike. Spectral patterns have been classified arbitrarily into discrete (or narrow-band) and continuous (or broad-band). A discrete spectrum (characteristic of periodic and some chaotic signals) contains one or more narrow spikes. The higher frequency spikes (the harmonics) are exact multiples of some lower frequency spike (the fundamental). A continuous spectrum (characteristic of random and some chaotic signals) exhibits curves that enclose a large number of frequencies bearing no numerical relation to each other. Often the distinction between a discrete and a continuous spectrum is qualitative rather than quantitative. Figure 10L illustrates the continuous frequency spectrum of a typical random signal.

Spectral analysis is insensitive to noise, but its application is limited to determining the presence or absence of periodic signals. It cannot distinguish between random, chaotic or periodic signals[18,111], although it has been used to detect bifurcations which manifest as new harmonics[9]. Although spectral analysis alone cannot distinguish a chaotic process, some investigators believe that a particular spectral pattern (one in which the power density is inversely related to the frequency) is highly suggestive of a nonlinear or chaotic process[67,74,75,81,112,113]. Others, however, question the diagnostic value of this so-called 1/f pattern[114].

Integrated Analysis. Table I integrates the various graphical and numerical methods of analysis into a coherent structure that demonstrates their relative ability to detect the characteristics of chaos in an unknown signal. Because no single method is sufficient to detect all the characteristics reliably, an investigator should use combinations of these methods[48,115,116]. Table II demonstrates the expected results of each of the tests on periodic, chaotic and random signals. The graphical demonstration of banding, forbidden zones, and sensitive dependence on initial conditions is highly suggestive of a chaotic process. Currently the numerical methods are all subordinate to the graphical methods, but if a reliable and rapid technique for the calculation of the Lyapunov exponent were to be developed, it would most likely be the only tool needed for the study of a stable system.

Future Implications

Only two decades have passed since Aristotle's prophetic description of chaos ("*The least initial deviation from the truth is multiplied later a thousandfold*") was recast with mathematical rigor. This "new math" has already helped explain a number of heretofore puzzling phenomena in the physical sciences, and its application to biology is likely to be similarly rewarding.

Applications of nonlinear dynamics to cardiology have become common over the last few years, and a broad range of subjects are being studied by many groups. Computer models of excitable tissue have demonstrated their utility in better understanding basic cardiac physiology[117,118,119]. An explanation for irregular action potential dynamics seen when Purkinje fibers are repetitively stimulated may be forthcoming[19]. Mechanisms of phase-locking, and chaotic ionic mechanisms in the cell membrane are also being investigated[120,121]. More direct clinical applications are being studied in the patterns of conduction through the AV node[44-48], mechanisms of parasystole[116], the nature of ventricular fibrillation, and whether chaos is normal or abnormal in physiology[121,122]. There is some evidence that the termination of reentry may be chaotic[122]. Also of interest is the fractal nature of blood flow through the coronary tree, which may give new insight into coronary flow dynamics and ischemia[123]. An interesting application of sensitive dependence on initial conditions, analogous to Lorenz' statement regarding the unpredictability of the weather, has been made regarding clinical prediction models[124] whereby outcome can never be reliably predicted because of initial uncertainties in a patient's condition.

Summary

Nonlinear dynamics is an exciting new way of looking at peculiarities that in the past have been ignored or explained away. We have attempted to give a general introduction to the basics of the mathematics, applications to cardiology, and a brief review of the new tools needed to use the concepts of nonlinear mathematics. The careful mathematical approach to problems in cardiac electrical dynamics and blood flow is opening a window on behaviors and mechanisms previously inaccessible.

References

1. Glass L, Mackey MC: From Clocks to Chaos: The Rhythms of Life, New Jersey, Princeton University Press, 1988.
2. Lorenz EN: Deterministic nonperiodic flow. J Atmospheric Sci 1963;20:130-141
3. Jensen RV: Classical Chaos. Amer Sci 1987;75:168-181
4. Olsen LF, Degn H: Chaos in biological systems. Q Rev Biophysics 1985;18:165-225
5. Holden AV. Chaos, New Jersey, Princeton University Press, 1986
6. Moon FC: Chaotic Vibrations, New York, John Wiley and Sons, 1987
7. Gleick J: Chaos: Making a New Science, New York, New York, 1987.
8. Stewart I: Does God play dice? The mathematics of chaos. Basil Blackwell Ltd., New York, 1989
9. Hofstadter DR: Metamagical Themas. Sci Amer 1981;245:22-43
10. Crutchfield JP, Farmer JD, Packard NH, Shaw RS: Chaos. Scientific American 1986;255:46-57
11. Kloeden PE, Mees AI: Chaotic phenomena. Bull Math Biol 1985;47:697-738
12. Grebogi C, Ott E, Yorke JA: Chaos, strange attractors, and fractal basin boundaries in nonlinear dynamics. Science 1987;238:632-638
13. Thompson JMT, Stewart HB: Nonlinear Dynamics and Chaos, New York, John Wiley and Sons, New York, 1986
14. Bergé P, Pomeau Y, Vidal C: Order within Chaos, New York, John Wiley and Sons, 1984.
15. Winfree, AT: When Time Breaks Down: The Three-Dimensional Dynamics of Electrochemical Waves and Cardiac Arrhythmias. New Jersey, Princeton University Press, 1987
16. Epstein IR: Oscillations and chaos in chemical systems. Physica D 1983;7:47-56
17. Roux JC: Experimental studies of bifurcations leading to chaos in the Belousof-Zhabotinsky reaction. Physica D 1983;7:57-68
18. Kaplan JL, Yorke JA: The onset of chaos in a fluid flow model of Lorenz. Ann NY Acad Sci 1979;316:400-407
19. Sussman GJ, Wisdom J: Numerical evidence that the motion of pluto is chaotic. Science 1988;241:433-437
20. Kurths J, Herzel H: An attractor in a solar time series. Physica D 1987;25:165-172
21. Spiegel EA, Wolf A: Chaos and the solar cycle. Ann NY Acad Sci 1987;497:55-60
22. Pool R: Seeing chaos in a simple system. Science 1988;241:787-788
23. Pool, R: Is something strange about the weather? Science 1989;243:1290-1293
24. Rothrock DA, Thorndike AS. Geometric properties of the underside of sea ice. J Geophys Res 1980;85:3955-3963
25. Pool, R: Is it chaos, or is it just noise? Science 1989;243:25-28
26. May RM: Biological populations with nonoverlapping generations: Stable points, stable cycles, and chaos. Science 1974;186:645-647
27. Pool, R: Ecologists flirt with chaos. Science 1989;243:310-313
28. Arneodo A, Coullet P, Peyraud J, Tresser C: Strange attractors in Volterra equations for species in competition. J Math Biol 1982;14:153-157
29. Rogers TD, Yang ZC, Yip LW: Complete chaos in a simple epidemiological model. J Math Biol 1986;23:263-268
30. May RM: Nonlinear phenomena in ecology and epidemiology. Ann NY Acad Sci 1980;357:267-281
31. Decker P: Spatial, chiral, and temporal self-organization through bifurcation in "Bioids", open systems capable of a generalized Darwinian evolution. Ann NY Acad Sci 1979;316:236-250
32. Kearney RE, Hunter IW: Nonlinear identification of stretch reflex dynamics. Ann Biomed Eng 1988;16:79-94

33. Goldberger AL, Shabetai R, Bhargava V, West BJ, Mandell AJ: Nonlinear dynamics electrical alternans and pericardial tamponade. Am Heart J 1984;107:1297-1299
34. Goldberger AL, Findley LJ, Blackburn MR, Mandell AJ: Nonlinear dynamics in heart failure: Implications of long-wavelength cardiopulmonary oscillations. Am Heart J 1984;107:612-615
35. Glass L, Mackey MC: Pathological conditions resulting from instabilities in physiological control systems. Ann NY Acad Sci 1979;316:214-235
36. Mackey MC, Glass L: Oscillation and chaos in physiological control systems. Science 1977;197:287-289
37. Pyeritz RE, Murphy EA: Genetics and congenital heart disease: Perspectives and prospects. JACC 1989;13:1458-1468
38. Meinhardt H. The random character of bifurcations and the reproducible processes of embryonic development. Ann NY Acad Sci 1979;316:188-202
39. Saperstein AM: Chaos - A model for the outbreak of war. Nature 1984;309:303-305
40. Sporns O, Roth S, Seelig F: Chaotic dynamics of two coupled biochemical oscillators. Physica D 1987;26:215-224
41. Decroly O, Goldbeter A: Birhythmicity, chaos and other patterns of temporal self-organization in a multiply regulated biochemical system. Proc Nat Acad Sci 1982;79:6917-6921
42. Decroly O, Goldbeter A. Selection between multiple periodic regimes in a biochemical system: Complex dynamic behavior resolved by use of one-dimensional maps. J Theor Biol 1985;113:649-671
43. Babloyantz A, Destexhe A: Low-dimensional chaos in an instance of epilepsy. Proc Natl Acad Sci USA 1986;83:3513-3517
44. Watt RC, Hameroff SR: Phase space electroencephalography (EEG): A new mode of intraoperative EEG analysis. Int J Clin Monit Comput 1988;5:3-13
45. Watt RC, Hameroff SR: Phase space analysis of human EEG during general anesthesia. Ann NY Acad Sci 1987;504:286-288
46. Mayer-Kress G, Layne SP: Dimensionality of the human electroencephalogram. Ann NY Acad Sci 1987;504:62-87
47. May RM: Simple mathematical models with very complicated dynamics. Nature 1976;261:459-467
48. Feigenbaum MJ: Universal behavior in nonlinear systems. Physica D 1983;7:16-39
49. Feigenbaum MJ: Universal behavior in nonlinear systems. Los Alamos Science 1980;1:4-27
50. Swinney HL: Observations of order and chaos in nonlinear systems. Physica D 1983;7:3-15
51. Procaccia I: Universal properties of dynamically complex systems: the organization of chaos. Nature 1988;333:618-623
52. Heppenheimer TA: Routes to Chaos. Mosaic 1986;17:3-13
53. Eckmann JP: Roads to turbulence in dissipative dynamic systems. Rev Mod Phys 1981;53:643-654
54. Wolf A: Simplicity and universality in the transition to chaos. Nature 1983;305:182-183
55. Manneville P, Pomeau Y: Different ways to turbulence in dissipative dynamic systems. Physica D 1980;1:219-226
56. Beloshapkin VV, Chernikov AA, Natenzon MY, Petrovichev BA, Sagdeev RZ, Zaslavsky GM: Chaotic streamlines in pre-turbulent states. Nature 1989;337:133-137
57. Devaney RL: Chaotic bursts in nonlinear dynamical systems. Science 1987;235:342-344
58. Ruelle D: Strange attractors. Math Intelligencer 1980;2:126-137
59. Ruelle D: Sensitive dependence on initial condition and turbulent behavior of dynamical systems. Ann NY Acad Sci 1979;316:408-416
60. Grassberger P, Procaccia I: Dimensions and entropies of strange attractors from a fluctuating dynamics approach. Physica D 1984;13:34-54
61. Guevara MR, Glass L, Shrier A: Phase locking, period-doubling bifurcations, and irregular dynamics in periodically stimulated cardiac cells. Science 1981;214:1350-1354
62. Glass L, Guevara MR, Shrier A: Bifurcation and chaos in a periodically stimulated cardiac oscillator. Physica D 1983;7:89-101
63. Guevara MR, Shrier A, Glass L. Phase-locked rhythms in periodically stimulated heart cell aggregates. Am J Physiol 1988;254:H1-H10
64. Glass L: Complex cardiac rhythms. Nature 1987;330:695-696
65. West BJ, Goldberger AL, Rovner G, Bhargava V: Nonlinear dynamics of the heartbeat: I. The AV junction: Passive conduit or active oscillator?. Physica D 1985;17:198-206
66. Glass L, Goldberger AL, Courtemanche M, Shrier A: Nonlinear dynamics, chaos and complex cardiac arrhythmias. Proc Royal Soc Lond A 1987;413:9-26
67. Goldberger AL, West BJ: Applications of nonlinear dynamics to clinical cardiology. Ann NY Acad Sci 1987;504:195-213
68. Glass L, Guevara MR, Shrier A: Universal bifurcations and the classification of cardiac arrhythmias. Ann NY Acad Sci 1987;504:168-178
69. Chialvo DR, Jalife J: Nonlinear dynamics of cardiac excitation and impulse propagation. Nature 1987;330:749-752
70. Ritzenberg AL, Adam DR, Cohen RJ: Period multupling - evidence for nonlinear behavior of the canine heart. Nature 1984;307:159-161
71. Adam DR, Smith JM, Akselrod S, Nyberg S, Powell AO, Cohen RJ. Fluctuations in T-wave morphology and susceptibility to ventricular fibrillation. J Electrocardiology 1984;17(3):209-218
72. Smith JM, Clancy EA, Valeri CR, Ruskin JN, Cohen RJ: Electrical alternans and cardiac electrical instability. Circulation 1988;77:110-121
73. Ritzenberg AL, Smith JM, Grumbach MP, Cohen RJ: Precursor to fibrillation in cardiac computer model. Computers in Cardiology 1984;171-174
74. Goldberger AL, West BJ: Chaos in Physiology: Health or Disease?, in Degn H, Holden AV, Olsen LF (eds): Chaos in Biological Systems. New York, Plenum Pub Corp, 1987, pp 1-4
75. Goldberger AL, Rigney DR: Sudden death is not chaos, in Kelso JAS, Mandell AJ (eds): Dynamic Patterns in Complex Systems. Singapore, World Scientific Pub, 1988, pp 248-264
76. Goldberger AL, Bhargava V, West BJ, Mandell AJ: Some observations on the question: Is ventricular fibrillation "chaos"?. Physica D 1986;19:282-289
77. Chen PS, Wolf PD, Dixon EG, Danieley ND, Frazier DW, Smith WM, Ideker RE: Mechanism of ventricular vulnerability to single premature stimuli in open-chest dogs. Circ Res 1988;62:1191-1209
78. El-Sherif N: The figure 8 model of reentrant excitation in the canine post-infarction heart, in Zipes DP and Jalife J (eds): Cardiac Electrophysiology and Arrhythmias New York, Grune and Stratton, 1985, pp 363-378
79. Garfinkel A, Karagueuzian H, Khan S, Diamond G: Is the proarrhythmic effect of quinidine a chaotic phenomenon? JACC 1989;13:186A
80. Evans SJ, Khan SS, Garfinkle A, Kass RM, Albano A, Diamond GA. Is ventricular fibrillation random or chaotic? Circulation 1989;80:II-134
81. Goldberger AL, Rigney DR, Mietus J, Antman EM, Greenwald S: Nonlinear dynamics in sudden cardiac death syndrome: heartrate oscillations and bifurcations. Experientia 1987;44:983-987
82. Goldberger AL, Bhargava V, West BJ, Mandell AJ: Nonlinear dynamics of the heartbeat II. Subharmonic bifurcations of the cardiac interbeat interval in sinus node disease. Physica D 1985;17:207-214

83. Myers GA, Martin GJ, Magid NM, Barnett PS, Schaad JW, Weiss JS, Lesch M, Singer DH: Power spectral analysis of heart rate variability in sudden cardiac death: Comparison to other methods. IEEE Trans Biomed Eng BME 1986;33:1149-1156
84. Shrier A, Dubarsky H, Rosengarten M, Guevara M, Nattel S, Glass L: Prediction of complex atrioventricular conduction rhythms in humans with use of the atrioventricular nodal recovery curve. Circulation 1987;76:1196-1205
85. Winfree AT: Sudden cardiac death: a problem in topology. Scientific American 1983;248:144-161
86. Winfree AT: Electrical instability in cardiac muscle: Phase singularities and rotors. J Theor Biol 1989;138:353-405
87. Frazier DW, Wolf PD, Wharton JM, Tang ASL, Smith WM, Ideker RE: Stimulus-induced critical point - Mechanism for electrical initiation of reentry in normal canine myocardium. J Clin Invest 1989;83:1039-1052
88. Shibata N, Peng-Sheng C, Dixon EG, Wolf PD, Danieley ND, Smith WM, Ideker RE: Influence of shock strength and timing on induction of ventricular arrhythmias in dogs. Am J Physiol 1988;255:H891-H901
89. Redwood DR, Borer JS, Epstein SE. Whither the ST segment during exercise? Circulation 1976;5:703-706
90. Pinsker HM, Bell J: Phase plane description of endogenous neuronal oscillators in aplysia. Biol Cybern 1981;39:211-221
91. Braunwald E, Ross J, Sonnenblick EH: Mechanisms of contraction of the normal and failing heart. N Engl J Med 1967;277:794-800, 853-863, 910-920, 962-971, 1012-1022 (four parts)
92. Shaw R: The Dripping Faucet as a Model Chaotic System. Ariel Press, Santa Cruz, California, 1984
93. Kaplan DT, Cohen RJ: Method and apparatus for quantifying beat-to-beat variability in physiologic waveforms. United States Patent Number 4,732,157, Issued March 22, 1988.
94. Eckmann JP, Ruelle D: Ergodic theory of chaos and strange attractors. Rev Mod Physics 1985;57:617-656
95. Grassberger P, Procaccia I: Measuring the strangeness of strange attractors. Physica D 1983;9:189-208
96. Benettin G, Galgani L, Giorgilli A, Strelcyn JM: Lyapunov characteristic exponents for smooth dynamical systems and for Hamiltonian systems; A method for computing all of them. Part 2: Numerical application. Meccanica 1980;15:21-30
97. Wolf A, Swift JB, Swinney HL, Vastano JA: Determining Lyapunov exponents from a time series. Physica D 1985;16:285-317
98. Grebogi C, Ott E, Pelikan S, Yorke JA: Strange attractors that are not chaotic. Physica D 1984;13:261-268
99. Mandelbrot BB: Discussion Paper: Fractals, attractors, and the fractal dimension. Ann NY Acad Sci 1979;316:463-464
100. Mandelbrot, B: The Fractal Geometry of Nature, New York, W.H. Freeman, 1983
101. Packard NH, Crutchfield JP, Farmer JD, Shaw RS: Geometry from a time series. Phys Rev Lett 1980;45:712-716
102. Havstad JW, Ehlers CL: Attractor dimension of nonstationary dynamical systems from small data sets. Phys Rev A 1989;39:845-853
103. Farmer JD, Ott E, Yorke JA: The dimension of chaotic attractors. Physica D 1983;7:153-180
104. Grassberger P, Procaccia I: Characterization of strange attractors. Physical Rev Letters 1983;50:346-349
105. Grassberger P, Procaccia I: Estimation of the Kolmogorov entropy from a chaotic signal. Phys Rev A 1983;28:2591-2593
106. Froehling H, Crutchfield JP, Farmer D, Packard NH, Shaw R: On determining the dimension of chaotic flows. Physica D 1981;3:605-617
107. Geisel T: Chaos, randomness and dimension. Nature 1982;298:322-323
108. Albano AM, Mees AI, deGuzman GS, Rapp PE: Data requirements for reliable estimation of correlation dimensions. In Holden AV (ed), Chaotic Biological Systems, New York, Pergamon Press, 1987
109. McGillem CD, Cooper GR: Continuous and Discrete Signal and System Analysis. New York, Holt, Rinehart and Winston, 1974
110. Ramirez RW: The FFT : Fundamentals and concepts. New Jersey, Prentice-Hall, 1985
111. Farmer D, Crutchfield J, Froehling H, Packard N, Shaw R: Power spectra and mixing properties of strange attractors. Annals NY Acad Sci 1980; 357:453-472
112. Goldberger AL, Bhargava V, West BJ, Mandell AJ: On a mechanism of cardiac electrical stability, the fractal hypothesis. Biophysical Journal 1985; 48:525-528
113. Goldberger AL, West BJ: Fractals in physiology and medicine. Yale J Biol Med 1987;60:421-435
114. Pool R: Is it healthy to be chaotic? Science 1989;243:604-607
115. Babloyantz A, Destexhe A: Is the normal heart a periodic oscillator? Biol Cybern 1988;58:203-211
116. Holden AV: Chaos in complicated systems. Nature 1983;305:183
117. Michaels DC, Chialvo DR, Matyas EP, Jalife J. Chaotic activity in a mathematical model of the vagally driven sinoatrial node. Circ Res 1989;65:1350-1360
118. Courtemanche M, Glass L, Rosengarten MD, Goldberger AL. Beyond pure parasystole: Promises and problems in modelling complex arrhythmias. Am J Physiol 1989;257:H693-H706
119. Chialvo DR, Michaels DC, Jalife J. Supernormal excitability as a mechanism of chaotic dynamics of activation in cardiac purkinje fibers. Circ Res 1989;66 (in press, for publication Feb 1990)
120. "Mathematical Approaches to Cardiac Arrhythmias", Workshop sponsored by the New York Academy of Sciences, November 1989.
121. "Is Cardiac Chaos Normal or Abnormal". Postgraduate Seminar, American Heart Association, 62nd Scientific Sessions, November, 1989, Chairman - MF Arnsdorf
122. Frame LH, Rhee EK. Chaotic cycle length oscillation and bifurcation during reentry. Circulation (Abstr) 1989;80:II-96
123. Bassingthwaighte JB, King RB, Roger SA. Fractal nature of regional myocardial blood flow heterogeneity. Circ Res 1989;65:578-590
124. Diamond GA. Future imperfect: The limitations of clinical prediction models and the limits of clinical prediction. J Am Coll Cardiol 1989;14:12A-22A
125. Gomes MAF. Fractal geometry in crumpled paper balls. Am J Physics 1987;55(7):649-650
126. Saaty TL, Bram J: Nonlinear Mathematics. Dover Publications, New York, 1964

Glossary

Aperiodic[67,74] - Irregular behavior that has no definite period. Aperiodic behavior is either random or chaotic. One exception is quasiperiodic behavior which is often considered a subset of periodic.

Attractor[44,114] - A geometric figure (or mathematical abstraction) in state space to which all trajectories in its vicinity (basin) are drawn. There are four types of attractors; point, limit cycle, toroidal and strange. A point attractor will draw all trajectories to a single point, like a pendulum spiraling to rest. A limit cycle is characteristic of periodic motion and a toroid represents quasiperiodic motion. A strange attractor is associated with chaotic motion.

The word attractor is classically associated with the solutions of differential equations (perfect mathematical models), but it has also been used to describe the behavior of unknown signals from physical or biological systems. Though its use in that regard is technically inaccurate, it persists in the literature.

Autocorrelation[110] - A measure of how closely a signal (time series) resembles a time-delayed image of itself. Periodic signals are highly autocorrelated whereas random signals are not.

Banding - Refers to bands of trajectories seen in plots of state space, inscribing zones that are not visited by the trajectories. These are analogous to the "swirls" seen in turbulent fluid. The presence of banding in state space is suggestive of chaotic behavior.

Bifurcation[67,44,9] - A point in which there is an abrupt change in behavior of a dynamic system which occurs when one of the parameters reaches a critical value.

Bifurcation diagram[144,74] - A graph that demonstrates the relation between the values of one parameter and the behavior of a system. An example is the bifurcation diagram for the logistic map where the x-axis represented all the values of k and the y-axis was all possible states of the system.

Bounded - A system's behavior is bounded if all of the behavior is in a limited region of state space. A bounded signal will not have any behavior that approaches infinity. "Constrained" is often used as a synonym for boundedness.

Broad-band spectrum - see Continuous spectrum.

Chaos - An aperiodic, seemingly random behavior in a deterministic system which exhibits sensitive dependence on initial conditions.

Continuous data[49] - In general terms, a time series that is continuous is "smooth" visually. From a mathematical viewpoint, if each point in the time series has only one derivative the time series is continuous. An alternate mathematical definition is that if the derivatives on both sides of all points are equal, then the series is continuous.

Continuous spectrum - A spectral pattern that includes a large number of frequencies with no numerical relation to one another. Also called broad-band; in contrast to discrete spectrum.

Deterministic - A system is deterministic if its behavior is governed by known equations and initial conditions, and is therefore predictable at any past or future time. A dynamical system is deterministic if its evolution is completely determined by its current state and past history. There is no stochastic (random) component in a deterministic system.

Difference equation[144,44,49] - An equation that is solved by successive iterations, using the solution of the equation at one time as an initial condition for the next solution: of the form $x(t+1) = f(x(t))$. The logistic map is an example.

Differential equation - An equation or series of coupled equations that contain(s) the derivative of one of the variables.

Dimension[68,108-110] - A measure of the amount of space an object occupies. There are only four topological dimensions (point, line, surface, volume). A fractal dimension is also a measure of the "space" an object occupies, but is measured by looking at the object at different scales. The fractal dimension can be integer or non-integer and may be greater than three. Fractal dimension is also a measure a system's complexity; the more complex, the higher the dimension.

Discretely sampled data[10] - Data collected at defined intervals in time, not continuously. Digitized data are discretely sampled, whereas analog data are continuous because a value is defined at any point in time.

Discrete spectrum - A spectral pattern that consists of a series of isolated spikes, often integer multiples of a fundamental frequency (harmonics). A discrete spectrum is sometimes referred to as narrow-band; in contrast to continuous spectrum.

Dynamic(al) system - Any system in which the state changes with time.

Exponential divergence[47,86,87] - A property of the trajectories in state space where nearby points on adjacent trajectories diverge from each other at an exponential rate.

Fast Fourier Transform (FFT)[110] - A specific method of calculating the frequency spectrum of a signal. See spectral analysis.

Forbidden zones - Areas in a graphic representation of state space that are never visited by the trajectories of the system. These are one of the two components of the "swirls" seen in turbulent systems.

Fractal[108,109] - An object that has detailed structure at many scales. A perfect cylinder has only one structure no matter how much you reduce or magnify it. A coastline as seen from space has an irregular structure. By magnifying the coastline (changing the scale of reference), one can see the irregularity of small inlets and sand bars. Another change in scale reveals logs and boulders that make the coastline rough. Further magnification reveals the jaggedness of grains of sand. Thus, at many different scales, a coastline is "rough", and therefore fractal. The term self-similarity is also used in this setting, in that at many scales, the coastline looks like itself, rough and jagged.

Fractal dimension[68,108] - Represents the way a set of points fills a given area of space. Defined as the slope of the function relating the number of points contained in a given radius ("magnification") to the radius itself. The operative dimensionality of a trajectory is defined by the flat region of the slope-radius plot.

Harmonic[10] - A frequency obtained by multiplying a fundamental frequency by an integer greater than zero.

Iteration[46] - A process in which the solution to an equation is fed back into the original equation as a new initial condition.

Lag - A difference in time between one point and another. For example, a return map (also called a lag plot) plots the relation between one point in a time series and a subsequent point. The difference in time between the two points is called the lag. The choice of the lag is somewhat arbitrary, and is based on optimizing the amount of information in the graph.

Linear equation[125] - An equation that meets both the following criteria:
$$F(x+y) = F(x) + F(y)$$
$$F(kx) = kF(x)$$
$2^2 + 3^2 \neq (2 + 3)^2$, and $\log(2x) \neq 2\log(x)$ are examples that do not meet the above criteria and are therefore nonlinear equations.

Linear divergence - A property of the trajectories in state space where adjacent trajectories diverge from each other at a linear rate.

Linear system[125] - A system in which the relation between input and output varies in a constant (linear) fashion. For example, if a system has a constantly increasing input, and the output increases proportionately (though perhaps at a different magnitude), the system is linear.

Logistic map[X,4,6] - A simple nonlinear (quadratic) equation, that with special initial conditions and parameters, exhibits chaotic behavior. It is the simplest and archetypical chaotic system. The mathematical form is as follows:
$$x_{n+1} = k \bullet x_n \bullet (1 - x_n)$$
This equation states that the behavior of the system $(x_{n+1})$ is a function of the initial value $(x_n$ between 0 and 1) and some parameter k (ranging between 0 and 4). From a technical standpoint, chaos occurs in this particular system when the slope of the descending arm of the parabola - as it crosses the line of identity - is less than -1. At this point, the nonlinear term in the equation is dominant.

Lorenz equations[L,4,4] - A series of three differential equations derived from a more complex system used in the study of fluid dynamics. The Lorenz system was used to study weather patterns, and ultimately lead to the discovery of sensitive dependence on initial conditions and chaos.

Lyapunov exponent[L,X,7] - A measure of the exponential divergence of a system named after the Russian mathematician Alexander Lyapunov (1857-1918). In multidimensional systems ($\geq 3$), an exponent of 0 indicates periodic or random systems (no net divergence of trajectories), and a positive exponent indicates a chaotic system (exponential divergence).

Mandelbrot set[125] - A simple series of two equations (containing real and imaginary components) that, when iterated and plotted on a two dimensional graph, depict an extremely complex and classic fractal pattern.

Narrow band spectrum - see Discrete spectrum.

Nonlinear equation[125] - Any equation that does not meet the criteria for linearity (see linear equation). The logistic map contains a linear (kx) and a nonlinear (kx²) portion, but it is a nonlinear equation because a portion of it is nonlinear.

Nonlinear system[125] - Any system in which the output is disproportionate to the input. An example would be a system that has a linear input, but an output that is sinusoidal.

Nonlinear dynamics - The study of nonlinear systems whose state changes with time.

Period-doubling[L,4,4] - A system that originally had X periodic states, and now, in response to a parameter change, has 2X periodic states, is said to have undergone period doubling; one form of bifurcation.

Periodic behavior (periodicity) - Behavior of a system in which the output repeats itself exactly over a given time interval (the "period").

22

Phase locking[l,ll,ss] - The behavior of a system in which a given number of input stimuli always generate a given number of output responses - the behavior of the system is "locked" to the input stimulus. For example, a system that is stimulated at one cycle per second and responds at one cycle per second has 1:1 phase locking. If there are three responses for each four stimuli there is 4:3 phase locking. A synonym is entrainment.

Phase plane plot[ss,ll,ll] - A graph of state space that has for its axes various combinations of the states of the system. May consist of the first, second, third or $n^{th}$ derivative of the system. Each axis may also represent a different variable of the system.

Poincaré section[ll] - Two techniques using plots of state space that allow closer scrutiny of the trajectories and their relation to each other. A lagged section plots points on the phase plane plot at defined intervals (lag). A cross section characterizes the relation between trajectories as they cross some region of interest.

Prechaotic behavior - Predictable behavior of a system before the onset of chaos. Period-doubling is one of them.

Quasiperiodic[c] - A behavior that consists of at least two frequencies in which the phases are related by an irrational number. An example would be the sum of two sine waves in which the phases are related by the square root of a prime number.

Random behavior[ss] - Behavior that can never be predicted, and can only be described by summary statistics such as the mean and standard deviation. Technically, a behavior can never be reliably described as random - only organized (deterministic) behavior can be excluded.

Return map[l,ll,ll] - A graphic technique that represents the relation between a point and any subsequent point in a time series. A lag 1 return map is a plot of an initial value on one axis and the succeeding value on the other axis. A lag 5 return map is a plot of the initial value on one axis and the $5^{th}$ succeeding value on the other axis.

Sensitive dependence on initial conditions[ll,ll,ss] - A property of chaotic systems whereby small changes in the state variables in a system at one point will make large differences in the behavior of the system at some future point.

Spectral analysis[ss,ll] - A technique that breaks a signal up into its fundamental frequencies. The Fourier transform is the most common form of spectral analysis.

State space - That area of the universe of behavior that contains the range of values for the behavior of a particular system.

Stochastic - Random from a mathematical (statistical) point of view.

Subharmonic[s] - A frequency obtained by dividing a fundamental frequency by an integer greater than zero.

Time series - A series of numbers, each representative of the behavior of a system at particular points in time.

Trajectory - The representation of the behavior of a system in state space over a short period of time; one cycle on a phase plane plot.

89

Figure Legends

Figure 1. (A) Hypothetical beat-to-beat QRS voltage (mV) as a function of time (200 cycles). (B) Hypothetical simultaneous beat-to-beat peak systolic blood pressure (mmHg) as a function of time. (C) QRS voltage of each beat (n) on the x-axis versus QRS voltage of the subsequent beat (n+1) on the y axis based on the data in panel A. (D) Peak systolic blood pressure of each beat (n) on the x-axis versus peak systolic blood pressure of the subsequent beat (n+1) on the y-axis based on the data in panel B.

Figure 2. (A) A typical linear function. For every value of Y, there is a unique value of X. (B) A typical nonlinear function. In this example, for any single value of Y (except its maximum) there are two possible values of X.

Figure 3. Iterative solutions of the logistic map. (A) When $k = 2.5$ the output of the system (y) exhibits a single state after a brief initial period of oscillation. (B) When $k=3.2$ the system alternates between two states. (C) When $k=3.5$ the system has four states. (D) When $k=4$, the system has an infinite number of states.

Figure 4. Bifurcation diagram for the logistic map. The x-axis represents values of the parameter k from 1 to 4, and the y-axis represents 100 iterated values of the variable x at each fixed value of k. Starting with $k=1$, the system has only one state (Figure 3A). At $k=3.0$ a bifurcation occurs and the system now has two states (as in Figure 3B). At $k=3.45$ another bifurcation occurs and the system now has four states (as in Figure 3C). At $k>3.57$ the system develops an infinite number of states (chaos). The letters in the diagram correspond to the four behaviors seen in Figure 3.

Figure 5. Geometric solution to the logistic map. Panel A demonstrates a periodic solution with values oscillating between a and b. Panel B is a chaotic solution, with the values (a through g) falling on irregular points of the parabola. See text for explanation of the solution technique.

Figure 6. Sensitive dependence on initial conditions. The solid line represents iterations of the logistic map ($k=3.99$) with initial $x=0.5$, and the dotted line represents the same number of iterations with initial $x=0.5000001$. The two signals are exactly the same until the $35^{th}$ cycle (point A) when they diverge. By the 42nd cycle (Point B) the peaks and nadirs are completely out of phase.

Figure 7. (A) Proximal and distal chamber action potential recordings of unstressed and stressed Purkinje fibers. The left sigmoid curve of each pair represents a depolarization in the proximal chamber and the right curve is the depolarization in the distal chamber. The time between the two curves is the conduction time between the chambers (latency). In the top series (no stress) all four depolarizations have the same conduction time. In the bottom series (stressed by compression) they oscillate; a long conduction time alternates with a short conduction time (shading). (B) A bifurcation diagram of the same system. The x-axis is the frequency of stimulation (the stress to the system) and the y-axis represents the latency (the difference in conduction time between proximal and distal chambers). There is a constant variance in latency (just as in the logistic map bifurcation diagram) until the system is stimulated at 325 beats per minute (arrow). At higher frequencies chaos occurs (compare this to Figure 4) and the variance in latency increases. Reprinted and modified by permission from Nature, Vol. 330, pp. 751 Copyright (c) 1987 Macmillan Magazines Limited.

Figure 8. (A) Portion of a typical chaotic signal (Duffing's equation). The x-axis is time (in arbitrary units) and the y-axis is amplitude (unitless). (B) The phase plane plot of the same chaotic signal. The x-axis is amplitude and the y-axis is the first derivative of the amplitude (the center of each axis is zero). The signal starts high and becomes slightly more positive for a short period of time. On the phase plane plot this is represented by starting at point a, moving slightly rightward (higher amplitude) and down (toward a derivative of zero). Point b represents an area of positive amplitude but of zero derivative. Point c represents a point in which the amplitude and the derivative are approaching zero. Point d has a slightly negative amplitude and

24 a derivative near zero. Point e is the minimum with a derivative of zero. Point f is a small loop that represents a smaller sub-oscillation. The signal now returns toward another peak value (positive amplitude and maximally positive derivative), and the phase plane plot returns toward the starting point, a. The second complex in A does not exactly superimpose over the first, indicating that this waveform is aperiodic. Note the incidental similarity of this signal to a surface electrocardiogram (lead I in left bundle branch block).

Figure 9. A phase plane plot of the action potentials arriving at the distal chamber in the Purkinje fiber model described in Figure 6. The pacing rate of 322 beats per minute corresponds to the aperiodic region in Figure 6B. The banding and forbidden zones (point 2) and the sensitive dependence on initial conditions (two trajectories are very close together at point 1, and far apart at point 2), are all characteristic of chaos. Reprinted and modified by permission from Nature, Vol. 330, pp. 751 Copyright (c) 1987 Macmillan Magazines Limited.

Figure 10. Analysis of periodic, chaotic and random signals. Panel A is an 8 Hz sine wave and B is its phase plane plot. Periodic signal trajectories all overlap; thus only a single circle is seen. Its return map (Panel C) is very similar in structure to the phase plane plot. Panel D is the FFT power spectrum, with one isolated spike at 8 Hz (a discrete spectrum). Panel E is a chaotic solution to Duffing's equation (see also Figure 7) and F is its phase plane plot. Note the banding and forbidden zones, consistent with a chaotic process. Panel G is the return map demonstrating the same structure as the phase plane plot. The spectrum (Panel H) has predominant spikes at 8 and 24 Hz, and very small amounts of continuous spectral power centered about 1, 16 and 19 Hz, which are the components of the signal that make it aperiodic. They are not random because Duffing's equation contains no stochastic components (note the similarity of Duffing's equation to polymorphous ventricular tachycardia). Panel I is a random, continuous, low frequency signal generated by successive smoothing of a pseudorandom number time series. Its phase plane plot (Panel J) and its return map (Panel K) reflect the underlying Gaussian distribution (non-structured) from which the data were generated. Its frequency spectrum (Panel G) is continuous with power at all frequencies between 0 and 14 Hz.

Figure 11. Return map of the time intervals (T) between successive drops of water from a conventional faucet. The x-axis is the duration (in msec) of the index interval (n) and the y-axis is the duration of the succeeding interval (n+1). Note the similarity of these empirical data to the hypothetical data in Figure 1C. The nonlinear relationship indicates that the process might be chaotic rather than random. Reproduced with permission of Ariel Press, copyright 1984[iii].

Figure 12. Poincaré section. Panel A is a phase plane plot of a typical chaotic system (Rössler system). The vertical line intersects ("sections") a selected portion of the phase plane plot. The distribution of the points along an expansion of this line (Panel B) reveals no apparent structure, but a return map constructed from these points, shows a nonlinear pattern suggestive of a parabola (Panel C). Compare this to Figures 1C and 10. The phase plane plot is not a series of spirals – each trajectory crosses the line irregularly. In panel B $X_9$ and $X_{10}$ are the 9$^{th}$ and 10$^{th}$ trajectories – they are not adjacent. The relation between $X_9$ and $X_{10}$ is shown in graph C.

Figure 13. Calculation of fractal dimension. For each panel, the y-axis is dimension and the x-axis is the "magnification" at which that dimension is calculated. The plateau portion of the curve (boxed, thick line) is an estimate of the dimension. Panel A is the dimension of an 8 Hz sine wave (Figure 9A). There is a long plateau that corresponds to a dimension close to 1. Panel B is a calculation using Duffing's equation (Figure 9E) and shows an approximate dimension of 2.4. Panel C is a random, continuous, low frequency signal (Figure 9I) with a dimension of 3.2. Note the difficulty in selecting a plateau, and thus the limitation in accuracy and precision in the calculation. Because of this, dimensions should probably be reported semiquantitatively as high, intermediate or low.

Table 1 - Ability of analytic methods to detect the characteristics of chaos.*

|  | Aperiodicity | Sensitive dependence | Boundedness |
|---|---|---|---|
| Phase plane plot | yes | yes | yes |
| Return map | yes | yes | yes |
| Poincaré section | yes | yes | yes |
| Lyapunov exponent | no | yes | no |
| Fractal dimension | no | no | yes |
| Spectral analysis | yes | no | no |

* This table is overly simplified and the investigator is referred to any of the comprehensive references for more detailed understanding.

Table 2 - Expected results of the analytic techniques on standard signals.

|  | Periodic | Chaotic | Random |
|---|---|---|---|
| Phase plane plot | trajectories overlap | banding, forbidden zones, sensitive dependence | no structure |
| Return map | points overlap | banding, forbidden zones, sensitive dependence | no structure |
| Poincaré section | uniform distribution of points | non-random distribution of points | random distribution of points |
| Lyapunov exponent | zero | positive | zero |
| Fractal dimension | usually low | usually low | often high, but can be low |
| Spectral analysis | discrete | discrete or continuous | continuous |

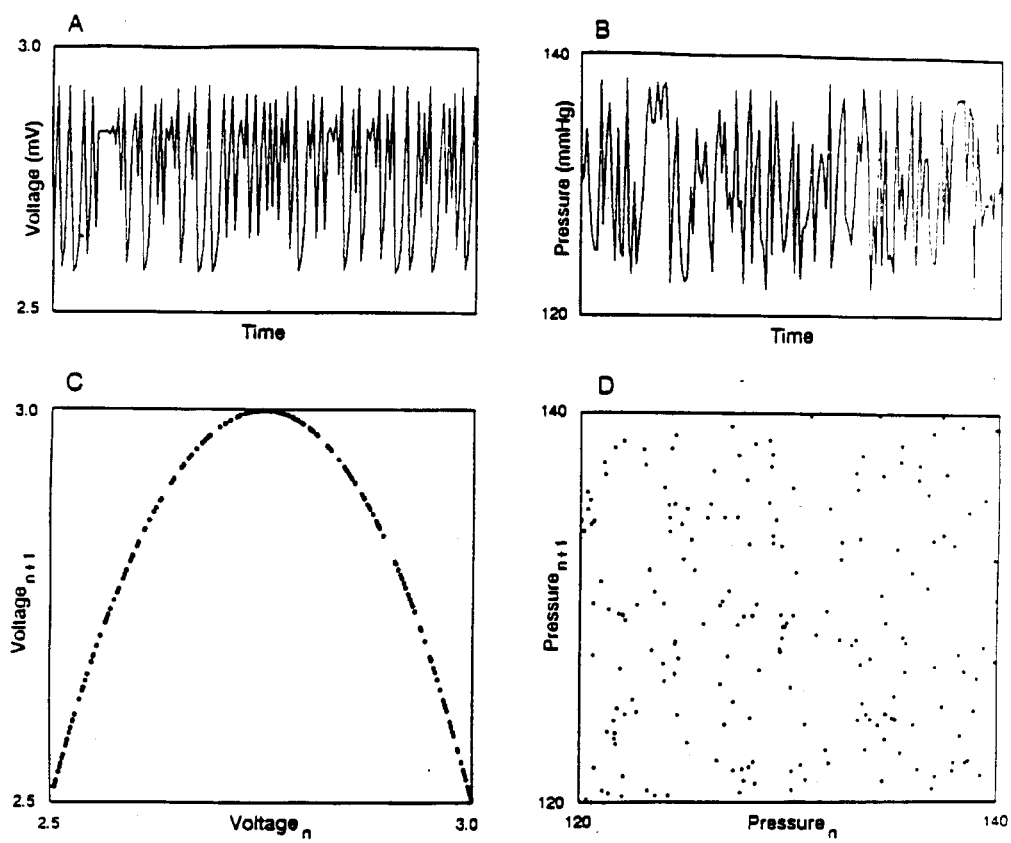

Figure 1. (A) Hypothetical beat-to-beat QRS voltage (mV) as a function of time (200 cycles). (B) Hypothetical simultaneous beat-to-beat peak systolic blood pressure (mmHg) as a function of time. (C) QRS voltage of each beat (n) on the x-axis versus QRS voltage of the subsequent beat (n+1) on the y axis based on the data in panel A. (D) Peak systolic blood pressure of each beat (n) on the x-axis versus peak systolic blood pressure of the subsequent beat (n+1) on the y-axis based on the data in panel B.

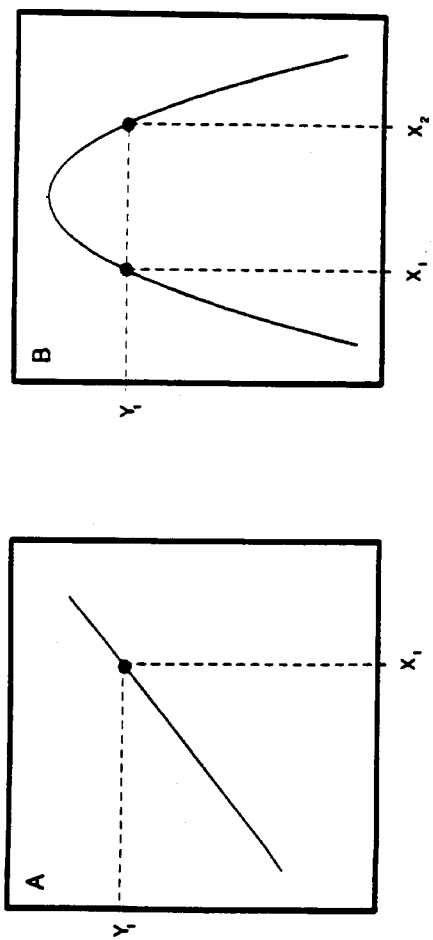
Figure 2. (A) A typical linear function. For every value of Y, there is a unique value of X. (B) A typical nonlinear function. In this example, for any single value of Y (except its maximum) there are two possible values of X.

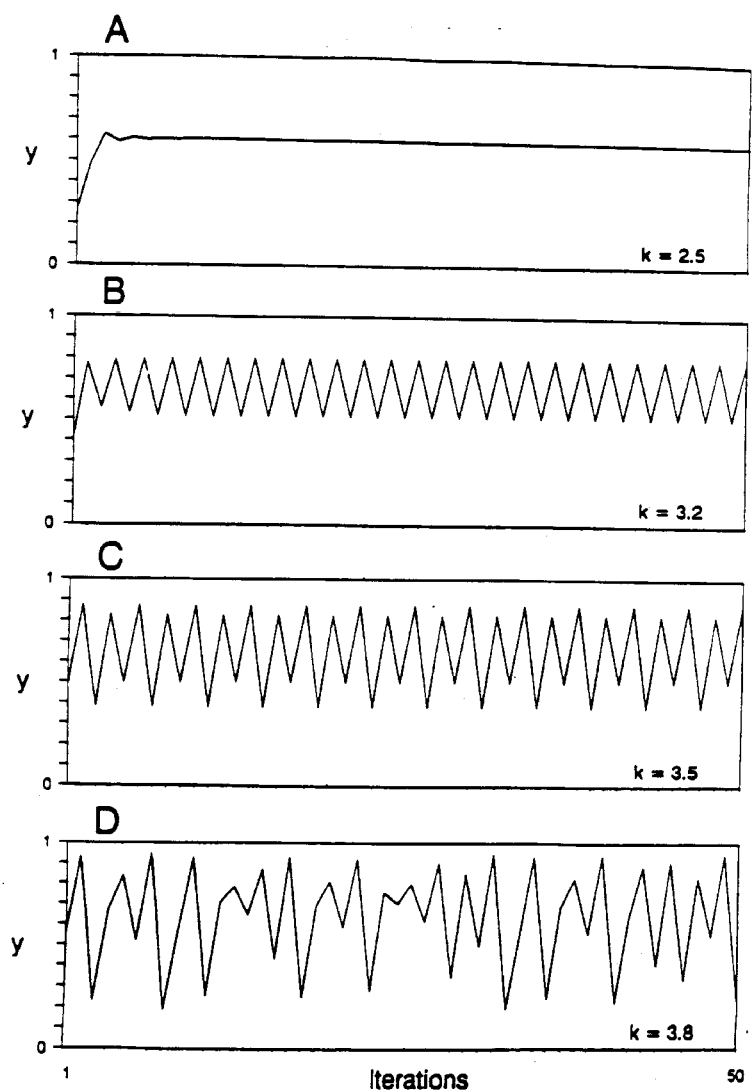
Figure 3. Iterative solutions of the logistic map. (A) When k = 2.5 the output of the system (y) exhibits a single state after a brief initial period of oscillation. (B) When k=3.2 the system alternates between two states. (C) When k=3.5 the system has four states. (d) When k=3.8, the system has an infinite number of states.

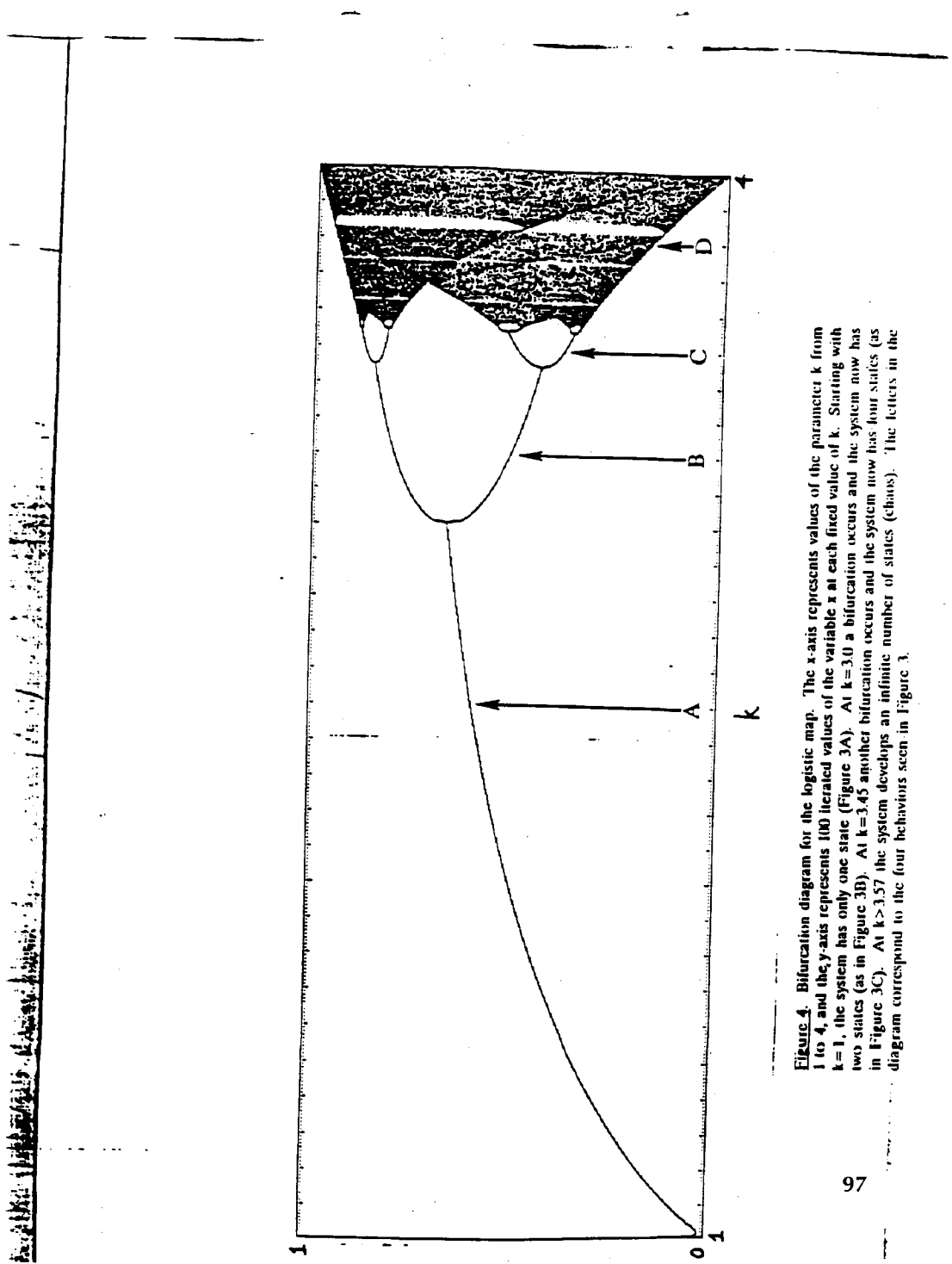

Figure 4. Bifurcation diagram for the logistic map. The x-axis represents values of the parameter k from 1 to 4, and the y-axis represents 100 iterated values of the variable x at each fixed value of k. Starting with k=1, the system has only one state (Figure 3B). At k=3.0 a bifurcation occurs and the system now has two states (as in Figure 3B). At k=3.45 another bifurcation occurs and the system now has four states (as in Figure 3C). At k>3.57 the system develops an infinite number of states (chaos). The letters in the diagram correspond to the four behaviors seen in Figure 3.

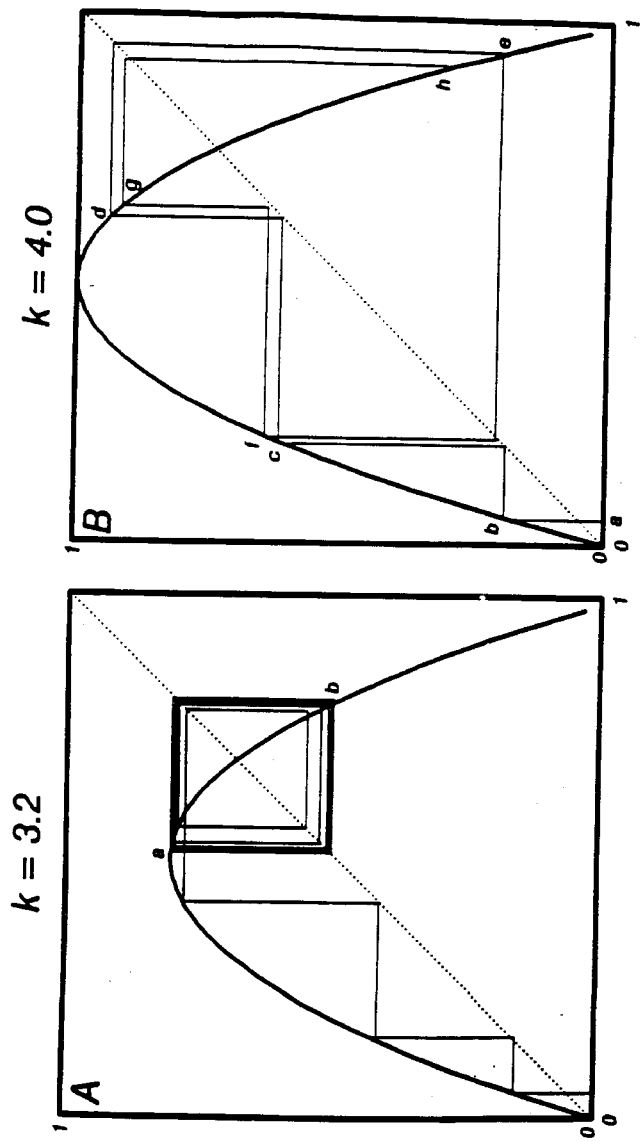
Figure 5. Geometric solution to the logistic map. Panel A demonstrates a periodic solution with values oscillating between a and b. Panel B is a chaotic solution, with the values (a through g) falling on irregular points of the parabola. See text for explanation of the solution technique.

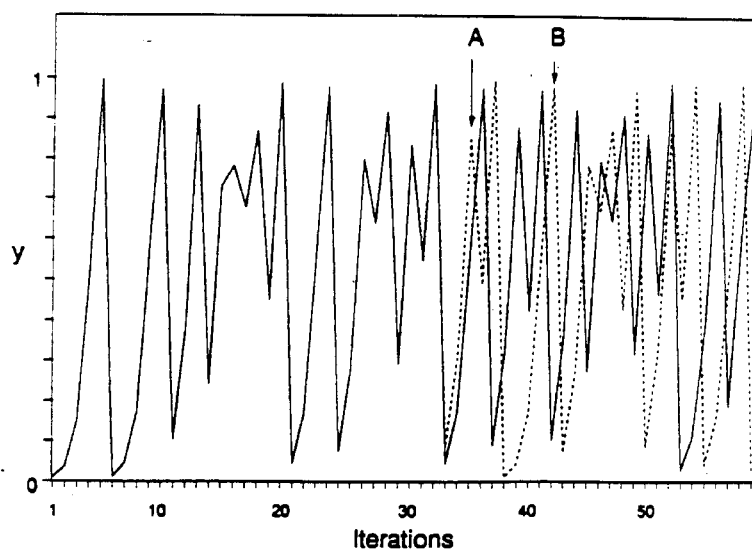
Figure 6. Sensitive dependence on initial conditions. The solid line represents iterations of the logistic map (k=3.99) with initial x=0.5, and the dotted line represents the same number of iterations with initial x=0.5000001. The two signals are exactly the same until the 35th cycle (point A) when they diverge. By the 42nd cycle (Point B) the peaks and nadirs are completely out of phase.

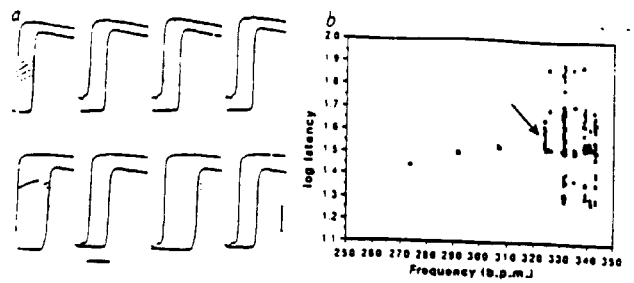

Figure 7. (A) Proximal and distal chamber action potential recordings of unstressed and stressed Purkinje fibers. The left sigmoid curve of each pair represents a depolarization in the proximal chamber and the right curve is the depolarization in the distal chamber. The time between the two curves is the conduction time between the chambers (latency). In the top series (no stress) all four depolarizations have the same conduction time. In the bottom series (stressed by compression) they oscillate; a long conduction time alternates with a short conduction time (shading). (B) A bifurcation diagram of the same system. The x-axis is the frequency of stimulation (the stress to the system) and the y-axis represents the latency (the difference in conduction time between proximal and distal chambers). There is a constant variance in latency (just as in the logistic map bifurcation diagram) until the system is stimulated at 325 beats per minute (arrow). At higher frequencies chaos occurs (compare this to Figure 4) and the variance in latency increases. Reprinted and modified by permission from Nature, Vol. 330, pp. 751 Copyright (c) 1987 Macmillan Magazines Limited.

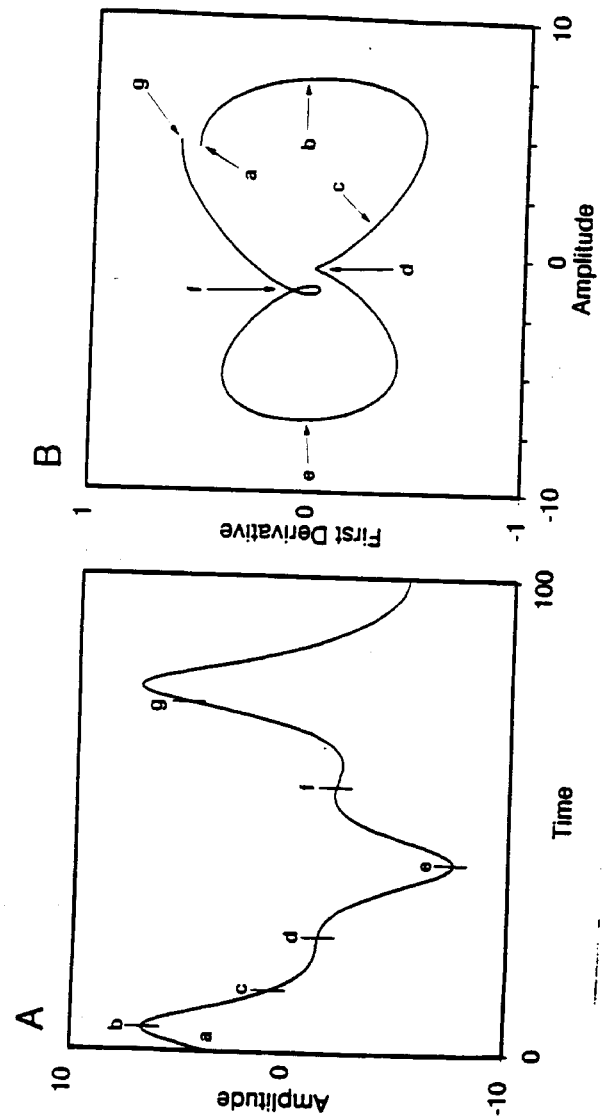

Figure 8. (A) Portion of a typical chaotic signal (Duffing's equation). The x-axis is time (in arbitrary units) and the y-axis is amplitude (unitless). (B) The phase plane plot of the same chaotic signal. The x-axis is amplitude and the y-axis is the first derivative of the amplitude (the center of each axis is zero). The x-axis is starts high and becomes slightly more positive for a short period of time. On the phase plane plot this is represented by starting at point a, moving slightly rightward (higher amplitude) and down (toward a derivative of zero). Point b represents an area of positive amplitude but of zero derivative. Point c represents a point in which the amplitude and the derivative are approaching zero. Point d has a slightly negative amplitude and a derivative near zero. Point e is the minimum with a derivative of zero. Point f is a small loop that represents a smaller sub-oscillation. The signal now returns toward another peak value (positive amplitude and maximally positive derivative), and the phase plane plot returns toward the starting point, a. The second complex in A does not exactly superimpose over the first, indicating that this waveform is aperiodic. Note the incidental similarity of this signal to a surface electrocardiogram (lead 1 in left bundle branch block).

101

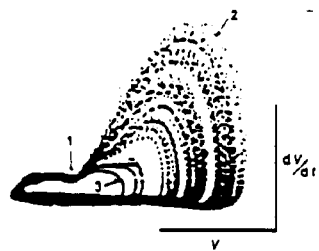

Figure 9. A phase plane plot of the action potentials arriving at the distal chamber in the Purkinje fiber model described in Figure 6. The pacing rate of 322 beats per minute corresponds to the aperiodic region in Figure 6B. The banding and forbidden zones (point 2) and the sensitive dependence on initial conditions (two trajectories are very close together at point 1, and far apart at point 2), are all characteristic of chaos. Reprinted and modified by permission from Nature, Vol. 330, pp. 751 Copyright (c) 1987 Macmillan Magazines Limited.

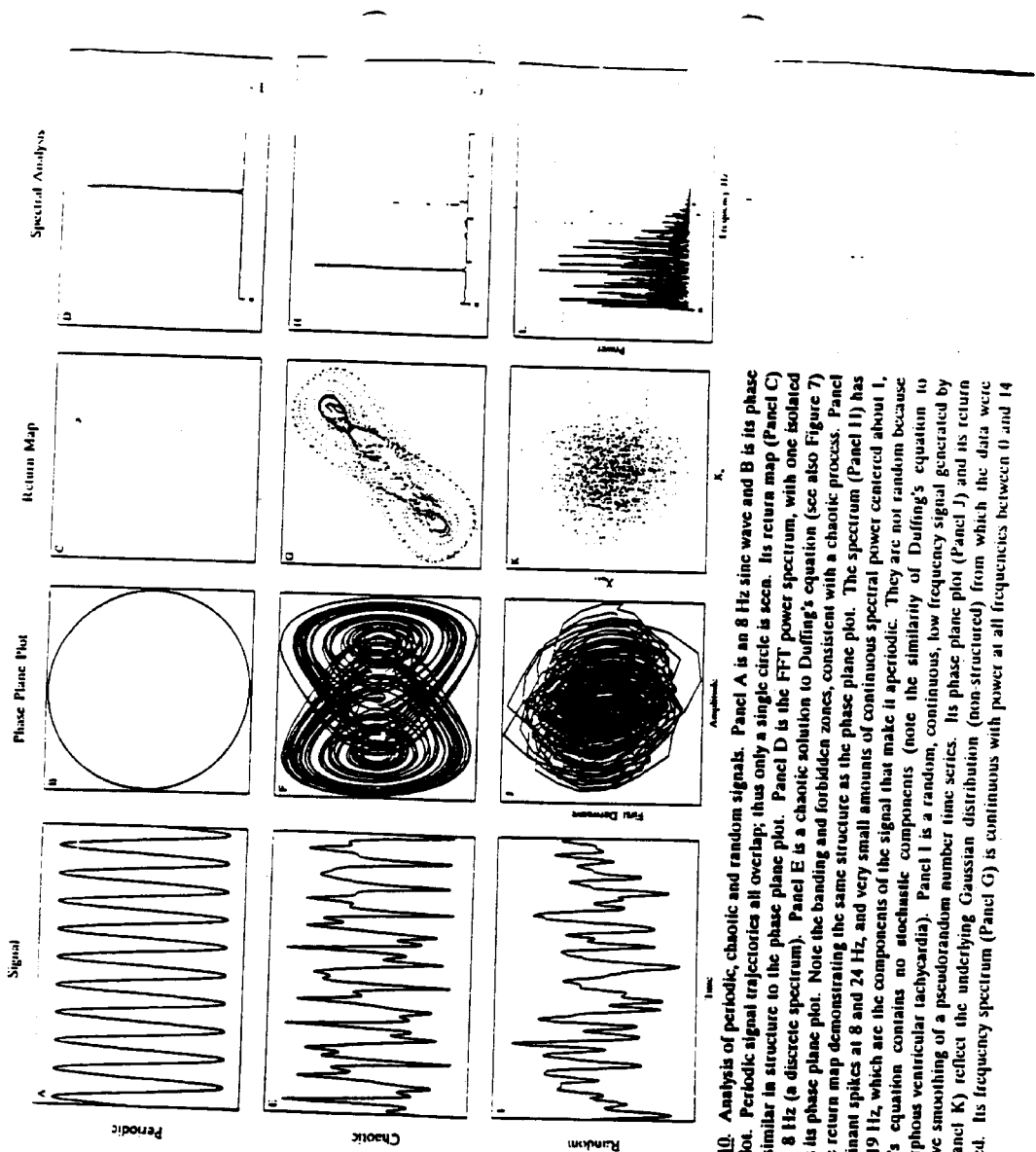

Figure 10. Analysis of periodic, chaotic and random signals. Panel A is an 8 Hz sine wave and B is its phase plane plot. Periodic signal trajectories all overlap; thus only a single circle is seen. Its return map (Panel C) is very similar in structure to the phase plane plot. Panel D is the FFT power spectrum, with one isolated spike at 8 Hz (a discrete spectrum). Panel E is a chaotic solution to Duffing's equation (see also Figure 7) and F is its phase plane plot. Note the banding and forbidden zones, consistent with a chaotic process. Panel G is the return map demonstrating the same structure as the phase plane plot. The spectrum (Panel H) has predominant spikes at 8 and 24 Hz, and very small amounts of continuous spectral power centered about 1, 16 and 19 Hz, which are the components of the signal that make it aperiodic. They are not random because Duffing's equation contains no stochastic components (note the similarity of Duffing's equation to polymorphous ventricular tachycardia). Panel I is a random, continuous, low frequency signal generated by successive smoothing of a pseudorandom number time series. Its phase plane plot (Panel J) and its return map (Panel K) reflect the underlying Gaussian distribution (non structured) from which the data were generated. Its frequency spectrum (Panel G) is continuous with power at all frequencies between 0 and 14 Hz.

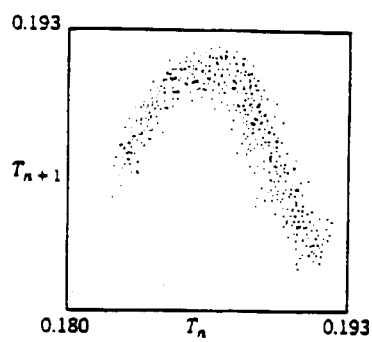

Figure 11. Return map of the time intervals (T) between successive drops of water from a conventional faucet. The x-axis is the duration (in msec) of the index interval (n) and the y-axis is the duration of the succeeding interval (n+1). Note the similarity of these empirical data to the hypothetical data in Figure 1C. The nonlinear relationship indicates that the process might be chaotic rather than random. Reproduced with permission of Ariel Press, copyright 1984[111].

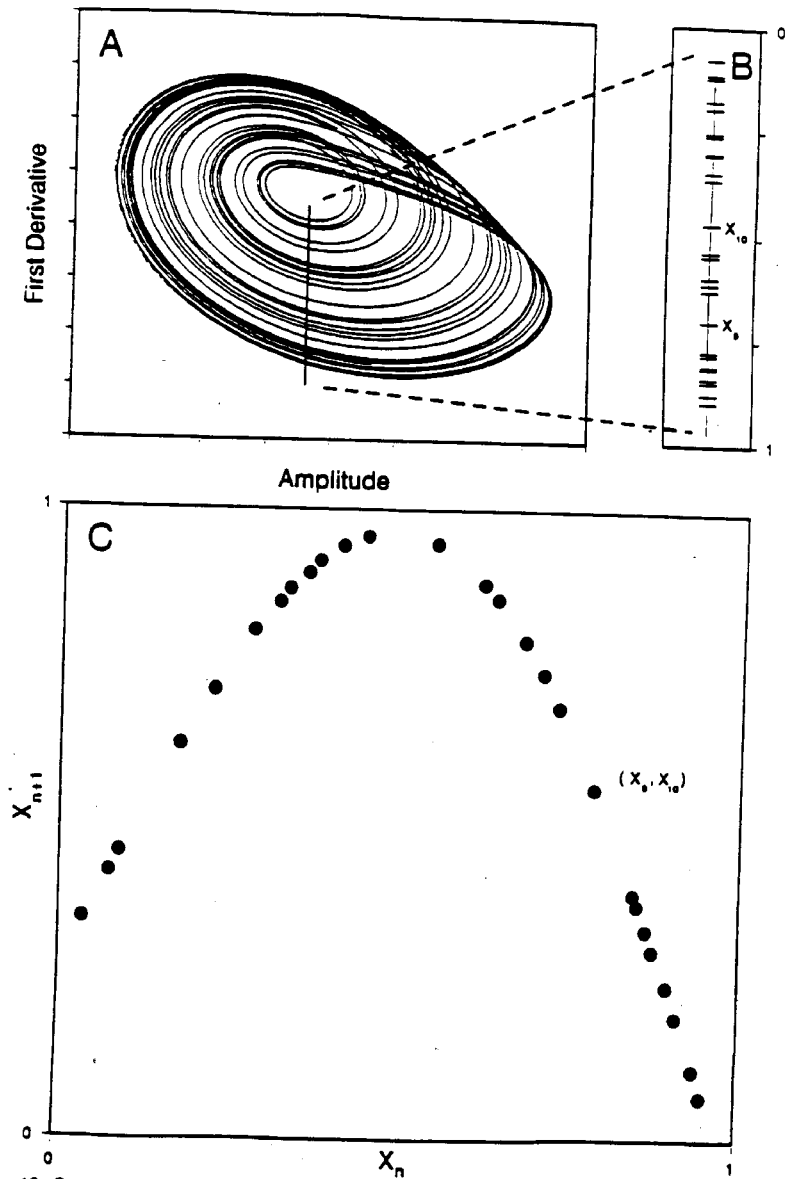

Figure 12. Poincaré section. Panel A is a phase plane plot of a typical chaotic system (Rössler system). The vertical line intersects ("sections") a selected portion of the phase plane plot. The distribution of the points along an expansion of this line (Panel B) reveals no apparent structure, but a return map constructed from these points, shows a nonlinear pattern suggestive of a parabola (Panel C). Compare this to Figures 1C and 10. The phase plane plot is not a series of spirals -- each trajectory crosses the line irregularly. In panel B $X_9$ and $X_{10}$ are the 9th and 10th trajectories -- they are not adjacent. The relation between $X_9$ and $X_{10}$ is shown in graph C.

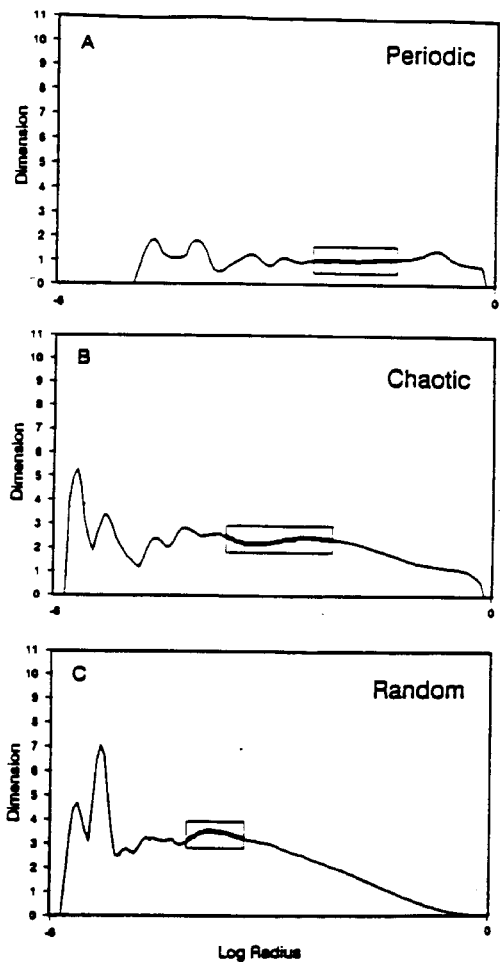

Figure 13. Calculation of fractal dimension. For each panel, the y-axis is dimension and the x-axis is the "magnification" at which that dimension is calculated. The plateau portion of the curve (boxed, thick line) is an estimate of the dimension. Panel A is the dimension of an 8 Hz sine wave (Figure 9A). There is a long plateau that corresponds to a dimension close to 1. Panel B is a calculation using Duffing's equation (Figure 9E) and shows an approximate dimension of 2.4. Panel C is a random, continuous, low frequency signal (Figure 9I) with a dimension of 3.2. Note the difficulty in selecting a plateau, and thus the limitation in accuracy and precision in the calculation. Because of this, dimensions should probably be reported semiquantitatively as high, intermediate or low.

106

NONHOMOGENEOUS LOCAL ATRIAL ACTIVITY
DURING ACUTE ATRIAL FIBRILLATION.
SPECTRAL AND DYNAMIC ANALYSIS.

Running Title: Local activity in Atrial fibrillation

Hrayr S Karagueuzian, Steven S Khan, Werner Peters,
William J Mandel, George A Diamond Division of Cardiology, Cedars-Sinai Medical Center,
and Department of Medicine, UCLA School of Medicine.

Address for Correspondence:
Hrayr S Karagueuzian, Ph.D.,
Division of Cardiology, Halper Bldg. #216
Cedars-Sinai Med Center
8700 Beverly Blvd
Los Angeles, CA, 90048.

ABSTRACT

Atrial fibrillation (A Fib) has been categorized into 4 different types (I-IV) based on the morphology of the epicardial bipolar electrogram. In the present study, we hypothesized that these same types of A Fib also exist at endocardial sites. Simultaneous high, mid and low right atrial endocardial bipolar electrograms were analyzed during acute A Fib induced by a rapid train of stimuli (20-40Hz) for 1-3sec in anesthetized closed-chest dogs (N=7, total of 72 episodes). A Fib lasted between 3 sec and a few minutes (22.3 ± 22.8sec). During A Fib, bipolar electrograms (0.5-500Hz) were both discrete (Types I and II) on electrograms recorded at one site and at the same time irregular (Type III) on electrograms recorded at another site. The 3 simultaneously recorded electrograms encompassed all combinations of the four types of A Fib. When A Fib had a discrete electrogram morphology (Types I and/or II), the mean rate of the A Fib was 494 ± 93beats/min. At a given site, electrogram morphology also changed type over time. Fast Fourier transform (FFT) of the digitized electrograms (8-10sec, 800Hz digitization) showed peaks mostly below 15Hz, (range 0-30Hz), that were either discrete (narrow band) with clear harmonic components, or had continuous (broad band) spectra, that changed in a time and site dependent manner. Phase plane plots (PPP), a plot of voltage versus rate of change of voltage, varied with respect to time and location. However, the morphology of these PPP often inscribed well defined structure suggesting dynamics compatible with deterministic chaos, rather than random dynamics. We conclude that AFib is both temporally and spatially heterogeneous and that all combinations of the 4 different types of AFib occur simultaneously. These findings may be helpful in developing robust algorithms for A Fib recognition for antitachycardia devices.

KEY WORDS: atrial fibrillation, phase plane plot, spectra, nonlinear dynamics, heterogeneity.

INTRODUCTION

Atrial fibrillation (A Fib) in man has been characterized as being one of four different types, types I to IV [1]. In Type I A Fib, discrete spikes of variable amplitude occur, separated by an isoelectric baseline; in Type II A Fib, the discrete spikes are not clearly separated by an isoelectric baseline and perturbations of the baseline are seen; in Type III A Fib, there are neither discrete spikes nor an isoelectric baseline, and in Type IV A Fib, the electrogram morphology alternates in an irregular manner between Type III and either Type I and/or Type II [1]. These studies describing the types of AFib used bipolar wire electrodes (0.5-1 cm apart) sutured on the epicardial surface of the right atrium [1]. So far, only limited information exists concerning endocardial local electrical activity during A Fib recorded with bipolar electrodes routinely used in the cardiac cath lab [2]. Therefore, the purpose of the present study was to determine: 1) if different Types of A Fib also exists on the endocardial surface of the atrium, as in the epicardial surface; 2) if the different Types of A Fib, when recorded on the endocardial surface, are mutually exclusive both in terms of time and space, and, finally, 3) to correlate the local dynamics and the spectra of A Fib to the underlying local electrical activity.

METHODS and MATERIALS:

Seven Mongrel dogs of either sex weighing between 24kg and 28kg were anesthetized with intravenous sodium pentobarbital (30-35mk/kg). Two bipolar and one quadripolar electrode catheters (USCI) with interelectrode distances of 1cm were introduced into the right atrium through the left internal jugular vein and positioned in the high, mid and low atrial endocardial surface under fluoroscopic control [3]. In two dogs after an initial study with 3 bipolar

4 atrial electrograms, the lower electrode catheter was advanced to the right ventricle to record bipolar activity from the ventricle at the apex. Atrial fibrillation (A Fib) was induced by a 1-2sec rapid train of stimuli (20-40Hz) at twice diastolic current threshold, applied in the high right atrium with a fourth bipolar electrode catheter. All atrial recordings obtained during A Fib (0.05-500HZ), along with lead II surface ECG were monitored on an Electronics for Medicine VR 16 system, with representative portions of the rhythm recorded on paper at paper speeds of 25-50mm/sec. In two dogs, filtered data (30-500Hz) was also analyzed in a total of 12 episodes. The entire study was taped on magnetic tape (Bell and Howel data tape CPR 4010) for subsequent selective retrieval and analysis.

Typically 8-10sec of data were digitized at 0.8-1kHz. Dynamic analysis of data was done by plotting voltage vs rate of change of voltage of the digitized data as othrogonal coordinates (state variables in phase space, or phase plane plot) [4] using SNIP waveform analysis software (Hodgsin, UCLA). In addition, spectral analysis was also performed on the same 8-10sec data used for the phase plane plot using the Fast Fourier Transform. In the present study, we acquired and analyzed data at 0.5-500Hz, as dynamic analysis with open filter settings would encompass the entire fast and slower frequency events, and thus would be more representative. Analog data acquired and analyzed at 30-500Hz also manifested the 4 Types of A Fib obtained at open filter setting. All data were analyzed using an Amiga 2000 and a PC/AT.

RESULTS

ELECTROGRAM MORPHOLOGY:

Figure 1 shows a typical example of electrically induced A Fib. Note that the activity in the high right atrium at the initial stage of the A Fib is consistent with Type IV A Fib with alternation between discrete and irregular activity. Ten seconds later, however, the A Fib changed to irregular (Type III) activity, and 20sec later the A Fib had a discrete, regular morphology (i.e., Type I). The electrogram morphologies on the simultaneously recorded mid and lower electrograms in figure 1 were different from the higher electrogram for the entire duration of the episode (which in this example lasted 26sec). A Fib at these sites was consistent with Type III activity in both leads. In a total of 72 episodes in all seven dogs, A Fib had a remarkably similar morphological pattern. All 4 Types of A Fib could be seen on a given lead in only 20% of the episodes (14 of 72 episodes). However, all 4 Types of A Fib could be seen in 90% of the episodes (65 of 72) when all three leads were taken into account.

The duration of a given episode ranged between 5sec to a few minutes, with a mean of $22.3 \pm 22.8$sec. In a given dog, the duration of a given episode was not constant, but varied from run to run encompassing the entire observable range of induced A Fib in all 7 dogs.

The rate of the A Fib when complexes were discrete, (Type I and II) ranged between 400 to 600 beats/min, with a mean of $494 \pm 93$ beats/min (mean $\pm$ S.D.) Ventricular response rate during A Fib was $170 \pm 25$beats/min (range 140-185beats/min) Figure 1.

PHASE PLANE PLOTS.

Sinus Rhythm: Figure 2 shows a typical example of a phase plane plot during sinus rhythm. The trajectories remain densely and uniformly packed together throughout both depolarization (larger loops) and repolarization (smaller loops) processes. This indicates constant dynamics of depolarization and repolarization of consecutive beats [4], a characteristic finding during sinus rhythm.

A Fib: During A Fib, however, (Figure 3) the trajectories of the phase plane plots and the resultant geometric forms were different from those of sinus rhythm and manifested both site- and time-dependent changes in their morphologies. In about 36% of the episodes (26 of 72 episodes) the trajectories inscribed a structure (form) that did not appear to result from random motion [Figures 4] because certain regions of the phase plane plots were never visited by the trajectories. If atrial fibrillation was a random process, all areas of the plot would have had similar chance of access by the trajectories.

FREQUENCY SPECTRA:

Sinus Rhythm: Spectra during sinus rhythm consistently showed discrete spikes at the fundamental and its harmonics clearly separated by flat (zero amplitude) interharmonics. (Figure 2). Such spectra were typically found during sinus rhythm at high, mid and low endocardial recording sites.

A Fib: In contrast, A Fib often had broad band (continuous) spectra with power at all frequencies (0-20Hz), (Figures 3 and 4). No discrete pattern, as in sinus rhythm, could be detected. During an episode of Fib however, there were site- and time-dependent differences in the spectra. Spectra could be quasi-discrete at one site (Figure 4, mid atrial recording) while continuous at others, encompassing a larger frequency band in a continuous manner (Figure 3,4).

DISCUSSION

This study demonstrates that endocardial electrical activity during A Fib, is not an homogeneous entity. Both time and site-dependent changes occurred in the electrogram, the phase plane plot and the frequency spectrum in this closed-chest canine model of A Fib. All 4 Types of A Fib described in man [1] using epicardial bipolar electrodes were also seen on the endocardial surface as well.

Mechanism of Atrial Fibrillation: The present study does not provide data to elucidate the mechanism of A Fib. Mapping studies using large number of electrodes strongly suggest that A Fib is caused by circus movement reentry that simultaneously incorporate 3 to 5 different reentry circuits. (Allessi M, Personal communication). Furthermore, in these studies it was emphasized that the reentry circuits constantly changed in number, site and configuration. Should similar mechanism(s) be operative in our model, then the dynamics of A Fib seen in our study could result from the constantly changing patterns of tthe reentry circuits during A Fib. This proposed mechanism of A Fib could also explain both site- and time-dependent changes in the dynamic and electrophysiological properties of local electrical activity during A Fib. Reentry in the normal atrium can be initiated by the mechanism of dispersion of repolarization, as atrial fibers have spatially distributed heterogeneous action potential durations [5]. In addition, structural complexities (anisotropy) of the atrial myocardium could also promote reentry, independent of the phenomenon of dispersion [6]. It therefore seems that the atrium has multiple intrinsic properties that promote reentry and as such it is highly likely that reentry was in fact the mechanism of induced A Fib in the present study.

Clinical Significance: As close similarity exists between our canine model and earlier clinical findings in man, our data suggest that heterogeneous A Fib may also exist on the endocardial surface of human A Fib. Should this be the case, algorithm development for recognition of A Fib with data obtained from endocardial electrograms must take into account the local heterogeneous nature. Should a given recording site manifest a transient period of relative constancy in the Type of A Fib, it will still not be possible to make definitive therapeutic and/or prognostic inferences as other sites could manifest different type(s) of A Fib at some point in time during the episode.

9

Figure Legends

Figure 1: Surface electrocardiograms (leads 1 and V3) and endocardial electrograms from the high right atrium (HRA), mid right atrium (MRA) and low right atrium (LRA) of electrically induced canine atrial fibrillation. The three panels demonstrate (from left to right) the induction of atrial fibrillation and waveform morphology at 10 and 20 seconds after induction of atrial fibrillation.

Figure 2: Atrial bipolar endocardial electrogram (BEG), phase plane plot, and spectral analysis of sinus rhythm. The BEG was recorded from the low right atrium (LRA). The phase plane plot is a graph of the rate of change of voltage (dV/dt) versus voltage (V) over 8 seconds of digitized data (800 Hz). The spectral analysis reveals discrete frequency spikes at harmonics (integer multiples) of the fundamental frequency (the heart rate). The discrete nature is shown by the lack of significant power between the harmonics and suggests a periodic signal.

Figure 3: Simultaneous HRA, MRA, and LRA endocardial electrograms, power spectra, and phase plane plots in canine atrial fibrillation. Note the discrete nature of the spikes in the electrogram in the HRA while the MRA and LRA electrogram are less discrete. This difference is also reflected in the discrete frequency and harmonics seen in the HRA power spectrum compared to the continuous frequency spectrum in the other leads. The phase plane plots of the HRA also differ with a clear central area in the HRA plot compared to the smeared out, space filling, phase plane plots of the MRA and LRA.

116

Figure 4: Simultaneous HRA, MRA, and LRA endocardial electrograms, power spectra, and phase plane plots in canine atrial fibrillation which suggest order. The HRA recording has a broad band power spectrum by FFT but the phase plane plots appear to show structure. See text for details.

REFERENCES

1. Wells JL Jr, Karp RB, Kouchoukos NT et al: Characterization of atrial fibrillation in man: studies following open heart surgery. PACE, 1:426-438, 1978.

2. Slocum J, Sahakian A, Swiryn S: Computer discrimination of atrial fibrillation and regular atrial rhythm from intra-atrial electrograms. PACE, 11:610-621, 1988.

3. Karagueuzian HS, Ohta M, Drury K et al: Coronary venous retroinfusion of procainamide: a new approach for the management of spontaneous and inducible sustained ventricular tachycardia during myocardial infarction. J Am Coll Cardiol, 7:551-563, 1986.

4. Pinsker HM, Bell J: Phase plane description of endogenous neuronal oscillator in Aplysia. Biol Cybern, 39:211-221, 1981.

5. Spach MS, Dolber PC, Anderson PAW: Multiple regional differences in cellular properties that regulate repolarization and contraction in the right atrium of adult and newborn dogs. Circ Res, 65:1594-1611, 1990.

6. Spach MS, Miller WT Jr, Dolber PC et al: The functional role of structural complexities in the propagation of depolarization in the atrium of the dog. Circ Res, 50:175-191, 1982.

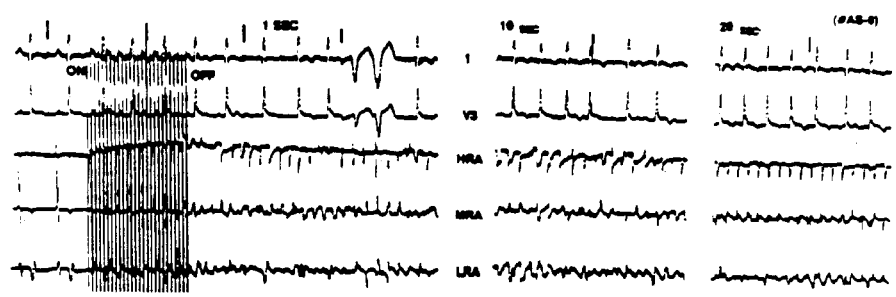
118

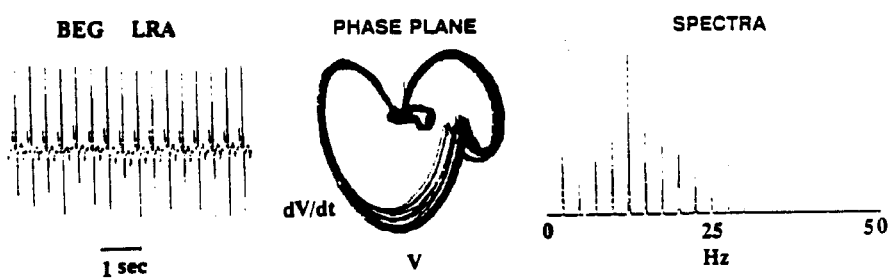

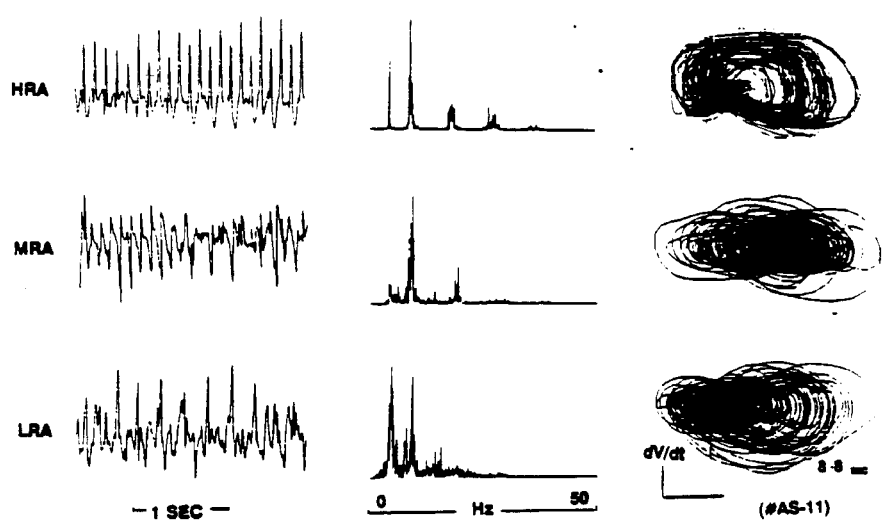

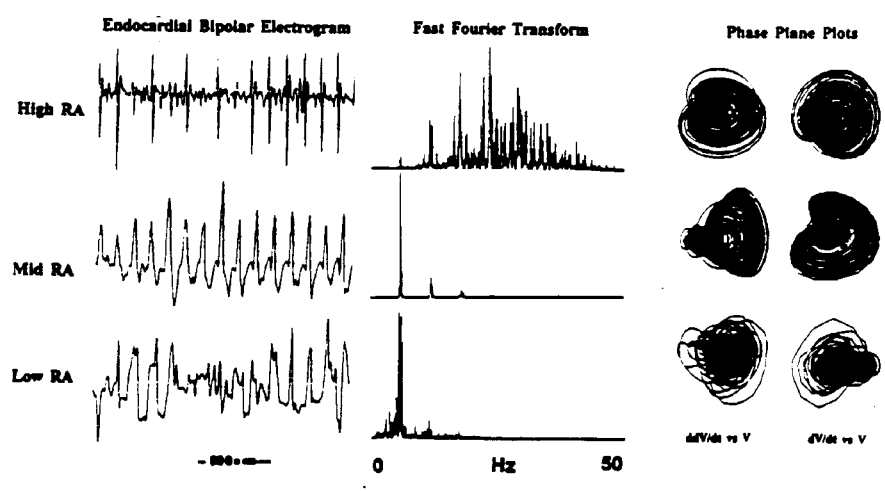
121

Nonlinear Dynamic Analysis of Temporally
Heterogenous Action Potential Characteristics Running Title: Action Potential Dynamics Hrayr S Karagueuzian, Steven S Khan,
William J Mandel, Kichol Hong, and George A Diamond.

From the Division of Cardiology, Cedars-Sinai Medical Center,
Department of Medicine UCLA, Los Angeles, California 90048, USA.

Abstract

Rate-dependent bifurcations and aperiodic changes in action potential duration and amplitude were observed in periodically stimulated cardiac Purkinje and ventricular muscle cells isolated from dogs with quinidine-induced ventricular fibrillation and ventricular tachycardia. The slope of the action potential duration restitution curve was higher in the quinidine intoxicated fibers than in normal untreated fibers. Aperiodicity and bifurcations in APD could not be observed in normal untreated cardiac fibers. The data suggest that induction of reentrant ventricular fibrillation and ventricular tachycardia could be brought about not by fixed but rather by changing alterations in cellular electrical activity. Theory based on nonlinear dynamics seems to provide a quantitative basis for such an analysis. This could have important implications in the issue of sudden cardiac death, a major problem in cardiology.

Key Words: Nonlinear dynamics, dispersion of repolarization, action potential duration restitution, phase plane plot, chaos.

INTRODUCTION

Nonlinear dynamic systems are characterized by their intrinsic ability to manifest increasingly complex behavior when subjected to constant periodic stress [1-5]. Recent findings indicate that cardiac excitability and cardiac impulse propagation behave in this nonlinear fashion [2,4]. Similar observations were also made with respect to cardiac automaticity in vitro [3], and by the analysis of QRS and T waves in intact in vivo hearts [5]. Recent theoretical arguments [4] suggest that the nonlinear behavior of ventricular activation and recovery promote dispersion of refractoriness and reentry [6,7]. So far, the dynamic response of cardiac cellular action potentials to repetitive electrical stimulation in the presence of toxic concentrations of antiarrhythmic drugs are still unknown. Since antiarrhythmic drugs may promote arrhythmias (proarrhythmic effect) [8], the present study was designed to evaluate the dynamic behavior of cardiac cell action potentials during quinidine toxicity.

METHODS AND MATERIALS

Mongrel dogs (N=5) of either sex weighing between 23-29kg were anesthetized with sodium pentobarbital (35mg/kg intravenously), intubated, and ventilated with room air with a Harvard respirator at 4cm H2O pressure. Two Tygon (Teflon) catheters (i.d. 1.58mm and o.d.3.17mm) were inserted through the right carotid artery and the right jugular vein for monitoring aortic blood pressure and for systemic drug injections respectively. A 6F USCI bipolar electrode catheter was introduced through the left jugular vein to the right ventricular apex, under fluoroscopic control for the purpose of pacing the ventricle. An in vivo model of ventricular tachycardia and ventricular fibrillation (VT/VF) was developed in our laboratory by administration of intravenous quinidine (Quinidine Gluconate Injection USP, Lilly) (10mg/kg over 2min), at 30min intervals, until a total of 90-100mg/kg (over 5hours) is administered or VT/VF occurs, whichever comes first. This model of global cardiac intoxication was used to allow each sampled cell for microelectrode study to be representative. Two minutes after each administered dose of quinidine, the ventricle was paced at cycle lengths of 500 and 300msec for periods of 5 to 10min, to enhance myocardial uptake and toxicity by quinidine

3

[9, 10]. All dogs developed VT/VF either spontaneously or during pacing at 300msec cycle length. Three dogs that received no quinidine were used as controls. The right ventricles of the arrhythmic hearts were isolated and mounted in a tissue bath, endocardial surface upward (2X2cm block). Tissue blocks isolated from treated and untreated dogs were of similar size and from similar locations. The bath was superfused with Tyrode's solution at 34° C and pH 7.4 [11,12]. The preparations were regularly stimulated and transmembrane action potentials recorded with glass capillary electrodes [11,12]. The effects of increasing rates of stimulation on the duration and amplitude of subendocardial Purkinje and ventricular muscle cells were evaluated in each isolated tissue preparation during progressive increase in the frequency of stimulation (2000-200msec). All action potentials were first recorded on an analog tape recorder (Bell and Howell, model 4010 CPR) and later digitized at 1kHz for analysis of the power spectrum and to construct phase plane plots [13,14]. Data was analyzed using SNIP signal processing software (Hodgsin, UCLA) on an Amiga-2000.

RESULTS

Figure 1 illustrates two such experiments, one in a control dog (A), and the other in a quinidine intoxicated dog (B). Recordings were made from right ventricular endocardial muscle cells [18,19]. Both preparations were first paced at relatively long cycle lengths, 2000msec (top panels), followed by shorter ones. In the normal non-intoxicated cell, each stimulus is followed by an action potential that has constant duration and amplitude for the entire range of frequencies (2000-300msec) used. However, in the intoxicated fiber when the cycle length was shortened to 1000msec, action potential duration

125 alternated between long and short duration (period doubling). Further shortening of the stimulating cycle length to 800 and then to 600msec caused the emergence of period 3 and period 4 alternans of the duration of the action potential respectively. At 500msec drive, a 4:3 phase locking pattern emerged (i.e., 4 applied stimuli were followed by 3 action potentials), which after 30sec progressed to aperiodic action potential duration pattern. Note the induction of a non-driven premature response (arrow), during this aperiodic activity. This could be caused by close juxtaposition of two cells with disparate APDs during repolarization that can generate an excitatory (depolarizing) current. If this current is of sufficient magnitude, it can reexcite the fiber with shorter duration [15].

The analysis of the steady-state restitution curves obtained at cycles lengths of 500-1500msec [16,17] (diastolic interval vs APD) obtained during periodic and aperiodic activity have shown that even large variations in the magnitude of diastolic intervals could have no predictable effect on the APD (Figure 2A). However, when "plateau" responses were analyzed at the exclusion of the non-plateau responses, the typical exponential curves described for Purkinje and ventricular muscle cells [16] were obtained (Figure 2A). The dynamic losses of action potential plateau could be caused by periodic and aperiodic inexcitability [2,4] of an electrically coupled cell to the cell from which recording is made. The unexcited cell can exert a strong repolarizing (hyperpolarizing) influence on the excited (depolarized) cell (because it is electrically well coupled) causing an abrupt abbreviation and loss of plateau of APD, by the all-or-none repolarization process [17]. Secondary depolarizations (Figures 1), may well be reflections of such "sub-threshold" hyperpolarizing influences from more distal unexcited sites. The initial slope of the APD restitution curve of quinidine intoxicated cells was much steeper (at least an order of magnitude) than the slope of normal cells (Figure 2A). Unlike in normal cells, quinidine toxicity caused rate-dependent APD bifurcations during stepwise increase in the frequency of stimulation similar to that in sheep Purkinje fibers stressed with heptanol [2]. With increasing frequency of stimulation APD and amplitude showed steady alternans (Figure 3) (bifurcation) of 108 ± 36msec and 12 ± 9mV respectively. Further increases in the frequency of stimulation resulted in irregular activity of the sort shown in Figure 1 and 4. In the three normal tissue preparations neither ventricular muscle cells nor Purkinje cells have shown such bifurcative behavior with respect to both APD and APA. During each frequency of stimulation (2000-300msec) a constant APD and APA were present for the duration of stimulation.

Phase plan plot of the irregular, aperiodic responses showed trajectories that manifested the property of sensitive dependence on initial conditions and the presence of forbidden zones (Figure 4A), similar to those seen in stressed cardiac Purkinje fibers [1]. Fast Fourier transforms (FFT) of these aperiodic responses (Figure 4B) showed continuous spectra ("broad band") consistent with chaotic dynamics. In normal cells the trajectories were uniform and densely packed and FFT showed discrete (discontinuous) spectra (Figure 3A) indicative of periodic activity.

DISCUSSION

Quinidine-induced, rate-dependent increase of nonlinearity of action potential duration and amplitude was found to occur in cells isolated from ventricles with tachyarrhythmias. Periodic and aperiodic cellular electrical responses enhance the dispersion of ventricular refractoriness and cause non-uniform recovery of excitability, thus setting the stage for reentrant sustained activation and ventricular fibrillation [6,7]. Use of nonlinear dynamic concepts may thus have important implications for monitoring cardiac electrical stability and drug-induced proarrhythmic effects by monitoring the slope of action potential duration restitution curve. Alternatively, the efficacy of an antiarrhythmic drug can be judged by its ability to decrease the strength of electro-dynamic nonlinearity of the ventricle, by decreasing the slope. The ionic mechanism(s) responsible for altered recovery of action potential duration are still undefined, and this study does not provide an explanation in this regard. While membrane kinetics of ionic current recovery may well be a possibility, intracellular events involving the sarcoplasmic reticulum (SR) can not be excluded. The intracellular handling of calcium ions by the SR appears to be a nonlinear phenomenon, due to its demonstrated ability to manifest an oscillatory behavior during a steady level of applied stress [18]. Since strictly linear systems lack such an oscillatory (period doubling) property [19], it is therefore possible that bifurcations of transmembrane action potential induced by quinidine intoxication may be nonlinear manifestations of intracellular homeostasis of calcium ions by the SR, that in turn may alter the kinetics of sarcolemmal ionic current flow [20]. These hypotheses need experimental verification.

The strong possibility that irregular and aperiodic activity may result from deterministic chaos is suggested by the intermediate dynamic stages that precede such activity, (i.e., bifurcations); the broad-band frequency spectra; and the apparent exquisite sensitivity to initial conditions during the irregular activity. Thus it seems possible to expect similar orderly cardiac

7 electro-dynamic transition sequences to occur in an in situ ventricle, should such intermediate dynamic stages be not interrupted by intrinsic and extrinsic noise, which could destroy the emergence of such an orderly sequences. These intermediate stages could thus serve as predictors of an impending aperiodic chaotic state that could precipitate VT/VF by reentry due to dispersion of repolarization [6,7].

This work was supported by ECHO Cedars-Sinai Research Fund. HSK was the recipient of NIH, RCDA Award. We thank Avile McCullen for excellent technical assistance.

REFERENCES

1. Swinney H: Observations of order and chaos in nonlinear systems. Physica, 7D, 3-15 (1983).

2. Chialvo DR & Jalife J: Non-linear dynamics of cardiac excitation and impulse propagation. Nature, 330, 749-752 (1987)

3. Guevara MR, Glass L , Shrier A, Class A: Phase locking, period doubling bifurcations, and irregular dynamics in periodically stimulated cardiac cells. Science, 214:1350-1353, 1981.

4. Chialvo DR, Michaels DC, Jalife J: Supernormal excitability as a mechanism of chaotic dynamics of activation in cardiac Purkinje fibers. Circ Res (In press).

5. Ritzenberg AL, Adam DR , Cohen RJ: Period multupling: evidence for nonlinear behaviour of the canine heart. Nature, 307:159-161, 1984.

6. Gadsby D, Wit AL: Normal and abnormal electrical activity in cardiac cells. In "Cardiac Arrhythmias, Their Mechanisms, Diagnosis and Management. Mandel WJ (ed), pp 53-80, Lippincott. Philadelphia, 1985.

8

7. Kuo CS, Reddy P, Munkata K, Surawicz: Arrhythmias dependent predominantly on dispersion of repolarization. In: "Cardiac Electrophysiology and Arrhythmias", Zipes DP and Jalife J (eds), pp 277-285, Grune and Stratton, 1985.

8. Stanton MS, Pryscowsky EN, Fineberg NS, Miles WM, Zipes DP, Heger JJ: J AM Coll Cardiol, 14:209-215 (1989)

9. Hondeghem LM & Katzung BG: Antiarrhythmic agents: the modulated receptor mechanism of action of sodium and calcium channel-blocking drugs. Ann Rev Pharmacol Toxicol, 24,387-423 (1984)

10. Davidenko JM, Cohen L, Goodrow R & Anzelevitch C: Circulation 79:674-686, 1989.

11. Sugi K, Karagueuzian HS, Fishbein MC, et al: Cellular electro-physiologic characteristics of surviving subendocardial fibers in chronically infarcted right ventricular myocardium susceptible to inducible sustained ventricular tachycardia. Am Heart J, 114:559-569,1987.

12. Karagueuzian HS, Fenoglio JJ Jr, Weiss MB ,Wit AL: Coronary occlusion and reperfusion: effects on subendocardial cardiac fibers. Am J Physiol, 238, H581-H595 (1980)

13. Pinsker HM, Bell J: Phase plane description of endogenous neuronal oscillators in Aplysia. Biol Cybern, 39:211-221, 1981.

14. Teresa R Chay: Abnormal discharges and chaos in a neuronal model system. Bio Cubern, 50:301-311, 1984.

15. Saitoh H, Bailey JC, Surawicz B: Alternans of action potential duration after abrupt shortening of cycle length: differences between dog Purkinje and ventricular muscle fibers. Circ Res,62:1027-1040 (1988)

16. Elharrar V, Atarashi H, Surawicz B: Cycle length-dependent action potential duration in canine Purkinje fibers. Am J Physiol, 247: H936-H945, 1984.

17. Noble D & Tsien RW: In "Electrical Phenomena in the Heart", WC de Mello (ed), pp.141-144. Academic Press, New York, 1972.

18. Karagueuzian HS, Katzung BG: Voltage-clamp studies of transient inward current and mechanical oscillations induced by ouabain in ferret papillary muscle. J Physiol (London) 327:255-271, 1982.

19. Feigenbaum MJ: Universal behavior in non linear systems. Los Alamos Science, 4-27, Summer, 1980.

20. Tsien RW: Ann Rev Physiol, 45, 341-358 (1983)

LEGENDS

FIGURE 1. A: Rate-dependent shortening of canine right ventricular endocardial ventricular muscle cell action potential duration (APD) isolated from a normal untreated dog. Note, stable and constant action potential response at each of the basic cycle length (BCL) tested, 2000-300msec of stimulation. B, Rate-dependent periodic and aperiodic ventricular muscle APD patterns, in a quinidine-intoxicated canine endocardial tissue. Note recordings at the slower sweep speed (bottom two tracings) are continuous. The arrow indicates the induction of a non-drive beat.

FIGURE 2. A, Action potential duration (APD) restitution curve of a ventricular muscle cell intoxicated with quinidine. Abscissa, diastolic interval; ordinate, APD for 100% repolarization. The curve was constructed during 800msec BCL. The kinetics of APD restitution during "plateau" responses

10 follows the typical exponential pattern [21,22] (filled circles). In contrast however, during non-plateau responses (open circles) no relation between diastolic interval and APD could be detected. Note the greater steepness of the slope of quinidine intoxicated cell compared with normal untreated cell (open squares).

FIGURE 3. Depolarization and repolarization alternans of endocardial cardiac cells isolated from quinidine intoxicated right ventricular endocardium, eight minutes after induction of ventricular tachyarrhythmia with quinidine overdose. Cells #2 and 3 are from one dog and the bottom recordings from another.

FIGURE 4. A; phase plane trajectories (state space) (top), and fast Fourier frequency spectra (bottom) of normal canine Purkinje fiber action potentials (middle) in Purkinje fibers isolated from a normal untreated dog during 1000msec BCL of stimulation. The phase plane plots are densely packed and uniformly thick, and the frequency spectra potentials are discrete. In contrast, the action potentials B: (middle) had an irregular and aperiodic pattern (monitoring of more than 100 beats failed to show a repeating pattern). Phase plane plots of these action potentials show a characteristic chaotic property known as "sensitive dependence on initial conditions". Frequency spectra associated with this irregular series of action potentials (B bottom) had a continuous spectra (broad-band) that was conspicuously absent in the normal fiber. Both preparations were stimulated at 1000msec cycle length.

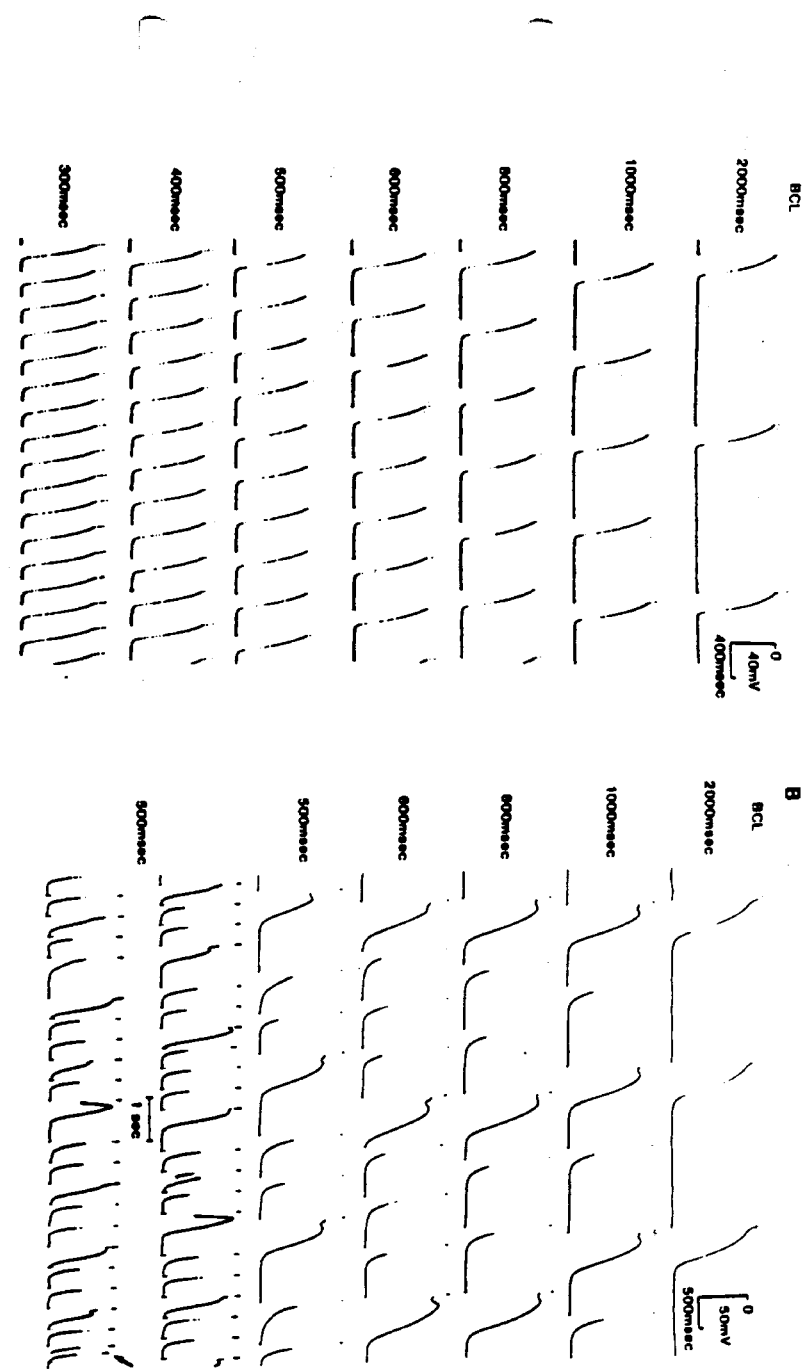
133

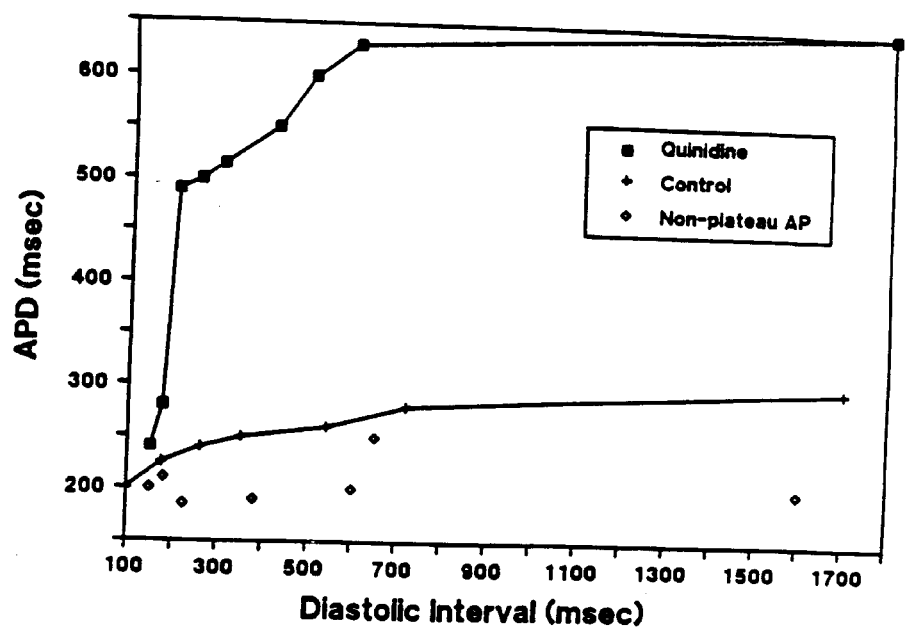

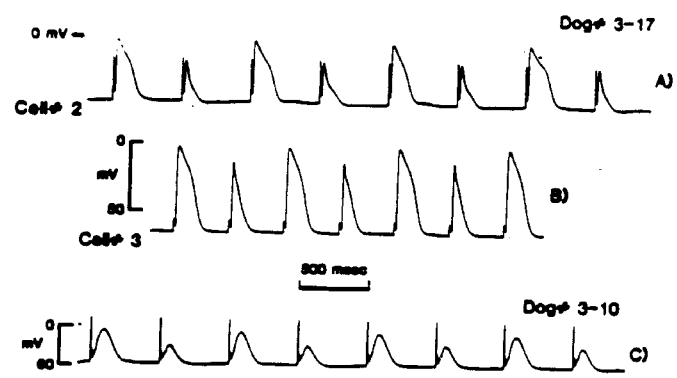
SINGLE CELL DEPOLARIZATION AND REPOLARIZATION ALTERNANS IN RV ENDOCARDIUM ISOLATED FROM TWO DOGS 8 MIN. AFTER INDUCTION OF VF BY QUINIDINE OVERDOSE

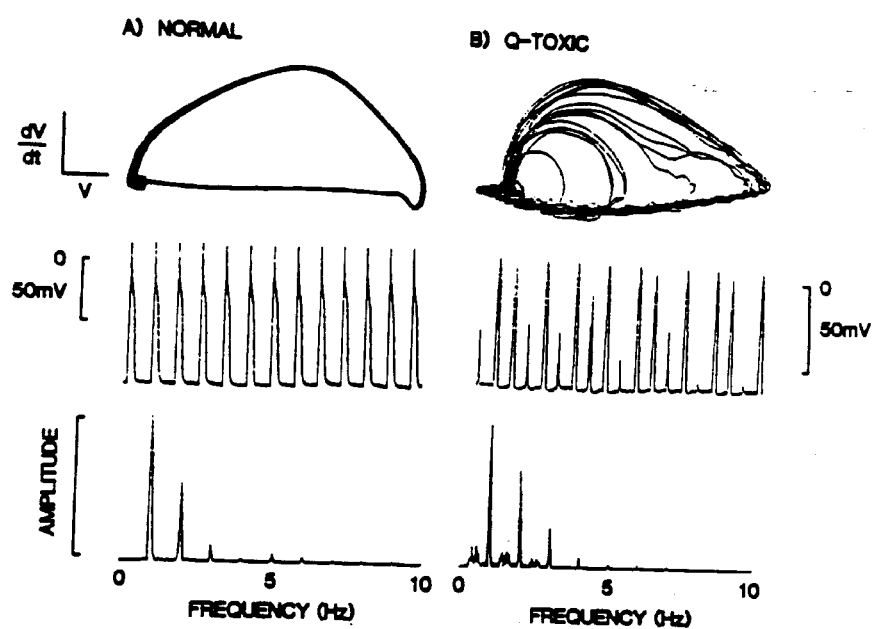

Nonlinear Dynamic Analysis of

Periodic, Random and Chaotic Signals

Timothy A. Denton, M.D.
George A. Diamond, M.D.

Short Title: Nonlinear Dynamics - Standard Signals

From the Division of Cardiology, Cedars-Sinai Medical Center
and the School of Medicine, University of California, Los Angeles, California This work was supported in part by an NHLBI Training Grant (2T32HL07380) from the National Institutes of Health, Bethesda, Maryland.

Address reprint requests to:
  George A. Diamond, M.D.
  Cedars-Sinai Medical Center
  Division of Cardiology
  Becker 210
  8700 Beverly Boulevard
  Los Angeles, California 90048

Abstract

Recent advances in the mathematical discipline of nonlinear dynamics has led to its use in the analysis of biological processes. We analyzed a series of standard signals with five tools of nonlinear dynamics. These signals were of three types: periodic, chaotic and random. Periodic signals were sine, square, triangular, sawtooth, modulated sine waves and quasiperiodic signals, generated at multiple amplitudes and frequencies. Chaotic signals were generated by solving standard sets of nonlinear equations including the logistic map, Duffing's equation, Lorenz equations and the Silnikov attractor. Random signals were both discontinuous and continuous. Gaussian noise was added to some signals at magnitudes of 1, 2, 5, 10 and 20% of the signal's amplitude. Each signal was then subjected to the five analytical techniques: phase plane plotting, Poincaré section, return map, correlation dimension (a specific type of fractal dimension) and spectral analysis. Periodic chaotic and random signals were compared to determine the relative sensitivity and specificity of each of the techniques to determine the underlying system. In the absence of noise, phase plane plots and return maps are the most sensitive detectors of chaotic behavior, and can also identify periodic processes. Spectral analysis can determine if a process is periodic or quasiperiodic, but cannot with any certainty tell the difference between a chaotic or random signal. Correlation dimension is useful to determine the overall complexity of a signal, but cannot be used in isolation to diagnose a chaotic process. Noise at any level effaces the structure of the phase plane plot. Return maps are relatively immune to noise at levels of up to 5%. Spectral analysis is noise insensitive as is the correlation dimension.

Based on these data, each signal of interest must be subjected to all of the techniques to increase the certainty of identification of the underlying process. No single test is sufficiently sensitive or specific to categorize an unknown signal as chaotic.

Introduction

Nonlinear dynamics is a branch of mathematics that has advanced significantly in theory and application over the last twenty years[1,3,4,6,7,12,119]. These developments have led to the explanation of seemingly complex phenomena that are now described as *chaotic*. The science has been applied to systems as diverse as planetary motion[18] and measles epidemics[5], and in the last eight years chaos theory has been used to explain many complex behaviors in biology and cardiology[1,13,14,16,a,13,66,14,67].

Nonlinear dynamicists have developed many tools to study complex behavior, and these tools are often able to reveal underlying order in seemingly random data. When certain patterns emerge in these complex data, they can form a basis for explaining mechanisms of the behaviors. Phase plane plots, Poincaré sections, return maps, correlation dimension and spectral analysis are five common techniques used to study mathematical and real world continuous signals[4,12,13,18]. Each tool, by either graphic or numeric techniques, is able to reveal different characteristics of a continuous signal's behavior not easily visible in the raw signal.

Many of the these new techniques are unfamiliar to the basic science researcher and clinician. Furthermore, these techniques have not been reviewed in an accessible fashion for biologic investigators who may want to apply them to their discipline. We undertook this study to (1) determine how known standard signals are interpreted by the techniques of nonlinear dynamics commonly used in the literature, (2) determine the relative ability of each of the techniques to detect periodicity, chaos and randomness and (3) determine the effects of noise on the interpretation of information obtained from these tools.

Materials and Methods

Standard Signal Generation

All programs used in this study were written in Turbo Pascal (Borland International, Scotts Valley, California), and run on an IBM-PC compatible computer (AST Premium-286). Three classes of signals were generated for analysis by the five tools of nonlinear dynamics - *periodic*, *chaotic* and *random*. The signal generation program produced signals in files of up to 10,190 points in length. The frequency and amplitude of each signal was controllable, and the putative digitization rate was a constant 1000 samples per second. Each signal was assumed to be generated for a 12 bit data path, and the amplitude of the signal was defined as a percentage of the 12 bit amplitude (amplitude between a maximum of +2048 and minimum of -2048). The amplitude of any given signal was defined as a percent of the theoretical maximum amplitude (a sine wave with an amplitude of 50% would vary between a maximum of +1024 and a minimum of -1024). Periodic signals included sine, square, triangular and sawtooth each at 8, 20, 40 and 100 Hz with amplitudes of 20, 50 and 90%.

Modulated sine waves were generated by multiplying two to five sine waves of varying frequency together and renormalizing the amplitudes such that they corresponded to 90% of maximum. The combinations of frequencies for the modulated sine waves were as follows: #1- 4, 6 Hz, #2- 4, 6, 8 Hz, #3- 4, 6, 8, 10 Hz, #4- 4, 6, 8, 10, 12 Hz and #5- 4, 6, 8, 10, 12, 14 Hz. Phase relations were not varied.

Quasiperiodic signals were considered a special case of modulated sine waves and five signals were produced by summing two sine waves in which the frequencies were irrationally (mathematically) related. The frequency relations were the square roots of 3, 7, 9, 11 and 13.

Chaotic signals were generated by the numeric integration or iteration of several well known nonlinear systems. The logistic map[2,6,8] was iterated at four values of the parameter k (2.5, 3.2, 3.5, 4). The continuous chaotic systems (flows) -- Duffing, Lorenz, Rössler, Silnikov -- were numerically integrated with a custom program utilizing a fourth-order Runge-Kutta algorithm. Chaotic solutions to the systems of differential equations were generated. Parameter values and step-sizes are reported in the results section.

Of the three random signals generated, the first was a discontinuous pseudorandom time series obtained from Turbo Pascal. The second was a continuous, low-frequency (0-25 Hz) random signal obtained by successive (nine times) smoothing (19 point moving average) of the discontinuous pseudorandom time series. The third random continuous signal was generated by convoluting a triangular function with the Fourier transformation of the pseudorandom number time series. A reverse Fourier transform was then performed to reconstitute the desired time series. The passband of the triangular function started at 1 Hz, peaked at 8 Hz and ended at 12 Hz.

Graphic Analysis Tools

*Phase plane plots* - Phase plane plots are one representation of phase space (state space) and demonstrate the behavior of a system (in two dimensions) by plotting the relation between a signal's amplitude and one or more of its derivatives[4,12,13]. The most common two dimensional plot is amplitude (abscissa) vs first derivative (ordinate). A phase space plot can be three-dimensional with the third axis being the second derivative. In multidimensional systems (for example, a system of three sets of differential equations), each variable represents the x, y and z axes. For the purposes of this study, we limited ourselves to two-dimensional phase plane plots of three different types. The first is that described above, signal amplitude versus the first derivative of amplitude, *(first order phase plane plot)*. The second type is a plot of first derivative versus second derivative *(second order phase plane plot)*. The third type is a plot of amplitude versus the second derivative of the amplitude *(double order phase plane plot)*. Derivatives were calculated at a point ($X_i$) by subtracting the value of the subsequent point ($X_{i+1}$) from the point in question. This is referred to as a "lag 1" derivative, and all derivatives for this paper were of this type.

A periodic phase plane plot was defined as a series of orbits that after a given time interval (the period), the orbit returns to the starting point and overlaps the previous one. A chaotic phase plane plot was defined as one that demonstrated sensitive dependence on initial conditions, banding and forbidden zones. We used a visual estimate of sensitive dependence and it was considered to exist when in either the phase plane plot or return map, multiple orbits passed very near each other at one point in the plot, and later had divergent trajectories in another area of the plot. Banding was defined as a series of orbits very close together, separated by a zone (forbidden zone) that contained few or no orbits. A random phase plane plot was defined as one showing no structure.

*Return maps* - Return maps demonstrate the relation between the amplitude at a given point in time ($X_t$) and the amplitude at some future point ($X_{t+\Delta t}$), where the difference between them (delta t) is called the lag. The construction of the return maps was performed by plotting the point in question ($X_t$) on the abscissa and the lagged point ($X_{t+\Delta t}$) on the ordinate. The lag was chosen such that the return map occupied the most space within the bounds of the graph. When discrete data are used to construct the plots, the phase plane plot and the return map (if appropriately lagged) are essentially the same. Therefore, in the analysis of return maps, the same criteria for periodicity, randomness and chaos were used as in the analysis of phase plane plots.

*Poincaré sections* - Two types of Poincaré sections have been described[4,12,13,14,123] – "stroboscopic" and planar sections. We used the stroboscopic technique, which has features of both the phase plane plot and the return map. Points and their first derivatives were chosen from a time series in question and plotted on the same graph as the phase plane plot. The time, or "best lag", between points was chosen by spectral analysis as the digitization rate divided by the fundamental frequency. That is, in a time series with a first harmonic of 10 Hz, and a digitization rate of 1000 Hz, the ideal lag would be 1000/10, or 100 points. Other lags were chosen around this best lag in an attempt to come closest to the effective fundamental frequency of the system as distinct from the analytic (measured) frequency.

A Poincaré section of a periodic signal consists of one isolated point or small group of points in phase space. Random systems have sections with no clear pattern (other than a Gaussian distribution), and chaotic systems have sections consisting of infinitely large, ordered sets of points that are arranged in a self-similar (fractal) structure.

Numeric Analysis Tools

*Correlation dimension* - Correlation dimension is a measure of a signal's complexity - the more complex a signal is, the higher its dimension[4,12,94,95,97,98]. We used a modification of a standard computational technique for correlation dimension[102,124]. The length of the time series used for the calculation varied between 1000 and 6000 points. The algorithm allows embedding dimension selection between 1 and 11. Eleven was always chosen so as to reduce the possibility that a high dimensional system was embedded in a dimension lower than its characteristic dimension. The algorithm analyzes a maximum of one thousand points (vectors). The *ideal lag* was calculated from the following formula using the first zero of the autocorrelation function (vide infra): Lag = Z / (D - 1), where Z = the first autocorrelation zero, and D is the embedding dimension[123,124]. Therefore, since our embedding dimension was constant (11), the ideal lag was the first autocorrelation zero divided by ten. In addition to using the ideal lag, two lags were chosen from each side of the ideal so as to bracket the preferred value. Most ideal lags were three, therefore lags of 1, 2, 4 and 5 were chosen in addition to three. One signal had an ideal lag of 5 and in that situation, additional lags of 1, 3, 7 and 9 were chosen. If the ideal lag was 1, then lags of 2 and 3 were also chosen for analysis. After the computation was complete, correlation dimension was estimated by a graphic representation of all the lag curves. The portions of all curves that were horizontal were visually identified. Mean values of those horizontal segments were calculated along with the standard deviation for the values and were reported to two decimal places.

Five signals were subjected to further analysis by calculation of correlation dimension on a series of windows in the time series. All windows were 1000 points in length and were contiguous. Therefore, a 6000 point time series was divided into six segments and dimension calculations were performed on each segment (window). We report the numbers obtained from all dimension calculations to two decimal places, but we realize the inaccuracy in doing so (vide infra).

*Spectral analysis* - This technique was performed using a standard fast Fourier transform (FFT) algorithm (Cooley-Tukey) on a time series of 8,192 points[104]. Raw spectra (sum of the absolute values of the real and imaginary components - also called the magnitude), power spectra (sum of the squares of the real and imaginary components), and log spectra (log of the raw spectrum) were calculated for each signal. There was no attempt to quantify the relative power of different frequencies in a given spectrum since the tools were designed only to determine which frequencies were present in a signal and whether or not the signal exhibited narrow or broadband characteristics.

For purposes of comparison between periodic, random and chaotic signals, the step size in the chaotic and random systems were arbitrarily defined as 1/1000th of a second (one digitization cycle). This allows the labeling of the FFT axes like those in the periodic signals. All signals were analyzed with a cosine (Kaiser-Bessel) window[126].

Raw spectra were classified into narrow and broadband by two techniques; visual and analytic. Visually, broad-band spectra were defined as those exhibiting energy enclosing a large range of frequencies. Narrow-band spectra were defined as isolated spikes in the spectrum with little or no broad-band component. In the analytic techniques, major peaks, and the central regions of energy distributions in the spectra were visually identified. The magnitude of the transform at that point (bin) and the surrounding 23 points (for a total of 3 Hz, given a 8192 point FFT) were summed. All harmonic values for that frequency were summed and added to the magnitude of the fundamental frequency. This magnitude, divided by the total magnitude of the transform (sum of all 8192 points), expressed as percent, was defined as the harmonic magnitude ratio (HMR). These values were calculated for all continuous signals.

*Autocorrelation* - Autocorrelation is a measure of a signal's self-similarity and is not a standard tool of nonlinear dynamics. In this study, it was used as an adjunct to the correlation dimension calculation. Autocorrelation was performed using a standard statistical package (BMDP Statistical Software, Inc., Los Angeles), on a minimum of 400 consecutive points. The first zero crossing was defined as the first point that was equal to or less than zero in the autocorrelation result.

Addition of Noise

Gaussian noise was added to each signal at levels of 1, 2, 5, 10 and 20% noise. The amplitude of the noise was defined as a function of the signal amplitude. Six standard deviations of the noise amplitude distribution was adjusted to the required percentage of the signal amplitude. Thus, 10% noise injected into a signal would consist of adjusting six standard deviations of the noise distribution to enclose 10% of the signal's amplitude.

Results

*Phase plane plots* - Figure 1 shows the three types of phase plane plots performed on a periodic signal. The first and second order phase plane plots always exhibited the most information on the signal's behavior. Trajectories were separated widely, were followed easily, and the figure occupied most of the plane. The trajectories on double order phase plane plots were always narrow, oriented at an angle to standard axes, and the trajectories were difficult to follow. Both first and second order plots exhibited the characteristics expected from periodic, chaotic and random signals, as opposed to the double order plot which was often difficult to interpret.

Figure 2 is an example of three periodic signals (A,B,C) and their phase plane plots (D,E,F). Panels D and E demonstrate the properties of periodic signals. The trajectory starts at its initial condition, traces the appropriate path, and returns to the initial point. From that point, the trajectory follows the same path exactly. The third panel is an example of a quasiperiodic signal, exhibiting the "periodic-like" structure, but also demonstrating that it never returns exactly to the initial point - it is slightly different from the previous. This difference between starting and ending points of the trajectories is maintained throughout the next trajectory, thus two adjacent trajectories will never overlap exactly. The trajectories will continue to fill the space of the phase plane plot until it is a complete torus.

Figure 3 shows the discontinuous (A), continuous (B) random signals and their phase plane plots (C,D). Note that in neither case is there any clear internal structure in the phase plane plots.

Figure 4 shows three chaotic signals and their phase plane plots demonstrating the classic banding, forbidden zones and sensitive dependence on initial conditions. There is an overall pattern seen in the plots with characteristics between periodic and random behavior. The overall form of the behavior can be predicted (trajectories will oscillate between two general areas or around one general area), but the exact behavior of a single orbit cannot be predicted. The figure legend gives parameter values, initial conditions and step sizes for each of the signals. Sensitive dependence on initial conditions is seen in all three plots. The trajectory originates at a point and return to near the original point. On the second orbit of the trajectory, the small difference between the starting point of the first and second orbits is amplified and the direction and location of the subsequent orbits cannot be predicted. This amplification of the small differences in position at the beginning of orbits is contrasted with the quasiperiodic behavior. The small differences there were not amplified. Therefore, the trajectory's behavior could be predicted.

While varying the frequency of the sine wave from 8 to 100 Hz, changes in the form of the phase plane plot were noted and figure 5 demonstrates this relation. Note that as the signal increases in frequency, the orbits do not maintain their smooth appearance but are made up of short, flat segments. This flattening is first noticeable at 40 Hz ($1/25^{th}$ the sampling rate) and very noticeable at 100 Hz ($1/10^{th}$ the sampling rate).

Phase plane plots were not performed on the discontinuous signals such as the logistic map, triangular, sawtooth and square wave signals.

*Poincaré Sections* - Poincaré sections of periodic signals all demonstrated isolated points in their graphs of state space. The random signals showed a Gaussian random distribution of points. Sections of chaotic signals showed patterns analogous to those observed in previous studies[125] - ordered areas of apparent self-similarity. The stroboscopic Poincaré sections of chaotic systems were very difficult and time-consuming to perform. The accuracy required in selecting the lag is greater than four significant digits. Sections of the computer generated periodic signals were easily performed because they are mathematically perfect - all zeros, minima and maxima correspond to points. This makes calculation of the fundamental frequency accurate and thus the choice of lag accurate. In the chaotic systems, step sizes as small as 0.001 were needed as well as lags greater than 6000 points. To construct plots with these parameters, over 4 million points were calculated, requiring ten hours on the personal computer.

*Return Maps* - Because digitally sampled data were used, there was a similarity between the return map and the phase plane plot - figure 6 demonstrates this similarity. Return maps compare one point in a time series to the next (X vs X + first derivative), while the phase plane plot compares a point to its first derivative (X vs first derivative). With the exception of noise effects (vide infra), the only major difference between the phase plane plot and the appropriately lagged return map is their 45° rotation with respect to each other.

*Correlation Dimension* - Table I shows the results of the autocorrelation zeros, correlation dimensions and standard deviations of the dimensions for all signals studied (first 1000 points). The sine and sawtooth waveforms all had correlation dimensions near 1. Note that as the frequency of the sine wave was increased, the apparent dimension also increased. This is explained by the change in the plateau region of the graph. As the ratio of frequency to sampling rate increases, the plateau region is shifted rightward and becomes smaller. This decrease in size changes the accuracy of the calculation as manifest by the increase in standard deviation. The square wave's dimension (1.42) was close to that of the 100 Hz sine wave (1.48), probably indicating that the undersampled sine wave appears more discontinuous to the algorithm, like the square wave.

The triangular wave's dimension (1.2) was intermediate to the sine and square waves, probably indicating that it has some discontinuities but they are not as dramatic as the square wave.

The dimension of modulated sine waves was relatively constant (approximately 1.5) when two, three and four sine waves were modulated. When five and six waves were modulated, a common plateau among the lags was not found, thus complicating the interpretation. With the exception of the first quasiperiodic signal (dimension = 1.76), all the other quasiperiodic signals had dimensions very near 2.2.

Dimensions of the periodic solutions of the logistic map were not measurable. The chaotic solution (k=4) had a dimension of 1.49. The chaotic solutions to the Duffing, Lorenz and Silnikov systems all had dimensions near 2.2.

The discontinuous random time series had an incalculable dimension since there was no clear plateau present and thus the reported dimension of greater than 10. Both continuous random signals had dimensions near 2.7. Figure 7 demonstrates three examples of graphic results of the dimension calculation on the first 1000 points of the time series.

The calculations described above were performed only on 1000 points. The periodic signals repeat at least once over that interval, thus calculation beyond 1000 points is unnecessary. The chaotic and random signals and one periodic signal were further analyzed beyond the 1000 point limit. Additional calculations of dimension were performed on 1000 point windows out to a maximum of 6000 points. These data are reported in Table II. Note that the quasiperiodic signal's dimension remained relatively constant varying only between 2.19 and 2.22, giving a coefficient of variation of only 0.5. The variability in the chaotic and random signals was much greater. Duffing's oscillator varied between 2.29 and 2.83, with a coefficient of variation of 7.9. Lorenz' system had a minimum of 1.62 and a maximum of 2.03, with a coefficient of variation of 7.5. The Silnikov system's minimum was 1.65, its maximum was 2.39 which gave a coefficient of variation of 13.7. The first continuous random signal had a minimum dimension of 2.12 and a maximum of 2.6, with a coefficient of variation of 6.7. The second random continuous signal varied between 2.87 and 4.25, giving a coefficient of variation of 14.5.

*Spectral Analysis* - The overall structure of the raw and power spectra were similar, but the major frequency spikes were amplified and the low power energies were attenuated in the power spectra. Log spectra attenuated the higher power spikes and amplified the lower power energy. Figure 8 shows examples of unwindowed periodic, chaotic and random signal spectra each displayed in the three forms.

All periodic signals exhibited classic narrow-band spectra in the raw and power spectra. Interpretation of the log spectrum was difficult because of the amplification of small spectral values. Figure 8C demonstrates what might be considered a broadband spectrum in a periodic signal. All random spectra were broad band, the only difference being the frequencies covered. The discontinuous spectrum displayed energy from zero Hz to the Nyquist limit (500 Hz). The heavy filtering of the continuous random signal limited its range of frequencies from 0 to 25 Hz. The FFT filtered random signals had a broadband spectrum that started at 1 Hz, peaked at 8 Hz and tapered to 12 Hz.

Figure 9 shows the spectra of the continuous chaotic signals (the logistic map was not analyzed because of its discontinuous nature). Duffing's oscillator is an example of a signal that appears to be a narrow band spectrum with small amounts of "noise". In contrast, Lorenz' system shows a broad-band spectrum. The Silnikov system has spectral characteristics between the two.

All periodic signals had HMR's greater than 97%. The random signals were approximately 40% and the chaotic signals varied between 17 and 80%.

*Effects of Noise* - The addition of Gaussian noise to the signals affected the analysis tools in different ways (Poincaré sections were not analyzed). The phase plane plot was probably the most affected by even small amounts of noise. Figure 10 demonstrates that 1% noise, not visible in the original signal, can severely disrupt a phase plane plot and 10% noise completely effaces the underlying structure. Noise significantly affected not only the periodic signal phase plane plots, but also the chaotic phase plane plots, such that the underlying structure was completely masked by small amounts of noise.

Return maps were also affected by noise, but in a much less dramatic fashion. Figure 11 shows the same noise levels used in the phase plane plots, but what little effect it had on the structure of the return map (contrast figure 11 to figure 10). All signals, periodic and random were easily interpretable with 1% noise, and many with 10% noise were identifiable as periodic or chaotic.

Figure 12 demonstrates the effect of progressive increases in noise on the fractal dimension calculation. Note that at small amounts of noise, a curve at low radius is formed and as the noise increases, the curve becomes taller, moving to larger radii. Even at 20% noise, the underlying dimension curve for the sine wave was always visible.

The power spectra exhibited a broad range of reactions to Gaussian noise. The raw FFT and power spectra were relatively immune to noise. There were no changes in the raw FFT spectrum until a noise level of 20% was reached. Then, only minor variations in the baseline could be observed (Figure 13). The power spectrum calculation showed no effect from noise up to 20%. The log FFT was the most sensitive, exhibiting easily detected noise at even 1%, and remaining unchanged to 20% (Figure 13).

HMR was also affected with noise levels of 1, 5 and 20% dropping the HMR to 80.3, 44.3 and 17.3% respectively.

Discussion

Since its original description in theoretical mathematics, nonlinear dynamics has been applied to diverse physical systems[17,18,21,25,26,28]. Many techniques are used by nonlinear dynamicists for the analysis of potentially chaotic behaviors[4,12,28]. Some techniques are used on discontinuous signals looking for bifurcation behavior, others on the analysis of continuous data[4,12,18]. A few of the latter techniques have been applied to limited areas of electroencephalography and electrocardiography[6,9,19], but not all techniques have been used or carefully applied to this area. We undertook this study to standardize the expected outputs from each of the chaotic tools, and determine the ability of each of the tools to determine whether a given signal is periodic, chaotic or random.

Phase plane plots and return maps are commonly used in the analysis of continuous signals. Periodic signals, by definition, repeat over their period, and this process is easily visualized with these tools. Random signals, in contrast, will have unpredictable trajectories and this is also readily visible. Chaotic signals, on the other hand, may or may not be easily identifiable using these techniques alone. Trajectories that show sensitive dependence on initial conditions, banding and forbidden zones would be highly suggestive of a chaotic process. But the absence of these structures would not exclude a high dimensional chaotic process embedded in a lower dimensional space. Based on the data presented here, we feel that periodic signals are easily identifiable with phase plane plots and return maps. The presence of sensitive dependence on initial conditions, banding and forbidden zones is highly suggestive of chaotic behavior, but not conclusive (vide infra).

Based on the data from our study we would recommend that the first and second order phase plane plots be studied because they reveal more information regarding the trajectories of the system than the double order phase plane plot. In addition, because of the effects of sampling rate on the phase plane plot, at least 25 times oversampling (25 times the maximum frequency of the signal) should be used to limit the flattening of trajectories.

Based on the data from our study, we would recommend the very careful use and interpretation of the Poincaré section in real signals of short duration. Not only is there the difficulty in selecting an exact lag, but there must be a sufficient number of points for the graph to be meaningful. A signal consisting of only 80 cycles of the fundamental frequency would produce a Poincaré section of only 80 points. If there were a clear pattern to the points then a chaotic process might be suggested. But proving that the pattern is fractal, a requirement for the diagnosis of chaos, would not be possible. In addition, the absence of a pattern would not exclude a chaotic process since this might imply an incorrect lag or insufficient sampling frequency.

In contrast to phase plane plots, return maps are relatively immune to low levels of noise. The addition of small amounts of noise to a signal did not change the ability of the tool to detect periodicity, randomness or chaos. We would recommend that in addition to plotting the first and second order phase plane plots, that an appropriately lagged return map also be studied.

Fractal (correlation) dimension has been used previously as an aid to diagnosing a chaotic process. It is used as a measure of a signal's complexity and, in this study, we have generally confirmed its use in that regard. We have demonstrated that many periodic signals are low dimensional (<2), and that the chaotic signals that we studied are higher in complexity (>2). But we have also demonstrated that a quasiperiodic signal can be constructed that equals or exceeds the dimension of a classic chaotic signal. In addition, a low frequency random process can also have a dimension near that of a chaotic process. The presence of a non-integer dimension has also been associated with fractal (chaotic) processes[94]. Given that many of our periodic waveforms and the two random continuous waveforms had non-integer dimension, the utility of non-integer dimensions is also in question. These findings suggest that fractal dimension may not be useful in diagnosing a chaotic process.

Furthermore, there are many technical problems in the use of fractal (correlation) dimension. First, there must be adequate sampling of the signal, and we recommend, as in the phase plane plot, a 25 times oversampling. In addition, the variability in the result was well demonstrated in the calculations over multiple windows (Table II). Dimension values obtained from the algorithm can vary as much as 15% in perfect mathematical systems. This stationarity is usually not seen in most biological systems, thus tending to widen the variability of the calculations. Based also on the data from window calculations, we recommend that instead of reporting dimension to multiple decimal places, only general categories be used (e.g., low, intermediate and high).

Spectral analysis is not a tool specific to nonlinear dynamics, but has been used in many studies to determine if a given signal is chaotic or not[71,72,73]. The presence of a broad-band spectrum has been attributed to chaotic processes, and in most cases, chaotic signals are broadband. But random signals are also broad band. In addition, some chaotic signals may have most of their energy in fundamental and harmonic frequencies. Based on these two findings, chaos cannot be detected with any certainty by spectral analysis alone. HMR may be useful in quantifying what our eye sees. It easily separated the periodic spectra from chaotic and random ones.

A problem with many of the applications of spectral analysis is the selection of type of spectrum used. Some have used power spectra, others have used log spectra and called them power spectra. We understand that this is an long-standing problem with the display of spectral data. Based on our data, we recommend the use of the raw spectrum because it does not "hide" small areas of broad band information, like the power spectrum, and it does not amplify very small amounts of noise like the log spectrum.

Another major problem with the use of spectral analysis is the definition of narrow and broad band. This in not a unique problem and our study will certainly not solve it, but HMR may be useful in quantifying what our eye sees in the spectrum.

Noise affects each of the tools in a different manner. Phase plane plots are most effected by noise, as little as 1% severely disrupting structure. In contrast, return maps seem somewhat immune to noise at low levels. Noise affects the curves obtained from the calculation of correlation dimension, but the dimension of the underlying waveform is not obscured and remains easily identifiable. The raw and power spectra are least affected by noise, but the log FFT demonstrates its effects at very low levels. Figure 14 demonstrates why phase plane plots are disrupted by noise. The upper three panels (A,B,C) are the time series of three sine waves with 0, 1% and 10% noise respectively. No irregularities are noted in the first two signals, and with 10% noise the underlying structure is still easily visible. Panels D, E and F show the derivatives of panels A, B, and C respectively (note the cosine function in the derivatives). Panel E shows that 1% noise is easily visible and in Panel F, 10% noise effaces the derivative almost completely. Panels A, B, and C represent the abscissa and panels D, E and F represent the ordinate in a phase plane plot. With substantial amounts of noise, filtering may be required so that the underlying structure of the plot is visible. But heavy filtering can disrupt the underlying structure and efface an ordered behavior.

Taking our data as a whole, table III demonstrates our interpretation of the relative abilities of the tools described here to detect periodic, chaotic and random signals. The table represents, in a qualitative way, the relative abilities to detect periodic, chaotic and random processes in signals without noise.

The ideal method for detection of chaos is the calculation of the Lyapunov exponent. This technique certainly works on mathematically generated time series, and even in very controlled physical experiments. But two factors limit its use in biological systems. The first is the problem of system stationarity. For an accurate calculation of the Lyapunov exponent, the system producing the signal must be stationary - that is, the parameters that affect its behavior must be maintained constant. This can rarely be assured in biological systems. Secondly, sufficient data must be available for an accurate calculation. At least 10,000 cycles of the fundamental frequency are needed for a reasonable calculation, and this is often difficult to achieve. For example, over 30 seconds of ventricular fibrillation would be needed to achieve this amount of data, and the underlying system is usually changing (nonstationary) during that time. Also, the computation time for analysis of 10,000 cycles may require the use of a super-computer.

There are many limitations to our study. One lies in the definition of randomness. Randomness can never be diagnosed with any certainty, and we cannot be assured that our "random" signals may not have an underlying structure visible with newer analytical techniques. Furthermore, any continuous random signal will have a structure that is predictable over the short term because the signal is continuous. We have made the assumptions that our random signals are random (unpredictable) at some lag.

Another weakness is that we have only used three chaotic systems in our study. Chaotic systems and their associated behaviors are truly pleomorphic, and the study of only three limits the available behaviors. Not only have we limited ourselves to three systems, we have not studied the rich behavior easily obtainable by varying the parameters of the individual systems. This limited analysis of chaotic systems was chosen because of the amount of data to analyze can become formidable with even one system.

We have also limited ourselves to mathematically "pure" systems. A more thorough study might include real data obtained from real physical and electrical systems that are affected by noise.

We have also limited ourselves to the use of one algorithm for correlation dimension calculation. Calculation of dimension itself is an art and many algorithms exist. But our purpose was not to study multiple dimension algorithms, but to study known behaviors using standard computational techniques.

In summary, we have analyzed a series of standard signals with five classic tools of nonlinear dynamic analysis. Based on these analyses, we feel that none of the tools used alone are sufficiently sensitive or specific for the diagnosis of chaos. We recommend that, after careful, noise-limited collection and filtering of all signals, that they be subjected to all of the tools of nonlinear dynamic analysis to determine whether a signal is periodic, chaotic or random.

Acknowledgements - We would like to express our gratitude to Dr. Alfonso Albano for supplying us with the program for the calculation of correlation dimension, and for his thoughtful review of the manuscript.

References

1. Glass L, Mackey MC: From Clocks to Chaos: The Rhythms of Life, New Jersey, Princeton University Press, 1988.
3. Jensen RV: Classical Chaos. Amer Sci 1987;75:168-181
5. Holden AV. Chaos, New Jersey, Princeton University Press, 1986
6. Moon FC: Chaotic Vibrations, New York, John Wiley and Sons, 1987
7. Gleick J: Chaos: Making a New Science, New York, New York, 1987.
12. Thompson JMT, Stewart HB: Nonlinear Dynamics and Chaos, New York, John Wiley and Sons, New York, 1986
13. Bergé P, Pomeau Y, Vidal C: Order within Chaos, New York, John Wiley and Sons, 1984.
17. Kaplan JL, Yorke JA: The onset of chaos in a fluid flow model of Lorenz. Ann NY Acad Sci 1979;316:400-407
18. Sussman GJ, Wisdom J: Numerical evidence that the motion of pluto is chaotic. Science 1988;241:433-437
20. Spiegel EA, Wolf A: Chaos and the solar cycle. Ann NY Acad Sci 1987;497:55-60
25. May RM: Biological populations with nonoverlapping generations: Stable points, stable cycles, and chaos. Science 1974;186:645-647
26. Pool, R: Ecologists flirt with chaos. Science 1989;243:310-313
28. Rogers TD, Yang ZC, Yip LW: Complete chaos in a simple epidemiological model. J Math Biol 1986;23:263-268
31. Kearney RE, Hunter IW: Nonlinear identification of stretch reflex dynamics. Ann Biomed Eng 1988;16:79-94
33. Goldberger AL, Findley LJ, Blackburn MR, Mandell AJ: Nonlinear dynamics in heart failure: Implications of long-wavelength cardiopulmonary oscillations. Am Heart J 1984;107:612-615
34. Glass L, Mackey MC: Pathological conditions resulting from instabilities in physiological control systems. Ann NY Acad Sci 1979;316:214-235
39. Sporns O, Roth S, Seelig F: Chaotic dynamics of two coupled biochemical oscillators. Physica D 1987;26:215-224
42. Babloyantz A, Destexhe A: Low-dimensional chaos in an instance of epilepsy. Proc Natl Acad Sci USA 1986;83:3513-3517
43. Watt RC, Hameroff SR: Phase space electroencephalography (EEG): A new mode of intraoperative EEG analysis. Int J Clin Monit Comput 1988;5:3-13
47. Feigenbaum MJ: Universal behavior in nonlinear systems. Physica D 1983;7:16-39
48. Feigenbaum MJ: Universal behavior in nonlinear systems. Los Alamos Science 1980;1:4-27
60. Guevara MR, Glass L, Shrier A: Phase locking, period-doubling bifurcations, and irregular dynamics in periodically stimulated cardiac cells. Science 1981;214:1350-1354
61. Glass L, Guevara MR, Shrier A: Bifurcation and chaos in a periodically stimulated cardiac oscillator. Physica D 1983;7:89-101
62. Glass L: Complex cardiac rhythms. Nature 1987;330:695-696
65. Goldberger AL, West BJ: Applications of nonlinear dynamics to clinical cardiology. Ann NY Acad Sci 1987;504:195-213
67. Chialvo DR, Jalife J: Nonlinear dynamics of cardiac excitation and impulse propagation. Nature 1987;330:749-752
71. Goldberger AL, West BJ: Chaos in Physiology: Health or Disease?, in Degn H, Holden AV, Olsen LF (eds): Chaos in Biological Systems, New York, Plenum Pub Corp, 1987, pp 1-4
72. Goldberger AL, Rigney DR: Sudden death is not chaos, in Kelso JAS, Mandell AJ (eds): Dynamic Patterns in Complex Systems, Singapore, World Scientific Pub, 1988, pp 248-264
73. Goldberger AL, Bhargava V, West BJ, Mandell AJ: Some observations on the question: Is ventricular fibrillation "chaos"?. Physica D 1986;19:282-289

88. Eckmann JP, Ruelle D: Ergodic theory of chaos and strange attractors. Rev Mod Physics 1985;57:617-656
89. Grassberger P, Procaccia I: Measuring the strangeness of strange attractors. Physica D 1983;9:189-208
94. Mandelbrot, B: *The Fractal Geometry of Nature*, New York, W.H. Freeman, 1983
96. Havstad JW, Ehlers CL: Attractor dimension of nonstationary dynamical systems from small data sets. Phys Rev A 1989;39:845-853
97. Farmer JD, Ott E, Yorke JA: The dimension of chaotic attractors. Physica D 1983;7:153-180
98. Grassberger P, Procaccia I: Characterization of strange attractors. Physical Rev Letters 1983;50:346-349
102. Albano AM, Mees AI, deGuzman GS, Rapp PE: Data requirements for reliable estimation of correlation dimensions. In Holden AV (ed), *Chaotic Biological Systems*, New York, Pergamon Press, 1987
104. Ramirez RW: *The FFT - Fundamentals and concepts*. New Jersey, Prentice-Hall, 1985
109. Babloyantz A, Destexhe A: Is the normal heart a periodic oscillator? Biol Cybern 1988;58:203-211
119. Stewart I: *Does God play dice? The mathematics of chaos*. Basil Blackwell Ltd., New York, 1989
124. Albano AM, Muench J, Schwartz C, Mees AI, Rapp PE. Singular value decomposition and the Grassberger-Procaccia algorithm. Phys Rev A, 1988.
125. Ueda Y, Hayashi C, akamatsu N. Computer simulation of nonlinear ordinary differential equations and nonperiodic oscillations. Elec Communic (Japan) 1973;56A:27-34
126. Harris FJ. On the use of windows for harmonic analysis with the discrete Fourier transform. Proc IEEE 1978;66(1):51-83

Figures

Figure 1. Three types of phase plane plots. Note that the first and second order plots, the trajectories are much easier to follow. In the double order plot, the trajectories are near each other and oriented at an angle to the standard axes.

Figure 2. (A) An example of the phase plane plot of a sine wave. After one cycle, the trajectory overlaps. (B) is an example of a modulated sine wave. Though obviously more complex than Figure 1A, it is also a periodic signal, repeating itself (overlapping) after one period. (C) A quasiperiodic signal - two sine waves multiplied together, the ratio of the frequencies being irrational. The trajectory never overlaps itself perfectly and will thus fill the space completely. The three dimensional representation of this figure would be a torus.

Figure 3. Discontinuous and continuous random signals. In neither case is there any structure observable in the phase plane plot other than regression toward the mean.

Figure 4. Time series and phase plane plots of Duffing's oscillator (B=7.5, k=0.05, x=3, dx=4, step size=0.01), the Lorenz attractor (Ro=15, Delta=10, Beta=8/3, x=0.1, y=0.1, z=0.1, stepsize=0.02) and the Silnikov attractor (a=0.5, b=0.5, c=0, d=1, x=0.123, y=0.2, z=0.1, stepsize=0.05). Note the characteristics of banding and forbidden zones in addition to sensitive dependence on initial conditions.

Figure 5. Effect of signals frequency on phase plane plot at constant sampling rate. At 50:1 sampling, the plot is smooth, forming a perfect circle. At 25:1 sampling, flattening between points is just visible. At 10:1 sampling, the trajectories are flattened, disrupting the expected structure seen in panel A.

Figure 6. Comparison between phase plane plot and return map of the same signal. Note that with the exception of a 45° rotation, they are equivalent. The lag (L) of the return map is 18.

Figure 7. Correlation dimension calculations of periodic, chaotic and random signals.

Figure 8. Three types of spectra for periodic, chaotic and random signals.

Figure 9. Spectra of the Duffing, Lorenz, Rossler and Silnikov chaotic attractors.

Figure 10. Effect of small amounts of noise on the phase plane plot. One percent noise cannot be visually detected in a raw signal, but the phase plane plot is severely disrupted by even this low amount. The plot is uninterpretable at noise levels of 10%.

Figure 11. The effect of noise on the return map is hardly noticeable at the 1% level, and at 10% noise, the structure is still visible.

Figure 12. Effect of noise on dimension. Note the curve at low radii starting at 1% noise, moving to higher radii and higher dimension. Even with 20% noise, the underlying plateau of the sine wave remains unchanged.

Figure 13. Spectra showing the effect of noise on each of the three types.

Figure 14. The effect of noise on a sine wave and its first derivative. The addition of noise to the sine wave does not significantly affect the structure of the signal until it reaches approximately 10% of the amplitude. But note that the first derivative is affected by as little as 1% noise - thus explaining the aberrations in the phase plane plot at low noise levels.

Table L Autocorrelation zero (Z) and correlation dimension (D) with standard deviation and harmonic magnitude ratio (HMR).

|  | Z | D | SD | HMR |
|---|---|---|---|---|
| Periodic |  |  |  |  |
| Sine |  |  |  |  |
| 8 Hz | 32 | 1.09 | 0.07 | 99.5 |
| 20 Hz | 13 | 1.15 | 0.09 | - |
| 40 Hz | 7 | 1.15 | 0.09 | - |
| 100 Hz | 3 | 1.48 | 0.46 | - |
| Square (8 Hz) | 33 | 1.42$^a$ | 0.17 | 98.8 |
| Triangular (8 Hz) | 32 | 1.20 | 0.13 | 99.5 |
| Sawtooth (8 Hz) | 27 | 0.96 | 0.09 | 98.7 |
| Modulated #1 | 42 | 1.40 | 0.28 | 99.6 |
| Modulated #2 | 32 | 1.54 | 0.23 | - |
| Modulated #3 | 16 | 1.63 | 0.32 | - |
| Modulated #4 | 31 | 1.00$^a$ | 0.20 | - |
| Modulated #5 | 24 | 2.74$^a$ | 0.15 | - |
| Quasiperiodic #1 | 27 | 1.76$^a$ | 0.12 | - |
| Quasiperiodic #2 | 20 | 2.22 | 0.09 | - |
| Quasiperiodic #3 | 18 | 2.18 | 0.10 | - |
| Quasiperiodic #4 | 15 | 2.17 | 0.14 | - |
| Quasiperiodic #5 | 14 | 2.20 | 0.04 | - |
| Chaotic |  |  |  |  |
| Logistic map |  |  |  |  |
| k = 2.5 | NA | 0.00$^b$ | - | - |
| k = 3.2 | NA | 0.00$^b$ | - | - |
| k = 3.5 | NA | 0.00$^b$ | - | - |
| k = 4 | NA | 1.49 | 0.46 | - |
| Duffing | 30 | 2.23 | 0.12 | 73.2 |
| Lorenz | 41 | 2.22 | 0.13 | 18.1 |
| Silnikof29 | 2.13 | 0.29 | 28.4 |  |
| Random |  |  |  |  |
| Discontinuous | NA | >10.00$^c$ | - | - |
| Continuous #1 | 49 | 2.76$^a$ | 0.27 | - |
| Continuous #2 | 33 | 2.72$^a$ | 0.11 | 43.0 | a - no common plateau among all lags calculated (only the ideal lag's plateau is reported)
b - fractal dimension indeterminate - dimension near zero.
c - fractal dimension indeterminate - no plateau was found.

Table II. Dimensions of quasiperiodic, chaotic and random continuous signals over different windows. The first window (1) was from 0 to 1000 points, the second (2) from 1001 to 2000 points, et. seq. Mean refers to the mean dimension of all windows and COV is the coefficient of variation.

| Signal | 1 | 2 | 3 | 4 | 5 | 6 | Mean | COV |
|---|---|---|---|---|---|---|---|---|
| Quasi | 2.22 | 2.21 | 2.21 | 2.21 | 2.19 | 2.20 | 2.21 | 0.5 |
| ±SD | 0.17 | 0.11 | 0.16 | 0.17 | 0.11 | 0.17 | 0.10 | |
| Duffing | 2.29 | 2.83 | 2.32 | 2.47 | 2.60 | 2.50 | 2.50 | 7.9 |
| ±SD | 0.21 | 0.40 | 0.18 | 0.20 | 0.09 | 0.19 | 0.20 | |
| Lorenz | 2.03 | 1.62 | 1.82 | 1.88 | 1.78 | 1.92 | 1.84 | 7.5 |
| ±SD | 0.15 | 0.16 | 0.12 | 0.24 | 0.24 | 0.21 | 0.14 | |
| Silnik | 2.06 | 1.65 | 2.39 | 2.20 | 1.84 | 2.30 | 2.07 | 13.7 |
| ±SD | 0.29 | 0.32 | 0.35 | 0.37 | 0.43 | 0.35 | 0.28 | |
| Rand #1 | 2.31 | 2.26 | 2.60 | 2.31 | 2.32 | 2.12 | 2.34 | 6.7 |
| ±SD | 0.33 | 0.24 | 0.54 | 0.46 | 0.38 | 0.47 | 0.16 | |
| Rand #2 | 3.24 | 2.87 | 3.80 | 3.21 | 4.25 | 3.85 | 3.54 | 14.5 |
| ±SD | 0.40 | 0.17 | 0.74 | 0.19 | 1.04 | 0.70 | 0.51 | |

Table III. Qualitative estimates overall value of a tool to diagnose periodicity, chaos and randomness. + = low, ++++ = high, ± = equivocal.

| Tool | Periodic | Chaotic | Random |
|---|---|---|---|
| Return map | ++++ | +++ | +++ |
| Phase plane plot | +++ | ++ | ++ |
| Spectral analysis | ++++ | + | + |
| Fractal dimension | ++ | ± | ++ |
| Poincaré section | +++ | ± | ± |

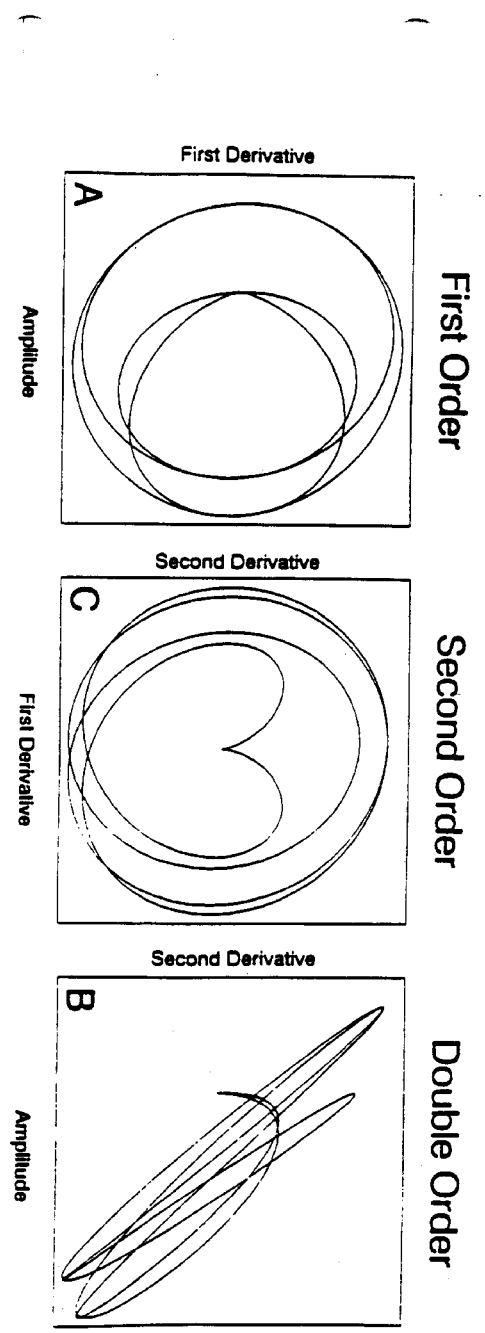
Figure 1. Three Types of Phase Plane Plots

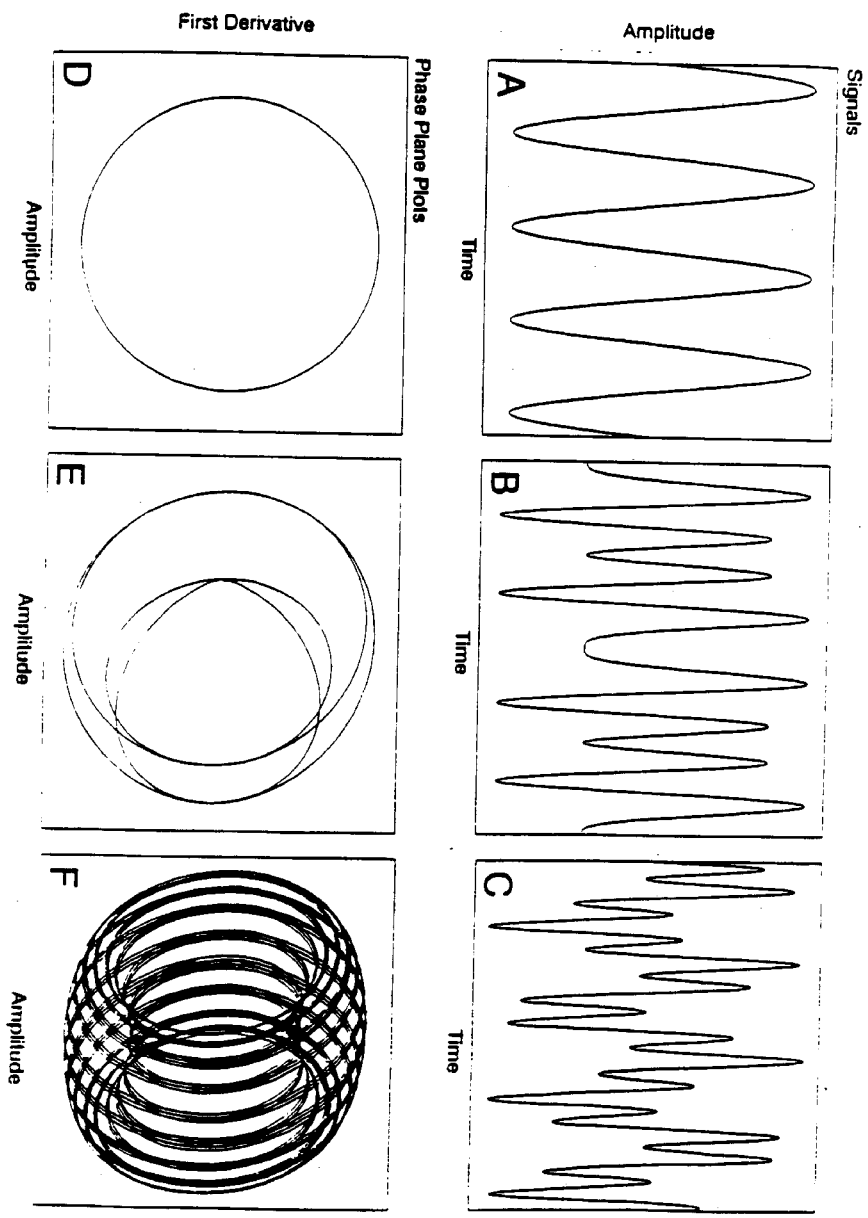
Figure 2. Periodic Signals and Phase Plane Plots

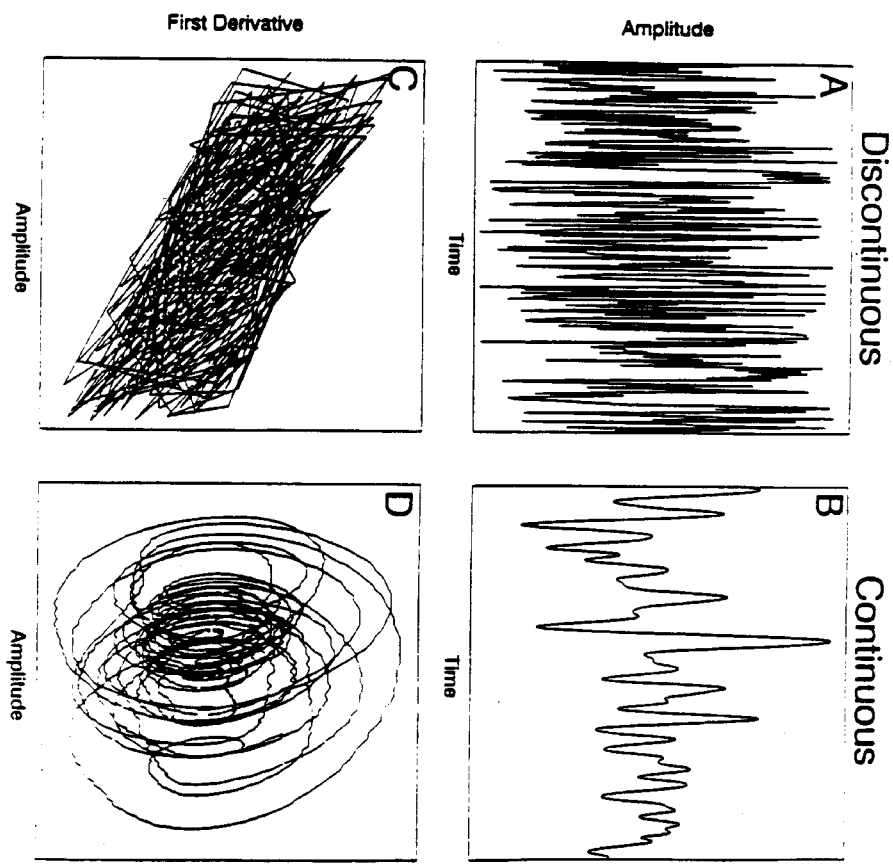
Figure 3. Random Signals and Phase Plane Plots

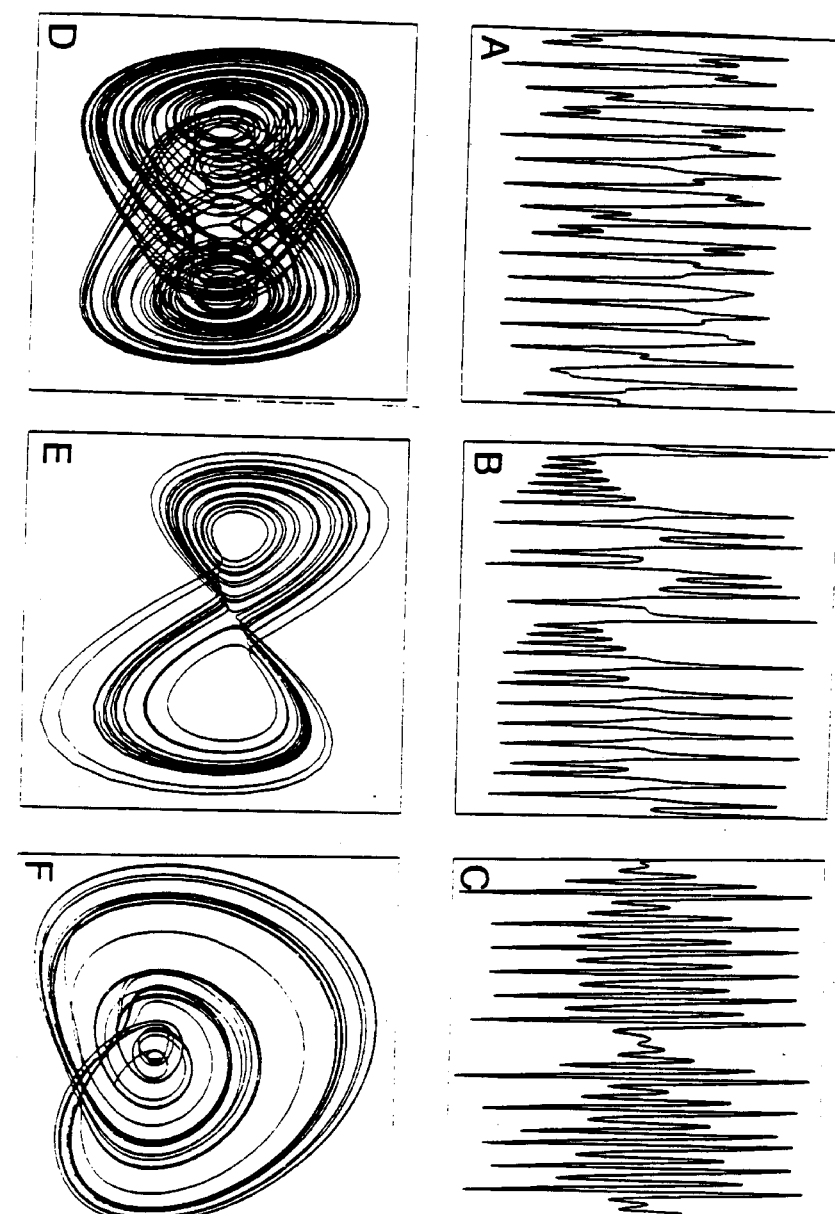
Figure 4. Three Chaotic Signals and Their Phase Plane Plots

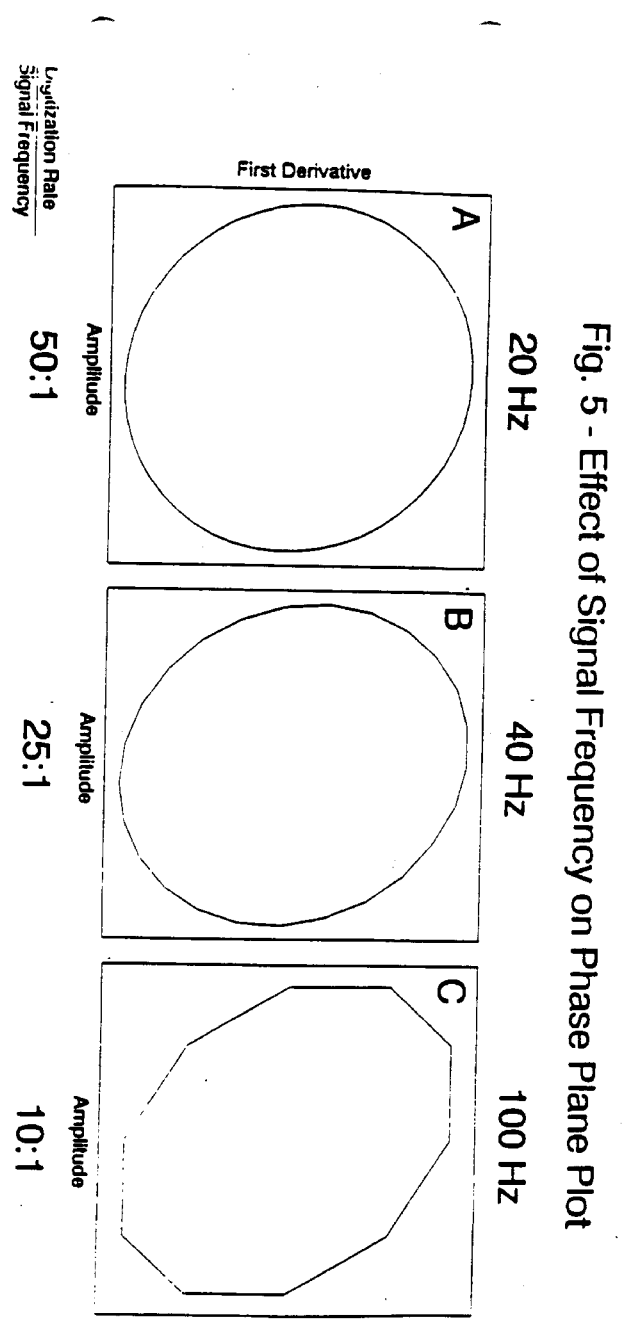
Fig. 5 - Effect of Signal Frequency on Phase Plane Plot

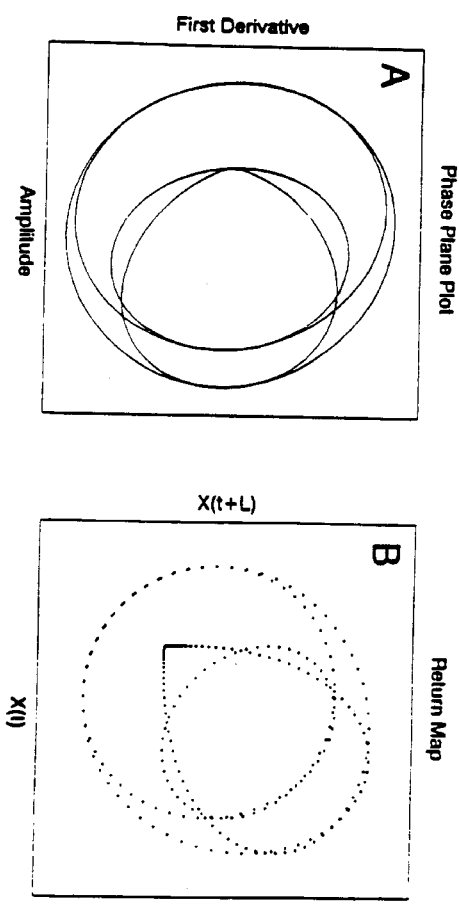
Figure 6. - Comparison of Phase Plane Plot and Return Map

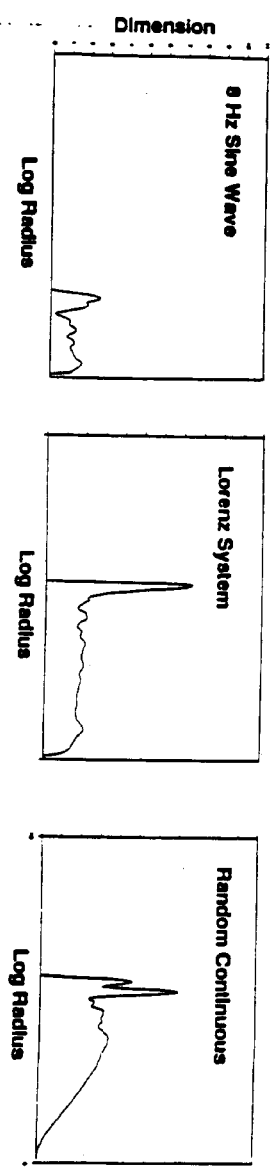
Figure 7. - Fractal Dimension of Periodic, Chaotic and Random Signals

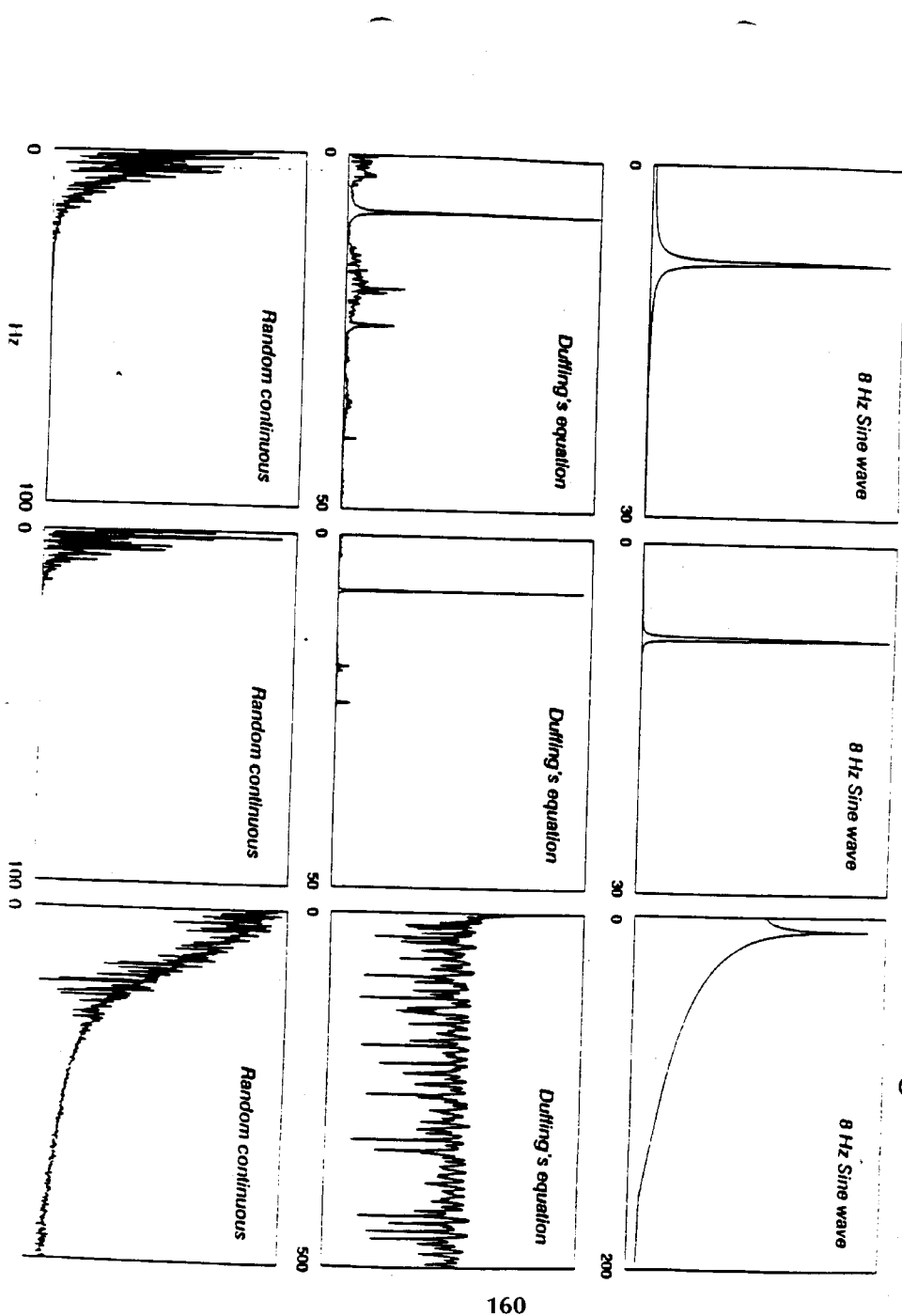
Figure 8. - Spectra of Periodic, Chaotic and Random Signals

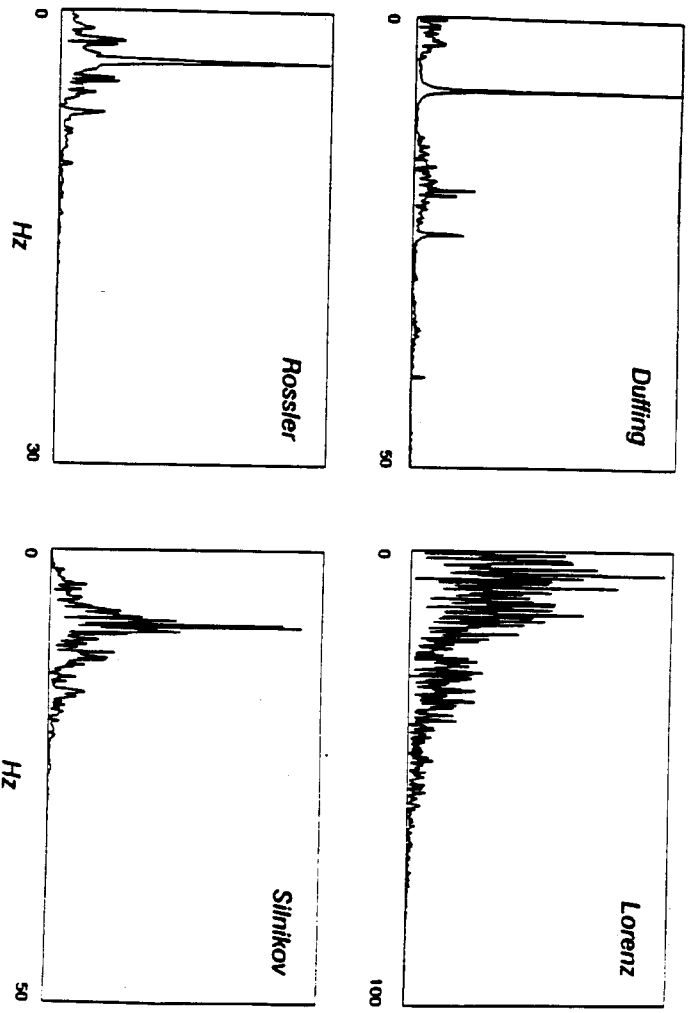
Figure 9. - Raw FFT of four chaotic signals

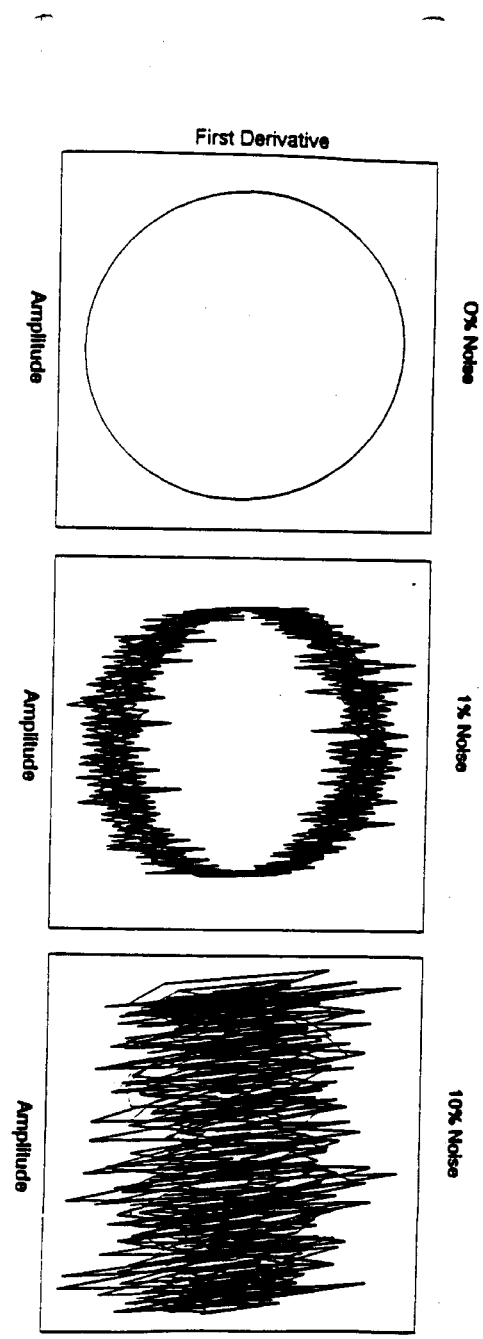
Figure 10. Effect of Noise on Sine Wave
First Order Phase Plane Plots

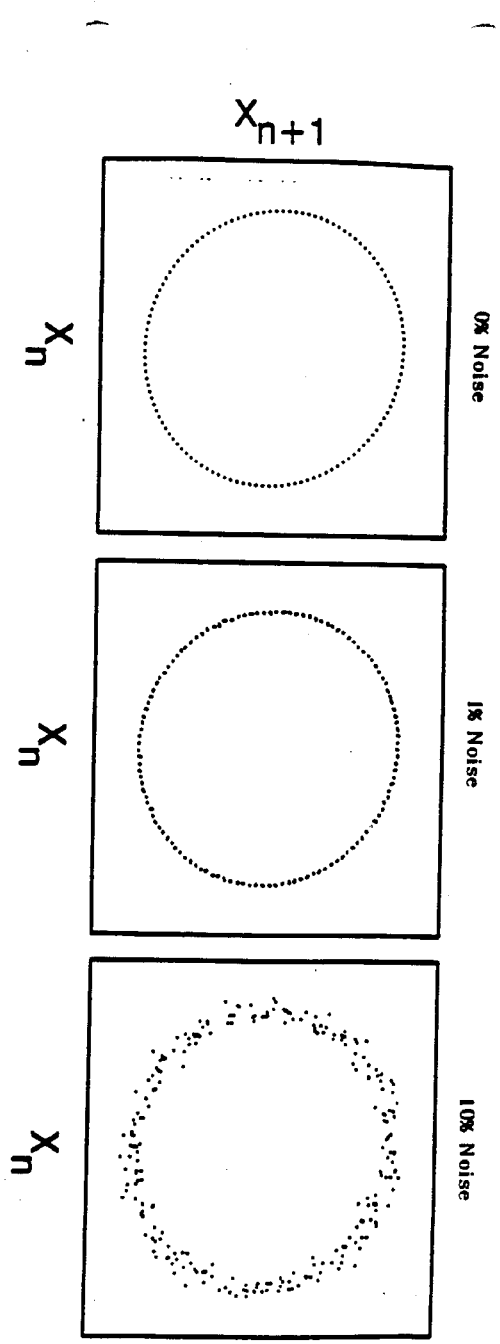
Figure 11. Effect of Noise on Sine Wave Return Maps

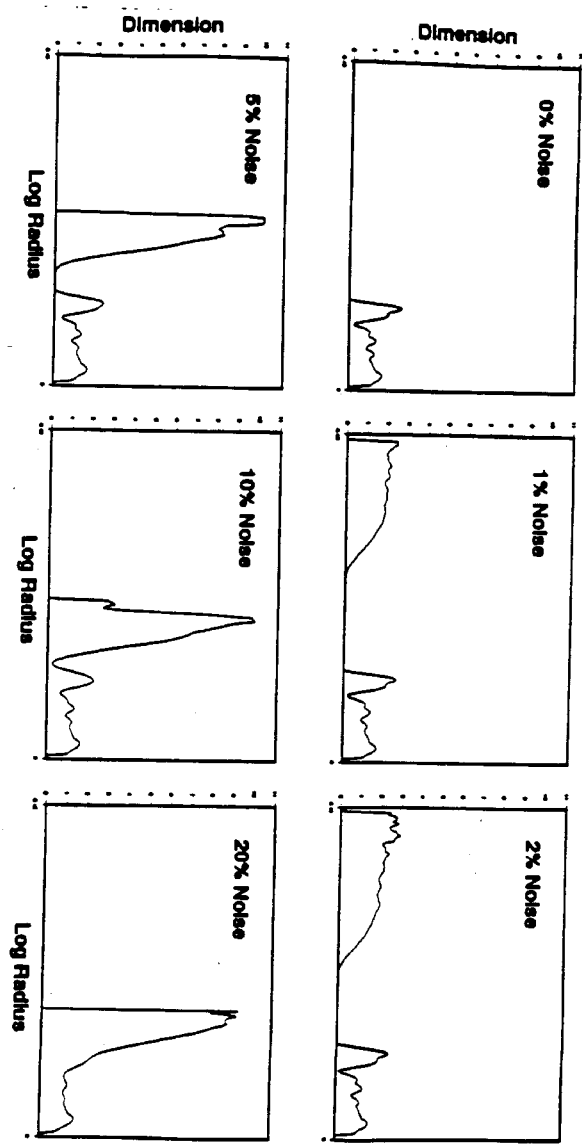
Figure 12. Effect of Noise on Dimension Calculations

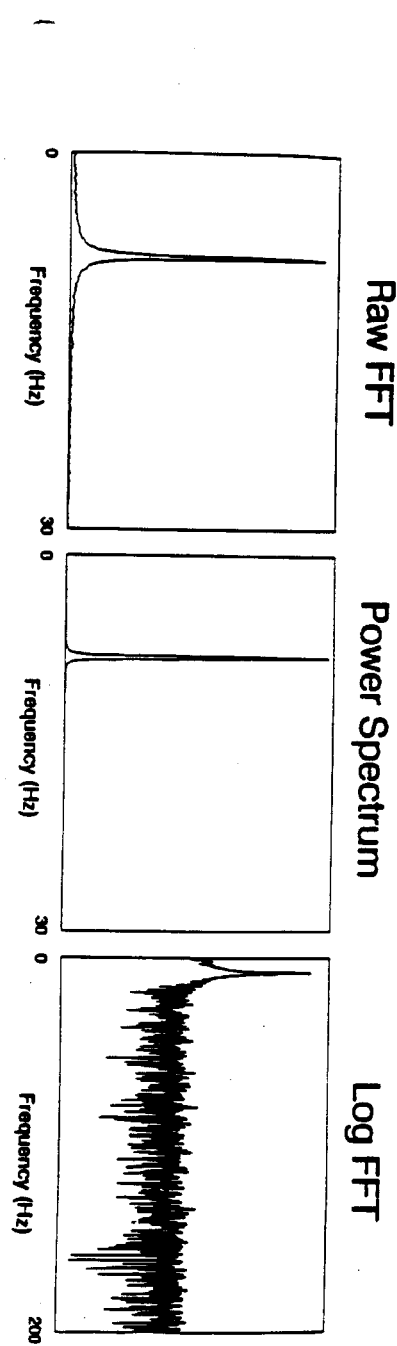
Figure 13. Spectra of an 8 Hz Sine Wave with 20% Noise
165

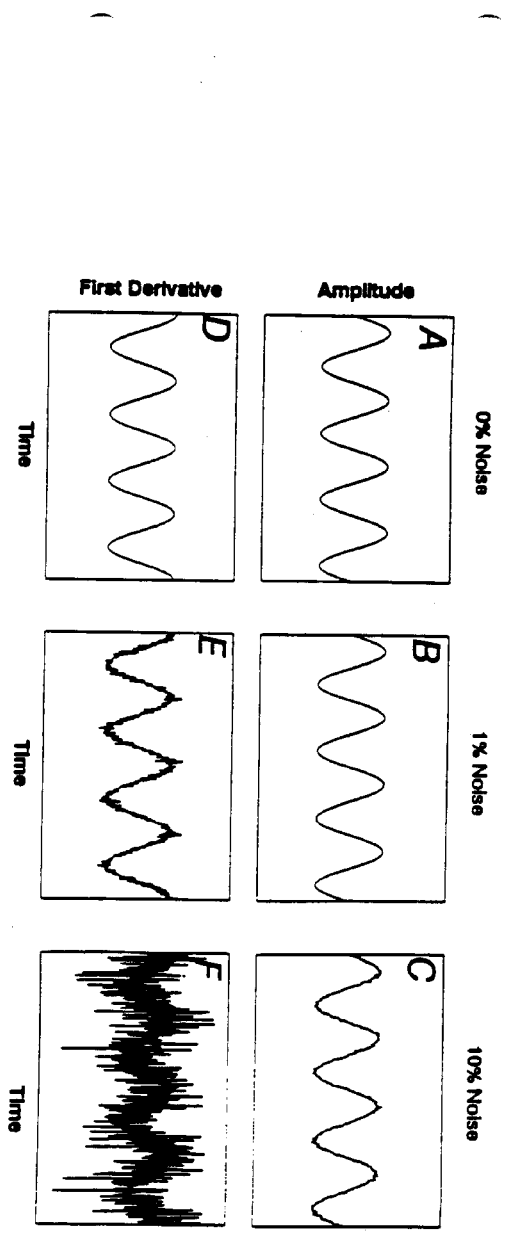
Figure 14. Effect of Noise on a Sine Wave And its First Derivative

PRINCIPAL INVESTIGATOR/PROGRAM DIREC Ifrayr Vatotyncuz..., ...

DESCRIPTION: State the application ... oad, long-term objectives and specific aims, making ... rence to the health relatedness of the project. Describe concisely the experimental design and methods for achieving these goals. Avoid summaries of past accomplishments and the use of the first person. This abstract is meant to serve as a succinct and accurate description of the proposed work when separated from the application. DO NOT EXCEED THE SPACE PROVIDED.

Despite major advances in the diagnosis and treatment of ischemic heart disease over the last decade, a substantial number of patients continue to suffer sudden cardiac death as a consequence of ventricular fibrillation. To date, no reliable predictive or preventive measures have been developed. This research proposal investigates a promising new approach. The recent discovery that very simple physical systems are capable of manifesting highly complex, seemingly random behavior has created a broad new field known as chaos theory. Classical chaos exhibits 3 characteristic features that allow it to be distinguished from random behavior: aperiodicity (absence of any strictly repetitive pattern), a bounded trajectory with definite form. (confinement to a limited region of phase space), and sensitive dependence on initial conditions (exponential divergence of adjacent events). A singularly important feature of chaos is that its evolution follows a well-defined, deterministic path, allowing its prediction.

By all outward appearances, ventricular fibrillation too is a highly complex, seemingly random phenomenon. If it can be shown to result from an underlying formal chaotic process, however, it should be possible to predict or prevent its occurrence. This research proposal therefore seeks to determine (i) if ventricular fibrillation is truly a chaotic process, (ii) if there are identifiable, intermediate dynamic stages that presage the onset of ventricular fibrillation, and (iii) if the transition to chaos can be interrupted by pharmacologic interventions.

We will use anesthetized closed and open chest dog preparations and induce ventricular fibrillation by a variety of interventions (quinidine overdose, acute coronary artery occlusion and reperfusion, regional hyperkalemia, hypothermia, and electrical stimulation). Whole animal studies will be complemented by isolated tissue studies designed to elucidate the underlying cellular mechanisms leading to chaos using microelectrode techniques. We will employ five different methods of dynamic analysis to detect chaos (power spectra, phase plane plots, Poincare sections, fractal dimension, and Lyapunov exponents). As a result of this research, we hope to develop and validate clinically relevant methods to detect ventricular fibrillation. These data will have direct relevance to a basic understanding of the pathophysiology and prevention of sudden cardiac death.

PRINCIPAL INVESTIGATOR/PROGRAM DIRECTOR: Hrayr Karagueuzian, Ph.D.

VENTRICULAR FIBRILLATION AS CHAOS

SPECIFIC AIMS

Despite major advances in the diagnosis and treatment of ischemic heart disease over the last decade, a substantial number of patients continue to suffer sudden cardiac death as a consequence of ventricular fibrillation. To this date, no reliable predictive or preventive measures have been developed. This research proposal investigates a promising new approach.

The recent discovery that very simple physical systems are capable of manifesting highly complex, seemingly random behavior has created a broad new field known as chaos theory [1-6]. A singularly important feature of chaos is that its evolution follows a well-defined, deterministic path -- allowing its occurrence to be predicted [3]. Although still in its infancy, chaos theory has already provided a deeper understanding of a wide variety of complex dynamic phenomena in physics, chemistry, and biology [4-8].

By all outward appearances, ventricular fibrillation too is a highly complex, seemingly random phenomenon. If it can be shown to result from an underlying formal chaotic process, however, it should be possible to predict or prevent its occurrence.

This research proposal therefore seeks answers to the following questions:

1. Is ventricular fibrillation truly a chaotic process?

2. Are there identifiable, intermediate dynamic stages that presage the onset of ventricular fibrillation as in other chaotic systems -- and if so, what are their mechanisms?

3. Can the transition to chaos be interrupted by pharmacologic interventions?

BACKGROUND AND SIGNIFICANCE

Background. Although 300,000 patients a year suffer sudden cardiac death -- 80% as a consequence of ventricular fibrillation -- reliable measures to predict or prevent its occurrence have not been developed [9-19]. Chaos theory [1-8,21-27] is a relatively new mathematical discipline that offers a new opportunity to better understand this fatal arrhythmia. Reports from four different laboratories [4,23,24,27] -- supplemented by our own preliminary data obtained from intact hearts and isolated cardiac tissue -- suggest that the insights embodied in chaos theory could lead to effective ways to predict or prevent the occurrence of ventricular fibrillation and sudden cardiac death.

What is chaos? Throughout this proposal we will use the term chaos strictly as a formal term to indicate seemingly complex and random behavior that has a mathematically simple and deterministic underlying mechanism. Classical chaos exhibits 3 characteristic features [21]: aperiodicity (absence of any strictly repetitive pattern), a bounded trajectory with definite form, (confinement to a limited region of phase space), and sensitive dependence on initial conditions (exponential divergence of adjacent events) -- the latter 2 features being those that distinguish chaotic behavior from stochastic (random) behavior. A number of quantitative measures of chaos are discussed in the Data Analysis section of Protocol 1.

Specific Aim 1: Is ventricular fibrillation truly a chaotic process?

Several recent investigations suggest that isolated cardiac tissue is capable of manifesting chaotic behavior. Guevara and associates induced both periodic and aperiodic rhythms in spontaneously depolarizing chick embryo heart cells by intracellular current injections, and observed a variety of phenomena (such as period-doubling and phase-locking) that are characteristic precursors of chaos [4,8]. Chialvo and Jalife observed these same phenomena following rapid pacing, tissue compression, and heptanol-induced cellular uncoupling in non-automatic driven adult sheep cardiac Purkinje fibers [23].

Similarly, Ritzenberg and associates observed a variety of electrophysiologic phenomena indicative of pre-chaotic behavior (QRS alternans, period-doubling, period-tripling, period-quadrupling, and period-quintupling) in anesthetized closed chest dogs following PRINCIPAL INVESTIGATOR/PROGRAM TOR: Hrayr Karagueuzian, Ph.D.

intravenous noradrenaline [24]. Using spectral analysis techniques, these investigators reported that both hypothermia (29 degrees C) and transient coronary artery occlusion caused changes in the magnitude of QRS alternans that followed a pattern of period-doubling. Whenever this characteristic precursor of chaos was observed, the ventricular fibrillation threshold was significantly decreased [25].

On the basis of these studies, these authors developed a simple computer model of ventricular activation. This model demonstrated beat-to-beat oscillations of period 2, 3, 6, and 24 during progressive increases in the rate of stimulation that eventually ended in chaos. The authors suggested that this terminal chaotic rhythm was analogous to ventricular fibrillation [26].

Goldberger et al, on the other hand, have questioned the hypothesis that ventricular fibrillation is chaotic [27]. They applied a rapid train of electrical stimuli to the heart of normal, open-chested, anesthetized dogs, and analyzed the resulting ventricular fibrillation by spectral analysis of the hand-digitized ECG waveforms. They observed this ventricular fibrillation was associated with a discrete ("narrow") frequency spectrum. Because chaos is characterized by a continuous ("broad") frequency spectrum [5,28], these authors concluded that ventricular fibrillation is not a chaotic process [27].

There is nevertheless ample reason to suspect that ventricular fibrillation is a chaotic process despite these observations. First, recent studies by Chen and associates [29] using a very similar model (canine ventricular fibrillation induced by a single premature stimulus) showed reentrant activation at the very onset of ventricular fibrillation in a figure eight pattern. This highly organized pattern of activation -- analogous to sustained monomorphic ventricular tachycardia [30] -- would explain the discrete frequency spectrum observed by Goldberger et al [27] at the onset of ventricular fibrillation.

Second, Goldberger et al restricted their analysis to conventional ECG leads recorded over the first two minutes of fibrillation. Our own preliminary data (presented below) suggest that the spectral and dynamic characteristics of ventricular fibrillation evolve over a longer time frame, and that conventional surface ECG leads and intracardiac electrograms differ with respect to their spectral characteristics.

Third, although all investigations aimed at determining if ventricular fibrillation is chaotic have so far relied exclusively on conventional spectral analysis [24,27], more sophisticated methods are now available. These include the analysis of phase plane plots [31], Poincare sections [8], Lyapunov exponents [32], and fractal dimension [33]. Our own preliminary data (presented below) indicate that these additional methods are necessary for the accurate diagnosis of chaos.

There are therefore a number of unanswered questions regarding our hypothesis that ventricular fibrillation represents a chaotic process:

1. Are there different types of ventricular fibrillation? Specifically, do various ventricular fibrillations, resulting from different etiologies, have a universal dynamic profile (whether chaotic or nonchaotic), or does the mode of induction (ischemia versus drugs) or time of recording (early versus late ventricular fibrillation) distinguish "chaotic" from "nonchaotic" fibrillation?

2. Do technical differences in the recording and analysis of data affect the sensitivity and specificity for detection of chaos? Specifically, does the position and type of recording lead (e.g. intracardiac versus surface) or the particular method of analysis (e.g. spectral versus phase plane) affect the diagnosis of chaos?

Our preliminary data (presented below) suggest that at least some ventricular fibrillation is indeed chaotic, and that both the method of recording and the method of analysis affect the results. We believe that the controversy surrounding the description of ventricular fibrillation as chaos can be resolved only by systematically applying a variety of stimuli and analytic methods to the same set of data. This is the first of our three Specific Aims.

169

PHS 398 (Rev. 9/86)

Specific Aim 2: Are there identifiable intermediate dynamic stages that presage the onset of ventricular fibrillation as in other chaotic systems -- and if so, what are their mechanisms?

Typically, a stressed physical system evolves to chaos in only a few ways. Each of these ways is characterized by a series of identifiable intermediate stages such as (i) period doubling (a sequence of subharmonic bifurcations -- beginning, for example, as QRS alternans) [8,22,25], (ii) spatial desynchronization (a process that is periodic in time and homogeneous in space loses spatial synchrony, and becomes irregular) [63], (iii) Ruelle-Takens bifurcation [34] (the sequential appearance of additional independent oscillations in a periodic process -- as seen in fluid turbulence) [34], and (iv) morphologic complexity (the appearance of qualitatively distinct changes of the periodic waveform -- such as the Rossler "funnel") [35]. We hypothesize that such "routes to chaos" can be identifed in experimental and clinical ventricular fibrillation.

Several groups have reported that cardiac electrical alternans (period doubling) is associated with an increased frequency of ventricular arrhythmias in patients with ischemic heart disease [25,36,37]. ST-T alternans has been reported to be a "reliable marker" of cardiac electrical instability [37], and QRS alternans has been shown to be associated with a lowering of the threshold of ventricular fibrillation [25]. Some investigators have related these observations to cellular action potential abnormalities. Thus, Kleinfeld and associates [38] induced alternation of the action potential duration and amplitude in the frog heart by the use of triiodothyronine, and found that alternation of a simultaneously recorded bipolar electrogram usually paralleled changes in the single cell action potential [38]. This observation has since been extended to guinea pig ventricular muscle cells intoxicated with aconitine [39], to canine ventricular muscle fibers and Purkinje fibers under a variety of stimuli (pacing [40,41], hypoxia and low pH [42], coronary artery occlusion [43], and occlusion-reperfusion [44]), to porcine ischemic muscle [45], and to diseased human ventricular muscle obtained at surgery [46]. Both animal [47] and human [48] studies have shown that ventricular action potential duration alternation was associated with concomitant refractory period alternation. Although none of these studies directly examined the relationship between the resting membrane potential, the type of action potential alternans, and the presence of higher order periodicities, their similarity implies a causal link between ventricular fibrillation and global precursors of chaos (i.e., alternans) at the cellular level.

On the other hand, it is not very likely that ventricular fibrillation induced in normal hearts by electrical stimuli would be associated with deranged cellular function (intra-cellular chaos) at the time of its induction. It is more likely, that such a phenomenon is a manifestation of temporal asynchrony between cells (inter-cellular chaos). The myocardium is known to manifest anisotropic properties whereby characteristics such as conduction velocity depend on myocardial fiber orientation [49], and this could serve as a basis for inter-cellular desynchrony and subsequent chaos. Do adjacent cells or nearby groups of cells actually alternate in synchrony with each other? Hirata et al [41] have shown that Purkinje fiber action potentials after a sudden increase in the pacing rate are longer on odd beats, whereas ventricular muscle action potentials are longer on even beats. Nevertheless, the temporal relationship of action potential duration for similar cell types over extended periods of time, and the relation to chaos in the ventricles remain undefined. Thus, we do not yet know if the periodicity observed on intracardiac bipolar or surface electrocardiogram is the result of the desynchronous temporal/spatial activity of a group of cells exhibiting individual normal function, or is the result of the synchronous activity of a group of cells exhibiting individual abnormal function.

During conventional (period doubling) electrical alternans of the QRS or ST-T wave, for example, it is possible that not all myocardial cells are excitable during every beat, but rather at every second beat, because of their relatively long refractory period duration [26,50]. A theoretical computer simulation model of cardiac membrane action potential (Beeler-Reuter Model [51]) by Jensen et al [52] has shown that single cells can demonstrate periodicity and chaos when driven at fast rates. However, simultaneous recordings of bipolar electrogram and single cell action potentials using microelectrodes are necessary to answer this question experimentally.

If the mechanism of chaos is related to differences among groups of cells, then there should be divergent changes in the local bipolar electrogram at different recording sites. But if the mechanism of chaos is related to global alteration in the properties of individual myocardial cells, there should be similar changes in the local bipolar electrograms recorded from different sites. We will examine these alternative hypotheses using an open-chest canine model by comparing simultaneous electrograms from sites affected by a local stress such as ischemia or hyperkalemia to remote unaffected sites.

Whether the mechanism is inter-cellular or intra-cellular, the similarities so far reported suggest that a common set of intermediate stages on the transition to chaos can be identified, and that these stages might serve as accurate harbingers of fibrillation.

There are therefore a number of unanswered questions regarding our hypothesis that ventricular fibrillation evolves from chaos:

1. Is the transition to chaos characterized by identifiable stages, and are these stages independent of the inciting stimulus?

2. Are these stages predictive of subsequent ventricular fibrillation?

3. Are there different routes to ventricular fibrillation? Specifically, is ventricular fibrillation a consequence of inter-cellular chaos or intra-cellular chaos, and is chaos a manifestation of anisotropy?

Our preliminary data (presented below) suggest that specific stages indicating a transition to chaos can be identified prior to ventricular fibrillation in the quinidine-intoxicated dog. If these preliminary data can be confirmed and expanded, they might serve as the basis for development of an early warning system to help predict cardiac drug toxicity and sudden cardiac death. This is the second of our three Specific Aims.

Specific Aim 3: Can the transition to chaos be interrupted by pharmacologic interventions?

Can pharmacologic interventions prevent, arrest, or reverse the evolution of electrical activity toward chaos? Unfortunately there are only a few studies that dealt with pharmacologic reversal of electrical alternans both in experimental and clinical settings. Hashimoto et al [53] have shown that cardiac electrical alternans induced during acute ischemia in the dog can be eliminated by verapamil, but did not characterize the associated benefits. More recently, Salerno et al [36] reported that neither lidocaine nor propranolol had any effect in 4 patients with acute ischemia, ST-T alternans, and ventricular arrhythmias. In contrast, diltiazem suppressed both the ST-T alternans and the ventricular arrhythmias in these patients.

Experimental studies in the setting of acute myocardial ischemia [53] also suggest that calcium channel blockers can eliminate ST-T alternans, and by doing so, also eliminate arrhythmias. These observations suggest that ST-T alternans is mediated by ionic mechanisms sensitive to myocardial calcium channels. However, the resolution of this question requires the demonstration at the cellular level that repolarization alternans can be eliminated by calcium channel blockers. Furthermore, the determination that alternans in fact plays a role in arrhythmogenesis will also largely depend on our ability to find a drug or drug combination that effectively suppresses the arrhythmia after it first suppresses the alternans. Should the effective drug or drug combination be devoid of calcium channel blocking activity, additional mechanisms other than calcium channel blocking effects must be invoked in the suppression of ST-T alternans.

If electrical alternans (period doubling) proves to be a harbinger of ventricular fibrillation, as we hypothesize, then its elimination by pharmacologic intervention might be expected to prevent or reduce the risk of subsequent ventricular fibrillation. This would simultaneously serve to define a new group of electrocardiographic parameters to monitor the proarrhythmic cardiotoxicity of a variety of pharmacologic agents, and (perhaps more importantly) define the dynamic correlates of effective drug therapy.

There are several unanswered questions regarding the interruption of chaos:

1. Can the transition to chaos be prevented, arrested, or reversed by drugs?
2. What are the dynamic correlates of an effective therapy (chaos interruption) by particular classes of agents?
3. Is effectiveness a function of the underlying mechanism (inter- vs intra-cellular)?
4. Is there a point of no return with respect to interruption of the transition? Specifically, is there some point beyond which fibrillation is inevitable?

Conventional endpoints for defining the antiarrhythmic and proarrhythmic effects of drugs are highly limited. If the transition to chaos can be interrupted by drug therapy, this would provide clinicians with a cellular basis for the prevention of sudden cardiac death, and would provide investigators with a new way to quantify the arrhythmic effectiveness of drugs. The demonstration of this dual potential is the third of our three Specific Aims.

Significance. There are no reliable predictors of sudden cardiac death. Even in survivors of myocardial infarction in whom the relationship between ventricular arrhythmias and sudden death is well established [21], therapy directed at reducing this risk has been notoriously ineffective [9-19]. Thus, no study has shown unequivocally that antiarrhythmic drug therapy or myocardial revascularization surgery is capable of preventing sudden death. As a result of this research, (i) we will have developed and validated clinically relevant methods to detect chaotic biologic processes, (ii) we will have used these methods to determine if ventricular fibrillation is one such chaotic process, and (iii) we will have characterized the means by which that process can be predicted and prevented. These achievements thereby have direct relevance to a basic understanding of the pathophysiology and prevention of sudden cardiac death. Our research group is in a unique position to advance our Specific Aims because (i) we have an extensive track record in investigative electrophysiology, (ii) we have considerable expertise in the mathematical analysis of nonlinear dynamic systems, (iii) and we have the dedication and resources to perform these complex analyses as evidenced by our promising preliminary data.

EXPERIMENTAL DESIGN AND METHODS

Specific Aim 1: Is ventricular fibrillation truly a chaotic process?

PROTOCOL 1: MATHEMATICAL ANALYSIS OF COMPUTER SIMULATED WAVEFORMS

Study Hypothesis: Chaotic signals can be differentiated from periodic, random, and noisy signals using a combination of analytic methods. The sensitivity and specificity for the detection of chaos varies with the particular method of analysis.

Study Population: The following computer generated periodic signals will be produced on a PC-AT computer using custom-developed software: sine wave, modulated sine wave, square wave, saw-toothed wave, and triangular wave. In addition, the following known chaotic oscillators (attractors) will be similarly generated and analyzed: Van der Pol, driven pendulum, Lorenz, Duffing, and Rossler.

Data Collection: Random noise at various levels (1, 10 and 20%) and with different spectral profiles (e.g. white and pink) will be injected into each of the above signals. Each signal/noise combination will be filtered at various levels using Butterworth and bidirectional digital filters. Fifty (50) cycles of each signal will be stored in digital form for subsequent analysis.

Data Analysis: The digitized signals will be analyzed on an Amiga 2000 and PC-AT computers to determine the influence of noise and filtering on the ability of each method of dynamic analysis to correctly characterize the waveforms as chaotic and nonchaotic (e.g. periodic or random). Signal length will be varied to determine if a given minimum number of points is required to reach the desired sensitivity and specificity for each criterion (described below).

As noted in the Background and Significance section, chaos is defined as an aperiodic phenomenon, exhibiting a bounded trajectory inscribing a form and sensitive dependence on initial conditions [21]. The table below summarizes the ability of 5 different quantitative measures to detect one or more of these characteristics:

| MEASURE | CHARACTERISTIC | | |
|---|---|---|---|
| | Aperiodicity | Bounded trajectory | Sensitive dependence |
| Spectral Analysis | yes | no | no |
| Phase-Plane Plots | no | yes | yes |
| Poincare Section | yes | yes | no |
| Lyapunov Exponent | no | no | yes |
| Dimensional Analysis | yes | no | no |

We need to employ multiple measures to detect chaos because no single measure is sufficient to detect all 3 characteristics, and because the relative sensitivity of different measures for the same characteristic are not well-known [20]. Thus, the identification of all 3 characteristics in a waveform by any combination of the 5 measures serves as a highly specific, but insensitive operative definition of chaos. We shall therefore classify each ensemble of waveforms -- in this and all subsequent protocols -- as *definitely* chaotic only if all 3 characteristics are present; as *possibly* chaotic if only 2 characteristics are present; as *equivocally* chaotic if only 1 characteristic is present; and as *not* chaotic if no characteristic is present. In addition, we will apply conventional discriminant function analysis to the simulation data in this protocol to develop a quantitative index of chaos based on the optimal combination of these 5 measures. We will prospectively evaluate this measure in subsequent protocols.

Spectral Analysis. We will perform spectral analysis using the fast Fourier transform (FFT) algorithm embodied in the SNIP program developed by Hodgson at UCLA. The output of this program is a raw power spectrum (unfiltered and unsmoothed). This spectrum can be analyzed quantitatively for the proportion of power contained over any specified set of frequencies. A *continuous* (sometimes called "broadband") power spectrum will be defined as one in which more than 10% of the spectral power is contained in frequencies other than (especially below) the fundamental frequency and its integer multiples (harmonics). In contrast, spectra with more than 90% of their power in fundamental-and-harmonic-frequencies will be called *discrete* (sometimes called "narrowband"). Because this conventional definition is arbitrary, we shall also characterize each spectrum in terms of a *power ratio* (the proportion of inter-harmonic and sub-harmonic power divided by the proportion of harmonic power). The higher this ratio, the more aperiodic the spectrum.

Phase-Plane Plots. These plots represent a geometric description of the dynamic state of a system in terms of two state variables (e.g. dx/dt versus x). These two measurements yield a point in the phase plane. As the state of the system changes it defines a curve or *trajectory* -- the phase plane plot. The same selected portions of the digitized rhythm strips used for FFT will be used to construct phase plane plots in SNIP. A subroutine numerically differentiates a given waveform with respect to time, and continuously plots the waveform on the x axis against its first derivative on the y axis [31]. These phase plane plots will be analyzed both qualitatively and quantitatively for the presence of *forbidden zones* (banded gaps resulting from non-uniform and non-random filling of the phase plane), *sensitive dependence on initial conditions* (differential thickening of the phase plane plots), and *qualitative morphologies* indicative of specific mechanisms. Forbidden zones and differential thickening are two indicators of non-randomness.

Forbidden zones are gaps in the phase plane plot. If the variance in the trajectory from cycle to cycle was produced by random factors such as noise we would not expect to see densly-filled bands separated by empty zones like the divisions in the rings of Saturn. The occurrence of this phenomenon can be quantified as follows: slice through the trajectory with a line roughly perpendicular to it. The result is a set of points representing the intersections of each cycle with the line of section. This set of points can then be tested for non-randomness by one-dimensional spatial statistical techniques [54]. For example, the presence of gaps can be diagnosed by the presence of significantly many randomly-chosen points whose nearest trajectory point is far away [67].

Differential thickening will be quantified as the ratio of the width of the widest region of the phase plane plot to the width of the narrowest region. The statistical significance of this ratio will be assessed by comparing it to expectations generated by a Monte Carlo simulation technique: take an actual normal cardiac record and add random noise to produce a test sample with the same number of cycles as in the actual data; calculate the widestto-narrowest ratio of this test sample; repeat the procedure 200 times. The 2nd and 10th largest of these 200 ratios represent 1% and 5% confidence levels for the hypothesis that the actual ratio is significantly larger than would be expected at random [67].

Poincare Sections. Even highly disordered phase plane plots can contain an underlying order. To detect this order, we construct a line segment roughly perpendicular to the trajectories of the phase plane plot at any region of interest. The set of points where the phase plane trajectory intersects that line is called the Poincare section. One then constructs a return map on the Poincare section in the following way: let the line segment have length 1. Let X1 be the location along the segment of the first crossing point and X2 the location of the 2nd crossing point, and so on. We then plot $X_{n+1}$ against $X_n$ (or $X_{t+T}$ against $X_t$). Nonrandom form in the return map (especially Cantor set-like patterns [20]), is indicative of chaos. We have developed a PASCAL computer program that allows a Poincare section and its return map to be displayed automatically for any specified pair of points in the phase plane. We will analyze the plots using conventional regression analysis, quadrat occupancy, spatial autocorrelation, and a method analogous to that used to characterize the large scale homogeneity and isotropy of the universe [54]. Assume there are N points in the return map. Drop 10 times N disks of arbitrary radius r with their centers located randomly and independently within the reference area, and find the vector average of all points within each disk. Display this as a vector centered at the disk center. Now consider the set of all such vectors, one for each disk. If the original set of points is homogeneous, the set of test vectors will have zero variance, regardless of its value. Similarly, if the original set of points is isotropic, each member of the set will have zero value. We can therefore test the difference between the observed and predicted values for each of these observations. If there is significant evidence (at the 0.05 level) for inhomogeneity or anisotropy, the return map is considered to have form.

Lyapunov Exponent. This measure quantifies the rate at which nearby points in a phase plane diverge from one another. A positive Lyapunov exponent indicates exponential divergence of adjacent trajectories (resulting in sensitive dependence) and indicates chaos. We calculate Lyapunov exponents using a BASIC transcription of a FORTRAN program written by Wolf and associates [32].

Dimensional Analysis. The dimensionality of a trajectory in state space is the number of independent degrees of freedom required to specify that trajectory. The basic idea is to create progressive pictures of the trajectory in increasing n-dimensional space, and to quantify the degree to which that space is filled by the trajectory. High dimensionality is characteristic of random noise, while low dimensionality -- usually between 3 and 7, and especially with a fractional (fractal) component -- is indicative of chaos [20]. We calculate dimensionality using a FORTRAN program developed by Albano [33]. The program calculates the apparent dimension of a trajectory (defined as the slope of the function relating the number of points contained in a given radius to the radius itself) as a function of increasing radius. The operative dimensionality of a trajectory is defined by the flat region of the slope-radius plot (represented by a linear regression slope not significantly different from zero).

Preliminary Results: Computer listings for our simulation and analysis programs are in the Appendix. Examples are given in the Preliminary Results for Protocol 2 and Protocol 6.

Sample size: While our study has numerous hypotheses to be tested, estimated variability and treatment effects are not readily available. As a consequence, classical sample size estimation techniques are not easily applied. However, a recurrent theme germane to the overall study is the ability to detect chaotic events under various controlled conditions in computer models (as in this protocol), and in biological models (as in all subsequent protocols). As such, it is believed that there exists some "threshold" beyond which one would conclude that the proportion of chaotic events detected were consistent with chaos theory. Specifically, let pi(0) be the threshold or null value to test against (the effective false positive rate of the interpretive criterion). If the phenomenon under study follows chaos theory, the actual proportion of chaotic events detected should be greater than pi(0), the actual value of which is taken to be pi(1). This hypothesis can be formally tested using a one-sample test for proportions, and the statistical power calculated given various sample sizes, and assumed pi(0) and pi(1) values. These "power"

PRINCIPAL INVESTIGATOR/PROGRAM DIR: Hrayr Karagueuzian, Ph.D.

calculations are presented in the Appendix as Table 1. For example, assuming a pi(0) value of 0.2, a sample size of 15 would yield a 15% chance of rejecting this value (power=0.849) if the actual proportion of chaotic events, pi(1), is greater than 0.50.

Additional hypotheses seek to compare two independent proportions, pi(1) versus pi(2). Using the normal approximation, the statistical power of a two-sample test for proportions was calculated under various hypothesized population proportions and sample sizes. These data are presented in the Appendix as Table 2.

Using these tables, we estimate that a sample size of 15 will be sufficient to test the hypotheses in protocols 1-7 with 80-90% power. Further refinements of this estimate based on preliminary data collected in conjunction with protocol 2 are presented below.

PROTOCOL 2: DYNAMICAL ANALYSIS OF CLOSED-CHEST CANINE VENTRICULAR FIBRILLATION

Study Hypothesis: Ventricular fibrillation induced by a variety of physical and chemical stimuli manifests characteristics predicted by chaos theory. Some of the characteristics will be independent of, and others particular to, the mode of induction.

Study Population: We shall use anesthetized, closed-chest, mongrel dogs of either sex, weighing between 20-26 Kg.

Data Collection: Dogs will be premedicated with morphine sulfate (1-1.5/Kg I.M.) to induce sedation, and 30-40 min later will be anesthetized with 30-35 mg/Kg intravenous sodium pentobarbital. They will then be intubated with cuffed endotracheal tubing and respiration maintained by a Harvard respirator with room air with an expiratory pressure of 4cm water. A three-lead ECG (I,aVF,V1) will be monitored continuously on an oscilloscopic-photographic recorder (VR-16; Honeywell Medical Electronics). A hexaplar catheter (USCI), with an interelectrode distance of 1 mm, will be inserted through the left internal jugular vein via a small (2cm) incision at the base of the neck, and guided into the right ventricle under fluoroscopic control (Philips C-ARM). The electrode catheter will be positioned to record two bipolar electrograms (2-500Hz), one from the right ventricular apical region, and the other from the right ventricular outflow tract. The third pair of the bipole will be used to stimulate the ventricle with a custom built digital constant current programmable stimulator. A quadripolar (6F USCI) electrode catheter will be inserted into the left ventricle via the left carotid artery, and positioned in the apex to record two bipolar electrograms. Two Tygon catheters (3.17 mm od and 1.58 mm id) will then be inserted through a small (2 cm) incision at the right base of the neck. One catheter will be placed in the ascending aorta via the right carotid artery to record aortic blood pressure, and the other catheter will be placed in the right jugular vein for systemic intravenous injections of various agents. All catheters will then be securely sutured in place to prevent dislodgement or change in position. Furthermore, the electrode positions will be checked periodically by fluoroscopy to insure stability at the recording sites. Surface ECGs, intracardiac recordings and aortic blood pressure will be recorded on magnetic tape (CPR 4010; Bell and Howell) for later selective retrieval and analysis. Control electrophysiological recordings will be obtained during normal sinus rhythm and during regular ventricular drive. Selected rhythm strips will be recorded with the respirator turned off and on, allowing us to detect the specific frequency component caused by respiratory modulation of the electrical signals [25]. The right ventricle will be regularly paced at 500-300 msec cycle length for 30-60 seconds at twice diastolic current threshold with a 2 msec pulse width. These regularly paced beats allow us to make comparisons at similar rates of the beat to beat variability in the electrocardiographic signals at various levels of toxicity in response to a variety of stimuli.

Ventricular fibrillation will be induced by a variety of stimuli -- one group of dogs per stimulus. Some of these stimuli are "global" in their effects (quinidine, hypothermia), and others are "regional" (ischemia, reperfusion, hyperkalemia, pacing). This spectrum will allow us to determine if the relationship between fibrillation and chaos is universal or stimulus-dependent:

Quinidine intoxication and spontaneous fibrillation. After obtaining the control recordings, quinidine gluconate, 10 mg/Kg, (USP-Lilly) will be injected intravenously through the jugular vein catheter over 2 minutes; 5 minutes later electrophysiological measurements will be repeated; 30 minutes after the first quinidine injection a second PRINCIPAL INVESTIGATOR/PROGRAM DIRECTOR: Hrayr Karagueuzian, Ph.D.

dose (10 mg/Kg) of quinidine will be injected (again over 2 minutes), and 5 minutes later electrophysiological studies will be repeated. This sequence will be continued until spontaneous ventricular fibrillation occurs (usually 85-100 mg/Kg over 4-5 hours based on our preliminary studies). Once it occurs, it will be recorded continuously on magnetic tape for 5 minutes, and the experiment will then be terminated. If fibrillation cannot be induced at the highest dose, the data will be analyzed with respect to Specific Aim 2.

We developed this model of ventricular fibrillation because of the global (rather than regional) nature of quinidine intoxication. This is important to our study design because intracardiac bipolar electrogram recordings obtained from an arbitrarily selected recording site on the ventricular endocardium must be representative. We believe that a relatively homogeneous degree of ventricular intoxication will occur with this model, which can be probed with reasonable degree of accuracy with one or two simultaneously recorded bipolar electrograms. As the level of quinidine intoxication is increased and the threshold of spontaneous ventricular fibrillation approached, the mean aortic blood pressure usually falls to about 40 mmHg. This could impart to the ventricle a certain degree of hypoxia that could further increase the vulnerability of the quinidine intoxicated ventricle to fibrillation. This additional "stress" could modify and conceivably accelerate the dynamics of electrophysiologic routes to chaos. Although this might have clinical relevance (to severely hypotensive patients, for example) it could also materially modify our hypothesized transition to chaos. Nevertheless, our intent is to study the transition to chaos, and not the effect of quinidine *per se*.

Quinidine intoxication and inducible fibrillation. In a separate group of dogs, the inducibility of ventricular fibrillation will be tested using premature electrical stimulation prior to quinidine administration and 5 minutes after each incremental dose (10 mg/kg) of quinidine (administered as above). Inducibility will be assessed by applying first a single premature stimulus (S2) scanning the entire cardiac cycle (twice diastolic current threshold, with 2 msec duration) during regular right ventricular drive at cycle lengths of 500-300 msec. If fibrillation is not induced, S2 will be fixed 10-15 msec outside the refractory period of S1 and a second premature stimulus (S3) with the same characteristics as S2 will be applied until refractoriness is encountered or ventricular fibrillation is induced. This protocol will be repeated, if needed, for S4 with S3 fixed 10 msec outside the refractory period of S2. Once ventricular fibrillation is induced all electrocardiographic signals will be recorded on magnetic tape for 5 minutes for selective retrieval and analysis of fibrillatory waveforms.

Coronary occlusion and acute fibrillation. In this group after the dogs are anesthetized and instrumented as described above, a preformed 8F radiopaque catheter (2.6 mm od and 1.4 mm id) will be placed in the left coronary ostium via the left carotid artery under fluoroscopic control [55]. The coronary vessels will be identified radiographically by injecting 1-2 ml Renografin-76 in the ostium. An inflatable balloon-tipped catheter (2 or 4 Fogarty Arterial Embolectomy Catheter; American Edwards) will then be inserted through the coronary catheter until it extends 15-20 mm beyond the left coronary ostium into the left anterior descending coronary artery, just proximal to the main diagonal branch. The catheter will then be exteriorized at the neck and sutured in place.

Control electrophysiologic and hemodynamic tracings will be recorded on magnetic tape during normal sinus rhythm for a period of 10 minutes. We will substitute V3 for V1 in this protocol because of its greater sensitivity for ischemic ST-T wave changes. The left anterior descending coronary artery will then be occluded by inflating the balloon. Occlusion of the artery will be confirmed by the lack of flow distal to the inflated balloon. The occlusion will be maintained for 60 minutes and all tracings will be recorded continuously on magnetic tape during this time. If ventricular fibrillation occurs during occlusion, the dogs will be cardioverted after 60 seconds, and occlusion continued to complete the 60 minute occlusion period. The same procedure will be followed should the dogs develop more than one episode of ventricular fibrillation. Selected portions of the fibrillatory waveforms will be retrieved later for analysis.

Reperfusion of acutely ischemic myocardium. After the termination of the 60 minute occlusion period, the occluded coronary artery will be reopened by deflating the balloon, allowing the resumption of blood flow [56]. Data will be recorded continuously on magnetic tape. If ventricular fibrillation occurs, it will be recorded continuously for a total of 5 minutes. If it does not occur for up to 5 minutes after reperfusion, it will be induced using the same pacing procedure described for quinidine intoxication.

Coronary occlusion and the time-course of fibrillation. In a separate series of dogs undergoing acute coronary occlusion, ventricular fibrillation will not be cardioverted within 60 seconds when it occurs spontaneously. Instead, it will be allowed to proceed uninterrupted for 5 minutes, to assess the time course of the phenomenon. This separate series of dogs will not undergo reperfusion (as in the occlusion series discussed earlier) because in our experience reperfusion 5 minutes after continuous and uninterrupted ventricular fibrillation is often unsuccessful. Again, all data will be recorded continuously on magnetic tape for later selective retrieval and analysis.

Regional hyperkalemia. Dogs will be anesthetized and instrumented as for the quinidine intoxication studies. Thereafter, a 2.5F end-hole catheter will be introduced via the left carotid artery, and positioned under fluoroscopic control in the left anterior descending coronary artery just proximal to the main diagonal branch, and sutured in place at the neck. We will perform intracoronary infusion of isotonic potassium chloride (KCl) according to the method of Ettinger et al [57], at a rate of 0.2 mcEq/Kg/second. Using this method, 100 per cent of the dogs can be expected to develop ventricular fibrillation after about 20 minutes of infusion [57]. Once ventricular fibrillation occurs, it will be taped continuously for 5 minutes for later retrieval and analysis.

Global hypothermia. Dogs will be anesthetized and instrumented as for the quinidine intoxication studies. Thereafter, a right carotid artery-jugular vein bypass heat exchanger will be used for cooling and maintaining the rectal temperature at 26-28 degrees C. Hypothermia will be induced by lowering the water temperature in the heat exchanger to 4 degrees C. Immediately before and after the induction of hypothermia, the right ventricle will be paced regularly at 500-300 msec cycle length for 5 seconds (twice diastolic current threshold with 2 msec pulse width) after each 2 degree C decrement in body temperature. This procedure will be continued until a temperature is reached whereby ventricular fibrillation is induced. If fibrillation does not occur spontaneously, it will be induced using the pacing procedure described for quinidine intoxication. Once fibrillation occurs, waveforms will be recorded continuously for 5 minutes.

Premature ventricular stimulation with high current strength. Dogs will be anesthetized and instrumented as for the quinidine studies. Ventricular fibrillation will be induced by applying 3 premature extrastimuli (S2 S3 S4) at 10 times diastolic current threshold, in normal dogs. The right ventricle will be regularly paced (S1 S1) at 400 msec cycle length at twice diastolic current threshold with 2 msec pulse width. After ten regularly driven beats, three premature extrastimuli (S2 S3 S4) at ten times diastolic current threshold will be applied at 120 msec coupling internal (S1 S2 = S2 S3 = S3 S4 = 120 msec). Slight adjustments of the premature stimuli may be needed to induce ventricular fibrillation. The sum of the coupling intervals of the premature stimuli (S1 S2 + S2 S3 + S3 S4) will be in the 365-370 msec range [58]. A 5 minute segment of induced-ventricular fibrillation will be taped continuously from its onset for later selective retrieval and analysis.

Data Analysis: All taped fibrillatory waveforms recorded by the electrocardiographic leads (I, aVF, V1 and all 3 bipolar electrograms -- 2 from the right, and 1 from the left ventricle) will be digitized using a custom-built (DM Auslander; UC Berkeley) 16 channel A/D converter. The sampling frequency will be 2KHz, and low pass filtering will be set at 900Hz to prevent aliasing. The digitized signals will be stored on 5 1/4 floppy disks using a PC-AT computer, and processed on an Amiga 2000 microcomputer using custom software developed by Hodgson (UCLA) in collaboration with one of our co-investigators (AG). All six methods of mathematical and dynamic computations described in Protocol 1 will be applied to each of the seven different ventricular fibrillation models in this protocol. Five minute long fibrillatory waveforms will be analyzed in the following manner. Six 15 second intervals of fibrillatory waveforms for each of the 5 electrocardiographic leads will be analyzed. The first two intervals will be the initial 15 seconds and the 45th-60th seconds of the fibrillation. Thereafter, the remaining 4 15 second intervals will be sampled at each of the 2nd to 5th subsequent minutes. The specific methods of analysis are identical to those described for Protocol 1. In addition three waveform parameters (QRS PRINCIPAL INVESTIGATOR/PROGRAM DIRECTOR: Hrayr Karagueuzian, Ph.D.

amplitude and duration and QT duration) will be measured at specified times for the purpose of comparing and complementing the dynamic data.

Preliminary Results: Progressive quinidine intoxication resulted in spontaneous ventricular fibrillation in 2 of 3 dogs when the total cumulative dose of intravenously administered quinidine reached 100 mg/kg (administered over 5 hours). In the third dog, when the total cumulative dose of quinidine was 80 mg/kg, progressive slowing of the heart rate occurred, with various degrees of AV block and ventricular escape beats. An additional 10 mg/kg of quinidine caused further cardiac slowing and eventual complete cardiac standstill. No spontaneous ventricular fibrillation occurred in this dog.

Figure 1A illustrates 7.9 seconds of quinidine induced ventricular fibrillation recorded from a bipolar RV electrogram in one dog. Figure 1B-F illustrate the analysis of these data by each of our 5 methods. The FFT power spectrum was continuous (Figure 1B), and the phase plane plot (Figure 1C) revealed a pattern of small loops and large loops to the left and right, reminiscent of the Lorenz attractor [35], a classic chaotic system. A Poincare return map (constructed along an axis indicated by the arrow in Figure 1C) revealed significantly non-random structure (Figure 1D) illustrated by linear regression (r=-0.41, p=0.02). However, the Lyapunov exponent for these data (Figure 1E) was negative (-0.08 compared to +2.16 for the Lorenz attractor), and no evidence of low dimensionality was observed (Figure 1F). In this case then there was positive evidence for aperiodicity (spectral analysis), and a bounded trajectory (phase plane plot and Poincare return map), but not sensitive dependence. Based on our semiquantitative scale, therefore, we would characterize this case of fibrillation as being possibly chaotic.

In two additional dogs, reperfusion ventricular fibrillation was analyzed during the initial 10 seconds of its onset. Spectral analysis of ECG lead I showed a highly discrete spectrum, not suggestive of chaos. It consisted of a major spike at 6 Hz, the dominant frequency, and much smaller spikes at 9 and 12 Hz. The significance of these spikes can be seen from a close reading of the waveform: it is not quite sinusoidal, but rather has sharp bottoms and rounded tops. There is also a small spike at around 3 Hz, representing a long-period oscillation in the amplitude. When we performed the same analysis on a simultaneously recorded right ventricular endocardial bipolar electrogram, however, a continuous (broadband) frequency spectrum consistent with chaos was observed. Phase plane plots of these same data have shown discrete bands and forbidden zones consistent with chaos. These preliminary findings suggest that ventricular fibrillation can be described as chaotic electrophysiologic behavior, but that single electrographic leads and single methods of analysis are not sufficient to detect such behavior.

Sample Size: According to the biostatistical tables provided in the Appendix, we will need to study 15 dogs to confirm the significance of this observation with an alpha error of 5% and a beta error of 10%. However, since only 2 out of 3 dogs develop spontaneous ventricular fibrillation, this increases the number to 20. Thus, a total of 40 dogs are needed for our 2 quinidine intoxication studies. In the acute myocardial ischemia and reperfusion protocols, only 1 in 2 dogs develop spontaneous ventricular fibrillation. Accordingly, we will need 30 dogs for this study. An additional 30 dogs unsuited for reperfusion studies will be needed for the protocol in which ischemic fibrillation is not cardioverted for five minutes. In each of the remaining protocols we will require 15 dogs in each group. Thus, we will employ seven different canine models of ventricular fibrillation induced by various means necessitating a total of 145 dogs. Since we expect that 10% of the dogs will fail to reach a successful termination for a variety of other reasons (defective instrumentation and/or premature death) we estimate that we will require a total of 161 (145/0.9) dogs to complete these studies.

PROTOCOL 3: DYNAMICAL ANALYSIS OF OPEN-CHEST CANINE VENTRICULAR FIBRILLATION

Study Hypothesis: Recording site affects the sensitivity of detecting chaos during regional myocardial alterations leading to ventricular fibrillation.

Study Population: We will use a total of 45 anesthetized, open-chest, Mongrel dogs of either sex, weighing between 20-26 Kg.

Data Collection: Dogs will be premedicated and initially instrumented as in Protocol 2, and an inflatable balloon-tipped end-hole catheter will be placed in the left anterior PRINCIPAL INVESTIGATOR/PROGRAM DIRECTOR: Hrayr Karagueuzian, Ph.D.

descending coronary artery (LAD) as described for the coronary occlusion and acute fibrillation study. Thereafter the chest will be opened by a mid-sternal approach and the heart suspended in a pericardial cradle. Twelve bipolar Teflon coated sliver electrodes (0.1 mm diameter) with 1 mm interelectrode distance and 8 mm distance between two consecutive bipoles will then be sewed on the left epicardium in the territory supplied by the LAD. The electrodes are mounted on a rectangular synthetic rubber block (2x4cm). An initial 5-10 seconds of transient ischemia will identify a cyanotic area that is perfused by the occluded artery. This area will be used for sewing the electrode array. Two to 3 pairs of the electrodes will likely be outside the LAD perfusion zone, and similar number of electrodes are likely to be on the border of ischemic zone. Five to six bipoles will end up in the ischemic zone. A second array of twelve bipolar electrodes, as above, will be sewn on the right ventricle near the outflow tract. This will serve as a remote, control, nonischemic zone. Bipolar electrograms recorded from these 24 sites along with the 3 bipolar endocardial electrograms recorded with 6F USCI catheters, two from the right and one from the left ventricle, along with three surface electrograms I, aVF, V3 will be digitized (2KHz sampling rate) and stored in the computer (VME). Sampling will be done at 2 minute interval. Samapling will continue until ventricular fibrillation occurs. The following two interventions will be studied:

Coronary artery occlusion and acute ventricular fibrillation. As in Protocol 2, five minutes prior to LAD occlusion, and during the entire 60 minutes of occlusion, 15 seconds of signals from all 30 leads will be recorded by our computerized multiplexor, every 5 minutes, until spontaneous ventricular fibrillation occurs (15 of 30 dogs). Fifteen seconds of data will be recorded during the first minute of fibrillation, and a second 15 second strip during the second minute, until 5 minutes lapses after the start of fibrillation (a total of 5 15 second samples, during fibrillation). The digitized data will be stored in the computer for later analysis. Our computerized cardiac mapping system (DM Auslander, UC Berkeley) can simultaneously record from 64 different sites by multiplexing. Data will be acquired at a rate of 1KHz with low pass filtering at 450 Hz.

Regional hyperkalemia. Intracoronary infusion of isotonic potassium chloride is initiated as described in Protocol 2. Recordings will be obtained from all 30 leads as above, until spontaneous fibrillation occurs (15 dogs). Data will be recorded as described above.

Data Analysis: The digitized signals will be analyzed by the 5 different methods described in Protocol 1 to determine if demonstrable evidence for chaos varies from one regional recording site to another, and from intracavitary sites to epicardial sites.

PROTOCOL 4: HUMAN VENTRICULAR FIBRILLATION DURING OPEN-HEART SURGERY

Study Hypothesis: Human ventricular fibrillation induced by hypothermia during open heart surgery is a chaotic process.

Study Population: Patients with coronary artery disease with normal ventricles and without a prior history of myocardial infarction who are undergoing cardiopulmonary bypass in conjunction with open heart surgery constitute the study population.

Data Collection: After the chest has been opened and aortic and venous cannulas placed for initiation of cardiopulmonary bypass 2 bipolar electrodes will be sewn onto the epicardium of the left ventricle and right ventricle. These electrodes, along with 3 standard EKG leads: I, AVL, and V1, and a myocardial temperature probe, will be connected to an Electronics for Medicine VR-16 recorder with a 60 Hz analog notch filter for paper recordings. Both the filtered (30-500 Hz) and unfiltered output of the VR-16 will be connected to a 14 channel Teac XR-510 physiologic recorder allowing the data to be recorded on standard VHS videotape. At a speed of 9.52 ips this recorder has a frequency response accurate to 2,500 Hz. The aortic and venous clamps will then be released and, after the proper flow rate has been achieved (about 2.2 l/min/M2), the patient will be cooled by lowering the water temperature in the heat exchanger to 4 degrees C. During this cooling process between 80% and 90% of patients spontaneously fibrillate. About 30 seconds of fibrillation will be recorded, after which the aorta will be cross clamped and cardioplegia solution administered through the proximal ascending aorta. Recording will continue during this process until cardiac standstill occurs and electrical activity has effectively ceased. This technique allows gradual varying of a measured parameter (the PRINCIPAL INVESTIGATOR/PROGRAM DIRECTOR: Hrayr Karagueuzian, Ph.D.

body temperature) until ventricular fibrillation develops. Patients with morphologically normal (and therefore presumably topographically normal) myocardium will be studied to reduce any possible variability in the characteristics of ventricular fibrillation caused by abnormal geometry of the heart.

Data Analysis: The recorded data will be played back through an antialiasing analog filter with a cutoff frequency of 1000 Hz, given appropriate gain and digitized at 2500 samples per second. About 5 second intervals will be digitized for each record resulting in 12,500 points per record and about 6 records per patient. The digitized data will be analyzed using the methods in Protocol 1 (spectral analysis, Poincare sections, phase plane plots, Lyapunov exponents, and dimensional analysis). Chaos will be diagnosed using the criteria outlined earlier. Records will be compared between patients to look for inter patient differences. Additionally, records will be compared within patients according to their time of collection (first 5 seconds, second 5 seconds, etc) to look for time dependent changes in these parameters.

PROTOCOL 5: VENTRICULAR TACHYARRHYTHMIAS DURING CLINICAL ELECTROPHYSIOLOGY TESTING

Study Hypothesis: Patients who have inducible tachyarrhythmias at the time of electrophysiologic testing will manifest alterations in their intracardiac electrograms consistent with chaos, and patients who do not have inducible tachyarrhythmias will not.

Study Population: Four groups of patients undergoing electophysiologic testing will be the subjects of this study: (i) survivors of sudden cardiac death who have inducible tachyarrhythmias, (ii) patients who have not experienced sudden cardiac death, but have inducible tachyarrhythmias, (iii) survivors of sudden cardiac death who do not have inducible tachyarrhythmias, and (iv) patients who have not experienced sudden cardiac death, and do not have inducible tachyarrhythmias.

Data Collection: Our clinical electrophysiologic methodology is published in detail elsewhere [59,60]. Briefly, all studies are performed in the postabsorptive state. All antiarrhythmic drugs are stopped for at least 5 half-lives prior to testing. Electrode catheters are inserted percutaneously or by cutdown, and are positioned under fluoroscopic control in the right atrium, right ventricular apex, and in the His bundle position. Intracardiac recordings are filtered at 30 to 500 Hz, are displayed simultaneously with three surface ECG leads on a multichannel oscilloscope, and recorded on a multichannel FM tape recorder (Teac) having a frequency response of 0-1250 Hz. Stimulation is performed using a programmable stimulator that delivers rectangular impulses of 2 msec duration at 2 and 5 times late diastolic threshold. The specific protocol is as follows:

Step 1: Ten minutes of baseline data recorded.

Step 2: Atrial pacing for 30 seconds at cycle lengths of 600 msec to 300 msec in 50 msec increments, or until the development of atrioventricular block.

Step 3: "Burst" ventricular pacing from the right ventricular apex for 8 to 10 beats at cycle lengths of 600 msec to 250 msec in 50 msec increments.

Step 4: Premature ventricular stimuli during ventricular pacing at cycle lengths of 550 msec. Ventricular extrastimuli are introduced at increasing prematurity beginning in late diastole and at progressively shorter coupling intervals until reaching ventricular refractoriness. The coupling interval of the first premature stimulus is then set at 10 msec longer than the effective refractory period. Single, double, and triple ventricular extrastimuli are introduced in this way at twice diastolic threshold.

Step 5: Ventricular stimulation with single, double, and triple extrastimuli is repeated at a paced cycle length of 400 msec at 2 times and then 5 times diastolic current threshold.

Step 6: Ventricular stimulation with single, double, and triple extrastimuli is then performed from the right ventricular outflow tract at a paced cycle length of 400 msec at 5 times diastolic threshold.

180

PRINCIPAL INVESTIGATOR/PROGRAM DIRECTOR: Hrayr Karagueuzian, Ph.D.

An abnormal electrophysiologic study is defined by the induction of monomorphic ventricular tachycardia at a rate greater than 120 per minute and less than 250 per minute, and lasting for at least 30 seconds or requiring therapeutic intervention.

Data analysis: The data will be played back and digitized at a sampling rate of 2 kHz. Once digitized, the individual electrogram complexes will be analyzed for frequency content, peak amplitude, maximum rate of rise, and duration. These parameters will then be examined for any underlying periodicity. Individual complexes, and groups of complexes at each stage of testing will be analyzed using each of the quantitative methods described in Protocol 1. Each of the four patient groups will be analyzed separately for differences in the frequency and magnitude of the various chaotic parameters.

Preliminary Results: We have, so far studied a single patient with a history of sudden cardiac death and inducible ventricular tachycardia. Phase plane plots of the RV electrogram during normal sinus rhythm revealed differential thickening consistent with sensitive dependence on initial conditions, but spectral analysis showed a discrete power spectrum. No change in this pattern was noted during ventricular tachycardia. These findings illustrate the greater sensitivity of phase plane plots compared to FFT power spectra for the detection of chaotic phenomena.

Specific Aim 2: Are there identifiable intermediate dynamic stages that presage the onset of ventricular fibrillation as in other chaotic systems -- and, if so, what are their mechanisms?

PROTOCOL 6: HOW ACCURATE ARE MARKERS OF CHAOS FOR PREDICTING VENTRICULAR FIBRILLATION?

Study Hypothesis: The transition to chaos is characterized by distinct intermediate stages that are predictive of the subsequent occurrence of ventricular fibrillation.

Study Population: The same dogs used in Protocol 2 and Protocol 3.

Data Collection: The methods of anesthesia, the instrumentation, and the particular interventions are described in Protocol 2 and Protocol 3.

Data Analysis: Whether or not spontaneous ventricular fibrillation occurs (and during the entire period preceding the emergence of fibrillation when it does occur), digitized rhythm strips will be analyzed at selected time intervals by all five different methods of analysis described in Protocol 1. In the series of dogs with quinidine intoxication, 15-second intervals of digitized rhythm strips during both normal sinus rhythm and regular ventricular pacing will be analyzed. Sampling will be done 5 minutes after each incremental dose of quinidine. For coronary occlusion, reperfusion, hyperkalemia and hypothermia, 15-second intervals of digitized rhythm strips will be analyzed at 2 minute intervals. The entire minute immediately preceding ventricular fibrillation will be analyzed in all groups. In the series of dogs with open chest studies (Protocol 3), all available data, collected and stored in the digitized form, preceding ventricular fibrillation, will also be analyzed by the 5 different methods as above. These data will show if intermediate dynamic markers of fibrillation during regional interventions are site specific. In cases where no fibrillation occurs, electrocardiographic data will be analyzed in a similar manner, for comparison to cases that develop ventricular fibrillation. In this way, both the sensitivity and specificity of each observational characteristic for the emergence of ventricular fibrillation will be defined.

The sensitivity and specificity for the development of spontaneous and inducible ventricular fibrillation will be determined separately for the following observations: spectral power, phase plane banding, Poincare return map structure, Lyapunov exponential divergence, and dimensionality. Subjective data (such as the visual assessment of phase plane plots for the occurrence of banding) will be interpreted on 2 separate occasions by 3 independent observers, to quantify interobserver and intraobserver variability. Because the defining thresholds for many of these observations are arbitrary (for example, the definition of a continuous spectrum as one containing more than 10% interharmonic power), accuracy will also be quantified independent of the particular defining threshold by (i) iterating the threshold of the underlying continuous variable over a range of values, (ii) constructing a receiver-operating characteristic (ROC) curve, and (iii) computing the area under this curve [61,62].

PRINCIPAL INVESTIGATOR/PROGRAM DIRECTOR: Hrayr Karagueuzian, Ph.D.

Preliminary Results: Figure 2 illustrates the RV electrograms (top panels A-C) and phase plane plots (middle panels A-C) for one dog during progressive quinidine intoxication. During the control state (A), the phase plane plot is uniformly thick (maximum ratio: 1.8 to 1) and shows no gaps. The Lyapunov exponent was -0.43. As the dose of quinidine is increased, to 40 mg/kg (B), the phase plane plot shows visible banding, and non-uniform thickening (maximum ratio: 5.0 to 1), representing <u>sensitive dependence on initial conditions</u>. The Lyapunov exponent at this dose remained negative (-0.62). At 100 mg/kg (C), the Lyapunov exponent becomes positive (+0.18), and the phase plane plots become even more complex, revealing the development of a "funnel" in the ST-T wave portion of the plot (inset to Figure 2C), similar to that seen with the Rossler attractor [35] as its stress parameter is raised (lower panels). We observed this phenomenon only in the two dogs that subsequently developed ventricular fibrillation (and not in the other). The spectra derived from these data, at all pre-fibrillatory doses, were discrete, with multiple peaks at harmonics of the fundamental frequency, or, in advanced stages of intoxication, at frequencies below the fundamental, representing long-period oscillations. This discordance between a "chaotic" phase plane plot and a "non-chaotic" periodic power spectrum illustrates again the limitation of using only a single analytic marker. Thus, power spectra alone are an insensitive index of chaos.

PROTOCOL 7: IS CHAOS AN INTER-CELLULAR OR AN INTRA-CELLULAR PROCESS?

Study Hypothesis: Chaos can arise by two different mechanisms. Pharmacologic and biochemical alterations are capable of initiating aperiodicities within individual cells. Alternatively, ensembles of cells, in the absence of similar alterations, exhibit periodicities, but chaos arises as a consequence of asynchrony between them.

Study Population: We will use right ventricular endocardial and epicardial tissue preparations isolated from the dogs used in Protocol 2 and protocol 3, in which ventricular fibrillation was induced by a variety of regional and global stimuli (quinidine, ischemia, reperfusion, hyperkalemia, hypothermia, pacing). In addition, similar tissue preparations will be isolated from 15 untreated, normal dogs.

Data Collection: After terminating the whole animal studies, the right ventricular endocardium from which bipolar electrograms were recorded will be isolated and evaluated for transmembrane potential using microelectrode techniques [64-66]. A left thoracotomy will be performed with a sharp scalpel at the fifth intercostal space while the dogs are still under general anesthesia. Supplemental doses (5-10mg/kg IV) of sodium pentobarbital will be administered, if necessary, to insure deep anesthesia. After the pericardium is incised, the heart will be removed rapidly by severing all major vessels, and placed in cold (4 degree C) oxygenated Tyrode's solution. A right ventricular endocardial block (2x2 cm) will then be excised from approximately the same site from which bipolar electrograms were recorded in situ. The block will be set and mounted with stainless steel insect pins in a Lucite tissue chamber (5x5x1 cm). For endocardial studies, the endocardium will be mounted upward, and for epicardial studies, the epicardium will be mounted upward. The tissue will be constantly superfused with normal Tyrode's solution at a rate of 8 ml per minute (37 degree C at pH=7.4±0.1) [65,66]. Similarly, epicardial strips will be isolated from left or right ventricular sites that do show various degrees of periodic and nonperiodic behavior during regional interventions (Protocol 3).

<u>Cellular basis of bipolar electrograms showing characteristic dynamic behaviors</u>: Two bipolar (USCI) electrodes with a 1 cm interelectrode distance (same as for the in vivo studies) will be placed on the surface of the tissue in orthogonal directions, such that one bipole is parallel to the myocardial fiber orientation, and the second bipole is perpendicular to it. The preparations will be paced regularly at 1000 msec cycle length with twice diastolic current threshold and 2 msec pulse width. The stimulating electrode (Teflon coated bipolar silver wire, 0.5 mm in diameter, except for their tips) will be placed near (1mm) the corner where the poles of the two recording bipolar electrodes meet. One microelectrode will be impaled in the middle of one bipolar electrode (stationary microelectrode) and another microelectrode will be used to map the endocardial surface (roving microelectrode) [65,66,71,72]. Recordings will be made, at progressively decreasing pacing cycle lengths, starting from 1000 msec and decreasing by 100 msec until one or the two bipolar electrograms manifest characteristic dynamic behavior indicative of evolution PRINCIPAL INVESTIGATOR/PROGRAM DIRECTOR: Hrayr Karagueuzian, Ph.D.

to chaos (e.g. a given order of periodicities or irregular aperiodic dynamics). At this cycle length, action potentials will be recorded from the 3-4 most superficial subendocardial layers with the roving microelectrode. Fifty consecutive action potentials and electrograms will then be recorded on a Gould recorder (2600-S), and the entire pacing sequence (1 minute) will be recorded on magnetic tape (CPR-4010) for later analysis. Similar recording will also be made at relatively longer cycle length during which no discernable dynamic events occur on the two bipolar electrograms. Mapping of the endocardial surface with the microelectrode will be done by recording action potentials sequentially from different sites. We will record from 20-25 different sites, and thus obtain 20-25 cell pairs along with two corresponding bipolar electrograms.

Anisotropy and chaos: As for the determination of the anisotropic effects of the myocardium on conduction and on bipolar electrogram properties, two microelectrodes will simultaneously be impaled near the distal poles of the bipolar electrodes (relative to the stimulating electrode). A third bipolar recording electrode (Teflon coated, not at the tip, silver wire, 0.5 mm diameter) will be placed within 200 microns of the stimulating electrode. The microelectrodes will be able to measure conduction along the longitudinal and transverse fiber orientation by measuring impulse arrival at the proximal (bipolar) and distal microelectrodes. The preparations will then be paced in decrements of 100 msec starting at 1000 msec cycle length while subjected to various interventions (see below). The filtered output of the signals of the entire experiment will be connected to an FM tape recorder (CPR-4010) with a frequency response of 0-2.5 kHz.

Superfusion media: Both endocardial and epicardial tissue isolated from quinidine intoxicated dogs will be superfused with normal drug-free Tyrode's solution maintained at 37 degrees C. Because quinidine washout is very slow (C Antzelevitch, Personal Communication) these tissue preparations remain intoxicated and manifest various cellular electrophysiological stigma (described below in the Preliminary Results section) for up to 2 1/2 hours. If the experiment lasts longer than 2 hours, 20 ug/ml quinidine gluconate will be added to the Tyrode's solution to maintain toxicity. Tissues isolated from acute ischemia and reperfusion studies will first be superfused with Tyrode's solution gassed with 5% oxygen and 95% nitrogen to mimic some of the effects of ischemia, and after termination of hypoxic conditions, the tissues will be reoxygenated with 95% oxygen and 5% carbon dioxide. Tissues isolated from studies of the effects of regional potassium infusion will be superfused with Tyrode's solution containing increasing potassium ion concentrations from 4 to 32 mm in 4 mm steps, and the effects of incremental potassium evaluated. Finally, tissues isolated from dogs used for the hypothermia studies will be superfused with normal Tyrode's solution, and the effect of progressive lowering of the tissue bath temperature from 37 degrees C to 27 degrees C in steps of 1 to 2 degrees C will be evaluated. The effects of 3 drugs will be studied: (i) lidocaine (1-5 ug/ml), a fast sodium inward current blocker acting primarily on the inactivated channel state (channel closed), [68], (ii) quinidine (1-10 ug/ml), a fast sodium channel blocker acting primarily on activated state (channel open) [68], and (iii) verapamil (0.5-5 ug/ml), a calcium channel blocker.

Data Analysis: Taped recordings from all five electrodes (three bipole and two microelectrodes) will be digitized at 2 KHz, and the digitized signals will be analyzed using the five different methods of analysis described in Protocol 1. Action potentials and bipolar electrograms will be analyzed over 30 to 60 second intervals. Single cell action potential variability (recorded from multiple sites) will be correlated with bipolar electrogram variability in orthogonal directions. This comparative approach will allow us to determine how, if at all, single cell activity correlates with multicellular activity as indicated by the bipolar electrograms. For example, will a single cell manifest chaos when the bipolar electrogram manifests chaos? If so, will there be dynamic directional differences in the electrograms as depicted by the two orthogonal bipolar electrodes. As for the effects of anisotropy on the induction of various periodic behaviors on the conduction time and conduction velocity [23], conduction velocity will be calculated by subtracting the time of arrival of the impulse at the proximal bipolar extacellular electrogram (0.5mm silver wires) from the the time of arrival at the two microelectrodes (distal). Conduction times and conduction velocities will then be plotted on a time versus next-time plot. For example, if conduction time at beat $x$ is $c$, and at PRINCIPAL INVESTIGATOR/PROGRAM DIRECTOR: Hrayr Karagueuzian, Ph.D.

beat x1 is c1, and at x2 is c2, and so on, we will plot c vs c1, c1 vs c2, c2 vs c3, and so on. The resulting plot will then indicate if pacing and interventions produce period two (alternans), higher order periodicities, phase locked patterns, or chaotic conduction patterns. This plotting technique has been successfully employed previouly [4,8,23]. By comparing conduction patterns in longitudinal and transverse directions, we will determine the effects of anisotropy on the dynamics of impulse propagation.

Furthermore, a simultaneously recorded pair of cells will be analyzed by electronically subtracting their action potential amplitudes and durations from each other over time, and then analyzing the resulting <u>difference signal</u> with the five different methods of analysis, and correlating this <u>difference signal</u> with the dynamic electrical activity of the bipolar electrogram in the transverse and longitudinal directions. The relation of the resting membrane potential to the type of periodicities in various action potential phases will be analyzed by comparison of slow response fibers (-50 to -65mv) to depressed fast (-63 to -75mv) and normal fast response (-75 to -90mv) fibers.

Preliminary Results: <u>Our initial isolated tissue studies have resulted in a rich array of periodicities that were neither anticipated by us nor reported previously by others</u>. In four right ventricular endocardial preparations isolated from quinidine intoxicated dogs, action potential amplitude and action potential duration alternans (period two) were seen in fast depressed fibers with resting potentials of -65 to -72 mV (Figure 3A and 3B), and in slow response fibers with resting potentials of -58mv to -62mv (Figure 3C). Phase 2 (plateau region) and phase 3 alternans appeared over a 5 minute interval of continuous monitoring during regular drive at a cycle length of 800 to 500 msec (Figures 3-5). In one fast depressed fiber (resting membrane potential of -70mv), graded increases in the driving rate resulted in the progressive emergence of period 2, period 3, period 4, and the eventual appearance of 4 to 3 phase locking (arrows in Figure 5). In another cell, a decrease in the pacing cycle length (from 1.0 to 0.8 seconds) resulted in aperiodic modulations of action potential amplitude (Figure 6). Simultaneous recordings of two cell action potentials has shown in-phase period two alternans that progressed transiently to out-of-phase alternans (arrows in Figure 3). A plot of the action potential difference signal from this pair of cells resulted in an even more irregular dynamic profile than observed on the bipolar electrogram. We have also observed a variety of periodic and phase-locked patterns prior to chaos in individual cardiac cells in both subendocardial ventricular muscle and Purkinje fibers (Figure 5). This dynamic pattern was also found to be in and out of phase during simultaneous recording of 2 cells with the microelectrode. <u>The identification of these predictable periodic patterns and their order of appearance are typical of chaos</u>.

Although some of the details of these sequential periodicities might be expected to be obscured or lost altogether by the high level of noise inherent in such relatively large (2x2 cm) tissue blocks [23], we have nevertheless been able to demonstrate unequivocal precursors to chaos in these isolated tissue studies. In all four quinidine intoxicated tissues, for example, period two was necessarily the initial step to aperiodicity. Our choice of a relatively larger tissue size is largely dictated by our ability to record bipolar electrograms (abbreviated 'BEg' in Figures 4 and 6), and by our desire to explain periodicities seen in the intact ventricle. Histology showed that the superficial endocardial 10-15 cell layers are parallel with the cardiac base-apex axis. Although epicardial fiber orientation can identified visually, it will be confirmed by histological analysis at the end of each experiment [65].

Specific Aim 3: Can the transition to chaos be interrupted by pharmacologic interventions?

PROTOCOL 8: INTERRUPTION OF CHAOS AND PREVENTION OF VENTRICULAR FIBRILLATION BY DRUGS

Study Hypothesis: Quinidine, verapamil, and diltiazem, and the combination of quinidine and metoprolol modify the transition to chaos produced by acute myocardial ischemia.

Study Population: We will use anesthetized closed chest dog preparations in which acute ischemia will be induced by transient left anterior descending coronary artery occlusion followed by reperfusion.

Data Collection: The dogs will be anesthetized and instrumented as in Protocol 2 for coronary occlusion. <u>Twenty minutes before coronary occlusion, 1 mg/kg/min of quinidine</u>

PRINCIPAL INVESTIGATOR/PROGRAM DIRECTOR: Hrayr Karagueuzian, Ph.D.

gluconate will be infused through the jugular vein for 15 minutes (loading dose), followed by 0.1 mg/Kg/minute as a maintenance dose for the entire duration of occlusion (60 minutes). In a second series of dogs, metoprolol will be administered in a single bolus injection (jugular vein) of 4 mg/Kg 20 minutes before coronary occlusion. In a third series of dogs, both drugs will be administered simultaneously using the above dosage protocols, again 20 minutes before coronary occlusion. In a fouth series of dogs, verapamil will be administered in a single bolus injection (jugular vein) of 0.15 mg/kg [69] followed by 7.5 ug/kg/min as maintenance intravenous infusion. Verapamil therapy will start 20 minutes prior to coronary artery occlusion. In a fifth series of dogs, diltiazem will be constantly infused through the jugular vein at 0.04 mg/kg/min [70], starting 20 minutes prior to coronary artery occlusion. All infusions of drugs will last for the entire duration of occlusion and reperfusion. The entire 20 minutes preceding the occlusion, 60 minutes of occlusion, and 20 minutes of reperfusion (100 minutes total) will be recorded continuously on magnetic tape.

Data Analysis: Thirty second intervals of digitized signals taken at 5 minute intervals will be analyzed by the methods of analysis described in Protocol 1 for all five groups (quinidine, metoprolol, quinidine-metoprolol, verapamil, and diltiazem). The entire 2 minute interval immediately preceding fibrillation will be analyzed in its entirety.

Preliminary Results: We have observed that the combination of metoprolol and quinidine is effective in suppressing ventricular fibrillation during acute myocardial ischemia and during acute reperfusion. In 12 dogs with no drug therapy ventricular fibrillation occurred in 7 dogs. In metoprolol treated dogs, fibrillation occurred in 4 out 10 dogs, and in quinidine treated dogs, it occurred in all 4 dogs tested. In contrast, in the quinidine-metoprolol group, ventricular fibrillation occurred only in 1 out 9 dogs tested. The degree of ischemia as judged by ST segment elevation and the myocardium at risk assessed by Monastral blue dye injection in the occluded artery was similar in all three groups. These data serve to support our selection of these agents for a preliminary study of chaos prophylaxis.

Sample Size: This protocol seeks to compare the proportion of chaotic events detected in each of 5 different treatment groups to a group of controls. Table 3 (in the Appendix) provides the statistical power achieved under various hypothesized treatment effects for sample sizes of 10 to 30 dogs in each group. Since each treatment will be compared to the control (5 pairwise comparisons) Dunnett's multiple comparison procedure was incorporated into the power calculations to control the familywise error rate. This has the effect of reducing the power of a particular sample in comparison to Tables 1 and 2. Accordingly, we will need 20 dogs in each treatment group for a total of 100 dogs (control dogs are the same as those in Protocol 2). Assuming we will be unable to successfully terminate the studies in approximately 10% of the dogs (no ischemia, inability to catheterize) we will require a total of 111 dogs for these studies (100/0.9).

STUDY SCHEDULE

| PROTOCOL | YEAR 1 | 2 | 3 | 4 | 5 |
|---|---|---|---|---|---|
| 1 Computer simulated waveforms | ****** | | | | |
| 2 Is VF chaos (closed-chest dogs)? | *** | ****** | ****** | *** | |
| 3 Is VF chaos (open-chest dogs)? | | *** | | | |
| 4 Is VF chaos (open-heart surgery)? | ****** | ****** | | | |
| 5 Is VT/VF chaos (EP testing)? | ****** | ****** | ****** | ****** | |
| 6 Dynamic stages of canine VF | | ****** | ****** | ****** | ****** |
| 7 Cellular basis of chaos | *** | ****** | ****** | ****** | ****** |
| 8 Interruption of chaos by drugs | | | | ****** | ****** |

Each symbol (*) represents 2 months

PRINCIPAL INVESTIGATOR/PROGRAM DIRECTOR: Hrayr Karagueuzian, Ph.D.

HUMAN SUBJECTS

1. Patients to be included in this study will be chosen from the population of patients undergoing coronary artery bypass surgery or electrophysiology testing at Cedars-Sinai Medical Center as part of their routine care. The mean age of our patient population is approximately 66, 20% are female and 80% male. Patients will be selected for inclusion between the ages of 35 and 90 regardless of sex. The patients in the clinical electrophysiology laboratory will be undergoing standard angiography or electrophysiologic testing. Their ages and sex distribution are approximately the same as for the cardiac surgery patients.

2. Data will be obtained from existing ECG recordings both in the operating room and in the electrophysiologic lab. The collected data wil be obtained from the output of a routine electrocardiographic monitor. There will be no modification to the procedure in the lab for the purposes of this study.

3. This study involves simple recording of signals which occur normally during the course of cardiac surgery and electrophysiologic testing, and does not call for modification of the procedures in any way. Patient consent for each of the protocols is already obtained for each of the procedures. Additional consent is unnecessary due to the nature of the protocol.

4. We believe that there is no additional risk to the patient at all resulting from this protocol, which is nothing more than simple recording of an existing signal. During routine electrocardiographic monitoring, the induced ventricular fibrillation will be taped. There is no risk to the patient while data are being recorded in the angiographic, surgical or electrophysiologic studies.

5. As stated above, there is no added risk to the patient.

6. In the absence of any added risk, we believe the information obtained from human ventricular fibrillation significantly add to our understanding of its dynamic behavior and determine the usefulness and the value of animal models of ventricular fibrillation.

PRINCIPAL INVESTIGATOR/PROGRAM DIRECTOR: Hrayr Karagueuzian, Ph.D.

VERTEBRATE ANIMALS

1) We will use Mongrel dogs of either sex, approximately two years old and weighing between 20-26Kg. All experimental protocols, will be done and completed while the dogs are under general anesthesia. Each dog experiment is terminal, in that, after the completion of the experiment, the dogs will not regain consciousness.

2) The dog model, by virtue of its remarkable tolerance to general anesthesia, heart size, anatomy, collateral circulation, and arrhythmic response to a variety of stimuli, has proven to be extemely useful. Furthermore, the similarities of the quality of the canine arrhythmias to humans, makes the canine model desirable for exploration.
The multiple lengthy methods of analysis, that will be done in each dog, will generate a huge data base that will contain a wealth of important information worth studying. Therefore, this very nature of the present proposal will necessitate relatively fewer number of dogs. We estimate, one successful and complete dog experiment per week will complete the intended experiment (about 90% of the present proposal's experiments, we estimate, are successful). This, we believe, justifies both the use and the relative high cost the of the dogs.

3) We have three house staff veterinarians, along with four other personnel who take around the clock care of the needs and the requirements of the animals in the vivarium. Furthermore, since our protocols do not require any special diatary care or medical attention. We will use the dogs in acute terminal experiments. Post-operative attention to possible complications would be of no concern in this proposal.

4) All the study protocols will be conducted on fully anesthetized dogs. There will be no discomfort or pain throughout the entire study period in each and every dog. Throughout the entire period of a given study, additional supplemental doses of anesthetic agents will be administered through indwelling catheters to insure that comlete anesthesia is adequately maintained throughout the entire study period.

5) At the end of the study, additional doses of anesthetic agent will be administered if needed to insure full and deep anesthesia. At this time, a thoracotony is done at the left fifth intercostal space, the heart rapidly removed by severing the major vessels and euthanasia induced by exsanguination.

187

PHS 398 (Rev. 9/86)

PRINCIPAL INVESTIGATOR/PROGRAM DIRECTOR: Hrayr Karagueuzian, Ph.D.

REFERENCES

1. May RM. Simple mathematical models with very complicated dynamics. Nature 1976;261:459-467.

2. Procaccia I. Universal properties of dynamically complex systems: the organization of chaos. Nature 1988;333:618.

3. Feigenbaum MJ. Universal behavior in nonlinear systems. Los Alamos Science, 1980;Summer:4-27.

4. Guevara MR. Glass L, Shrier A, Class A. Phase locking, period doubling bifurcations, and irregular dynamics in periodically stimulated cardiac cells. Science 1981;214:1350-1353.

5. Olsen LF, Degn H. Chaos in biological systems. Quart Rev Biol 1985;18:165-255

6. Garfinkel A. A mathematics for physiology. Am J Physiol 1983;14:R455-466.

7. Goldberger AL, West BJ. Applications of nonlinear dynamics to clinical cardiology. Ann NY Acad Sci 1987;504:195-213.

8. Guevara MR, Glass L. Phase locking, period doubling bifuractions and chaos in a mathematical model of a periodically driven oscillator: a theory for the entrainment of biological oscillators and the generation of cardiac dysrhythmias. J Math Biol 1982;14:1-23.

9. Moss AJ. Clinical significance of ventricular arrhythmias in patients with and without coronary artery disease. Prog Cardiovasc Dis 1980;23:33-52.

10. May GS, Eberlein KA, Furberg CD, Passamani ER, DeMets D. Secondary prevention after myocardial infarction: A review of long term trials. Prog Cardiovasc Dis 1982;24:331-352.

11. DeSoyza et al. Ventricular arrhythmia before and after aorta coronary bypass surgery. Internat J Cardiol 1981;1:123.

12. Codini MA, Sommerfeldt L, Ebel CE, et al. Efficacy of coronary bypass grafting in excercise-induced ventricular tachycardia J Thorac Cardiovasc Surg 1981;81:502.

13. Leutenegger F, Giger G, Fuhr P, et al. Evaluation of aortic coronary venous bypass for prevention of cardiac arrhythmias. Am J Cardiol 1979;98:15.

14. Nordstrom LA, Lillehei JP Adicoff A, et al. Coronary artery surgery for recurrent ventricular arrhythmias in patients with variant angina. Am Heart J 1975;89:236.

15. Bonchek LI, Olinger GN, Keelan MH, et al. Management of sudden coronary death. Ann Thorac Surg, 1977;24:337.

16. Tabri IF, Geha AS, Hammond GL, Baue A E. Effective surgery on ventricular tachyarrhythmias associated with coronary arterial occlusive disease. Circulation 1978;58:167.

17. Ricks WB, Vinkle RA, Shumway NW, Harrison DC. Surgical management of life-threatening ventricular arrhythmias in patients with coronary artery disease. Circulation 1977;56:38.

18. Gallagher JJ, Oldham H N, Wallace AG, et al. Ventricular aneurysm with ventricular tachycardia. Am J Cardiol 1975;35:696.

19. Graboys TB, Lown B, Podrid PJ, DeSilva R: Long term survival of patients with with malignant ventricular arrhythmias treated with antiaarhthmic drugs. Am J Cardiol 1982;50:436-443

20. Moon FC. Chaotic vibrations. John Wiley:New York; 1987:37-66.

21. Cipra BA. Computer-drawn pictures stalk the wild trajectory. Science 1988;241:1162-1163.

PRINCIPAL INVESTIGATOR/PROGRAM DIRECTOR: Hrayr Karagueuzian, Ph.D.

22. Glass L, Guevara MR, Shrier A. Universal bifurcations and the classification of cardiac arrhythmias. Ann NY Acad Sci 1987;504:168-178.

23. Chialvo DR, Jalife J. Non-linear dynamics of cardiac excitation and impulse propagation. Nature 1987;330:749-752.

24. Ritzenberg AL, Adam DR, Cohen RJ. Period multupling-evidence for nonlinear behaviour of the canine heart. Nature 1984;307:159-161.

25. Smith JM, Clancy EA, Valeri CR, Ruskin JN, Cohen RJ. Electrical alternans and cardiac electrical instability. Circulation 1988;77:110-121.

26. Ritzenberg AL, Smith JM, Grumbach MP, Cohen RJ. Precursor to fibrillation in cardiac computer model. Computers in Cardiology, 1984;171-174.

27. Goldberger AL, Bhargava V, West BJ, Mandell AJ. Some observations on the question: Is ventricular fibrillation "CHAOS"? Physica D 1986;19:282-289.

28. Farmer D, Crutchfield J, Froehling H, Packard N, Shaw R. Power spectra and mixing properties of stange attractors. Annals NY Acad Sci 357;1980,453-472.

29. Chen PS, Wolf PD, Dixon EG, Danieley ND, Frazier DW, Smith WM, Ideker RE. Mechanism of ventricular vulnerability to single premature stimuli in open-chest dogs. Circ Res 1988;62:1191-1209.

30. El-Sherif N. The figure 8 model of reentrant excitation in the canine post-infarction heart. In Cardiac Electrophisiology and Arrhythmias 1985. Zipes DP and Jalife J (eds). Crune and Stratton, pp 363-378.

31. Pinsker HM, Bell J. Phase plane description of endogenous neuronal oscillators in aplysia. Biol Cybern 1981;39:211-221.

32. Wolf A, Swift JB, Swinney HL, Vastano JA. Determining Lyapunov exponents from a time series. Physica D 1985;16:285-317.

33. Albano AM, Mees AI, deGuzman GC, Rapp PE; Data requirements for reliable estimations. In "Chaotic Biological Systems". Holden AV (ed), Pergamon Press 1987

34. Eckmann JP. Roads to tubulence in dissipative dynamical systems. Rev Mod Phys 53;1981;643-654.

35. Abraham R, Shaw C. Dynamics: The Geometry of Behavior, Part Two: Chaotic Behavior. Santa Cruz CA: Aerial Press, 1983, pp77-84.

36. Salerno JA, Previtali M, Pancirolli C, et al. Ventricular arrhythmias during acute myocardial ischaemia in man. The role and significance of R-ST-T alternans and the prevention of ischaemic sudden death by medical treatment. Eur Heart J 1986;7(Supp. A):63-75.

37. Rozansky JJ, Kleinfeld M; Alternans of ST segment and T wave. A sign of electrical instability in Prinzmetal's angina. PACE 1982;5:359-365.

38. Kleinfeld M, Stein E, Magin J. Electrical alternans in single ventricular fibers of the frog heart. Am J Physiol 1956;187:139-142.

39. Hogancamp CE, Kardesh M, Danforth WH, Bing RJ. Transmembrane electrical potentials in ventricular tachycardia and fibrillation. Am Heart J 1959;57:214-222.

40. Hoffman BF, Suckling EE. Effect of heart rate on cardiac membrane potentials and the unipolar electrogram. Am J Physiol 1954;179:123-130.

41. Hirata Y, Kodama I, Iwamura N, Shimizu T, Toyama J, Yamada K. Effects of verapamil on canine Purkinje fibres and ventricular muscle fibres with particular reference to the alternation of action potential duration after a sudden increase in driving rate. Cardiovascular Res 1979;13:1-8.

42. Hirata Y, Toyama J, Yamada K. Effects of hypoxia or low pH on the alternation of canine ventricular action potentials following an abrupt increase in driving rate. Cardiovascular Res 1980;14:108-115.

189

PRINCIPAL INVESTIGATOR/PROGRAM DIRECTOR: Hrayr Karagueuzian, Ph.D.

43. Russel DC, Smith HJ, Oliver MF. Transmembrane potential changes and ventricular fibrillation during repetitive myocardial ischaemia in the dog. Brit Heart J 1979;42:88-98.

44. Akiyama T. Intracellular recording of in situ ventricular cells during ventricular fibrillation. Am J Physiol 1981;240:465-471.

45. Downar E, Janse MJ, Durrer D. The effect of acute coronary artery occlusion on subepicardial transmembrane potentials in the intact porcine heart. Circulation 1977;56:217-224.

46. Spear JF, Horowitz LN, Hodess AB, MacVaugh H, Moore EN. Cellular Electrophysiology of human myocardial infarction. Circulation 1979;59:247-256.

47. Janse ME, van der Steen ABM, van Dam R Th, Durrer D. Refractory period of the dog's ventricular myocardium following sudden changes in frequency. Circ Res 1969;26:251-262.

48. Marchlinski FE. Characterization of oscillations in ventricular refractoriness in man after an abrupt increment in heart rate. Circulation 1987;75:550-556.

49. Spach MS, Dolber PC, Heidlage JF, Kootsey JM, Johnson EA. Propagating depolarization in anisotropic human and canine cardiac muscle: Apparent directional differnces in membrane capacitance. Circ Res 1987;60:206-219.

50. Carson DL, Cardinal R, Savard P, Vermeulen M. Characterization of unipolar waveform alternation in acutely ischaemic porcine myocardium. Cardiovascular Res 1986;20:521-527.

51. Beeler GW, Reuter H. Reconstruction of the action potential of ventricular myocardial fibres. J Physiol 1977;268:177-210.

52. Jensen JH, Christiansen PL, Scott AC. Chaos in the Beeler-Reuter system for the action potential of ventricular myocardial fibres. Physica D 1984;13:269-277.

53. Hashimoto H, Suzuki K, Miyake S, Nakashima M. Effects of calcium antagonists on the electrical alternans of the ST segment and on associated mechanical alternans during acute coronary occlusion in dogs. Circulation 1983;68:667-672.

54. Ripley, B.D., Spatial Statistics, John Wiley and Sons, New York 1981

55. Karagueuzian HS, Ohta M, Drury JK et al,. Coronary venous retroinfusion of procainamide: a new approach for the menagementof spontaneous and inducible sustained ventricular tachycardia during myocardial infarction. J Am Coll Cardiol 1986;7:551-563.

56. Meesmann M, Karagueuzian,Ino T, et al; Selective perfusion of ischemic myocardium during coronary venous retroinjection: a study of the causative role of venoarterial and venoventricular pressure gradients. J Am Coll Cardiol 1987;10:887-897.

57. Ettinger PO, Regan TJ, Oldewurtel HA. Ventricular delay and arrhythmias during regional hyperkalemia in the dog. Circ Res 1973;33:521-531.

58. Hamer A, Karagueuzian HS, Sugi K, et al. Factors related to the induction of ventricular fibrillation in the normal canine heart by programmed electrical stimulation. J Am Coll Cardiol 1984;3:729-751.

59. Nalos PC, Gang ES, Mandel WJ, Ladenheim ML, Lass Y, Peter T. The signal-averaged electrocardiogram as a screening test for inducibility of sustained ventricular cardia in high risk patients: a prospective study. J Am Coll Cardiol 1987;9:539-548.

60. Oseran DS, Gang ES, Hamer AW, Zaher CA, Rosenthal ME, Mandel WJ, Peter T. Mode of stimulation versus response: validation of a protocol for induction of ventricular tachycardia. Am Heart J 1985;110:646-651.

61. Diamond GA. ROC steady: a receiver operating characteristic curve that is invariant relative to selection bias. Med Decis Making 7:1987;238-243.

62. Hanley JA, McNeil BJ. The meaning and use of the area under a receiver operating characteristic (ROC) curve. Radiology 1982;143:29-36.

63. Howard LN. Time periodic and spatially irregular patterns. In: Dynamics and Modelling of Reactive Systems, Stewart WE et al (eds), Academic Press, NY, 1980

64. Katoh T, Karagueuzian HS, Jordan J, Mandel WJ. The cellular electrophysiologic mechanisms of the dual actions of disopyramide on rabbit sinus node function. Circulation 1982;66:1216-1224.

65. Sugi K, Karagueuzian, Fishbein MC, Mandel WJ, Peter T. Cellular electrophysiologig characteristics of surviving subendocardial fibers in chronically infarcted right ventricular myocardium susceptible to inducible sustained ventricular tachycardia. Am Heart J 1987;114:559-569.

66. Ino T, Karagueuzian HS, Hong K, et al. Relation of monophasic action potential recorded with contact electrode to underlying transmembrane action potential properties in isolated cardiac tissues: a systematic microelectrode validation study. Cardiovasc Res 1988;22:255-264.

67. Bodine SC, Garfinkel A, Roy RR, Edgerton. Spatial distribution of motor unit fibers in the cat soleus and tibialis anterior muscles: local interactios. J Neuroscience 1988;8:2145-2152.

68. Hondeghem LM, Katzung BG. Antiarrhythmhic agents: the modulated receptor mechanism of action of sodium and calcium channel-blocking drugs. Ann Rev Pharmacol Toxicol 1984;24:387-423.

69. Karagueuzian HS,Sugi K,Ohta M,Mandel WJ,Peter T; The efficacy of lidocaine and verapamil alone and in combination on spontaneously occuring automatic ventricular tachycardia in conscious dogs one day after right coronaray artery occlusion. Am Heart J 1986;111:438-446.

70. Peter T, Fujimoto T, Hamamoto H, McCullen A, Mandel WJ. Electrophysiologic effects of diltiazem in canine myocardium, with special reference to conduction delay during ischemia. Am J Cardiol 1982;49:602-605.

71. Karagueuzian HS, Fenoglio JJ Jr, Weiss MB, Wit AL. Coronary occlusion and reperfusion: effects on subendocardial cardiac fibers. Am J Physiol 1980;238:H581-H595.

72. Fenoglio JJ Jr, Karagueuzian HS, Friedman PL, Albala A, Wit AL. Time course of infract growth toward the endocardium after coronary occlusion. Am J Physiol 1979;236:H370-H384.

NONLINEAR DYNAMICS AND VENTRICULAR FIBRILLATION

SPECIFIC AIMS

The recent discovery that very simple physical systems are capable of manifesting highly complex, seemingly random behavior has created a broad new field of study based on the mathematics of nonlinear dynamics, also known as chaos [1-6]. A singularly important feature of nonlinear dynamic behavior is that its evolution follows a well-defined, deterministic path — allowing its occurrence to be predicted [3]. Although still in its infancy, nonlinear dynamics has already provided a deeper understanding of a wide variety of complex dynamic phenomena in physics, chemistry, and biology [4-8].

By all outward appearances, ventricular fibrillation is a highly complex, seemingly random phenomenon, and if it too can be shown to result from an underlying aperiodic nonlinear dynamic process, it might be possible to better understand, predict, and even design novel strategies for its prevention.

This research proposal therefore seeks answers to the following questions:

1. Is ventricular fibrillation an aperiodic nonlinear electrodynamic process?
2. Are there identifiable, intermediate stages that presage the onset of ventricular fibrillation as in other nonlinear dynamic systems — and what are their mechanisms?
3. Can the transition to nonlinear electrodynamic behavior be interrupted by pharmacologic interventions?

BACKGROUND AND SIGNIFICANCE.

Background. Although 300,000 patients a year suffer sudden cardiac death — 80% as a consequence of ventricular fibrillation — reliable measures to predict or prevent its occurrence have not been developed [9-19]. Nonlinear dynamics [1-8,21-27] is a relatively new mathematical discipline that offers a new opportunity to better understand this fatal arrhythmia. Reports from four different laboratories [4,23,24,27] — supplemented by our own preliminary data obtained from isolated cardiac tissue, intact canine hearts, and from patients undergoing cardiac surgery or electrophysiologic testing — suggest that the insights embodied in nonlinear dynamics could lead to more effective ways to predict or prevent the occurrence of ventricular fibrillation and sudden cardiac death.

What is nonlinear dynamics? Nonlinear dynamics is concerned with systems whose output is not a linear function of their input. In this proposal we will use the term aperiodic nonlinear dynamic behavior to indicate seemingly complex and random behavior that has a mathematically simple and deterministic underlying mechanism (chaos). Classical chaos (aperiodic nonlinear dynamics) exhibits 3 characteristic features [21]: aperiodicity (absence of any strictly repetitive pattern), a bounded trajectory with definite form, (confinement to a limited region of phase space), and sensitive dependence on initial conditions (exponential divergence of adjacent events) — the latter 2 features being those that distinguish chaotic from stochastic (random) behavior. A number of quantitative measures of nonlinear dynamic behavior are discussed in the Data Analysis section of Protocol 1.

Specific Aim 1: Is ventricular fibrillation an aperiodic nonlinear electrodynamic process?

Several recent investigations suggest that isolated cardiac tissue is capable of manifesting nonlinear electrodynamic behavior. Guevara and associates induced both periodic and aperiodic rhythms in spontaneously-depolarizing chick embryo heart cells by intracellular current injections, and observed a variety of phenomena (such as period-doubling and phase-locking) that are characteristics of nonlinear dynamic behavior [4,8]. Chialvo (a consultant on this proposal) and Jalife also observed in sheep cardiac Purkinje fibers [23], nonlinear electrical activity (with respect to conduction and excitability) in response to periodic stimulation.

Similarly, Ritzenberg and associates observed a variety of electrophysiologic phenomena indicative of nonlinear dynamic behavior (QRS alternans, period-doubling, period-tripling, period-quadrupling, and period-quintupling) in anesthetized closed chest dogs following intravenous noradrenaline [24]. Using spectral analysis techniques, these investigators reported that hypothermia (29 degrees C) and transient coronary artery occlusion — two models that we shall employ in our proposal — both caused changes in the magnitude of QRS alternans that followed a pattern of period-doubling. Whenever this characteristic precursor was observed, the ventricular fibrillation threshold was significantly decreased [25].

On the basis of these studies, these authors developed a simple computer model of ventricular activation. This model demonstrated beat-to-beat oscillations of period 2, 3, 6, and 24 during progressive increases in the rate of stimulation that eventually ended in aperiodic nonlinear dynamic behavior. The authors suggested that this terminal aperiodic behavior was analogous to ventricular fibrillation [26].

Goldberger et al, on the other hand, have questioned the hypothesis that ventricular fibrillation is the result of a chaotic dynamic process [27]. They applied a rapid train of electrical stimuli to the heart of normal, open-chested, anesthetized dogs, and analyzed the resulting ventricular fibrillation by fast Fourier transform (FFT) spectral analysis of the hand-digitized ECG waveforms. They observed this ventricular fibrillation was associated with a discrete ("narrow") frequency spectrum. Because nonlinear dynamic behavior is characterized by a continuous ("broad") frequency spectrum [5,28], these authors concluded that ventricular fibrillation is not a nonlinear dynamic process [27].

There is nevertheless ample reason to suspect that ventricular fibrillation is a nonlinear dynamic process despite these observations. First, recent studies by Chen and associates [29] using a very similar model (canine ventricular fibrillation induced by a single premature stimulus) showed reentrant activation at the very onset of ventricular fibrillation in a figure eight pattern. This highly organized pattern of activation — analogous to sustained monomorphic ventricular tachycardia [30] — would explain the discrete frequency spectrum observed by Goldberger et al [27] at the onset of ventricular fibrillation.

Second, Goldberger et al restricted their analysis to conventional ECG leads recorded over the first two minutes of fibrillation. Our own preliminary data (presented below) suggest that the spectral and dynamic characteristics of ventricular fibrillation evolve over a longer time frame, and that conventional surface leads and intracardiac electrograms differ with respect to their spectral characteristics.

Third, although all investigations aimed at determining if ventricular fibrillation is a nonlinear dynamic process have so far relied exclusively on conventional spectral analysis [24,27], more sophisticated methods are now available. These include the analysis of phase plane plots [31], Poincare sections [8], Lyapunov exponents [32], and fractal dimension [33].

Our own preliminary data indicate that these additional methods are necessary for the accurate diagnosis of an aperiodic nonlinear dynamic behavior. For example, to determine if chaotic electrodynamic behavior occurs in the intact human heart, we recently analyzed ventricular fibrillation induced by hypothermia in 8 patients undergoing open heart surgery, and monomorphic ventricular tachycardia induced by ventricular pacing in 3 patients undergoing clinical electrophysiologic testing. FFT spectra, phase-plane plots, Poincare sections, and fractal dimension of the digitized waveforms were compared to those for computer generated control waveforms known to be random. The random waveforms were characterized by high dimension (more than 9), and their phase-plane plots and return maps had no structure. In contrast, the 8 ventricular fibrillation and 3 ventricular tachycardia waveforms were characterized by low dimension (range, 2 to 5), and the phase-plane plots and return maps exhibited characteristic non-random structure ("forbidden zones" and "sensitive dependence on initial conditions"). All spectra — whether from computer controls or ventricular arrhythmia — were similarly broadband. These preliminary data indicate that clinical ventricular tachycardia and fibrillation represent aperiodic nonlinear dynamic behavior, (chaos) and they further demonstrate that methods other than spectral analysis are required to identify such behavior.

Despite these promising preliminary data, there are a number of unanswered questions regarding our 1. Are there different types of ventricular fibrillation? Specifically, do various ventricular fibrillations, resulting from different etiologies, have a universal dynamic profile, or does the mode of induction (e.g. ischemia versus drugs) or time of recording (e.g. early versus late ventricular fibrillation) affect the development and detection of chaos?

2. Do technical differences in the recording and analysis of data affect the sensitivity and specificity for detection of nonlinear dynamic behavior? Specifically, does the position and type of recording lead (e.g. intracardiac versus surface) or the particular method of analysis (e.g. spectral versus phase plane) affect the detection of chaos?

Our preliminary canine data (presented below) suggest that at least some ventricular fibrillation is indeed consistent with aperiodic nonlinear electrodynamic process (chaos), and that both the method of recording and the method of analysis affect the results. We believe that the controversy surrounding the description of ventricular fibrillation as chaos can be resolved only by systematically applying a variety of stimuli and analytic methods to the same set of data. This is the first of our three Specific Aims.

Specific Aim 2: Are there identifiable intermediate stages that presage the onset of ventricular fibrillation Page 196
as in other nonlinear dynamic systems - and what are their mechanisms?

Typically, a stressed physical system evolves to nonlinear dynamic behavior in only a few ways. Each of these ways is characterized by a series of identifiable intermediate stages such as (i) period doubling (sequence of subharmonic bifurcations - beginning, for example, as QRS alternans) [822.25], (ii) spatial desynchronization (a process that is periodic in time and homogeneous in space loses spatial synchrony, and becomes irregular) [63], (iii) Ruelle-Takens bifurcation [34] (the sequential appearance of additional independence oscillations in a periodic process - as seen in fluid turbulence) [34], and (iv) morphologic complex (the appearance of qualitatively distinct changes of the periodic waveform - such as the Rossler "funnel" [35]. We hypothesize that such phenomena can be identified in experimental ventricular fibrillation and that these phenomena provide information about the underlying causal mechanism.

Several groups have reported that cardiac electrical alternans (period doubling) is associated with an increased frequency of ventricular arrhythmias in patients with ischemic heart disease [25,36,37], ST-T alternans has been reported to be a "reliable marker" of cardiac electrical instability [37] and QRS alternans has been shown to be associated with a lowering of the threshold of ventricular fibrillation [25]. Some investigators have related these observations to cellular action potential abnormalities. Thus, the early work of Klonfeld and associates [38] has shown alternation of the action potential duration and amplitude in the frog heart by the use of triiodothyronine. This observation has since been extended to guinea pig ventricular muscle cells intoxicated with aconitine [39], to canine ventricular muscle fibers and Purkinje fibers under a variety of stimuli (pacing [40,41] hypoxia and low pH [42], coronary artery occlusion [43], and occlusion-reperfusion [44] to porcine ischemic muscle [45] and to diseased human ventricular muscle obtained at surgery [46]. Both animal [47] and human [48] studies have shown that ventricular action potential duration alternation was associated with concominant refractory period alternation. It has been suggested that action potential duration alternation in Purkinje fibers during sudden increase in rate, is caused by incomplete recovery kinetics of the membrane current (Isi and ix1) by the preceding action potential [59], along with the combined effects of electrical restitution and declining memory effect [57]. It was further suggested that electrical restitution was controlled by a TTX-sensitive current (sodium window current) [60]. Recently, Chialvo et al. [64] have reported that phase locking, period doubling bifurcations and chaos can be predicted in vitro cardiac tissues (Purkinje fibers), when the restitution of action potential duration and the recovery of excitability show a critical degree of nonlinearity. The emergence of period two alternans, higher order periodicities and deterministic chaos, in the mathematical computations were the obligatory consequences of an increase in the degree of nonlinearity in such recovery [64]. The mechanism of ventricular muscle action potential alternans is still undefined. The concept of nonlinear recovery may provide important clues about the mechanism of cardiac electrical instability. Nonlinearity (aperiodic cellular response pattern during periodic stimulation) can create a heterogeneous electrophysiologic milieu, that can set the stage for reentrant ventricular tachyarrhythmias [65,71].

On the other hand, it is not very likely that ventricular fibrillation induced in normal hearts by electrical stimuli would be associated with deranged cellular function (intra-cellular nonlinear dynamics, i.e., heterogeneity) at the time of its induction. It is more likely, that such a phenomenon is a manifestation of temporal asynchrony between cells (inter-cellular nonlinear dynamics, i.e., heterogeneity). The myocardium is known to manifest anisotropic properties whereby characteristics such as conduction velocity depend on myocardial fiber orientation [49], and this could serve as an additional mechanism for inter-cellular asynchrony and subsequent nonlinear dynamics (heterogeneity).

Do adjacent cells or nearby groups of cells actually alternate in synchrony with each other? Hirano et al. (Ref #) have shown that Purkinje fiber action potentials after a sudden increase in the pacing rate are longer on odds beats whereas ventricular muscle action potentials are longer on even beats. These effects are lasting for only a few dozen beats. The temporal relationship of action potential duration for similar cell types over extended periods of time remain undefined. Thus, we do not yet know if the mechanism for the periodicity observed on intracardiac bipolar or surface electrocardiogram represents synchronous temporal/spatial activities of a group of cells exhibiting individual normal function, or synchronous activity of a group of cells exhibiting individual abnormal function or both. Our preliminary data in Protocol 5 indicate that it is possible that both temporal and spatial heterogeneity may coexist, and that a phenomenon that is homogenous in space can become heterogeneous over time (i.e. transition from in phase alternans of cells to out of phase alternans). The property may even further enhance the electrophysiological heterogeneity of the ventricle and increase the susceptibility to ventricular fibrillation. Furthermore, a theoretical computer simulation model of cardiac membrane action potential (Beeler-Reuter model [511]) by Jensen et al. [52] has shown that single cells can demonstrate periodiety and speriodicity during progressive increase in drive rate. However, simultaneous Page 197 recordings of bipolar electrogram and single cell action potentials using microelectrodes are necessary to shower the question experimentally.

~~In the previous section dealing with microelectrode studies, it becomes clear that these should be divergent changes in the local bipolar electrograms at different recording sites. But if its mechanisms is similar~~ to global alteration in the properties of individual myocardial cells, there should be similar changes in the local bipolar electrograms recorded from different sites. We will examine these alternative hypotheses using an open-chess canine model by comparing simultaneous electrograms from sites affected by a local stress such as ischemia or hyperkalemia to remote unaffected sites.

Whether the mechanism of transition to aperiodic (chaotic) dynamics is inter- or intracellular electrophysiologic heterogeneity, the evidence [22,23] suggest to the existence of a common set of intermediate stages that can be identified. These stages might serve as accurate harbingers of ventricular fibrillation.

These are therefore a number of unanswered questions regarding our hypothesis that ventricular fibrillation is a chaotic dynamic process:

1. Is the transition from periodic to aperiodic (chaotic) dynamic behavior characterized by identifiable stages, and are these stages independent of the inciting stimulus?

2. Are these stages predictive of subsequent ventricular fibrillation?

3. Are there different electrodynamic routes to ventricular fibrillation? Specifically, is ventricular fibrillation a consequence of inter-cellular, and/or intra-cellular nonlinear dynamics, and is this a manifestation of anisotropy?

Our preliminary data (presented below) suggest that specific electrodynamic stages can be identified prior to onset of ventricular fibrillation in two different dog models of ventricular fibrillation one; ischemia caused by coronary preclusion, and two: systemic quinidine-intoxication. If these preliminary data can be confirmed and expanded, they might serve as the basis for development of an early warning system to help predict an impending ventricular fibrillation and sudden cardiac death. This is the second of our three Specific Aims.

Specific Aim 3: Can the transition to aperiodic nonlinear dynamic behavior be interrupted by pharcamologic intervention?

Can pharmacologic interventions prevent, arrest, or reverse the evolution of electrical activity toward nonlinear dynamics? Unfortunately there are only a few studies that dealt with pharmacologic reversal of electrical alternans both in experimental and clinical settings. Hashimoto et al [53] have shown that cardiac electrical alternans induced during acute ischemia in the dog can be eliminated by verapamil, but did not characterize the associated benefits. More recently, Salerno et al [36] reported that neither lidocaine nor propanolol had any effect in 4 patients with acute ischemia, ST-T alternans, and ventricular arrhythmias. In contrast, diltiazem suppressed both the ST-T alternans and the ventricular arrhythmias in these patients.

Experimental studies in the setting of acute myocardial ischemia [53] also suggest that calcium channel blockers can eliminate ST-T alternans, and by doing so, also eliminate arrhythmias. These observations suggest that ST-T alternans is mediated by ionic mechanisms sensitive to myocardial calcium channels. However, the resolution of this question requires the demonstration at the cellular level that repolarization alternans can be eliminated by calcium channel blocking activity, additional mechanisms other than calcium channel blocking effects must be invoked in the suppression of ST-T alternans. As mentioned above, using the concept of nonlinear recovery of excitability and restitution of action potential duration [64], antirrhythmic drugs may suppress electrical alternans by <u>decreasing</u> cardiac nonlinearity, i.e. by a process of "linearization." We will investigate these analytical approaches in protocol S.

If electrical alternans (period doubling) proves to be a harbinger of ventricular fibrillation, as we hypothesize, then is elimination by pharmacologic intervention might be expected to prevent or reduce the risk of subsequent ventricular fibrillation. This would simultaneously serve to define a now group of electrocardiographic parameters to monitor the proarrhythmic cardiotoxicity of a variety of pharmacologic agents and (perhaps more importantly) define the dynamic correlates of effective drug therapy.

PRINCIPAL INVESTIGATOR/PROGRAM DIRECTOR: C. Karagueuzian

There are several unanswered questions regarding the interruption of the evolution nonlinear dynamic processes to chaotic aperiodic regime:

1. Can the transition to aperiodic nonlinear dynamic behavior (chaos) be prevented, arrested, or reversed by drugs?

2. What are the dynamic correlates of an effective therapy by particular classes of agents?

3. Is there a point of no return with respect to interruption of the transition? Specifically, is there some point beyond which fibrillation is inevitable?

Conventional endpoints for defining the antiarrhythmic and proarrhythmic effects of drugs are highly limited. These often consist of monitoring ventricular ectopy and/or assessing susceptibility to tachycardia inducibility. Dynamic analysis however, does not rely on ectopy. It rather determines the degree of nonlinearity (a measure of electrical heterogeneity), either during normal sinus rhythm or during regular pacing, and thus provides information on the stability of the ventricle. Our preliminary results suggest that the electrodynamics of normal sinus rhythm, (using phase plane plot) of an ischemic ventricle (caused by coronary occlusion) that is destined to degenerate to ventricular fibrillation, is different from the dynamics of sinus rhythm of an ischemic ventricle, that does not degenerate to ventricular fibrillation. Therefore, these novel observations would provide investigators a new way, that is both sensitive and independent of ectopy, to quantify the antiarrhythmic and/or proarrhythmic effects of drugs. The demonstration of this dual potential is the third of our three Specific Aims.

Significance. As a result of this research, (i) we will have developed and validated methods to detect aperiodic nonlinear dynamic biologic processes that can be applied in subsequent studies to relevant clinical populations. (ii) we will have used these methods to determine if ventricular fibrillation is one such (chaotic) process, and (iii) we will have characterized more sensitive means by which that process can be predicted and perhaps even prevented. These achievements thereby have potential relevance to a basic understanding of the pathophysiology and prevention of sudden cardiac death.

Our research group is in a unique position to advance our Specific Aims because (i) we have an extensive track record in investigative electrophysiology, (ii) we have considerable expertise in the mathematical analysis of nonlinear dynamic systems, (iii) and we have the dedication and resources to perform these complex analyses as evidenced by our promising preliminary data.

PRINCIPAL INVESTIGATOR/PROGRAM DIRECTOR  _____

EXPERIMENTAL DESIGN AND METHODS

<u>Specific Aim 1</u>: Is ventricular fibrillation an aperiodic nonlinear dynamic process

PROTOCOL 1: MATHEMATICAL ANALYSIS OF COMPUTER SIMULATED WAVEFORMS

Study Hypothesis: Aperiodic nonlinear dynamic signals (chaotic signals) can be differentiated from periodic, random, and noisy signals using a combination of analytic methods. The sensitivity and specificity for the detection of nonlinear dynamic behavior varies with the particular method of analysis.

Study Population: The following computer generated periodic signals will be produced on a PC-AT computer using custom-developed software: sine wave, modulated sine wave, square wave, saw-toothed wave, and triangular wave. In addition, the following known nonlinear oscillators (attractors) will be similarly generated and analyzed: Van der Pol, driven pendulum, Lorenz, Duffing, and Rossler, classic models of chaotic dynamics.

Data Collection: Random noise at various levels (1, 10 and 20%) and with different spectral profiles (e.g. white and pink) will be injected into each of the above signals. Each signal/noise combination will be filtered at various levels using Butterworth and bidirectional digital filters. Fifty (50) cycles of each signal will be stored in digital form for subsequent analysis.

Data Analysis: The digitized signals will be analyzed on an Amiga 2000 and PC-AT computer to determine the influence of noise and filtering on the ability of each method of dynamic analysis to correctly characterize the waveforms as periodic or random. Signal length will be varied to determine if a given minimum number of points is required to reach the desired sensitivity and specificity for each criterion (described below).

As noted in the Background and Significance section, aperiodic nonlinear dynamic behavior is defined as an <u>aperiodic</u> phenomenon, exhibiting a <u>bounded trajectory</u> inscribing a form and <u>sensitive dependence on initial conditions</u> [21]. The table below summarizes the ability of 5 different quantitative measures to detect one or more of these characteristics:

| MEASURE | CHARACTERISTIC | | |
|---|---|---|---|
| | Aperiodicity | Bounded trajectory | Sensitive dependence |
| Spectral Analysis | yes | no | no |
| Phase-Plane Plots | no | yes | yes |
| Poincare Section | yes | yes | no |
| Lyapunov Exponent | no | no | yes |
| Dimensional Analysis | yes | no | no |

We need to employ multiple measures to detect nonlinear dynamic behavior because no single measure is sufficient to detect all 3 characteristics, and because the relative sensitivity of different measures for the same characteristic are not well-known [20]. Thus, the identification of all 3 characteristics in a waveform by any combination of the 5 measures serves as a highly specific, but insensitive operative definition of nonlinear dynamic behavior. We shall therefore classify each ensemble of waveforms — in this and all subsequent protocols — as <u>definitely</u> chaotic only if all 3 characteristics are present; as <u>possibly</u> chaotic if only 2 characteristics are present; as <u>equivocally</u> chaotic if only 1 characteristic is present; and as <u>not</u> chaotic if no characteristic is present. In addition, we will apply conventional discriminant function analysis to the simulation data in this protocol to develop a quantitative index of nonlinear dynamic behavior based on the optimal combination of these 5 measures. We will prospectively evaluate this measure in subsequent protocols.

<u>Spectral Analysis</u>. We will perform spectral analysis using the fast Fourier transform (FFT) algorithm embodied in the SNIP program developed by Hodgson at UCLA. The output of this program is a raw power spectrum (unfiltered and unsmoothed). This spectrum can be analyzed quantitatively for the proportion of power contained over any specified set of frequencies. A <u>continuous</u> (sometimes called "broadband") power spectrum will be defined as one in which more than 10% of the spectral power is contained in frequencies other than (especially below) the fundamental frequency and its integer multiples (harmonics). In contrast, spectra with more than 90% of their power in fundamental-and-harmonic- frequencies will be called <u>discrete</u> (sometimes called "narrowband"). Because this conventional definition is arbitrary, we shall also characterize each spectrum in terms of a power ratio (the proportion of inter-harmonic and sub-harmonic power divided by the proportion of harmonic power). The higher this ratio, the more aperiodic the spectrum.

Phase-Plane Plots. These plots represent a geometric description of the dynamic state of a system in terms of two state variables (e.g. dx/dt versus x). These two measurements yield a point in the phase plane. As the state of the system changes it defines a curve or trajectory — the phase plane plot. The same selected portions of the digitized rhythm strips used for FFT will be used to construct phase plane plots in SNIP. A subroutine numerically differentiates a given waveform with respect to time, and continuously plots the waveform on the x axis against its first derivative on the y axis [31]. These phase plane plots will be analyzed both qualitatively and quantitatively for the presence of forbidden zones (banded gaps resulting from non-uniform and non-random filling of the phase plane), sensitive dependence on initial conditions (differential thickening of the phase plane plots), and qualitative morphologies indicative of specific mechanisms. Forbidden zones and differential thickening are two indicators of non-randomness.

Forbidden zones are gaps in the phase plane plot. If the variance in the trajectory from cycle to cycle was produced by random factors such as noise we would not expect to see densely-filled bands separated by empty zones like the divisions in the rings of Saturn. The occurrence of this phenomenon can be quantified as follows: slice through the trajectory with a line roughly perpendicular to it. The result is a set of points representing the intersections of each cycle with the line of section. This set of points can then be tested for non-randomness by one-dimensional spatial statistical techniques [54]. For example, the presence of gaps can be diagnosed by the presence of significantly many randomly-chosen points whose nearest trajectory point is far away [67].

Differential thickening will be quantified as the ratio of the width of the widest region of the phase plane plot to the width of the narrowest region. The statistical significance of this ratio will be assessed by comparing it to expectations generated by a Monte Carlo simulation technique: take an actual normal cardiac record and add random noise to produce a test sample with the same number of cycles as in the actual data; calculate the widest- to-narrowest ratio of this test sample; repeat the procedure 200 times. The 2nd and 10th largest of these 200 ratios represent 1% and 5% confidence levels for the hypothesis that the actual ratio is significantly larger than would be expected at random [67].

Poincare Sections. Even highly disordered phase plane plots can contain an underlying order. To detect this order, we construct a line segment roughly perpendicular to the trajectories of the phase plane plot at any region of interest. The set of points where the phase plane trajectory intersects that line is called the Poincare section. One then constructs a return map on the Poincare section in the following way: let the line segment have length 1. Let $X1$ be the location along the segment of the first crossing point and $X2$ the location of the 2nd crossing point, and so on. We then plot $Xn+1$ against $Xn$ (or $Xt+T$ against $Xt$). Nonrandom form in the return map (especially Cantor set-like patterns [20]), is indicative of nonlinear dynamic behavior. We have developed a PASCAL computer program that allows a Poincare section and its return map to be displayed automatically for any specified pair of points in the phase plane. We will analyze the plots using conventional regression analysis, quadrant occupancy, spatial autocorrelation, and a method analogous to that used to characterize the large scale homogeneity and isotropy of the universe [54]. Assume there are N points in the return map. Drop 10 times N disks of arbitrary radius r with their centers located randomly and independently within the reference area, and find the spatial vector of all points within each disk. Display this as a vector centered at the disk center. Now consider the set of all such vectors, one for each disk. If the original set of points is homogeneous, the set of test vectors will have zero variance, regardless of its value. Similarly, if the original set of points is isotropic, each member of the set will have zero value. We can therefore test the difference between the observed and predicted values for each of these observations. If there is significant evidence (at the 0.05 level) for inhomogeneity or anisotropy, the return map is considered to have form. Return maps will also be constructed from time series using the lag time method [5]. Each point of the signal will be plotted against a specified preceding lag (T) time value. (see preliminary results).

Lyapunov Exponent. This measure quantifies the rate at which nearby points in a phase plane diverge from one another. A positive Lyapunov exponent indicates exponential divergence of adjacent trajectories (resulting in sensitive dependence) and indicates nonlinear dynamic behavior. We calculate Lyapunov exponents using a BASIC transcription of a FORTRAN program written by Wolf and associates [32].

ICIPAL INVESTIGATOR/PROGRAM DIRECTOR  HE   S. Karague...

Dimensional Analysis. The dimensionality of a trajectory in state space is the number of independent degrees of freedom required to specify that trajectory. The basic idea is to create progressive pictures of the trajectory in increasing n-dimensional space, and to quantify the degree to which that space is filled by the trajectory. High dimensionality is characteristic of random noise, while low dimensionality — usually between 3 and 7, and especially with a fractional (fractal) component — is indicative of nonlinear dynamic behavior [20]. We calculate dimensionality using a FORTRAN program developed by Albano [33]. The program calculates the apparent dimension of a trajectory (defined as the slope of the function relating the number of points contained in a given radius to the radius itself) as a function of increasing radius. The operative dimensionality of a trajectory is defined by the flat region of the slope-radius plot (represented by a linear regression slope not significantly different from zero).

Preliminary Results: Computer listings for our simulation and analysis programs are in the Appendix. Examples are given in the Preliminary Results for Protocol 2 and Protocol 4. Three types of signals were used in this portion of the study: 1.periodic (truly periodic, quasiperiodic, and modulated sine waves), 2. random signals, and 3. chaotic signals. Phase plane plots of standard periodic signals a typical periodic behavior, i.e., the successive trajectories overlap each other in a uniform manner oveer the entire trajectories. Signal amplitude had no effect on the phase plane plot, but high frequencies tended to flatten the trajectories. As the frequency of the signal increased to approximately 1/20 of the digitization frequency, phase plane plot lost much of the smoothness associated with lower frequencies. Return maps were similar in form to phase plane plots, but were less sensitive to noise. No significant differences were seen between linear and Gaussian noise injections. Spectral analysis, done using custom computer software is based on the standard Cooley-Tukey fast Fourier transform with a resolution of 8192 points, of the three types of signals indicate the lack of ability of this method of analysis to differentiate chaotic from random signals. Periodic signals exhibited discrete spectra exclusively, whereas random signals had continuous spectra. The spectrum from Duffing's equations exhibited components of both, but with isolated discrete spikes at 8 and 24 Hz respectively (arbitrary frequency assuming sampling interval of 1msec). Dimensional calculations revealed fractal dimensions of 1.07, 1.87, and 2.78 (all low) for the sine wave, Duffing's equations and random signals respectively. Signal amplitude had no effect on the calculations. Furthermore, choice of lag had no significant effect on the calculation of dimension. These data indicate: 1. the noise in the signal for analysis must be minimized; 2. for smooth trajectories on the phase plane plot, sampling at a rate at least 20 times the maximum signal frequency is necessary; 3. if the phase plane does not adequately represent the signal, the return map is a reasonable substitute; 4. spectral analysis is inadequate to differentiate between periodic, chaotic and random signals.

Sample size: While our study has numerous hypotheses to be tested, estimated variability and treatment effects are not readily available. As a consequence, classical sample size estimation techniques are not easily applied. However, a recurrent theme germane to the overall study is the ability to detect nonlinear dynamic events under various controlled conditions in computer models (as in this protocol), and in biological models (as in all subsequent protocols). As such, it is believed that there exists some "threshold" beyond which one would conclude that the proportion of nonlinear dynamic events detected were consistent with the mathematics of nonlinear dynamics. Specifically, let pi(0) be the threshold or null value to test against (the effective false positive rate of the interpretive criterion). If the phenomenon under study follows the mathematics of nonlinear dynamics, the actual proportion of nonlinear dynamic events detected should be greater than pi(0), the actual value of which is taken to be pi(1). This hypothesis can be formally tested using a one-sample test for proportions, and the statistical power calculated given various sample sizes, and assumed pi(0) and pi(1) values. These "power" calculations are presented in the Appendix as Table 1. For example, assuming a pi(0) value of 0.2, a sample size of 15 would yield a 15% chance of rejecting this value (power=0.849) if the actual proportion of nonlinear dynamic events, pi(1), is greater than 0.50.

Additional hypotheses seek to compare two independent proportions, pi(1) versus pi(2). Using the normal approximation, the statistical power of a two-sample test for proportions was calculated under various hypothesized population proportions and sample sizes. These data are presented in the Appendix as Table 2.

Using these tables, we estimate that a sample size of 15 will be sufficient to test the hypotheses in protocols 1-5 with 80-90% power. Further refinement of this estimate based on preliminary data collected with respect to protocol 2 are presented below.

PRINCIPAL INVESTIGATOR/PROGRAM DIRECTOR #: S. Karagueuzian

PROTOCOL 2: DYNAMICAL ANALYSIS OF CLOSED-CHEST CANINE VENTRICULAR FIBRILLATION

Study Hypothesis: Ventricular fibrillation induced by a variety of physical and chemical stimuli manifests characteristics predicted by the mathematics of nonlinear dynamics. Some of the characteristics will be independent of, and others particular to, the mode of induction.

Study Population: We shall use anesthetized, closed-chest, mongrel dogs of either sex, weighing between 20-26 Kg.

Data Collection: Dogs will be premedicated with morphine sulfate (1-1.5/Kg I.M.) to induce sedation, and 30-40 min later will be anesthetized with 30-35 mg/Kg intravenous sodium pentobarbital. They will then be intubated with cuffed endotracheal tubing and respiration maintained by a Harvard respirator with room air with an expiratory pressure of 4cm water. A three-lead ECG (I,aVF,V1) will be monitored continuously on an oscilloscopic- photographic recorder (VR-16; Honeywell Medical Electronics). A hexapolar catheter (USCI), with an interelectrode distance of 1 mm, will be inserted through the left internal jugular vein via a small (2cm) incision at the base of the neck, and guided into the right ventricle under fluoroscopic control (Philips C-ARM). The electrode catheter will be positioned to record two bipolar electrograms (0.5-500Hz), one from the right ventricular apical region, and the other from the right ventricular outflow tract. The third pair of the bipole will be used to stimulate the ventricle with a custom built digital constant current programmable stimulator. A quadripolar (6F USCI) electrode catheter will be inserted into the left ventricle via the left carotid artery, and positioned in the apex to record two bipolar electrograms. Two Tygon catheters (3.17 mm od and 1.58 mm id) will then be inserted through a small (2 cm) incision at the right base of the neck. One catheter will be placed in the ascending aorta via the right carotid artery to record aortic blood pressure, and the other catheter will be placed in the right jugular vein for systemic intravenous injections of various agents. All catheters will then be securely sutured in place to prevent dislodgement or change in position. Furthermore, the electrode positions will be checked periodically by fluoroscopy to insure stability at the recording sites. Surface ECGs, intracardiac recordings and aortic blood pressure will be recorded on magnetic tape (CPR 4010; Bell and Howell) for later selective retrieval and analysis. Control electrophysiological recordings will be obtained during normal sinus rhythm and during regular ventricular drive. Selected rhythm strips will be recorded with the respirator turned off and on, allowing us to detect the specific frequency component caused by respiratory modulation of the electrical signals [25]. The right ventricle will be regularly paced at 500-300 msec cycle length for 30-60 seconds at twice diastolic current threshold with a 2 msec pulse width. These regularly paced beats allow us to make comparisons at similar rates of the beat to beat variability in the electrocardiographic signals at various levels of toxicity in response to a variety of stimuli.

Ventricular fibrillation will be induced by a variety of stimuli — one group of dogs per stimulus. Some of these stimuli are "global" in their effects (quinidine, hypothermia), and others are "regional" (ischemia, reperfusion, hyperkalemia, pacing). This spectrum will allow us to determine if the relationship between fibrillation and nonlinear dynamics is universal or stimulus-dependent:

Quinidine intoxication and spontaneous fibrillation. After obtaining the control recordings, quinidine gluconate, 10 mg/Kg, (USP-Lilly) will be injected intravenously through the jugular vein catheter over 2 minutes; 5 minutes later electrophysiological measurements will be repeated; 30 minutes after the first quinidine injection a second dose (10 mg/Kg) of quinidine will be injected (again over 2 minutes), and 5 minutes later electrophysiological studies will be repeated. This sequence will be continued until spontaneous ventricular fibrillation occurs (usually 85-100 mg/Kg over 4-5 hours based on our preliminary studies). Once it occurs, it will be recorded continuously on magnetic tape for 5 minutes, and the experiment will then be terminated. If fibrillation cannot be induced at the highest dose, the data will be analyzed with respect to Specific Aim 2.

We developed this model of ventricular fibrillation because of the global (rather than regional) nature of quinidine intoxication. This is important to our study design because intracardiac bipolar electrogram recordings obtained from an arbitrarily selected recording site on the ventricular endocardium must be representative. We believe that a relatively homogeneous degree of ventricular intoxication will occur with this model, which can be probed with reasonable degree of accuracy with one or two simultaneously recorded bipolar electrograms.

As the level of quinidine intoxication is increased and the threshold of spontaneous ventricular fibrillation is approached, the mean aortic blood pressure usually falls to about 40 mmHg. This could impart to the ventricle a certain degree of hypoxia that could further increase the vulnerability of the quinidine intoxicated ventricle to fibrillation. This additional "stress" could modify and conceivably accelerate the electrophysiologic routes to nonlinear dynamic behavior. Although this might have clinical relevance (to severely hypotensive patients, for example) it could also materially modify our hypothesized transition to nonlinear dynamic behavior. Nevertheless our intent is to study the transition to such nonlinear behavior, and not the effect of quinidine per se.

Quinidine intoxication and inducible fibrillation. In a separate group of dogs, the inducibility of ventricular fibrillation will be tested using premature electrical stimulation prior to quinidine administration and 5 minutes after each incremental dose (10 mg/kg) of quinidine (administered as above). Inducibility will be assessed by applying first a single premature stimulus (S2) scanning the entire cardiac cycle (twice diastolic current threshold with 2 msec duration) during regular right ventricular drive at cycle lengths of 500-300 msec. If fibrillation is not induced, S2 will be fixed 10-15 msec outside the refractory period of S1 and a second premature stimulus (S3) with the same characteristics as S2 will be applied until refractoriness is encountered or ventricular fibrillation is induced. This protocol will be repeated, if needed, for S4 with S3 fixed 10 msec outside the refractory period of S2. Once ventricular fibrillation is induced all electrocardiographic signals will be recorded on magnetic tape for 5 minutes for selective retrieval and analysis of fibrillatory waveforms.

Coronary occlusion and acute fibrillation. In this group after the dogs are anesthetized and instrumented as described above, a preformed 8F radiopaque catheter (2.6 mm od and 1.4 mm id) will be placed in the left coronary ostium via the left carotid artery under fluoroscopic control [55]. The coronary vessels will be identified radiographically by injecting 1-2 ml Renografin-76 in the ostium. An inflatable balloon-tipped catheter (2 or 4 Fogarty Arterial Embolectomy Catheter; American Edwards) will then be inserted through the coronary catheter until it extends 15-20 mm beyond the left coronary ostium into the left anterior descending coronary artery, just proximal to the main diagonal branch. The catheter will then be exteriorized at the neck and sutured in place.

Control electrophysiologic and hemodynamic tracings will be recorded on magnetic tape during normal sinus rhythm for a period of 10 minutes. We will substitute V3 for V1 in this protocol because of its greater sensitivity for ischemic ST-T wave changes. The left anterior descending coronary artery will then be occluded by inflating the balloon. Occlusion of the artery will be confirmed by the lack of flow distal to the inflated balloon. The occlusion will be maintained for 60 minutes and all tracings will be recorded continuously on magnetic tape during this time. If ventricular fibrillation occurs during occlusion, the dogs will be cardioverted within 60 seconds, and occlusion continued to complete the 60 minute occlusion period. The same procedure will be followed should the dogs develop more than one episode of ventricular fibrillation. Selected portions of the fibrillatory waveforms will be retrieved later for analysis.

Reperfusion of acutely ischemic myocardium. After the termination of the 60 minute occlusion period, the occluded coronary artery will be reopened by deflating the balloon, allowing the resumption of blood flow [56]. Data will be recorded continuously on magnetic tape. If ventricular fibrillation occurs, it will be recorded continuously for a total of 5 minutes. If it does not occur for up to 5 minutes after reperfusion, it will be induced using the same pacing procedure described for quinidine intoxication.

Coronary occlusion and the time-course of fibrillation. In a separate series of dogs undergoing acute coronary occlusion, ventricular fibrillation will not be cardioverted within 60 seconds when it occurs spontaneously. Instead, it will be allowed to proceed uninterrupted for 5 minutes, to assess the time course of the phenomenon. This separate series of dogs will not undergo reperfusion (as in the occlusion series discussed earlier) because in our experience reperfusion 5 minutes after continuous and uninterrupted ventricular fibrillation is often unsuccessful. Again, all data will be recorded continuously on magnetic tape for later selective retrieval and analysis.

Regional hyperkalemia. Dogs will be anesthetized and instrumented as for the quinidine intoxication studies. Thereafter, a 2.5F end-hole catheter will be introduced via the left carotid artery, and positioned under fluoroscopic control in the left anterior descending coronary artery just proximal to the main diagonal branch, and sutured in place at the neck. We will perform intracoronary infusion of isotonic potassium chloride (KCl) according to the method of Ettinger et al [57], at a rate of 0.2 mcEq/Kg/second. Using this method, 100 pecent of the dogs can be expected to develop ventricular fibrillation after about 20 minutes of infusion [57]. Once ventricular fibrillation occurs, it will be taped continuously for 5 minutes for later retrieval and analysis.

Global hypothermia. Dogs will be anesthetized and instrumented as for the quinidine intoxication studies. Thereafter, a right carotid artery-jugular vein bypass heat exchanger will be used for cooling and maintaining the rectal temperature at 26-28 degrees C. Hypothermia will be induced by lowering the water temperature in the heat exchanger to 4 degrees C. Immediately before and after the induction of hypothermia, the right ventricle will be paced regularly at 500-300 msec cycle length for 5 seconds (twice diastolic current threshold with 2 msec pulse width) after each 2 degree C decrement in body temperature. This procedure will be continued until a temperature is reached whereby ventricular fibrillation is induced. If fibrillation does not occur spontaneously, it will be induced using the pacing procedure described for quinidine intoxication. Once fibrillation occurs, waveforms will be recorded continuously for 5 minutes.

Premature ventricular stimulation with high current strength. Dogs will be anesthetized and instrumented as for the quinidine studies. Ventricular fibrillation will be induced by applying 3 premature extrastimuli (S2 S3 S4) at 10 times diastolic current threshold, in normal dogs. The right ventricle will be regularly paced (S1 S1) at 400 msec cycle length at twice diastolic current threshold with 2 msec pulse width. After ten regularly driven beats three premature extrastimuli (S2 S3 S4) at ten times diastolic current threshold will be applied at 120 msec coupling internal (S1 S2 = S2 S3 = S3 S4 = 120 msec). Slight adjustments of the premature stimuli may be needed to induce ventricular fibrillation. The sum of the coupling intervals of the premature stimuli (S1 S2 - S2 S3 + S3 S4) will be in the 365-370 msec range [58]. A 5 minute segment of induced-ventricular fibrillation will be taped continuously from its onset for later selective retrieval and analysis.

Data Analysis: All taped fibrillatory waveforms recorded by the electrocardiographic leads (I, aVF, V1 and all 3 bipolar electrograms — 2 from the right, and 1 from the left ventricle) will be digitized using a custom-built (DM Auslander; UC Berkeley) 16 channel A/D converter. The sampling frequency will be 2KHz, and low pass filtering will be set at 900Hz to prevent aliasing. The digitized signals will be stored on 5 1/4 floppy disks using a PC-AT computer, and processed on an Amiga 2000 microcomputer using custom software developed by Dr. J.Hodgson, UCLA. All six methods of mathematical and dynamic computations described in Protocol 1 will be applied to each of the seven different ventricular fibrillation models in this protocol. Five minute long fibrillatory waveforms will be analyzed in the following manner. Six 15 second intervals of fibrillatory waveforms for each of the 5 electrocardiographic leads will be analyzed. The first two intervals will be the initial 15 seconds and the 45th-60th seconds of the fibrillation. Thereafter, the remaining 4 15 second intervals will be sampled at each of the 2nd to 5th subsequent minutes. The specific methods of analysis are identical to those described for Protocol 1. In addition three waveform parameters (QRS amplitude and duration and QT duration) will be measured at specified times for the purpose of comparing and complementing the dynamic data.

Preliminary Results: Progressive quinidine intoxication resulted in spontaneous ventricular fibrillation in 2 of 3 dogs when the total cumulative dose of intravenously administered quinidine reached 100 mg/kg (administered over 5 hours). In the third dog, when the total cumulative dose of quinidine was 80 mg/kg, progressive slowing of the heart rate occurred, with various degrees of AV block and ventricular escape beats. An additional 10 mg/kg of quinidine caused further cardiac slowing and eventual complete cardiac standstill. No spontaneous ventricular fibrillation occurred in this dog.

Figure 1A illustrates 7.9 seconds of quinidine induced ventricular fibrillation recorded from a bipolar RV electrogram in one dog. Figure 1B-F illustrate the analysis of these data by each of our 5 methods. The FFT power spectrum was continuous (Figure 1B), and the phase plane plot (Figure 1C) revealed a pattern of small loops and large loops to the left and right, reminiscent of the Lorenz attractor [35], a classic nonlinear dynamic system. A Poincare return map (constructed along an axis indicated by the arrow in Figure 1C) revealed significantly non-random structure (Figure 1D) illustrated by linear regression (r=-0.41, p=0.02). However, the Lyapunov exponent for these data (Figure 1E) was negative (-0.08 compared to +2.16 for the Lorenz attractor), and no evidence of low dimensionality was observed (Figure 1F). In this case then there was positive evidence for aperiodicity (spectral analysis), and a bounded trajectory (phase plane plot and Poincare return map), but not sensitive dependence. Based on our semiquantitative scale, therefore, we would characterize this case of fibrillation as possibly chaotic.

In two additional dogs, reperfusion ventricular fibrillation was analyzed during the initial 10 seconds of its onset. Spectral analysis of ECG lead I showed a highly discrete spectrum, not suggestive of aperiodic (chaotic) nonlinear dynamic behavior. It consisted of a major spike at 6 Hz, the dominant frequency, and much smaller spikes at 9 and 12 Hz. The significance of these spikes can be seen from a close reading of the waveform. It is not quite sinusoidal, but rather has sharp bottoms and rounded tops. There is also a small spike at around 3 Hz, representing a long-period oscillation in the amplitude. When we performed the same analysis on a simultaneously recorded right ventricular endocardial bipolar electrogram, however, a continuous (broadband) frequency spectrum consistent with chaotic dynamics was observed. Phase plane plots of these same data have shown discrete bands and forbidden zones consistent with nonlinear dynamic behavior. These preliminary findings suggest that ventricular fibrillation can be described as aperiodic nonlinear electrodynamics, and that single electrographic leads and single methods of analysis are not sufficient to detect such behavior.

Sample Size: According to the biostatistical tables provided in the Appendix, we will need to study 15 dogs to confirm the significance of this observation with an alpha error of 5% and a beta error of 10%. However, since only 2 out of 3 dogs develop spontaneous ventricular fibrillation, this increases the number to 20. Thus, a total of 40 dogs are needed for our 2 quinidine intoxication studies. In the acute myocardial ischemia and reperfusion protocols, only 1 in 2 dogs develop spontaneous ventricular fibrillation. Accordingly we will need 30 dogs for this study. An additional 30 dogs unsuited for reperfusion studies will be needed for the protocol in which ischemic fibrillation is not cardioverted for five minutes. In each of the remaining protocols we will require 15 dogs in each group. Thus, we will employ seven different canine models of ventricular fibrillation induced by various means necessitating a total of 145 dogs. Since we expect that 10% of the dogs will fail to reach a successful termination for a variety of other reasons (defective instrumentation and/or premature death) we estimate that we will require a total of 161 (145/0.9) dogs to complete these studies.

PROTOCOL 3: DYNAMICAL ANALYSIS OF OPEN-CHEST CANINE VENTRICULAR FIBRILLATION

Study Hypothesis: Recording site affects the sensitivity of detecting aperiodic nonlinear dynamic behavior during regional myocardial alterations leading to ventricular fibrillation.

Study Population: We will use a total of 45 anesthetized, open-chest, Mongrel dogs of either sex, weighing between 20-26 Kg.

Data Collection: Dogs will be premedicated and initially instrumented as in Protocol 2, and an inflatable balloon-tipped end-hole catheter will be placed in the left anterior descending coronary artery (LAD) as described for the coronary occlusion and acute fibrillation study. Thereafter the chest will be opened by a mid-sternal approach and the heart suspended in a pericardial cradle. Twelve bipolar Teflon coated sliver electrodes (0.1 mm diameter) with 1 mm interelectrode distance and 8 mm distance between two consecutive bipoles will then be sewed on the left epicardium in the territory supplied by the LAD. The electrodes are mounted on a rectangular synthetic rubber block (2x4cm). An initial 5-10 seconds of transient ischemia will identify a cyanotic area that is perfused by the occluded artery. This area will be used for sewing the electrode array. Two to 3 pairs of the electrodes will likely be outside the LAD perfusion zone, and similar number of electrodes are likely to be on the border of ischemic zone. Five to six bipoles will end up in the ischemic zone. A second array of twelve bipolar electrodes, as above, will be sewn on the right ventricle near the outflow tract. This will serve as a remote, control, nonischemic zone. Monophasic action potentials (MAP), will be recorded with our contact (pressure) electrode [66], to determine restitution of action potential duration by the S1S2 method [59,60,64]. (see below protocol 5) in ischemic and nonischemic epicardial and endocardial sites. All recordings will be digitized (2KHz sampling rate) and stored in the computer (VME). Sampling will be done at 2 minute interval. Samapling will continue until ventricular fibrillation occurs. The following two interventions will be studied:

Coronary artery occlusion and acute ventricular fibrillation. As in Protocol 2, five minutes prior to LAD occlusion, and during the entire 60 minutes of occlusion, 15 seconds of signals from all 30 leads will be recorded by our computerized multiplexor, every 5 minutes, until spontaneous ventricular fibrillation occurs (15 of 30 dogs). Fifteen seconds of data will be recorded during the first minute of fibrillation, and a second 15 second strip during the second minute, until 5 minutes lapses after the start of fibrillation (a total of 5 15 second samples, during fibrillation). The digitized data will be stored in the computer for later analysis. Our PRINCIPAL INVESTIGATOR/PROGRAM DIRECTOR   He    S. Karagueuzian, computerized cardiac mapping system (DM Auslander, UC Berkeley) can simultaneously record from 64 different sites by multiplexing. Data will be acquired at a rate of 1KHz with low pass filtering at 450 Hz.

Regional hyperkalemia. Intracoronary infusion of isotonic potassium chloride is initiated as described in Protocol 2. Recordings will be obtained from all 30 leads as above, until spontaneous fibrillation occurs (15 dogs). Data will be recorded as described above.

Data Analysis: The digitized signals will be analyzed by the 5 different methods described in Protocol 1 to determine if demonstrable evidence for nonlinear dynamic behavior varies from one regional recording site to another, and from intracavitary sites to epicardial sites.

Specific Aim 2: Are there identifiable intermediate stages that presage the onset of ventricular fibrillation as in other nonlinear dynamic systems — and what are their mechanisms?

PROTOCOL 4: HOW ACCURATE ARE NONLINEAR DYNAMIC MARKERS FOR PREDICTING VENTRICULAR FIBRILLATION?

Study Hypothesis: The transition to aperiodic nonlinear dynamic behavior is characterized by distinct intermediate stages that are predictive of the subsequent occurrence of ventricular fibrillation.

Study Population: The same dogs used in Protocol 2 and Protocol 3.

Data Collection: The methods of anesthesia, the instrumentation, and the particular interventions are described in Protocol 2 and Protocol 3.

Data Analysis: Whether or not spontaneous ventricular fibrillation occurs (and during the entire period preceding the emergence of qualitative change in some aspect of nonlinear dynamics will be analyzed at selected time intervals by all five different methods of analysis described in Protocol 1. In the series of dogs with quinidine intoxication, 15-second intervals of digitized rhythm strips during both normal sinus rhythm and regular ventricular pacing will be analyzed. Sampling will be done 5 minutes after each incremental dose of quinidine. For coronary occlusion, reperfusion, hyperkalemia and hypothermia, 15-second intervals of digitized rhythm strips will be analyzed at 2 minute intervals. The entire minute immediately preceding ventricular fibrillation will be analyzed in all groups. In the series of dogs with open chest studies (Protocol 3), all available data, collected and stored in the digitized form, preceding ventricular fibrillation, will also be analyzed by the 5 different methods as above. These data will show if intermediate dynamic markers of fibrillation during regional interventions are site specific. In cases where no fibrillation occurs, electrocardiographic data will be analyzed in a similar manner, for comparison to cases that develop ventricular fibrillation. In this way, both the sensitivity and specificity of each observational characteristic for the emergence of ventricular fibrillation will be defined.

The sensitivity and specificity for the development of spontaneous and inducible ventricular fibrillation will be determined separately for the following observations: spectral power, phase plane banding, Poincare return map structure, Lyapunov exponential divergence, and dimensionality. Subjective data (such as the visual assessment of phase plane plots for the occurrence of banding) will be interpreted on 2 separate occasions by 3 independent observers, to quantify interobserver and intraobserver variability. Because the defining thresholds for many of these observations are arbitrary (for example, the definition of a continuous spectrum as one containing more than 10% interharmonic power), accuracy will also be quantified independent of the particular defining threshold by (i) iterating the threshold of the underlying continuous variable over a range of values, (ii) constructing a receiver-operating characteristic (ROC) curve, and (iii) computing the area under this curve [61,62].

Preliminary Results: Figure 2 illustrates the RV electrograms (top panels A-C) and phase plane plots (middle panels A-C) for one dog during progressive quinidine intoxication. During the control state (A), the phase plane plot is uniformly thick (maximum ratio: 1.8 to 1) and shows no gaps. The Lyapunov exponent was -0.43. As the dose of quinidine is increased, to 40 mg/kg (B), the phase plane plot shows visible banding, and non-uniform thickening (maximum ratio: 5.0 to 1), representing sensitive dependence on initial conditions. The Lyapunov

| PRINCIPAL INVESTIGATOR/PROGRAM DIRECTOR | |
|---|---| exponent at this dose remained negative (-0.62). At 100 mg/kg (C), the Lyapunov exponent became positive (+0.18), and the phase plane plots become even more complex, revealing the development of a "tunnel" in the ST-T wave portion of the plot (inset to Figure 2C), similar to that seen with the Rossler attractor [35] as its stress parameter is raised (adjacent panels). We observed this phenomenon only in the two dogs that subsequently developed ventricular fibrillation (and not in the other). The spectra derived from these data at all pre-fibrillatory doses, were discrete, with multiple peaks at harmonics of the fundamental frequency, or in advanced stages of intoxication, at frequencies below the fundamental, representing long period oscillations. These data indicate that power spectra alone are insensitive index of chaotic dynamics. Figure 3 illustrates phase plane plots of sinus rhythm from two dogs during control, 20 and 25min post LAD occlusion periods. The dog (HQ-7), upper panels, developed ventricular fibrillation (VF) immediately after the last sinus beat was recorded. In contrast the dog (LQ-4), did not develop ventricular fibrillation, despite obvious signs of acute ischemia (ST elevation). Note, right ventricular (RV) bipolar phase plane plots (PPP), in both dogs remained relatively constant before an at increasing durations after coronary occlusion (non-ischemic zone). In contrast however PPP of the left ventricular bipolar electrograms (LV) during sinus rhythm, in the dog that eventually developed VF has shown forbidden zones (banding), and non-uniform thickening (0.9:9 ratio, during control and 1:24 rows before VF) reflecting sensitive dependence on initial conditions (arrows). Precordial lead (V3 in the fibrillating dog had also more discernible changes in the PPP than the dog that did not fibrillate. These data strongly suggest that the site of origin of ischemic VF demonstrates two major markers of chaotic dynamics. These markers can be used to predict an impending ventricular fibrillation in the intact dog.

PROTOCOL 5: IS APERIODIC NONLINEAR DYNAMICS (CHAOS), A REFLECTION OF INTER- OR INTRA- CELLULAR HETEROGENEOUS ACTION POTENTIAL PROPERTIES?

Study Hypothesis: Aperiodic nonlinear dynamic behavior can arise by two different mechanisms. Pharmacologic and biochemical alterations are capable of initiating aperiodicities within individual cells (temporal heterogeneity). Alternatively, ensembles of cells, in the absence of similar alterations, exhibit periodicities, but aperiodic dynamics (chaos) arise as a consequence of asynchrony between them (spatial heterogeneity).

Study Population: We will use right ventricular endocardial and epicardial tissue preparations isolated from the dogs used in Protocol 2 and protocol 3, in which ventricular fibrillation was induced by a variety of regional and global stimuli (quinidine, ischemia, reperfusion, hyperkalemia, hypothermia, pacing). In addition, similar tissue preparations will be isolated from 15 untreated, normal dogs.

Data Collection: After terminating the whole animal studies, the right ventricular endocardium, from which bipolar electrograms were recorded, will be isolated and evaluated for transmembrane action potentials, using microelectrode techniques [64-66,71]. A left thoracotomy will be performed at the fifth intercostal space, while the dogs are still under general anesthesia. After the pericardium is incised, the heart will be removed rapidly by severing all major vessels, and placed in cold (4 degree C) oxygenated Tyrode's solution. A right ventricular endocardial block (2x2 cm) will then be excised from approximately the same site from which bipolar electrograms were recorded in situ. The block will be set and mounted with stainless steel insect pins in a Lucite tissue chamber (5x5x1 cm). For endocardial studies, the endocardium will be mounted upward, and for epicardial studies, the epicardium will be mounted upward. The tissue will be constantly superfused with normal Tyrode's solution at a rate of 8 ml per minute (37 degree C at pH=7.4+0.1) [65,66]. Similarly, epicardial strips will be isolated from left or right ventricular sites that do show various degrees of periodic and nonperiodic behavior during regional interventions (Protocol 3).

Cellular basis of bipolar electrograms showing characteristic dynamic behaviors: Two bipolar (USCI) electrodes with a 1 cm interelectrode distance (same as for the in vivo studies) will be placed on the surface of the tissue in orthogonal directions, such that one bipole is parallel to the myocardial fiber orientation, and the second perpendicular to it. The preparations will be paced regularly at 1000 msec cycle length with twice diastolic current threshold and 2 msec pulse width. The stimulating electrode (Teflon coated bipolar silver wire, 0.5 mm in diameter, except for their tips) will be placed near (1mm) the corner where the poles of the two recording bipolar electrodes meet. One microelectrode will be impaled in the middle of one bipolar electrode (stationary microelectrode) and another microelectrode will be used to map the endocardial surface (roving microelectrode) [65,66,71,72]. Recordings will be made, at progressively decreasing pacing cycle lengths, starting from 1000 msec and decreasing by 50 msec until one or the two electrograms manifest characteristic dynamic behavior indicative of evolution, to nonlinear dynamics (e.g. a given order of periodicities or irregular aperiodic dynamics). At this cycle length, action potentials will be recorded from the 3-4 most superficial subendocardial layers with the roving microelectrode. Fifty consecutive action potentials along with their associated electrograms will then be recorded on a Gould recorder (2600- S). The entire pacing sequences will be recorded on a magnetic tape (CPR-4010) for later analysis. Similar recording will also be made at relatively longer cycle length during which no discernable nonlinear dynamic events occur on the two bipolar electrograms ("control", i.e.,stable steady-state). Mapping of the endocardial surface with the microelectrode will be done by recording action potentials sequentially from different sites (65,71). We will record from 20-25 different sites, and thus obtain 20-25 cell pairs along with two corresponding bipolar electrograms.

Anisotropy and nonlinear dynamics: As for the determination of the anisotropic effects of the myocardium on conduction and on bipolar electrogram properties, two microelectrodes will simultaneously be impaled near the distal poles of the bipolar electrodes (relative to the stimulating electrode). A third bipolar recording electrode (Teflon coated, not at the tip, silver wire, 0.5 mm diameter) will be placed within 200 microns of the stimulating electrode. The microelectrodes will be able to measure conduction along the longitudinal and transverse fiber orientation by measuring impulse arrival at the proximal (bipolar) and distal microelectrodes. The preparations will then be paced in decrements of 100 msec starting at 1000 msec cycle length while subjected to various interventions (see below). The filtered output of the signals of the entire experiment will be connected to an FM tape recorder (CPR-4010) with a frequency response of 0-2.5 kHz.

Restitution af action potential duration will constructed by the S1S2 method [59,60,64], where premture, late premature and postmature S1S2 impulses will be applied after 10 regularly driven beats at cycle lengths of 500-2000msec. The duration of these S1S2 action potentials will then be plotted as a function of S1S2, and the time constant of recovery of action potential duration evaluated experimentally [64]. Data thus obtained will be analyzed for nonlinearity of restitution of action potential duration and for recovery of excitability. Attention will be focused on supernormal excitability as this parameter was found to increase nonlinearity and cause aperiodic response patterns during periodic stimulation [64].

Superfusion media: Both endocardial and epicardial tissue isolated from quinidine intoxicated dogs will be superfused with normal drug-free Tyrode's solution maintained at 37 degrees C (65,71). Because quinidine washout is very slow (C Antzelevitch, Personal Communication) these tissue preparations remain intoxicated and manifest various cellular electrophysiological stigma (described below in the Preliminary Results section) for up to 2 1/2 hours. If the experiment lasts longer than 2 hours, 20 ug/ml quinidine gluconate will be added to the Tyrode's solution to maintain toxicity. Tissues isolated from acute ischemia and reperfusion studies will first be superfused with Tyrode's solution gassed with 5% oxygen and 95% nitrogen to mimic some of the effects of ischemia, and after termination of hypoxic conditions, the tissues will be reoxygenated with 95% oxygen and 5% carbon dioxide. Tissues isolated from studies of the effects of regional potassium infusion will be superfused with Tyrode's solution containing increasing potassium ion concentrations from 4 to 32 mm in 4 mm steps, and the effects of incremental potassium evaluated. Finally, tissues isolated from dogs used for the hypothermia studies will be superfused with normal Tyrode's solution, and the effect of progressive lowering of the tissue bath temperature from 37 degrees C to 27 degrees C in steps of 1 to 2 degrees C will be evaluated. The effects of 4 drugs will then be evaluated on nonlinear electrophysiologic dynamics induced by : (i) lidocaine (1-5 ug/ml), a fast sodium inward current blocker acting primarily on the inactivated channel state (channel closed), [68], (ii) quinidine (1-10 ug/ml), a fast sodium channel blocker acting primarily on activated state (channel open) [68], (iii) verapamil (0.5-5 ug/ml), a calcium channel blocker, and (iv) tetrodotoxin (TTX), (0.5-2 uM/ml), a specific sodium channel blocker; window sodium current at low and phase zero action potential at higher concentrations [60,66].. Data thus obtained will provide clues as to the possible ionic mechanism(s), responsible for the induction of nonlinear electrophysiologial dynamics.

Data Analysis: Taped recordings from all five electrodes (three bipole and two microelectrodes) will be digitized at 2 KHz, and the digitized signals will be analyzed using the five different methods of analysis described in Protocol 1. Action potentials and bipolar electrograms (0.5-500 Hz) will be analyzed over 30 to 60 second intervals. Single cell action potential variability (recorded from multiple sites) will be correlated with bipolar electrogram variability in orthogonal directions. This comparative approach will allow us to determine how, if at all, cellular electrical activity correlates with bipolar electrograms showing periodic and aperiodic nonlinear dynamics (chaos) in orthogonal directions. To evaluate the effects of anisotropy on the induction of nonlinear dynamics in propagation [23], we will use the method of this time vs next time plot of conduction time. Conduction times, (time of impulse propagation from the proximal electrogram to the two distal microelectrodes), at successive beats will then be plotted [4,8,23]. The presence or absence of period two (alternans), higher order periodicities and aperiodicity (chaos) on orthogonal leads can then be determined. The results of this study, will demonstrate if and under what circumstances, anisotropy makes a contribution to the nonlinear dynamic behavior of impulse propagation.

Preliminary Results: Our initial isolated quinidine-intoxicated tissue studies have shown a rich array of transmembrane action potential profiles, that changed on a beat to beat basis. These cellular electrical activity were neither anticipated by us nor reported previously by others [Figures 4-8]. Tissues (RV endocardium) were isolated from dogs (n=3) with ventricular tachycardia and fibrillation (VT/VF) induced by intravenous quinidine (100mg/kg over 5hrs), and continuous pacing. Steady-state, rate-dependent changes in action potential duration and amplitude (Figures 4 and 5 ) occurred as cycle length was reduced from 1000 to 300 msec. Period 2 action potential duration alternans amounted to 108±36msec at 50% repolarization), and action potential amplitude alternans to 9±8mV. Period 3 and 4 action potential duration/amplitude alternans and phase-locking emerged at shorter cycle lengths also emerged (Figure 5), eventually leading to aperiodic dynamics with respect to both action potential duration and amplitude (Figures 7 and 8A). Figure 8B illustrates the dynamics of one such aperiodic action potential responses (Figure 8A) in a state-space representation [i.e., phase-plane plot of voltage (V) vs its first derivative (dV/dT) in an arbitrary scale. During the xth beat the state variables describing the dynamics of the impaled cell (V vs dV/dT) are at point 1. Five msec later they are at point 2. During the subsequent beat (x+1), the variables are again very close to each other near point 1, but not axactly at point 1. As a result of this small displacement in the initial condition, the location of the trajectory 5msec later is at point 3. This phenomenone,described as "sensitive dependence on initial conditions", [23], is a marker of chaotic dynamics [1,5,23]. The second important hallmark of chaos (forbidden zones) 1,5,23] is also shown in Figure 8B. Certain areas of the phase plane plot are not crossed by trajectories (nonrandom, deterministic dynamics). These preliminary findings suggest that chaotic action potential dynamics, does in fact occur in our quinidine-intoxicated endocardial fibers. These findings are similar to those reported by Chialvo and Jalife [23], in heptanol-intoxicated sheep Purkinje fibers during very fast drive rate (>300beat/min). In dogs (n=3), intoxicated with quinidine that did not develop VF, no such cellular chaotic action potential dynamics coud be induced, at all pacing cycle lengths attempted (2000 to 200msec).

In one right ventricular endocardial preparation isolated from quinidine intoxicated dog with VF, action potential amplitude and action potential duration alternans (period two) were seen both in fast depressed fibers, resting potentials of -65 to -72 mV, (Figure 3A and 3B), and in slow response fibers, resting potentials of -58mv to -62mv (Figure 3C). Phase 2 (plateau region) and phase 3 alternans appeared over a 5 minute interval of continuous monitoring during regular drive at a cycle length of 800 to 500 msec (Figures 4-7). In one fast depressed fiber (resting membrane potential of -70mv), graded increases in the driving rate resulted in the progressive emergence of period 2, period 3, period 4, and the eventual appearance of 4 to 3 phase locking (arrows in Figure 5). Various periodicitties emerged after transients of 3-7msec and lasted for 3-5 minutes duration of monitoring. The dynamics and the time course of appearance of these periodicitiesin, are different from the electrical restitution and declining memory effects described in normal ventricular and Purkinje fibers [59,60]. This indicates, that quinidine-induced alterations in the kinetics of transmembrane ionic current flow, brings about chaotic dynamics, that did not occur neither in normal (3 dogs), nor in nonarrhythmic quinidine treated tissues . The ionic mechanism(s) are undefined at the present. Our systematic pharmacologic evaluation with antiarrhythmic drugs acting on specific ion channel and on specific ion channel state, could provide clues as to the probable ionic mechanism(s). Periodic and aperiodic action potential dynamics could suddenly be terminated by abrupt slowing of the drive rate. Simultaneous recordings of action potentials from two cells, has shown in-phase period two alternans that progressed transiently to out-of-phase alternans (arrows in Figure 6). All of these observations were made on endocardial Purkinje fibers, most superficial (1 to 3) cell layers [65], and in ventricular muscle cells, deeper cell layers (4 to 7) [65]. <u>These cellular chaotic dynamics, seen in quinidine-intoxicated fibers, provide electrophysiological heterogeneity that may be responsible for the induction of ventricular tachycardia and ventricular fibrillation seen in vivo.</u>

To determine if the Beeler-Reuter computer model of myocardial cell action potential [51,52] is capable of mimicking the nonlinear dynamic behavior that we have observed, we implemented the model in PASCAL on _____ PRINCIPAL INVESTIGATOR/PROGRAM DIRECTOR H. S. Karagueuzian ____ a microcomputer, and paced it at increasing frequencies, until periodic bifurcation occurred (manifest as afterpotentials). Driving the model at still higher frequencies caused a transition from periodic to aperiodic nonlinear dynamics. The use of this model, with manipulations of various ionic currents (time constants of activation and inactivation), with pharmacologic probes, will provide important details on the ionic mechanisms leading to cellular chaotic electrodynamics.

Specific Aim 3: Can the transition to aperiodic nonlinear dynamics (chaos) be interrupted by pharmacologic interventions?

PROTOCOL 6: INTERRUPTION OF APERIODIC NONLINEAR DYNAMICs (CHAOS) AND PREVENTION OF VENTRICULAR FIBRILLATION BY DRUGS

Study Hypothesis: Quinidine, verapamil, and diltiazem, and the combination of quinidine and metoprolol modify arrhythmic response produced by acute myocardial ischemia, and by doing so also modify the electrodynamics of ventricular depolarization and repolarization during sinus rhythm.

Study Population: We will use anesthetized closed chest dog preparations in which acute ischemia will be induced by transient left anterior descending coronary artery occlusion followed by reperfusion.

Data Collection: The dogs will be anesthetized and instrumented as in Protocol 2 for coronary occlusion. Twenty minutes before coronary occlusion, 1 mg/kg/min of quinidine gluconate will be infused through the jugular vein for 15 minutes (loading dose), followed by 0.1 mg/Kg/minute as a maintenance dose for the entire duration of occlusion (60 minutes). In a second series of dogs, metoprolol will be administered in a single bolus injection (jugular vein) of 4 mg/Kg 20 minutes before coronary occlusion. In a third series of dogs, both drugs will be administered simultaneously using the above dosage protocols, again 20 minutes before coronary occlusion. In a fouth series of dogs, verapamil will be administered in a single bolus injection (jugular vein) of 0.15 mg/kg [69] followed by 7.5 ug/kg/min as maintenance intravenous infusion. Verapamil therapy will start 20 minutes prior to coronary artery occlusion. In a fifth series of dogs, diltiazem will be constantly infused through the jugular vein at 0.04 mg/kg/min [70], starting 20 minutes prior to coronary artery occlusion. All infusions of drugs will last for the entire duration of occlusion and reperfusion. The entire 20 minutes preceding the occlusion, 60 minutes of occlusion, and 20 minutes of reperfusion (100 minutes total) will be recorded continuously on magnetic tape.

Data Analysis: Thirty second intervals "normal" sinus rhythm of digitized signals taken at specified times, (5 minute intervals if ventricular ectopy permits), will be analyzed by the methods of analysis described in Protocol 1 for all five groups (quinidine, metoprolol, quinidine-metoprolol, verapamil, and diltiazem). The entire 2-5 minute ectopy-free interval immediately preceding ventricular fibrillation will always be attempted to be analyzed.

Preliminary Results: We have observed that the combination of metoprolol and quinidine is effective in suppressing ventricular fibrillation during acute myocardial ischemia and during acute reperfusion. In 12 dogs with no drug therapy ventricular fibrillation occurred in 7 dogs. In metoprolol treated dogs, fibrillation occurred in 4 out 10 dogs, and in quinidine treated dogs, it occurred in all 4 dogs tested. In contrast, in the quinidine-metoprolol group, ventricular fibrillation occurred only in 1 out 9 dogs tested. The degree of ischemia as judged by ST segment elevation and the myocardium at risk assessed by Monastral blue dye injection in the occluded artery was similar in all three groups. These data serve to support our selection of these agents, to simulataneously evaluate modification of ventricular rhythm patterns and their associated electrodynamics.

Sample Size: This protocol seeks to compare the proportion of nonlinear dynamic events detected in each of 5 different treatment groups to a group of controls. Table 3 (in the Appendix) provides the statistical power achieved under various hypothesized treatment effects for sample sizes of 10 to 30 dogs in each group. Since each treatment will be compared to the control (5 pairwise comparisons) Dunnett's multiple comparison procedure was incorporated into the power calculations to control the familywise error rate. This has the effect of reducing the power of a particular sample in comparison to Tables 1 and 2. Accordingly, we will need 20 dogs in each treatment group for a total of 100 dogs (control dogs are the same as those in Protocol 2). Assuming we will be unable to successfully terminate the studies in approximately 10% of the dogs (no ischemia, inability to catheterize) we will require a total of 111 dogs for these studies (100/0.9).

APERIODICITY DURING QUINIDINE INTOXICATION

PCL = 800msec       FIGURE 7

Phase Plane Plots of "Normal Sinus Rhythm"

QUINIDINE: INCREASING DOSES

ROSSLER EQUATIONS: INCREASING STRESS PARAMETER

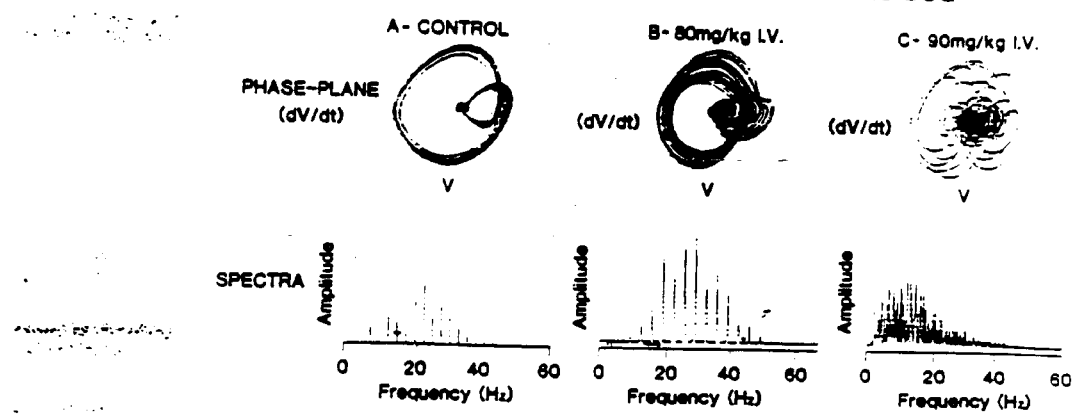
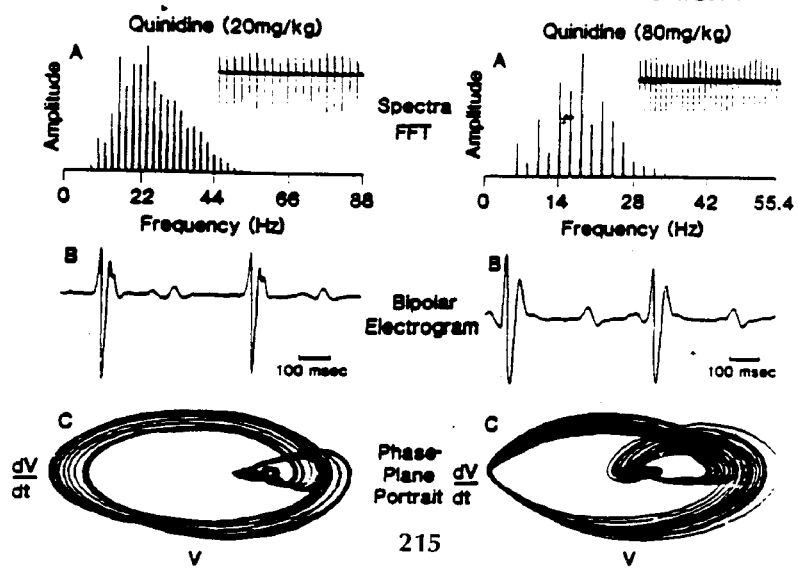

PAL INVESTIGATOR/PROGRAM DIRECTOR  J. Karagueuzian, Ph.D.

VERTEBRATE ANIMALS

1) We will use Mongrel dogs of either sex, approximately two years old and weighing between 20-26Kg. All experimental protocols, will be done and completed while the dogs are under general anesthesia. Each dog experiment is terminal, in that, after the completion of the experiment, the dogs will not regain consciousness.

2) The dog model, by virtue of its remarkable tolerance to general anesthesia, heart size, anatomy, collateral circulation, and arrhythmic response to a variety of stimuli, has proven to be extemely useful. Furthermore, the similarities of the quality of the canine arrhythmias to humans, makes the canine model desirable for exploration.
The multiple lengthy methods of analysis, that will be done in each dog, will generate a huge data base that will contain a wealth of important information worth studying. Therefore, this very nature of the present proposal will necessitate relatively fewer number of dogs. We estimate, one successful and complete dog experiment per week will complete the intended experiment (about 90% of the present proposal's experiments, we estimate, are successful). This, we believe, justifies both the use and the relative high cost the of the dogs.

3) We have three house staff veterinarians, along with four other personnel who take around the clock care of the needs and the requirements of the animals in the vivarium. Furthermore, since our protocols do not require any special diatary care or medical attention. We will use the dogs in acute terminal experiments. Post-operative attention to possible complications would be of no concern in this proposal.

4) All the study protocols will be conducted on fully anesthetized dogs. There will be no discomfort or pain throughout the entire study period in each and every dog. Throughout the entire period of a given study, additional supplemental doses of anesthetic agents will be administered through indwelling catheters to insure that comlete anesthesia is adequately maintained throughout the entire study period.

5) At the end of the study, additional doses of anesthetic agent will be administered if needed to insure full and deep anesthesia. At this time, a thoracotony is done at the left fifth intercostal space, the heart rapidly removed by severing the major vessels and euthanasia induced by exsanguination.

PRINCIPAL INVESTIGATOR/PROGRAM DIRECTOR: /r S. Karagueuzian, Ph.D

REFERENCES

1. May RM. Simple mathematical models with very complicated dynamics. Nature 1976;261:459-467.

2. Procaccia L. Universal properties of dynamically complex systems: the organization of chaos. Nature 1988;333:618.

3. Feigenbaum MJ. Universal behavior in nonlinear systems. Los Alamos Science, 1980;Summer:4-27.

4. Guevara MR, Glass L, Shrier A, Class A. Phase locking, period doubling bifurcations, and irregular dynamics in periodically stimulated cardiac cells. Science 1981;214:1350-1353.

5. Olsen LF, Degn H. Chaos in biological systems. Quart Rev Biol 1985;18:165-255

6. Garfinkel A. A mathematics for physiology. Am J Physiol 1983;14:R455-466.

7. Goldberger AL, West BJ. Applications of nonlinear dynamics to clinical cardiology. Ann NY Acad Sci 1987;504:195-213.

8. Guevara MR, Glass L. Phase locking, period doubling bifurcations and chaos in a mathematical model of a periodically driven oscillator: a theory for the entrainment of biological oscillators and the generation of cardiac dysrhythmias. J Math Biol 1982;14:1-23.

9. Moss AJ. Clinical significance of ventricular arrhythmias in patients with and without coronary artery disease. Prog Cardiovasc Dis 1980;23:33-52.

10. May GS, Eberlein KA, Furberg CD, Passamani ER, DeMets D. Secondary prevention after myocardial infarction: A review of long term trials. Prog Cardiovasc Dis 1982;24:331-352.

11. DeSoyza et al. Ventricular arrhythmia before and after aorta coronary bypass surgery. Internat J Cardiol 1981;1:123.

12. Codini MA, Sommerfeldt L, Ebel CE, et al. Efficacy of coronary bypass grafting in excercise-induced ventricular tachycardia J Thorac Cardiovasc Surg 1981;81:502.

13. Leutenegger F, Giger G, Fuhr P, et al. Evaluation of aortic coronary venous bypass for prevention of cardiac arrhythmias. Am J Cardiol 1979;98:15.

14. Nordstrom LA, Lillehei JP Adicoff A, et al. Coronary artery surgery for recurrent ventricular arrhythmias in patients with variant angina. Am Heart J 1975;89:236.

15. Bonchek LI, Olinger GN, Keelan MH, et al. Management of sudden coronary death. Ann Thorac Surg. 1977;24:337.

16. Tabri IF, Geha AS, Hammond GL, Baue A E. Effective surgery on ventricular tachyarrhythmias associated with coronary arterial occlusive disease. Circulation 1978;58:167.

17. Ricks WB, Winkle RA, Shumway NW, Harrison DC. Surgical management of life-threatening ventricular arrhythmias in patients with coronary artery disease. Circulation 1977;56:38.

18. Gallagher JJ, Oldham H N, Wallace AG, et al. Ventricular aneurysm with ventricular tachycardia. Am J Cardiol 1975;35:696.

19. Graboys TB, Lown B, Podrid PJ, DeSilva R: Long term survival of patients with with malignant ventricular arrhythmias treated with antiarrhthmic drugs. Am J Cardiol 1982;50:436-443

20. Moon FC. Chaotic vibrations. John Wiley:New York; 1987:37-66.

21. [illegible reference]

22. Glass L, Guevara MR, Shrier A. Universal bifurcations and the classification of cardiac arrhythmias. Ann NY Acad Sci 1987;504:168-178.

23. Chialvo DR, Jalife J. Non-linear dynamics of cardiac excitation and impulse propagation. Nature 1987;330:749-752.

24. Ritzenberg AL, Adam DR, Cohen RJ. Period multupling-evidence for nonlinear behaviour of the canine heart. Nature 1984;307:159-161.

25. Smith JM, Clancy EA, Valeri CR, Ruskin JN, Cohen RJ. Electrical alternans and cardiac electrical instability. Circulation 1988;77:110-121.

26. Ritzenberg AL, Smith JM, Grumbach MP, Cohen RJ. Precursor to fibrillation in cardiac computer model. Computers in Cardiology, 1984;171-174.

27. Goldberger AL, Bhargava V, West BJ, Mandell AJ. Some observations on the question: Is ventricular fibrillation "CHAOS"? Physica D 1986;19:282-289.

28. Farmer D, Crutchfield J, Froehling H, Packard N, Shaw R. Power spectra and mixing properties of stange attractors. Annals NY Acad Sci 357;1980,453-472.

29. Chen PS, Wolf PD, Dixon EG, Danieley ND, Frazier DW, Smith WM, Ideker RE. Mechanism of ventricular vulnerability to single premature stimuli in open-chest dogs. Circ Res 1988;62:1191-1209.

30. El-Sherif N. The figure 8 model of reentrant excitation in the canine post-infarction heart. In Cardiac Electrophisiology and Arrhythmias 1985. Zipes DP and Jalife J (eds). Crune and Stratton, pp 363-378.

31. Pinsker HM, Bell J. Phase plane description of endogenous neuronal oscillators in aplysia. Biol Cybern 1981;39:211-221.

32. Wolf A, Swift JB, Swinney HL, Vastano JA. Determining Lyapunov exponents from a time series. Physica D 1985;16:285-317.

33. Albano AM, Mees AI, deGuzman GC, Rapp PE: Data requirements for reliable estimations. In "Chaotic Biological Systems". Holden AV (ed), Pergamon Press 1987

34. Eckmann JP. Roads to tubulence in dissipative dynamical systems. Rev Mod Phys 53;1981;643-654.

35. Abraham R, Shaw C. Dynamics: The Geometry of Behavior, Part Two: Chaotic Behavior. Santa Cruz CA: Aerial Press, 1983, pp77-84.

36. Salerno JA, Previtali M, Pancirolli C, et al. Ventricular arrhythmias during acute myocardial ischaemia in man. The role and significance of R-ST-T alternans and the prevention of ischaemic sudden death by medical treatment. Eur Heart J 1986;7(Supp. A):63-75.

37. Rozansky JJ, Kleinfeld M; Alternans of ST segment and T wave. A sign of electrical instability in Prinzmetal's angina. PACE 1982;5:359-365.

38. Kleinfeld M, Stein E, Magin J. Electrical alternans in single ventricular fibers of the frog heart. Am J Physiol 1956;187:139-142.

PRINCIPAL INVESTIGATOR/PROGRAM DIRECTOR: H. S. Karagueuzian, Ph.D

39. Hogancamp CE, Kardesh M, Danforth WH, Bing RJ. Transmembrane electrical potentials in ventricular tachycardia and fibrillation. Am Heart J 1959;57:214-222.

40. Hoffman BF, Suckling EE. Effect of heart rate on cardiac membrane potentials and the unipolar electrogram. Am J Physiol 1954;179:123-130.

41. Hirata Y, Kodama I, Iwamura N, Shimizu T, Toyama J, Yamada K. Effects of verapamil on canine Purkinje fibres and ventricular muscle fibres with particular reference to the alternation of action potential duration after a sudden increase in driving rate. Cardiovascular Res 1979;13:1-8.

42. Hirata Y, Toyama J, Yamada K. Effects of hypoxia or low pH on the alternation of canine ventricular action potentials following an abrupt increase in driving rate. Cardiovascular Res 1980:14:108-115.

43. Russel DC, Smith HJ, Oliver MF. Transmembrane potential changes and ventricular fibrillation during repetitive myocardial ischaemia in the dog. Brit Heart J 1979;42:88-98.

44. Akiyama T. Intracellular recording of in situ ventricular cells during ventricular fibrillation. Am J Physiol 1981;240:465-471.

45. Downar E, Janse MJ, Durrer D. The effect of acute coronary artery occlusion on subepicardial transmembrane potentials in the intact porcine heart. Circulation 1977;56:217-224.

46. Spear JF, Horowitz LN, Hodess AB, MacVaugh H, Moore EN. Cellular Electrophysiology of human myocardial infarction. Circulation 1979;59:247-256.

47. Janse ME, van der Steen ABM, van Dam R Th, Durrer D. Refractory period of the dog's ventricular myocardium following sudden changes in frequency. Circ Res 1969;26:251-262.

48. Marchlinski FE. Characterization of oscillations in ventricular refractoriness in man after an abrupt increment in heart rate. Circulation 1987;75:550-556.

49. Spach MS, Dolber PC, Heidlage JF, Kootsey JM, Johnson EA. Propagating depolarization in anisotropic human and canine cardiac muscle: Apparent directional differnces in membrane capacitance. Circ Res 1987;60:206-219.

50. Carson DL, Cardinal R, Savard P, Vermeulen M. Characterization of unipolar waveform alternation in acutely ischaemic porcine myocardium. Cardiovascular Res 1986;20:521-527.

51. Beeler GW, Reuter H. Reconstruction of the action potential of ventricular myocardial fibres. J Physiol 1977;268:177-210.

52. Jensen JH, Christiansen PL, Scott AC. Chaos in the Beeler-Reuter system for the action potential of ventricular myocardial fibres. Physica D 1984;13:269-277.

53. Hashimoto H, Suzuki K, Miyake S, Nakashima M. Effects of calcium antagonists on the electrical alternans of the ST segment and on associated mechanical alternans during acute coronary occlusion in dogs. Circulation 1983;68:667-672.

54. Ripley, B.D., Spatial Statistics, John Wiley and Sons, New York 1981

55. Karagueuzian HS, Ohta M, Drury JK et al,. Coronary venous retroinfusion of procainamide: a new approach for the menagementof spontaneous and inducible sustained ventricular tachycardia during myocardial infarction. J Am Coll Cardiol 1986;7:551-563.

56. Meesmann M, Karagueuzian,Ino T, et al; Selective perfusion of ischemic myocardium during coronary venous retroinjection: a study of the causative role of venoarterial and venoventricular pressure gradients. J Am Coll Cardiol 1987;10:887-897.

57. Ettinger PO, Regan TJ, Oldewurtel HA. Ventricular delay and arrhythmias during regional hyperkalemia in the dog. Circ Res 1973;33:521-531.

58. Hamer A, Karagueuzian HS, Sugi K, et al. Factors related to the induction of ventricular fibrillation in the normal canine heart by programmed electrical stimulation. J Am Coll Cardiol 1984;3:729-751.

59. Saitoh H, Bailey JC, Surawicz B: Alternans of action potential duration after abrupt shortening of cycle length: differences between dog Purkinje and ventricular muscle fibers. Circ Res 1988;62:1027-1040.

60. Elharrar V, Atarashi H, Surawicz B: Cycle length-dependent action potential duration in canine Purkinje fibers. Am J Phsysiol 1984,247:H936-H945.

61. Diamond GA. ROC steady: a receiver operating characteristic curve that is invariant relative to selection bias. Med Decis Making 7:1987;238-243.

62. Hanley JA, McNeil BJ. The meaning and use of the area under a receiver operating characteristic (ROC) curve. Radiology 1982;143:29-36.

63. Howard LN. Time periodic and spatially irregular patterns. In: Dynamics and Modelling of Reactive Systems, Stewart WE et al (eds), Academic Press, NY, 1980

64. Chialvo DR, Michaels D, Jalife J. Supernormal excitability as a mechanism of chaotic dynamics of activation in cardiac Purkinje fibers. Circ Res (Submitted).

65. Sugi K, Karagueuzian, Fishbein MC, Mandel WJ, Peter T. Cellular electrophysiologig characteristics of surviving subendocardial fibers in chronically infarcted right ventricular myocardium susceptible to inducible sustained ventricular tachycardia. Am Heart J 1987;114:559-569.

66. Ino T, Karagueuzian HS, Hong K, et al. Relation of monophasic action potential recorded with contact electrode to underlying transmembrane action potential properties in isolated cardiac tissues: a systematic microelectrode validation study. Cardiovasc Res 1988;22:255-264.

67. Bodine SC, Garfinkel A, Roy RR, Edgerton. Spatial distribution of motor unit fibers in the cat soleus and tibialis anterior muscles: local interactios. J Neuroscience 1988;8:2145-2152.

68. Hondeghem LM, Katzung BG. Antiarrhythmhic agents: the modulated receptor mechanism of action of sodium and calcium channel-blocking drugs. Ann Rev Pharmacol Toxicol 1984;24:387-423.

69. Karagueuzian HS,Sugi K,Ohta M,Mandel WJ,Peter T; The efficacy of lidocaine and verapamil alone and in combination on spontaneously occuring automatic ventricular tachycardia in conscious dogs one day after right coronaray artery occlusion. Am Heart J 1986;111:438-446.

70. Peter T, Fujimoto T, Hamamoto H, McCullen A, Mandel WJ. Electrophysiologic effects of diltiazem in canine myocardium, with special reference to conduction delay during ischemia. Am J Cardiol 1982;49:602-605.

71. Karagueuzian HS, Fenoglio JJ Jr, Weiss MB, Wit AL. Coronary occlusion and reperfusion: effects on subendocardial cardiac fibers. Am J Physiol 1980;238:H581- H595.

72. Fenoglio JJ Jr, Karagueuzian HS, Friedman PL, Albala A, Wit AL. Time course of infract growth toward the endocardium after coronary occlusion. Am J Physiol 1979;236:H370-H384.

INDUCTION OF CHAOTIC DYNAMICS IN QUINIDINE INTOXICATED CARDIAC FIBERS. IMPLICATION TO ARRHYTHMIA GENESIS.
Hrayr S Karagueuzian, Ph.D., Steven Khan, M.D., Richard Helfant, M.D., William Mandel, M.D., George Diamond, M.D. Cedars-Sinai Medical Center, Los Angeles CA.

The dynamic response of cardiac cells to repetitive stimulation (RS) in the presence of toxic levels of antiarrhythmic drugs are unknown. We used arguments based on chaos theory to describe action potential (AP) response patterns to RS of right ventricular subendocardial fibers isolated from dogs intoxicated with quinidine (Q). In five closed-chest anesthetized dogs incremental I.V. doses of Q (80-100mg/kg over 5 hours) induced various forms of ventricular tachyarrhythmias (VT/VF). The dynamics of AP patterns of these arrhythmic tissues to RS was evaluated with microelectrode in tissue bath. With increasing RS frequency (2000-300msec) AP duration and amplitude showed steady alternans (bifurcation) of $108\pm36$ msec and $12\pm9$mV respectively. Further increase in RS frequency gave rise to irregular dynamics. This transition was preceded by various repeating stimulus-response ratios (phase-locking) for up to 50 consecutive beats. No such dynamics could be induced in 3 non treated (control) tissues. AP duration restitution curve had significantly ($p<0.05$) steeper slope than control fibers (n=6). Stimulus-response latency remained constant (6-9msec). Phase plane plots of the APs (digitized at 800Hz) during the irregular dynamics showed sensitive dependence on initial conditions and forbidden zones consistent with chaos theory. Conclusion: Q-intoxicated fibers manifest increased slope of AP duration restitution curve that could, in part, be responsible for the aperiodic, chaotic cellular dynamics. Such irregular dynamics may set the stage for reentrant VT/VF seen in vivo.

2 ABSTRACT REPRODUCTION SPACE

LACK OF DYNAMIC AND SPECTRAL HOMOGENEITY OF LOCAL ATRIAL ACTIVITY DURING ACUTE ATRIAL FIBRILLATION.
Hrayr S Karagueuzian, Werner Peters, Steven Khan, George Diamond, Richard Helfant, William J Mandel. Cedars-Sinai Medical Center, Los Angeles CA.

It has been suggested that atrial fibrillation (AF) can be typed to Types I-IV, based on local bipolar electrogram morphology. We hypothesized that various Types of AF can coexist at different locations at a given time, and that a given Type of AF can change to another with time at a given site. Simultaneous high, mid and low right atrial endocardial bipolar electrograms (BEg, 6F USCI) were analyzed during acute AF induced by 2-5sec rapid train of stimuli in anesthetized closed-chest dogs (n=5, 45 episodes, at rates of 400-600beats/min, with a mean of 490beats/min). AF lasted from 5sec to 45min (mean of 45sec). BEgs (0.05-500HZ) at a given time could be discrete, continuous or both at different recording sites, encompassing all 4 Types of AF. Similarly, BEg at a given site changed Type over time. Fast Fourier transform (FFT) of digitized BEgs (8-15sec, 800Hz digitization) showed peaks mostly below 15Hz (range 5-30Hz) that were either discrete (narrow-band) with clear harmonic components, or continuous (broad-band) spectra, that changed in a time and site dependent manner. Phase plane plots (PPP), a plot of voltage vs its first derivative varied both with respect to time and location. However, the morphology of these PPP often inscribed well defined structures (forms) suggesting dynamics compatible with deterministic chaos rather than random motion. We conclude that AF in this model is both temporally and spatially heterogenous encompassing all different Types of AF. These findings should be helpful in developing robust algorithms for AF recognition for antitachycardia devices.

Type in English only

3

ATRIAL ACTIVITY AND VENTRICULAR RESPONSE DURING ATRIAL FIBRILLATION. TWO INDEPENDENT APERIODIC PHENOMENA?

Werner U Peters, Hrayr S Karagueuzian, Steven S Khan, William J Mandel
Division of cardiology, Cedars-Sinai Medical Center, Los Angeles, CA It has been suggested that both atrial activity and ventricular response during atrial fibrillation (AF) are aperiodic phenomena. In the present study we tested the hypothesis that these two aperiodic phenomena are related using serial cross-correlation (CC) and phase-plane-plots (PPP), a plot of voltage vs its first derivative. AF was induced in closed-chest anesthetized dogs (n= 5) by rapid trains of stimuli (40 ms CL). Simultaneous recordings of high, mid and low right atrial (HRA, MRA and LRA respectively) bipolar electrograms (BEg's) and surface electrograms (ECG's) were digitized (800 Hz for PPP and 200 Hz for CC). Autocorrelation of atrial and ventricular activities established their aperiodic nature. CC analysis of HRA and MRA revealed no relationship to ventricular responses but CC of LRA showed in some runs of AF a single peak at 0 +/- 10 ms most probably representing ventricular potential detected in the LRA. However, there was no correlation of LRA at other lag-times. The QRS-occurance on the PPP of all three atrial BEg's was not confined to any specific phase of atrial activity (e.g. peak V, peak dV/dt) as it appeared randomly scattered on the PPP.

We conclude, that the aperiodic ventricular response during AF is not related in an obvious manner to the aperiodic atrial activity. This lack of correlation may be due to concealed conduction in the AV-node and/or complex local atrial mechanisms near the AV-node.

TYPE ABSTRACT IN THIS SPACE
Read Instructions Carefully Before Typing

IS THE PROARRHYTHMIC EFFECT OF QUINIDINE A CHAOTIC PHENOMENON? Alan Garfinkel, Ph.D, Hrayr S. Karagueuzian, Ph.D, FACC, Steven Khan, M.D., George A. Diamond, M.D., FACC. Cedars-Sinai Medical Center, Los Angeles, CA We used dynamic markers based on recent mathematical developments in chaos theory to predict the onset of ventricular fibrillation (VF) during progessive quinidine intoxication. Three closed-chest anesthetized dogs were infused with quinidine (up to 100mg/kg over 5 hours). RV endocardial bipolar electrograms were recorded and analyzed by frequency spectra, phase plane plots, Poincare section return maps and Lyapunov exponents. In the control state and at therapeutic doses the phase plane plots were uniformly thick and showed no gaps, indicating that cycle-to-cycle variation was due to normal biological 'noise'. But as the quinidine dose was increased to intermediate levels (40-50 mg/kg), phase plane plots showed clear non-uniform thickening, (indicating sensitive dependence on initial conditions), and also showed marked banding (densely filled regions separated by divisions or gaps). Both these phenomena are strong indicators of deterministic chaos as opposed to random noise. At these intermediate doses, Lyapunov exponents became positive and poincare return maps also indicated non-random chaos. At still higher doses, phase plane plots became more complex. In the two dogs that did exhibit VF (and not in the other) there was a significant change in the phase plane plot at the last pre-fibrillatory dose: the development of a 'funnel', a classic mechanism of chaos. The frequency spectra at all pre-fibrillatory doses were discrete, with peaks at a fundamental frequency and multiple harmonics. We conclude that chaos does in fact occur during progessive quinidine intoxication, and that phase plane plots are better indicators of chaos than frequency spectra.

CHAOTIC DYNAMICS IN QUINIDINE INTOXICATED ISOLATED CARDIAC FIBERS. Hrayr S Karagueuzian, Ph.D., FACC, Alan Garfinkel, Ph.D., Kichol Hong MD, George A. Diamond, MD, FACC. Division of Cardiology, Cedars-Sinai Med. Ctr. Los Angeles., CA Chaos theory has been used to explain complex dynamic behaviors of spontaneously beating and driven cardiac fibers. In the present study we investigated whether chaos theory would explain complex beat to beat fluctuations in action potential duration (APD) and action potential amplitude (APA) during quinidine intoxication. RV endocardial tissue blocks (2X2 cm) were isolated from anesthetized dogs (n=4) in which spontaneous ventricular fibrillation (VF) was induced with quinidine (100 mg/kg i.v. over 5 hours). Single cell simultaneous recordings were made from multiple (10-15) sites at various driving rates (1000 to 500 msec). APA and APD alternans (period 2) were observed in 35 of 42 cells on the endocardium. Increase in the driving rate from 1000 to 500 msec, caused the progressive appearance of higher order periodicities (period 3 and 4). Phase-locking, a stimulus (S) response (R) pattern repeating periodically were seen in all 4 preparations at S:R ratios of 2:1, 5:3, 3:2, a known precursor of chaos. Furthermore, at faster drive rates irregular, i.e. aperiodic variations in APA and APD were observed. No obvious relation could be found between the resting membrane potential and the nature of the periodicity. Cells could be in or out of synchrony with each other. Conclusion: A number of intermediate stages that presage chaos were seen in our quinidine intoxicated fibers. These dynamic changes could increase the heterogeneity of myocardial fibers, and predispose the ventricle to fibrillation.

TYPE ABSTRACT IN THIS SPACE
Read Instructions Carefully Before Typing

CAN THE COMPLEXITY OF VENTRICULAR FIBRILLATION BE MEASURED?

Timothy A. Denton, M.D., Hideaki Okazaki, M.D., George A. Diamond, M.D. F.A.C.C., and Hrayr S. Karagueuzian, Ph.D., F.A.C.C. Division of Cardiology, Cedars-Sinai Medical Center, Los Angeles California.

Ventricular fibrillation (VF) is a visually complex process that seems to defy simple explanation. Recent studies, which may help explain the mechanism of VF, have shown that the response of stressed ventricular myocardium to periodic stimulation varies on a beat to beat basis. The degree of variability increases as the applied stress increases in a manner consistent with a nonlinear dynamic process. Thus, the transitions from one dynamic state to another follow well defined routes characteristic of the system, and the final state is characterized by the emergence of complex, aperiodic, nonrandom behavior. In this study we tested the hypothesis that VF is one such final state, in that it exhibits characteristics consistent with aperiodic, nonrandom behavior. We used ischemia and reperfusion as stress factors in closed-chest anesthetized dogs (n=3) by intracoronary (LAD) balloon inflation and deflation. Three analytic techniques of nonlinear dynamics were applied during both normal sinus rhythm (NSR) and VF on 2 surface ECG leads and 2 intracardiac bipolar electrograms (RV and LV). The techniques used were spectral analysis (SA-fast Fourier transformation), phase plane plots (PPP-which describe the dynamic behavior's geometry) and fractal dimension (a measure of a signal's complexity). In NSR, SA revealed narrow-band spectra with fundamental frequencies at the sinus rate and harmonics extending beyond 50 Hz. PPP were consistent with periodic dynamics. Fractal dimension analysis in all cases revealed low dimensional behavior (1-2.5). SA of VF showed broad-band behavior with most of the energy at 6 Hz and with energy at all frequencies between 1 and 25 Hz. PPP showed constrained aperiodic behavior. Dimensional analysis revealed higher dimensions than NSR (4-6).

Conclusions: These data demonstrate that NSR is a simple, periodic process, whereas VF is a semi-complex, aperiodic, non-random process. These findings suggest that intermediate transitional dynamic states might exist that serve as sensitive indices of ventricular electrical stability.

B

GENERAL OUTLINE

Prediction of Sudden Coronary Death and Proarrhythmic Effects of Drugs Using Nonlinear Dynamic Methodology and Theory.

Introduction and Hypothesis.

The evolution of nonlinear dynamical systems under stress follows a deterministic and a well defined pathway that is characteristic to the system in question. The electrophysiologic properties of the heart muscle of the ventricle have been shown to manifest nonlinear dynamic properties. Furthermore, our preliminary data suggest that once the heart muscle is stressed with ischemia (coronary obstruction) or intoxicated with antiarrhythmic drug overdose (quinidine), characteristic changes of the dynamics of the electrophyiology of the ventricle occur. As these noxious stimuli eventually lead to ventricular fibrillation (sudden death), we are therefore hypothesizing in this research proposal that increased vulnerability of the ventricular myocardium to fibrillation, can be predicted by dynamic criteria, as is the case in other nonlinear dynamical physical systems that degenerate to chaotic dynamic regime.
Should our preliminary results prove to be reproducible, we will thus have achieved a method that will allow us to predict an impending ventricular fibrillation and assess the potential of proarrhythmic effects of antiarrhythmic drugs.
Additional information and discussion on the background, theory and significance of our approach for dynamical analysis please confer pages 24 to 56 of grant proposal (Nonlinear Dynamics and Ventricular fibrillation).

Protocols of the Study:

I. Antiarrhythmic Drugs, Proarrhythmia and Predictive Dynamic Markers:

In this portion of the project we will deliberately induce intoxication with quinidine (Class IA), either lidocaine or mexiletine (Class IB) and flecainide (Class IC) to cover all three subcalsses of Type I antiarrhythmic drugs, all of which have been reported to aggravate existing arrhythmias (i.e., proarrhythmic effects of antiarrhythmic drugs). The study design of progressive drug intoxication, the methodology and our preliminary results can be found on pages 31-32 and Figures 1, 2 and 3 on pages 45-47.

II. Acute Ischemia and Spontaneous Ventricular Fibrillation.
The study design and the methods of dynamic analysis can be found on pages 32--33 and preliminary results on page 48, Figure 4.

III. Chronic Ischemia and Inducible Ventricular Tachycardia and Ventricular Fibrillation.

Study design can be found in Appendix I and II, and the methods of analysis are the same as in the acute ischemia studies (above).

IV. Ventricular Tachyarrhythmias During Clinical Electrophysiology Testing:
Study design and methods of analysis can be found on pages 38-39.

V. Human Ventricular Fibrillation During Open Heart Surgery:
Study design and methods of analysis can be found on page 40 and in Figures 5 and 6 on pages 49-50.

VI. Cellular Electrophysiologic Basis of Nonlinear Dynamical Behavior of Drug-Intoxicated Cardiac Cells.
Study design and method of analysis and preliminary results can be found on pages 41-43, and in Figure 7 on page 51.

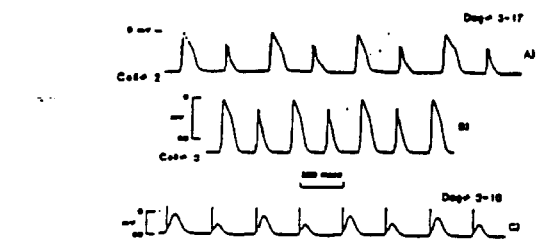
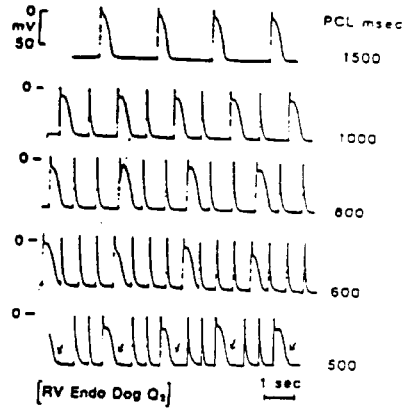
INDUCTION OF PERIODICITIES AND PHASE-LOCKING
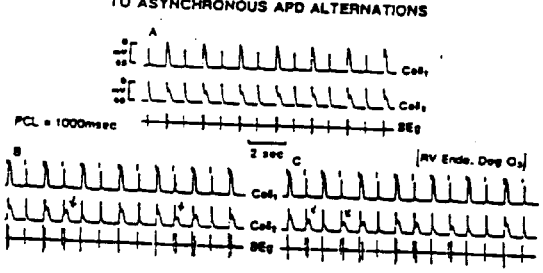
TRANSITION FROM SYNCHRONOUS TO ASYNCHRONOUS APD ALTERNATIONS
FIGURE 6
FIGURE 5
APERIODICITY DURING QUINIDINE INTOXICATION
PCL = 800msec    FIGURE 7
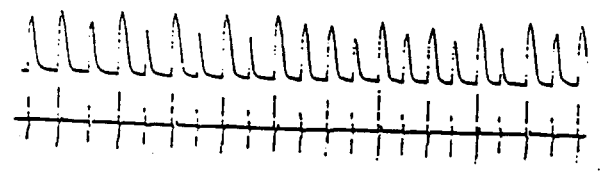
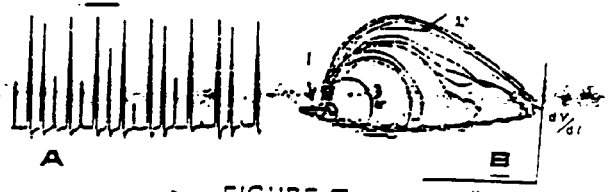
Phase Plane Plot
FIGURE 8

Phase Plane Plots of "Normal Sinus Rhythm"

Five Different Dynamic Methods of Analysis

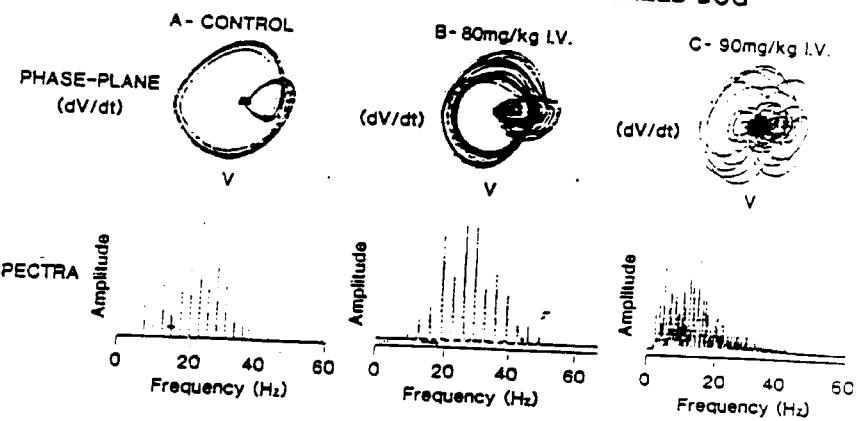
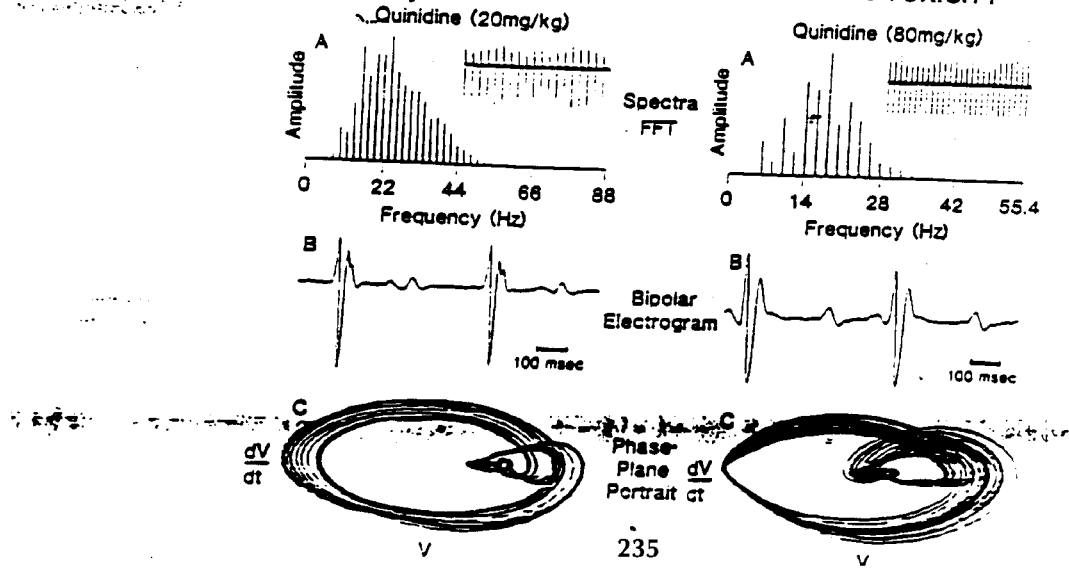

EVIDENCE FOR CHAOS IN HUMAN ATRIAL FIBRILLATION

Steven S. Khan, M.D., Alan Garfinkel, Ph.D, C. Thomas Peter, M.D., F.A.C.C., George A. Diamond, M.D., F.A.C.C. Cedars-Sinai Medical Center and UCLA School of Medicine, Los Angeles, CA.

A recently developed branch of mathematics, chaos theory, provides new insight into seemingly random processes. In order to determine whether the ventricular response in human atrial fibrillation is chaotic rather than random, we studied 16 patients, 4 by Holter monitoring and 12 by surface ECG; 4 of these patients were on a type I antiarrhythmic. RR intervals were measured by hand from ECG recordings, and by computer analysis of the Holter recordings using a specially developed analysis package (QRSDK; Marquette Electronics).

One dimensional next amplitude plots (RR interval vs prior RR interval) from the 4 patients on type I antiarrhythmics revealed an organized pattern, but those from patients not on type 1 agents did not. The Lyapunov exponent (an index of chaos when positive) ranged from 0.15 to 0.25. Fractal dimension (an index of the complexity of chaos) ranged between 6 and 7 for the untreated patients, and between 1 and 3 for patients on type I antiarrhythmics.

Conclusion: the ventricular response in clinical atrial fibrillation is chaotic rather than random. The lower fractal dimension associated with type I antiarrhythmic treatment is consistent with a beneficial therapeutic response.

Is Ventricular Fibrillation Random or Chaotic?

Steven J. Evans, Steven S. Khan, Alan Garfinkel, Robert M. Kass, Alfonso Albano, George A. Diamond. Cedars-Sinai Medical Center & UCLA, Los Angeles, CA, and Bryn Mawr College, Bryn Mawr, PA Although ventricular fibrillation (VF) appears random, order has been reported during the onset of VF. To determine if identifiable order is present throughout VF, we recorded hypothermia-induced VF in 8 patients during open heart surgery (a stable, perfused model of VF), and in 3 awake, normothermic patients with VF induced during electrophysiology testing. Analyses by 1) Fourier spectrum; 2) phase-plane plots (PP): (waveform voltage vs. its first derivative); 3) temporal return lag maps (TR): (waveform voltage vs. its voltage at a later fixed time interval); and 4) dimension (D) calculations (a measure of the number of independent variables necessary to define a system) were performed. All patients had a broad-band frequency spectrum (0-12 Hz), a low D (range: 2-5), and non-random structure (banding, forbidden zones) observed on PP and TR. In contrast, computer generated random waveforms had a broad-band spectrum but a high D($>9$), with no underlying structure apparent on PP or TR.

Conclusions: VF is not random, but has an identifiable underlying order which exhibits non-linear dynamical behavior suggestive of chaos. The ability to detect this order has important implications for the diagnosis and therapy of ventricular fibrillation.

ADEQUACY AND LIMITATIONS OF A NON-LINEAR COMPUTER MODEL OF VENTRICULAR MYOCARDIAL CELL MEMBRANE. TA Denton*, HS Karagueuzian*, GS Diamond*. Division of Cardiology, Cedars-Sinai Medical Center, Los Angeles, California.

The purpose of this study was to determine to what extent a computer model of the stressed myocardial cell membrane action potential (AP) could mimic in vitro behavior of the same. Computer models of myocardial APs have been constructed to study membrane behavior under various conditions, and such models have shown non-linear (chaotic) behavior (Jensen, et.al., Physica 13D:269, 1984). Driving the model at increasing rates, a periodic bifurcation was manifest as afterpotentials. Driving the model still faster caused a transition from periodic to aperiodic dynamics (chaos). Using this model as a guide, we studied normal and quinidine (Q) intoxicated canine right ventricular endocardial fibers (RVF) during stepwise increases in driving rates. RVF were isolated from six anesthetized dogs in which ventricular fibrillation was induced by stepwise increases with intravenous Q. Tissues were studied with the microelectrode technique in a bath maintained at 37 degrees C and superfused with Tyrode's solution. Controls were treated in the same fashion but without the Q intoxication. Control tissues showed no chaotic behavior with increasing drive rates as described in the model. Period doubling (alternation in AP duration and amplitude) was seen in all six intoxicated dogs. Two of the dogs exhibited phase locking and four showed aperiodic dynamics.

There is a discrepancy between the Jensen model and our in vitro results. Non-linear behavior would be predicted in a control preparation of myocardium but this was not seen in vitro. But with the addition of an agent that modifies ionic channel conductance (Q), non-linear behavior was demonstrable. Thus although this model has the potential for describing membrane dynamics after pharmacologic stress, our findings demonstrate its incompleteness in the absence of such stress. Accounting for the effects of Q may be instrumental in reformulating the model.

In summary, we have been unable to verify predicted behavior of myocardial membrane under stress, but non-linear behavior is easily demonstrable following Q intoxication. The Jensen computer model therefore needs further refinement.

INABILITY OF SPECTRAL ANALYSIS TO DISTINGUISH BETWEEN CHAOTIC AND RANDOM SIGNALS. TA Denton*, GS Diamond*. Division of Cardiology, Cedars-Sinai Medical Center, Los Angeles, California.

This study was undertaken to test the ability of spectral analysis (SA) to distinguish between chaotic and random signals. Mathematical techniques of chaos theory have been applied to the study of electrocardiographic signals. These methods attempt to determine if there is an underlying mechanism to a seemingly random process (VF, VT, inter-beat variability of sinus rhythm). SA by Fourier transformation (most often used is the Fast Fourier Transform [FFT]) is a common technique. The presence of broad band spectra (BBS), or a change from narrow band to BBS is often considered diagnostic of chaos. Nevertheless, although chaotic signals characteristically exhibit BBS the observation need not be specific. We performed this study to determine if random signals also exhibit BBS.

Random signals were obtained from two sources. A series of 5000 pseudo-random numbers were smoothed using the method of least squares approximation. The resultant was then analyzed by phase-plane plotting, return maps and FFT. A second series of random signals was obtained by smoothing white noise obtained from an analog to digital conversion board. These points were analyzed using the same techniques described above.

The random waveform was shown to be continuous on the basis of return maps and phase plane plots. The form of the return map was consistent with Gaussian randomness. The phase-plane plot showed a bounded trajectory without any clear pattern, again consistent with a random continuous signal. The FFT revealed a BBS with most of the power under 100Hz. The results from white noise were equivalent.

These data document that BBS are not unequivocally diagnostic of chaos, and can result from random signals. Additional tests (phase-plane plot, return map) are therefore necessary before concluding that a particular continuous signal is chaotic. In summary, SA may be necessary to verify the presence of a chaotic signal (to rule-out a periodic signal), but is insufficient by itself to make that determination. Additional tests such as evaluation of state space, return maps and Poincare' sections are required to diagnose a chaotic signal.

Temporal and Spatial Heterogeneity of Local
Atrial Activity During Acute Atrial
Fibrillation, Spectral and Dynamic Analysis.

Hrayr S. Karagueuzian, Werner W Peters, Steven S
Khan, George Diamond, Richard Helfant, William J
Mandel. Cedars-Sinai Med Center, Los Angeles, CA.

We simultaneously analyzed high, mid, and low right atrial endocardial bipolar electrograms (BEg) during acute atrial fibrillation (AF) in order to determine the dynamic nature of local atrial activity. AF was induced in dogs (n=6) by a 3-5 sec train of rapid stimuli. BEgs (7-10sec duration) were digitized at 833 Hz and analyzed using the fast Fourier transform (FFT) and phase plane plots (PPP). BEgs had no consistent temporal relationship with each other. At a given time, BEg morphology differed at different recording sites, and, at a given site, changed with time. FFT showed different peaks (5-30 Hz) with either discrete (periodic) or continuous (aperiodic) spectra in a time and site dependent manner. Spectra always became discrete immediately prior to spontaneous termination of AF. Similarly, PPP: a plot of voltage vs its first derivative, varied with respect to time and location. However, the morphology of the PPP were not random and had well defined features (structure) suggesting non-random dynamics.
Conclusion: AF in this model is both temporally and spatially heterogenous. Aperiodic local activity during AF may represent deterministic chaos.

Phase Plane Plots in Atrial Fibrillation: Initial Results and Clinical Implications

Werner W. Peters, Steven S. Khan, William J. Mandel, George Diamond, Hrayr S. Karagueuzian. Cedars-Sinai Medical Center, Los Angeles.

In order to develop algorithms to distinguish atrial arrhythmias from sinus rhythm (SR) and noise we evaluated the use of phase plane plots (PPP) in six mongrel dogs. Recordings of bipolar atrial electrograms (BE) were made from high, mid and low right atrium (HRA, MRA, LRA) and atrial fibrillation (AF) was induced electrically. BE were digitized and 2 seconds of data analyzed using PPP: plots of the voltage vs its first derivative; and lag plots (LP): plots of the signal vs its value at a fixed delay in time. PPP of atrial BE during AF and of noise revealed non-repetitive cycles (orbits) which filled the V-dV/dt plane and, in AF, resembled constrained randomness. In contrast, SR and atrial flutter revealed repetitive cycles constrained to distinct orbits. A box counting algorithm was developed to quantitate the percent of area visited by the orbits. PPP of LRA plots in SR demonstrated less structure than either MRA or HRA PPP due to detection of ventricular excitation and all PPP demonstrated susceptibility to noise. LP were less sensitive to noise but had a similar structure.
Conclusion: PPP and LP may be useful in developing algorithms to distinguish between AF and SR.

Chaotic Dynamics of Cardiac Action
Potential Duration and Amplitude.

Hrayr S. Karagueuzian, George A. Diamond, Kichol Hong, Richard H. Helfant, Steven S. Khan. Division of Cardiology, Cedars-Sinai Medical Center, Los Angeles, CA.

To determine if action potential duration (APD) and amplitude (APA) manifest deterministic chaos, we studied right ventricular (RV) endocardial tissue isolated from dogs (n=3) with ventricular tachycardia and fibrillation (VT/VF) induced by pacing and quinidine (Q)(100mg/kg iv over 5hrs). Period 2 alternans of APD ($\Delta$msec=108±36, at 50% repolarization) and of APA ($\Delta$mV=9±8) emerged at cycle length (CL) of 1 sec. At shorter CLs, period 3 and 4 alternans were evident, eventually leading to aperiodic APD/APA behavior at CL<600msec. Phase-plane plot of these aperiodic responses showed forbidden zones and sensitive dependence on initial conditions, 2 hallamarks of deterministic chaos. Although period 2 alternans of APD/APA also occurred in fibers isolated from Q-intoxicated dogs (n=3) with no VT/VF, threshold CL was shorter ($p<0.05$), (375±51 vs 740±199msec). No other form of periodicity and/or chaos ever occurred in the no VT/VF group or in control untreated dogs (n=3). We conclude that Q overdose can induce chaos in APD and APA. Such dynamics provide a novel cellular mechanism for the development of VT/VF in vivo.

NONLINEAR DYNAMIC ANALYSIS OF ELECTROCARDIOGRAPHIC SIGNALS

Timothy A. Denton, M.D., George A. Diamond, M.D., F.A.C.C., Cedars-Sinai Medical Center, Los Angeles, California.

Recent advances in the mathematics of nonlinear dynamics have led to its application in biology and cardiology. A series of graphical programs have been written to aid the understanding of chaotic signals and processes, and to analyze biological signals. All programs were written in Pascal for use on IBM personal computers.

The first program generates standard signals. Sine, square, triangular, sawtooth, quasiperiodic and modulated (amplitude and frequency) sine waves of any desired frequency, digitization rate and amplitude can be produced in files up to 10,190 points in length. Linear or Gaussian noise of any amplitude can be added to the signals.

Chaotic signals are generated by using a fourth-order Runge-Kutta algorithm for the solution of systems of differential equations (e.g., Lorenz, Rossler, Duffing, Silnikov, Van der Pol). Length of data files generated is limited only by the size of the hard disk. Programs for production of chaotic maps (logistic, Henon) and for the bifurcation diagram of the logistic map are also included. Random signals are constructed by filtering a pseudorandom number series, or any other random time-series.

Standard and electrocardiographic signals (digitized at 1000 kHz) are analyzed by phase plane plots, return maps and spectral analysis. Three types of phase plane plots are constructed (amplitude vs first derivative, amplitude vs second derivative, and first vs second derivative), but the program can be modified to generate any desired combination of amplitude or derivative. Return maps are constructed by choosing a lag of interest, and maps with that lag and three multiples of that lag are displayed.

Spectral analysis by fast Fourier transformation (FFT) is performed at a resolution of 8,192 points on data files of any length (by truncation or zero padding). The spectrum is displayed as either the raw FFT, power spectrum, or log FFT. Hard copy of all the graphs can be obtained by a screen dump.

Application/Control Number: 948,095

Page 3

Art Unit: 3737

--INABILITY OF SPECTRAL ANALYSIS TO DISTINGUISH BETWEEN CHAOTIC AND RANDOM SIGNALS TA Denton; GS Diamond, Division of Cardiology, Cedars-Sinai Medical Center, Los Angeles, California.

This study was undertaken to test the ability of special analysis (SA) to distinguish between chaotic and random signals. Mathematical techniques of chaos theory have been applied to the study of electrocardiographic signals. These methods attempt to determine if there is an underlying mechanism to a seemingly random process (VF, VT, inter-beat variability of sinus rhythm). SA by Fourier transformations (most often used is the Fast Fourier Transform [FFT]) is a common technique. The presence of broad band spectra (BBS), or a change from narrow band to BBS is often considered diagnostic of chaos. Nevertheless, although chaotic signals characteristically exhibit BBS the observation need not be specific. We performed this study to determine if random signals also exhibit BBS.

Random signals were obtained from two sources. A series of 5000 pseudo-random numbers were smoothed using the method of least squares approximation. The resultant was then analyzed by phase-plane plotting, return maps and FFT. A second series of random signals was obtained by smoothing white noise obtained from an analog to digital conversion board. These points were analyzed using the same technique described above.

The random waveform was shown to be continuous on the basis of return maps and phase plane plots. The form of the return map was consistent with Gaussian randomness. The phase-plane plot showed abounded trajectory without any clear pattern, again consistent with a random continuous signal. The FFT revealed a BBS with most of the power under 100Hz. The results from white noise were equivalent.

These data document that the BBS are not unequivocally diagnostic of chaos, and can result from random signals. Additional tests (phase-plane plot, return map) are therefore necessary before concluding that a particular continuous signal is chaotic. In summary, SA may be necessary to verify the presence of a chaotic signal (to rule out a periodic signal), but it is insufficient by itself to make that determination. Additional tests such as evaluation of state space, return maps and Poincare sections are required to diagnose a chaotic signal.

ADEQUACY AND LIMITATIONS OF A NON-LINEAR COMPUTER MODEL OF VENTRICULAR MYOCARDIAL CELL MEMBRANE TA Denton; HS Karagueuzian, GS Diamond. Division of Cardiology, Cedars-Sinai Medical Center, Los Angeles, California.

The purpose of this study was to determine to what extent a computer model of the stressed myocardial membrane action potential (AP) could mimic in vitro behavior of the same. Computer models of myocardial APs have been constructed to study membrane behavior under under various conditions, and such models have shown non-linear (Chaotic) behavior (Jensen et al., Physics 13D:269, 1964). Driving the model at increasing rates, a periodic bifurcation was manifest as afterpotentials. Driving the model still faster caused a transition from periodic to aperiodic dynamics (chaos). Using this model as a guide, we studied normal and quinidine (Q)

Application/Control Number: 948,095 Page 4

Art Unit: 3737 intoxicated canine right ventricular endocardial fibers (RVF) during stepwise increases in driving rates. RVF were isolated from six anthesthetized dogs in which ventricular fibrillation was induced by stepwise increases with intravenous Q. Tissues were studied with the microelectrode technique in a bath maintained at 37 degrees C and superfused with Tyrode's solution. Controls were treated in the same fashion but without Q intoxication. Control tissues showed no chaotic behavior with increasing drive rates as described in the model. Period doubling (alternation in AP duration and amplitude) were seen in all six intoxicated dogs. Two of the dogs exhibited phase locking and four showed aperiodic dynamics.

There is a discrepancy between the Jensen model and our in vitro results. Non-linear behavior would be predicted in a control preparation of myocardium but this was not seen in vitro. But with the addition of an agent that modifies ionic channel conductance (Q), non-linear behavior was demonstrable. Thus although this model has the potential for describing membrane dynamics after pharmacologic stress, our findings demonstrate its incompleteness in the absence of such stress. Accounting for the effects of Q may be instrumental in reformulating the model.

In summary, we have been unable to verify predicted behavior of myocardial membrane under stress but non-linear behavior is easily demonstrable following Q intoxication. The Jensen computer model therefore needs further refinement.--

Any inquiry concerning this communication or earlier communications from the examiner should be directed to Mr. Kamm whose telephone number is (703) 308-2994

Technology Center 3700 fax number is (703)305-3580.

wek
November 1, 1999

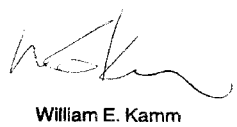

William E. Kamm
Primary Examiner

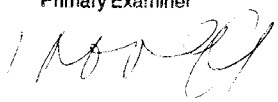

Application/Control Number: 948,095                                           Page 2

Art Unit: 3737

An examiner's amendment to the record appears below. Should the changes and/or additions be unacceptable to applicant, an amendment may be filed as provided by 37 CFR 1.312. To ensure consideration of such an amendment, it MUST be submitted no later than the payment of the issue fee.

The application has been amended as follows in accordance with the information received from applicant's attorney on 28 October 1999:

Lines 2-3 of the last paragraph on page 196 have been rewritten to read:

--et al [41] have shown that Purkinje fiber action potentials after a sudden increase in the pacing rate are longer on odd beats whereas ventricular muscle action potentials are longer on even beats. These effects were transient--

Lines 3-4 of page 197 have been rewritten to read:

--In the previous section dealing with microelectrode studies, it becomes clear that there should be divergent changes in the local bipolar electrogram at different recording sites. But if its mechanism is related--.

Page 243 has been entirely replaced by the following:

What is claimed is:

1. A method for detecting a propensity for ventricular fibrillation comprising applying a stimulus to heart muscle cells;

measuring the signal response of said heart muscle cells;

identifying a resting period and time duration for recovery from said signa;

measuring values for said resting period and time duration for recovery of action potential duration for said cells;

measuring the value of said plateau action potential duration;

fitting a curve to said detected values for the restitution period and time duration for recovery using the exponential equation $APD = APD_{P_1} - Ae^{-DI/\tau}$ where APD represents the time duration for recovery of action potential duration, $APD_{P_1}$ is the plateau action potential duration, A is a proportionality constant, DI is said resting period, and $\tau$ is the time constant;

determining the aforestated equation parameters so as to determine the value of $\tau$ for said fitted curve;

providing the value of $\tau$ for a normal patient;

comparing the value of $\tau$ for said fitted curve with the value of $\tau$ for a normal patient;

registering the propensity for ventricular fibrillation at a time when the value of the time constant $\tau$ for said fitted curve is larger than the value of $\tau$ for a normal patient.

2. A method for detecting a propensity for ventricular fibrillation comprising applying a stimulus to heart muscle cells;

measuring the signal response of said heart muscle cells;

measuring values for the resting period and time duration for recovery of action potential duration for said cells;

constructing an action potential duration curve using said detected values;

determining the slope of said constructed curve;

providing the slope of the action potential duration curve for a normal patient;

comparing the slope of said constructed action potential duration curve with the slope of said action potential duration curve for a normal patient;

registering the propensity for ventricular fibrillation where the slope of the said constructed curve is at least steeper than the slope of said action potential duration curve for a normal patient.

3. The method for detecting a propensity for ventricular fibrillation of claim 2 wherein the step of determining the slope of said constructed curve includes fitting a curve to said detected values and using said fitted curve to determine the slope of said constructed curve.

* * * * *

UNITED STATES PATENT AND TRADEMARK OFFICE
CERTIFICATE OF CORRECTION

PATENT NO. : 6,094,593
DATED : July 25, 2000
INVENTOR(S) : Hrayr S. Karagueuzian et al.

It is certified that error appears in the above-identified patent and that said Letters Patent is hereby corrected as shown below:

In the Title:

Please correct the title of the patent as follows:

Delete "Method and Apparatus for Detecting Prospenity for Ventricular Fibrillation Using Action Potential Curves" and insert -- Method and Apparatus for Detecting Propensity for Ventricular Fibrillation Using Action Potential Curves --.

Signed and Sealed this

Twenty-second Day of May, 2001

*Attest:*

NICHOLAS P. GODICI

*Attesting Officer*    Acting Director of the United States Patent and Trademark Office